US009879053B2

(12) United States Patent
Nicolette et al.

(10) Patent No.: US 9,879,053 B2
(45) Date of Patent: Jan. 30, 2018

(54) STRAIN-INDEPENDENT AMPLIFICATION OF PATHOGENS AND VACCINES THERETO

(71) Applicant: Argos Therapeutics, Inc., Durham, NC (US)

(72) Inventors: Charles Nicolette, Durham, NC (US); Irina Tcherepanova, Chapel Hill, NC (US); Jason Harris, Durham, NC (US); Donald Healey, Anderson, TX (US)

(73) Assignee: Argos Therapeutics, Inc., Durham, NC (US)

(*) Notice: Subject to any disclaimer, the term of this patent is extended or adjusted under 35 U.S.C. 154(b) by 117 days.

(21) Appl. No.: 14/659,487

(22) Filed: Mar. 16, 2015

(65) Prior Publication Data

US 2015/0252083 A1    Sep. 10, 2015

Related U.S. Application Data

(62) Division of application No. 11/662,828, filed as application No. PCT/US2005/032710 on Sep. 14, 2005, now Pat. No. 9,085,807.

(60) Provisional application No. 60/522,310, filed on Sep. 14, 2004, provisional application No. 60/665,130, filed on Mar. 25, 2005.

(51) Int. Cl.
| | |
|---|---|
| *A61K 45/06* | (2006.01) |
| *C07K 14/005* | (2006.01) |
| *C12Q 1/70* | (2006.01) |
| *A61K 39/21* | (2006.01) |
| *C12N 7/00* | (2006.01) |
| *A61K 39/00* | (2006.01) |

(52) U.S. Cl.
CPC ............ *C07K 14/005* (2013.01); *A61K 39/21* (2013.01); *C12N 7/00* (2013.01); *C12Q 1/703* (2013.01); *A61K 2039/5154* (2013.01); *A61K 2039/5156* (2013.01); *C12N 2740/16041* (2013.01); *C12N 2740/16234* (2013.01); *C12N 2740/16334* (2013.01)

(58) Field of Classification Search
None
See application file for complete search history.

(56) References Cited

U.S. PATENT DOCUMENTS

| | | |
|---|---|---|
| 5,386,022 A | 1/1995 | Sninsky et al. |
| 5,599,662 A | 2/1997 | Respess |
| 5,908,743 A | 6/1999 | Christopherson et al. |
| 6,001,558 A | 12/1999 | Backus et al. |
| 6,030,769 A | 2/2000 | Simon |
| 6,043,081 A | 3/2000 | Cohen et al. |
| 6,090,392 A * | 7/2000 | Berman ............... C07K 14/005 424/184.1 |
| 6,194,142 B1 | 2/2001 | Moncany et al. |
| 6,232,455 B1 | 5/2001 | Kroeger et al. |
| 6,379,957 B1 | 4/2002 | Johnston-Dow et al. |
| 6,531,588 B1 | 3/2003 | Johnston-Dow et al. |
| 6,627,442 B1 | 9/2003 | Humeau et al. |
| 6,670,186 B1 | 12/2003 | Nair et al. |
| 8,221,981 B2 | 7/2012 | Tcherepanova et al. |
| 2003/0148280 A1 | 8/2003 | Harris et al. |
| 2004/0009194 A1 | 1/2004 | Andreiu et al. |
| 2004/0081962 A1 | 4/2004 | Chen et al. |
| 2007/0054311 A1 | 3/2007 | Kamberov et al. |
| 2007/0248578 A1 | 10/2007 | Tcherepanova et al. |
| 2008/0311155 A1 | 12/2008 | Nicolette et al. |
| 2012/0231509 A1 | 9/2012 | Tcherepanova et al. |

FOREIGN PATENT DOCUMENTS

| | | |
|---|---|---|
| WO | 1999016910 A1 | 4/1999 |
| WO | 1999047102 A2 | 9/1999 |
| WO | 2001011067 A1 | 2/2001 |
| WO | 2004050856 A2 | 6/2004 |
| WO | 2005052128 A2 | 6/2005 |
| WO | 2009017743 A2 | 2/2009 |

OTHER PUBLICATIONS

Zhao et al. (Journal of Experimental Medicine, 2003, vol. 197, p. 153-162).*
Ejaz et al. (PLOS, Sep. 2012, vol. 7, p. 1-14).*
Weissman (Journal of Imunology, 2000, vol. 165, p. 4710-4717).*
Tcherepanova et al., "Multiplex RT-PCR amplification of HIV genes to create a completely autologous DC-based immunotherapy for the treatment of HIV infection," PLoS One, 2008, p. e1489, vol. 3.
Tcherepanova et al., "The Immunosuppressive Properties of the HIV Vpr Protein Are Linked to a Single Highly Conserved Residue, R90," PLoS One, 2009, pp. 1-10, vol. 4.
Thornburg et al., "Induction of cytotoxic T lymphocytes with dendritic cells transfected with human papillomavirus E6 and E7 RNA: implications for cervical cancer immunotherapy," (Jul. 2000) J. Immunother. 23(4): 412-18.

(Continued)

*Primary Examiner* — Agnieszka Boesen
(74) *Attorney, Agent, or Firm* — Elaine T. Sale; Leigh W. Thorne

(57) ABSTRACT

This in invention relates to methods for the nucleic acid amplification of multiple variants (strains) of any pathogen present in a sample, and preferably in a sample from a pathogen infected individual. In preferred embodiments, the pathogen is a retrovirus, such as HIV. The amplified pathogen nucleic acid can be used to identify the pathogen variants present in a sample, to quantitate the pathogen present in a sample, and as a nucleic acid vaccine, or in the preparation of antigen presenting cell vaccines. Nucleic acids produced by the methods of the invention or the proteins encoded thereby can be used to transfect/load antigen presenting cells. The loaded antigen presenting cells can then be used as a vaccine for the treatment of pathogen infection. In another embodiment, nucleic acids produced by the methods of the invention can be used directly as nucleic acid vaccines without prior loading into antigen presenting cells.

11 Claims, 62 Drawing Sheets

(56) References Cited

OTHER PUBLICATIONS

Tovanabutra et al., "The changing molecular epidemiology of HIV Type 1 among Northern Thai Drug Users . . . ," AIDS Res. and Hum. Retroviruses, 2004, vol. 20, pp. 465-475.
Wang et al., "Gene defects clustered at the C-terminus of the vpr gene of HIV-1 in long-term nonprogressing mother and child pair . . . ," Virology (1996) 223: 224-232.
Weissman et al., "HIV Gag mRNA transfection of dendritic cells (DC) delivers encoded antigen to MHC class I and II molecules, causes DC maturation, and induces a potent human in vitro primary immune response," J. Immunol. (2000) vol. 165, pp. 4710-4717.
Zazzi et al., "Simultaneous amplification of multiple HIV-1 DNA sequence from clinical specimens by using nested-primer [PCR]," AIDS Res. Hum. Retroviruses (Apr. 1993) 9(4): 315-322.
Zhao et al., "Functional conservation of HIV-1 Vpr and variability in a mother-child pair of long-term non-progressors," Virus. Res. (2002) 89: 103-121.
Routy et al., "Arcelis™ AGS-004 dendritic cell-based immunotherapy for HIV infection," Immunotherapy, 2010, pp. 467-476, vol. 2.
Kikuchi et al., "Dendritic cells genetically modified to express CD40 ligand and pulsed with antigen can initiate antigen-specific humoral immunity independent of CD4+ T cells," Nat Med. (Oct. 2000), vol. 6, No. 10, pp. 1154-1159.
Letvin et al., "Progress and obstacles in the development of an AIDS vaccine," Nat. Immunol. (2006), pp. 930-939, vol. 6.
Lu et al., "Therapeutic dendritic-cell vaccine for chronic HIV-1 infection," Nat. Med. (Dec. 2004), pp. 1359-1365, vol. 10, No. 12.
Lu et al., "Therapeutic dendritic-cell vaccine for simian AIDS," Nat. Med. (Jan. 2003) vol. 9, No. 1, pp. 27-32.
Lu et al., "In Vitro Human Immunodeficiency Virus Eradication by Autologous CD8+ T Cells Expanded with Inactivated-Virus-Pulsed Dendritic Cells," J. Virol., Oct. 2001, pp. 8949-8956, vol. 75.
Ludewig, "Dendritic cell vaccination and viral infection—animal models," Current Topics in Microbiology & Immunology (2003), vol. 276, pp. 199-214.
Lum et al., "Vpr R77Q is associated with long-term nonprogressive HIV infection and impaired induction of apoptosis," J. Clin. Invest. (2003) 111: 1547-54.
Machuca et al. (1999), "Human Immunodeficiency Virus Type 2 Infection in Spain," 1999, Intervirology, pp. 37-42, vol. 42.
Michael et al., "Defective accessory genes in a human immunodeficiency virus type I-infected long-term survivor lacking recoverable virus," J. Virol. (1995) 69: 4228-36.
Michael et al., "Development of calibrated viral load standards for Group M subtypes of [HIV] type 1 and performance of an improved Amplicor HIV-1 Monitor test with isolates of diverse subtypes," J. Clin. Microbiol. (Aug. 1999) pp. 2557-2563.
Mirani et al., "HIV-1 protein Vpr suppresses IL-12 production from human monocytes by enhancing glucocorticoid action . . . ," J. Immunol. (2002) 169: 6361-68.
Nehete et al., "Dendritic cells enhance detection of antigen-specific cellular immune responses by lymphocytes from rhesus macaques immunized with an HIV envelope peptide cocktail vaccine," J. Med. Primatol. (Apr. 2003) 32(2): 67-73.
Ponsaerts et al., "Cancer immunotherapy using RNA-loaded dendritic cells," Clin. Exp. Immunol. (Dec. 2003) 124: 378-384.
Pope, "Dendritic cells as a conduit to improve HIV vaccines," Curr. Mol. Med. (2003), vol. 3, pp. 229-242.
Routy et al., "Immunologic activity and safety of autologous HIV RNA-electroporated dendritic cells in HIV-1 infected patients receiving antiretroviral therapy," Clin. Immunol. (Feb. 2010) vol. 132, No. 2, pp. 140-147.
Singh et al., "A long-term follow-up of an HIV type 1-infected patient reveals a coincidence of Nef-directed cytotoxic T lymphocyte effectors and high incidence of epitope-deleted variants," AIDS Res. Hum. Retroviruses, 2001, pp. 1265-1271, vol. 17.
Strobel et al., "Human dendritic cells transfected with either RNA or DNA encoding influenza matrix protein M1 differ in their ability to stimulate cytotoxic T lymphocytes," Gene Therapy (Dec. 2000) 7(23): 2028-35.
Su et al., "The generation of LMP 2a-specific cytotoxic T lymphocytes for the treatment of patients with Epstein-Barr virus-positive Hodgkin disease," Eur. J. Immunol. (Mar. 2001) 31(3): 947-958.
Tcherepanova, "Declaration under Rule 132 of Dr. Irina Tcherepanova," submitted Apr. 2, 2010, in U.S. Appl. No. 11/662,828.
Abravaya et al., "Performance of a multiplex qualitative PCR LCx assay for detection of human . . . (HIV-1) group M subtyes, group O, and HIV-2," J. Clin. Microbiol., Feb. 2000, pp. 716-723, vol. 38.
Argos Therapeutics, Press release dated Jan. 9, 2015, "Argos Therapeutics Provides Update on Clinical Research for Investigational Fully Personalized Immunotherapy for the Treatment of HIV".
Bartido et al., "T-cell responses to multiple antigens presented by RNA-transfected APCs: a possible immunomonitoring tool," Cancer Immunol. Immunother., Feb. 2004, pp. 100-109, vol. 53(2).
Berman et al., "Genetic and immunologic characterization of viruses infecting MN-RGP120 vaccinated volunteers," International Conference on AIDS, Jul. 1996, p. 10, Supp. 3, No. 10.
Candotti et al., "Multiplex real-time quantitative RT-PCR assay for hepatitis B virus, hepatitis C virus, and [HIV] type 1," J. Virol. Meth., 2004, pp. 39-47, vol. 118.
Cham et al., "Development of a one-tube multplex reverse transcriptase-[PCR] assay for the simultaneous amplification of HIV type 1 group M gag and env heteroduplex mobility assay fragments," AIDS Res Hum Retroviruses, Oct. 2000, pp. 1503-1505, vol. 16, No. 15.
Christopherson et al., "PCR-based assay to quantify human immunodeficiency virus type 1 DNA in peripheral blood mononuclear cells," J. Clin. Microbiol., Feb. 2000, pp. 630-634.
Christopherson et al., "The effects of internal primer-template mismatches on RT-PCR: HIV-1 model studies," Nucl. Acids Res., 1997, pp. 654-658, vol. 25, No. 3.
Compton, "Degenerate primers for DNA amplification," Chapter 5 in PCR Protocols: A Guide to Methods and Applications (1990), pp. 39-45, Academic Press, Inc.
DeBenedette et al., "AGS-004 induces multi-functional CTL responses in chronically infected HIV subjects treated with autologous dendritic cell therapy," poster presented at Keystone Symposium on Molecular and Cellular Biology, Mar. 22-27, 2015, Alberta, Canada.
Defoort et al., "Simultaneous detection of multiplex-amplified [HIV] type 1 RNA, hepatitis C virus RNA, and hepatitis B virus DNA using a slow cytometer microsphere-based hybridization assay," J. Clin. Microbiol. (Mar. 2000) vol. 30, No. 3, pp. 1066-1071.
Evans et al., "Virus-specific cytotoxic T-lymphocyte responses select for amino-acid variation in [SIV] virus Env and Nef," Nat Med. (Nov. 1999) vol. 5, No. 11, pp. 1270-1276.
Garcia et al., "Therapeutic immunization with dendritic cells loaded with heat-inactivated autologous HIV-1 in patients with chronic HIV-1 infection," J. Infect. Dis. (May 15, 2005), vol. 191, pp. 1680-1685.
Gilboa et al., "Cancer immunotherapy with mRNA-transfected dendritic cells," Imm. Rev. (Jun. 2004) 199: 251-263.
Giri et al., "DNA vaccines against [HIV] type 1 in the past decade," Clin. Microbiol. Rev. (Apr. 2004) 17(2): 370-89.
Granelli-Piperno et al., "HIV-1-infected monocyte-derived dendritic cells do not undergo maturation but can elicit IL-10 production and T cell regulation," PNAS (May 18, 2004), vol. 101, No. 20, pp. 7669-7674.
Heiser et al., "Autologous dendritic cells transfected with prostate-specific antigen RNA stimulate CTL responses against metastatic prostate tumors," J. Clin. Invest. (Feb. 2002) 109(3): 409-17.
Huang et al., "Priming of [HIV] type 1 . . . -specific CD8+ T cell responses by dendritic cells loaded with HIV-1 proteins," J. Infect. Dis. (Jan. 15, 2003), vol. 187, pp. 315-319.
Idemyor, "[HIV]: scientific challenges impeding candidate vaccines," HIV Clin. Trials (Nov. 2003) vol. 4, No. 6, pp. 421-424.

(56) References Cited

OTHER PUBLICATIONS

Innis et al., "Optimization of PCRs," PCR Protocols: A Guide to Methods and Applications (1990), pp. 3-12.
Kellogg et al., "Detection of Human Immunodeficiency Virus," PCR Protocols: A Guide to Methods and Applications (1990), pp. 337-347.

* cited by examiner

PCR PRIMERS & REFERENCE
REF SEQUENCE        ACCESSION
HIV-1               NC001802

| PRIMER #/SEQ ID# | PRIMER NAME | PRIMER SEQUENCE 5' TO 3' | TM |
|---|---|---|---|
| 1 | GAG F 124 | ACTCTGGTAACTAGAGATCC | 58.35 |
| 2 | GAG F 124.1 | ACTCTGATAACTAGAGATCC | |
| 3 | GAG F 124.2 | ACTCTGGTAGCTAGAGATCC | |
| | | | |
| 4 | GAG F 304 | AATTTTGACTAGCGGAGGC | 58 |
| 5 | GAG F 304.1 | AAATTTTGACTAGCGGAGGC | |
| 6 | GAG F 304.2 | AAATTTTTGACTAGCGGAGGC | |
| 7 | GAG F 304.3 | TATTTTGACTAGCGGAGGC | |
| 8 | GAG F 304.4 | ATTTTTGACTAGCGGAGGC | |
| 9 | GAG F 304.5 | ACTTT-GACTAGCGGAGGC | |
| 10 | GAG F 304.6 | TTTTTTGACTAGCGGAGGC | |
| 11 | GAG F 304.7 | AATTTTTGACTAGCGGAGGC | |
| 12 | GAG F 304.8 | A-TTTTGACTAGCGGAGGC | |
| 13 | GAG F 304.9 | AAATTTTGACTAGCGGAGGC | |
| 14 | GAG F 304.10 | CATTTTGACTAGCGGAGGC | |
| 15 | GAG F 304.11 | -ATTTTGACTAGCGGAGGC | |
| | | | |
| 16 | GAG F 334 | AGATGGGTGCGAGAGCGT | 62.18 |
| 17 | GAG F 334.1 | AGATGGGTGCGAGACCGT | 62.18 |
| 18 | GAG F 334.2 | AGAGAGGGTGCGAGAGCGT | |
| 19 | T7 GAG F 334 | TAATACGACTCACTATAGGGAGACCACCATGGGTGCGAGAGCGT | 59.5 |
| 20 | T7 GAG F 334.1 | TAATACGACTCACTATAGGGAGACCACCATGGGTGCGAGACCGT | 59.5 |
| | | | |
| 21 | GAG R 1833 | GTGACGAGGGGTCGTTG | 62.02 |
| 22 | GAG R 1833.1 | GTGACGAGGGGTCGCTG | 64.43 |
| 23 | GAG R 1833.2 | GTGACGATGGGTCGTTG | |
| 24 | GAG R 1833.3 | GAGACGAGGGGTCGTTG | |
| 25 | GAG R 1833.4 | TTGACGAGGGGTCGTTG | |
| 26 | GAG R 1833.5 | GTAACGAGGGGCGTTG | 62.02 |
| 27 | GAG R 1833.6 | GTGTCGAGGGGCGTTG | 64.43 |
| 28 | GAG R 1833.7 | GTGACAAGGGGTCGTTG | |

FIGURE 1A

| | | | |
|---|---|---|---|
| 29 | GAG R 1833.8 | GTAACGAGGGGTCGTTG | |
| 30 | GAG R 1833.9 | GCAACGAGGGGTCGTTG | |
| 31 | GAG R 1833.10 | GCGACGAGGGGTCGTTG | |
| 32 | GAG R 1881 | GCTCCTGTATCTAATAGAGC | 58.35 |
| 33 | GAG R 1881.1 | GCTCCTGTATCTAATAAAGC | 56.3 |
| 34 | GAG R 1881.2 | GCTCCTGTATCTAACAGAGC | 60.4 |
| 35 | GAG R 1881.3 | GCTCCTGTGTCTAATAGAGC | |
| 36 | GAG R 1913 | TTTGGTTTCCATCTTCCTGG | 58.35 |
| 37 | GAG R 1913.1 | TTTGGTTTCCATCTTCCTGC | 58.35 |
| 38 | GAG R 1913.2 | TTTGGCTTCCATCTCCCTGG | 62.45 |
| 39 | GAG R 1913.3 | TTTGGCTTCCATCTTCCTGG | |
| 40 | GAG R 1913.4 | TTTGGTTTCCATTTCCCTGG | 58.35 |
| 41 | GAG R 1913.5 | TTTGGTTTCCATTTTCCTGG | 56.3 |
| 42 | GAG R 1913.6 | TTTGGCTTCCATCTTCCTGG | |
| 43 | GAG R 1913.7 | TTCGGTTTCCATCTTCCTGG | |
| 44 | VPR F 4995 | GCAGGACATAACAAGGTAGG | 60.4 |
| 45 | VPR F 4995.1 | GCAGGACATAGCAAGGTAGG | |
| 46 | VPR F 4995.2 | GCAGGACATAACAAAGTAGG | |
| 47 | VPR F 4995.3 | GCAGGACATAACAAGATAGG | |
| 48 | VPR F 4995.4 | GCAGGACATAACAAAGTAGA | 56.3 |
| 49 | VPR F 5058 | AAGATAAAGCCACCTTTGCC | 58.35 |
| 50 | VPR F 5058.1 | CAGATAAAGCCACCTTTGCC | |
| 51 | VPR F 5058.2 | AAGGTAAAGCCACCTTTGCC | |
| 52 | VPR F 5058.3 | AAGATAAGGCCACCTTTGCC | |
| 53 | VPR F 5090 | ACTGACAGAGGATAGATGG | 58 |
| 54 | VPR F 5090.1 | ACTGATAGAGGATAGATGG | |
| 55 | VPR F 5090.2 | ACTAACAGAGGATAGATGG | |
| 56 | VPR F 5090.3 | ACTGACAGAGGACAGATGG | 60.16 |
| 57 | T7 VPR F 5090 | TAATACGACTCACTATAGGGAGACCACC ATGGA ACAAGCCCCAG | 57 |
| 58 | T7 VPR F 5090.1 | TAATACGACTCACTATAGGGAGACCACCATGGA ACAAGCCCCGG | 59.5 |

FIGURE 1B

| | | | |
|---|---|---|---|
| 60 | VPR R 5296 | GGATAAACAGCAGTTGTTGC | 58.35 |
| 61 | VPR R 5296.1 | GAATAAACAGCAGTTGTTGT | 54.25 |
| 62 | VPR R 5296.2 | GGATAAACGGCAGTTGTTGC | |
| 63 | VPR R 5296.3 | GAATAAACAACAGTTGTTGC | |
| 64 | VPR R 5296.4 | GAATAAACAGCAGCTGTTGC | 58.35 |
| | | | |
| 65 | VPR R 5328 | ATTCTGCTATGTCGACACCC | 60.4 |
| 66 | VPR R 5328.1 | ATTCTGCTATGTCGGCGCCC | 64.5 |
| 67 | VPR R 5328.2 | ATTCTGCTATGTCGGCACCC | 62.45 |
| 68 | VPR R 5328.3 | ATTCTGCTATGTTGACACCC | 58.35 |
| | | | |
| 69 | VPR R 5363 | CTCCATTTCTTGCTCTCCTC | 60.4 |
| 70 | VPR R 5363.1 | CTCCATTTCTTGCTCTTCTC | 58.35 |
| 71 | VPR R 5363.2 | CTCCATTCCTTGCTCTCCTC | |
| 72 | VPR R 5363.3 | CTCTATTTCTTGCTCTCCTC | |
| 73 | VPR R 5363.4 | TTCCATTTCTTGCTCTCCTC | |
| | | | |
| 74 | REV F 7791 | ACATAACAAATTGGCTGTGG | 56.3 |
| 75 | REV F 7791.1 | ACATATCAAGTTGGCTGTGG | |
| 76 | REV F 7791.2 | ACATAACAAAATGGCTGTGG | 56.3 |
| 77 | REV F 7791.3 | ACATAACAAACTGGCTGTGG | 58.35 |
| 78 | REV F 7791.4 | ACATAACAGATTGGCTGTGG | |
| | | | |
| 79 | REV F 7832 | ATAGTAGGAGGCTTGGTAGG | 60.4 |
| 80 | REV F 7832.1 | ATAGTAGGAGGCTTAGTAGG | 58.35 |
| 81 | REV F 7832.2 | ATAGTAGGAGGCTTGATAGG | 58.35 |
| | | | |
| 82 | REV F 7912 | ATTATCGTTTCAGACCCACC | 58.35 |
| 83 | REV F 7912.1 | ATTATCGTTTCAGACCCGCC | 60.4 |
| 84 | REV F 7912.2 | ATTATCGTTTCAGACCCTCC | 58.35 |
| 85 | REV F 7912.3 | ATTGTCGTTTCAGACCCACC | |
| 86 | REV F 7912.4 | ATTGTCGTTTCAGACCCGCC | 62.45 |
| 87 | T7 REV F 7912 | TAATACGACTCACTATAGGGAGACCACCATGGACCCACCTCCC | 54.6 |
| 88 | T7 REV F 7912.1 | TAATACGACTCACTATAGGGAGACCACCATGGACCCGCCTCCC | 58 |

FIGURE 1C

| | | | |
|---|---|---|---|
| 89 | REV R 8186 | CCTGACTCCAATACTGTAGG | 60.4 |
| 90 | REV R 8186.1 | CCTGACTCCAATACTGCAGG | 62.45 |
| 91 | REV R 8186.2 | CCTGACTCCAATATTGTAGG | 58.35 |
| 92 | REV R 8186.3 | CCTGAATCCAATACTGTAGG | |
| 93 | REV R 8186.4 | CCTGGCTCCAATACTGTAGG | |
| | | | |
| 94 | REV R 8220 | GCATTGAGCAAGCTAACAGC | 60.4 |
| 95 | REV R 8220.1 | GCATTGAGCAAGCTAACTGC | 60.4 |
| 96 | REV R 8220.2 | GCATTGAGCAAGTTAACAGC | 58.35 |
| 97 | REV R 8220.3 | ACATTAAGCAAGTTAACAGC | |
| 98 | REV R 8220.4 | GCATTAAGCAAACTAACAGC | 56.3 |
| 99 | REV R 8220.5 | GCATTGACGAAGCTAACAGC | |
| 100 | REV R 8220.6 | GCATTAAGCAAGCTAACAGC | |
| 101 | REV R 8220.7 | GCGTTGAGCAAGCTAACAGC | |
| | | | |
| 102 | GAG R 1833 64T | TTTTTTTTTTTTTTTTTTTTTTTTTTTTTTTTTTTTTTTTTTTTTTTTTTTTTTGTGACGAGGGGTCGTTG | 62.02 |
| 103 | GAG R 1833.1 64T | TTTTTTTTTTTTTTTTTTTTTTTTTTTTTTTTTTTTTTTTTTTTTTTTTTTTTTGTGACGAGGGGTCGCTG | 64.43 |
| 104 | GAG R 1833.5 64T | TTTTTTTTTTTTTTTTTTTTTTTTTTTTTTTTTTTTTTTTTTTTTTTTTTTTTTGTAACGAGGGGGCGTTG | 62.02 |
| 105 | GAG R 1833.6 64T | TTTTTTTTTTTTTTTTTTTTTTTTTTTTTTTTTTTTTTTTTTTTTTTTTTTTTTGTGTCGAGGGGGCGTTG | 64.43 |
| | | | |
| 106 | GAG R 1881 64T | TTTTTTTTTTTTTTTTTTTTTTTTTTTTTTTTTTTTTTTTTTTTTTTTTTTTTTGCTCCTGTATCTAATAGAGC | 58.4 |
| 107 | GAG R 1881.1 64T | TTTTTTTTTTTTTTTTTTTTTTTTTTTTTTTTTTTTTTTTTTTTTTTTTTTTTTGCTCCTGTATCTAATAAAGC | 56.3 |
| 108 | GAG R 1881.2 64T | TTTTTTTTTTTTTTTTTTTTTTTTTTTTTTTTTTTTTTTTTTTTTTTTTTTTTTGCTCCTGTATCTAACAGAGC | 60.4 |
| | | | |
| 109 | GAG R 1913 64T | TTTTTTTTTTTTTTTTTTTTTTTTTTTTTTTTTTTTTTTTTTTTTTTTTTTTTTGGTTTCCATCTTCCTGG | 58.35 |
| 110 | GAG R 1913.1 64T | TTTTTTTTTTTTTTTTTTTTTTTTTTTTTTTTTTTTTTTTTTTTTTTTTTTTTTGGTTTCCATCTTCCTGC | 58.35 |
| 111 | GAG R 1913.2 64T | TTTTTTTTTTTTTTTTTTTTTTTTTTTTTTTTTTTTTTTTTTTTTTTTTTTTTTGGCTTCCATCTCCCTGG | 62.45 |
| 112 | GAG R 1913.4 64T | TTTTTTTTTTTTTTTTTTTTTTTTTTTTTTTTTTTTTTTTTTTTTTTTTTTTTTGGTTTCCATTTCCCTGG | 58.35 |
| 113 | GAG R 1913.5 64T | TTTTTTTTTTTTTTTTTTTTTTTTTTTTTTTTTTTTTTTTTTTTTTTTTTTTTTGGTTTCCATTTTCCTGG | 56.3 |
| | | | |
| 114 | VPR R 5296 64T | TTTTTTTTTTTTTTTTTTTTTTTTTTTTTTTTTTTTTTTTTTTTTTTTTTTTTTGGATAAACAGCAGTTGTTGC | 58.35 |
| 115 | VPR R 5296.1 64T | TTTTTTTTTTTTTTTTTTTTTTTTTTTTTTTTTTTTTTTTTTTTTTTTTTTTTTGAATAAACAGCAGTTGTTGT | 54.25 |
| 116 | VPR R 5296.4 64T | TTTTTTTTTTTTTTTTTTTTTTTTTTTTTTTTTTTTTTTTTTTTTTTTTTTTTTGAATAAACAGCAGCTGTTGC | 58.35 |
| | | | |
| 117 | VPR R 5328 64T | TTTTTTTTTTTTTTTTTTTTTTTTTTTTTTTTTTTTTTTTTTTTTTTTTTTTTTATTCTGCTATGTCGACACCC | 60.4 |
| 118 | VPR R 5328.1 64T | TTTTTTTTTTTTTTTTTTTTTTTTTTTTTTTTTTTTTTTTTTTTTTTTTTTTTTATTCTGCTATGTCGGCGCCC | 64.5 |

FIGURE 1D

| | | | |
|---|---|---|---|
| 119 | VPR R 5328.2 64T | TTTTTTTTTTTTTTTTTTTTTTTTTTTTTTTTTTTTTTTT<br>TTTTTTTTTTTTTTTTTTTTTTTTTATTCTGCTATGTCGGCACCC | 62.45 |
| 120 | VPR R 5328.3 64T | TTTTTTTTTTTTTTTTTTTTTTTTTTTTTTTTTTTTTTTT<br>TTTTTTTTTTTTTTTTTTTTTTTTTATTCTGCTATGTTGACACCC | 58.35 |
| 121 | VPR R 5363 64T | TTTTTTTTTTTTTTTTTTTTTTTTTTTTTTTTTTTTTTTT<br>TTTTTTTTTTTTTTTTTTTTTTTTTCTCCATTTCTTGCTCTCCTC | 60.4 |
| 122 | VPR R 5363.1 64T | TTTTTTTTTTTTTTTTTTTTTTTTTTTTTTTTTTTTTTTT<br>TTTTTTTTTTTTTTTTTTTTTTTTTCTCCATTTCTTGCTCTTCTC | 58.35 |
| 123 | REV R 8186 64T | TTTTTTTTTTTTTTTTTTTTTTTTTTTTTTTTTTTTTTTT<br>TTTTTTTTTTTTTTTTTTTTTTTTTCCTGACTCCAATACTGTAGG | 60.4 |
| 124 | REV R 8186.1 64T | TTTTTTTTTTTTTTTTTTTTTTTTTTTTTTTTTTTTTTTT<br>TTTTTTTTTTTTTTTTTTTTTTTTTCCTGACTCCAATACTGCAGG | 62.45 |
| 125 | REV R 8186.2 64T | TTTTTTTTTTTTTTTTTTTTTTTTTTTTTTTTTTTTTTTT<br>TTTTTTTTTTTTTTTTTTTTTTTTTCCTGACTCCAATATTGTAGG | 58.35 |
| 126 | REV R 8220 64T | TTTTTTTTTTTTTTTTTTTTTTTTTTTTTTTTTTTTTTTT<br>TTTTTTTTTTTTTTTTTTTTTTTGCATTGAGCAAGCTAACAGC | 60.4 |
| 127 | REV R 8220.1 64T | TTTTTTTTTTTTTTTTTTTTTTTTTTTTTTTTTTTTTTTT<br>TTTTTTTTTTTTTTTTTTTTTTTGCATTGAGCAAGCTAACTGC | 60.4 |
| 128 | REV R 8220.2 64T | TTTTTTTTTTTTTTTTTTTTTTTTTTTTTTTTTTTTTTTT<br>TTTTTTTTTTTTTTTTTTTTTTTGCATTGAGCAAGTTAACAGC | 58.35 |
| 129 | REV R 8220.4 64T | TTTTTTTTTTTTTTTTTTTTTTTTTTTTTTTTTTTTTTTT<br>TTTTTTTTTTTTTTTTTTTTTTTGCATTAAGCAAACTAACAGC | 56.3 |
| 130 | ENV F 5503 | TTAGGCATCTCCTATGGC | 57 |
| 131 | ENV F 5503.1 | TTAGGCATTTCCTATGGC | 55 |
| 132 | ENV F 5503.2 | TTAGGCATCTCCAATGGC | 57 |
| 133 | ENV R 8615 | CCAGTCCCCCCTTTTCTTTT | 60.4 |
| 134 | T7 ENV F 5784 | TAATACGACTCACTATAGGGAGACCACCATGGGAGTGATGG | 48 |
| 135 | T7 ENV F 5784.1 | TAATACGACTCACTATAGGGAGACCACCATGGGAGTGAAGG | 48 |
| 136 | T7 ENV F 5784.2 | TAATACGACTCACTATAGGGAGACCACCATGGGAGTGAGGG | 51 |
| 137 | ENV R 8324 64T | TTTTTTTTTTTTTTTTTTTTTTTTTTTTTTTTTTTTTTTT<br>TTTTTTTTTTTTTTTTTTTTTTTTTATAGCAAAGCCCTTTC | 51 |
| 138 | NEF F 8235 | TAGCTGAGGGGACAGATAG | 60.5 |
| 139 | NEF F 8235.1 | TAGCTGAGGGAACAGATAG | 58.3 |
| 140 | NEF F 8343 | ATGGGTGGCAAGTGGTCAAAAAG | 63.5 |
| 141 | NEF F 8343.1 | ATGGGTGGCAAGTGGTCAAAACG | 65.3 |
| 142 | NEF F 8343.2 | ATGGGTGGCAAATGGTCAAAAAG | 61.7 |
| 143 | NEF F 8343.3 | ATGGGTGGCAAGTGGTCAAAAGG | 65.3 |
| 144 | NEF R 9069 | CCAGTACAGGCAAAAAGC | 58.4 |
| 145 | NEF R 9069.1 | CAGTACAGGCGAAAAGC | 57.6 |
| 146 | NEF R 9069.2 | CAGTACAGGCAAGAAGC | 57.6 |

FIGURE 1E

| | | | |
|---|---|---|---|
| 147 | T7 NEF F 8343 | TAATACGACTCACTATAGGGAGACCACCATGGGTGGCAA GTGGTCAAAAAG | 63.5 |
| 148 | T7 NEF F 8343.1 | TAATACGACTCACTATAGGGAGACCACCATGGGTGGCAA GTGGTCAAAACG | 65.3 |
| | | | |
| 149 | NEF R 9069 64T | TTTTTTTTTTTTTTTTTTTTTTTTTTTTTTTTTTTTTTTT TTTTTTTTTTTTTTTTTTTTTTTTCCAGTACAGGCAAAAAGC | 58.4 |
| 150 | NEF R 9069.1 64T | TTTTTTTTTTTTTTTTTTTTTTTTTTTTTTTTTTTTTTTT TTTTTTTTTTTTTTTTTTTTTTTTCAGTACAGGCGAAAAGC | 57.6 |
| 151 | NEF R 9069.2 64T | TTTTTTTTTTTTTTTTTTTTTTTTTTTTTTTTTTTTTTTT TTTTTTTTTTTTTTTTTTTTTTTTCCAGTACAGGCAAGAAGC | 57.6 |
| | | | |
| 152 | NEF R 8952 64T | TTTTTTTTTTTTTTTTTTTTTTTTTTTTTTTTTTTTTTTT TTTTTTTTTTTTTTTTTTTTTTTTTGTCAGCAGTCTTT | |
| 153 | NEF R 8952.1 64T | TTTTTTTTTTTTTTTTTTTTTTTTTTTTTTTTTTTTTTTT TTTTTTTTTTTTTTTTTTTTTTTTTGTCAGCAGTCTCA | |
| | | | |
| 154 | ENV R 8634 | TTTTTGACCACTTGCCACCC | 60.4 |
| 155 | ENV R 8634.1 | TTTTTGACCACTTGCCACTC | 58.4 |
| 156 | ENV R 8634.2 | TTTTTGACCACTTGCCCCCC | 62 |
| | | | |
| 157 | ENV R 8634 64T | TTTTTTTTTTTTTTTTTTTTTTTTTTTTTTTTTTTTTTTT TTTTTTTTTTTTTTTTTTTTTGACCACTTGCCACCC | 60.4 |
| 158 | ENV R 8634.1 64T | TTTTTTTTTTTTTTTTTTTTTTTTTTTTTTTTTTTTTTTT TTTTTTTTTTTTTTTTTTTTTGACCACTTGCCACTC | 58.4 |
| 159 | ENV R 8634.2 64T | TTTTTTTTTTTTTTTTTTTTTTTTTTTTTTTTTTTTTTTT TTTTTTTTTTTTTTTTTTTTTGACCACTTGCCCCCC | 62 |
| | | | |
| 160 | NEF DELTA 29 T7 | TAATACGACTCACTATAGGGAGACCACCATGGTGGGAGC AGTGTCTCA | |
| 161 | NEF DELTA 58 T7 | TAATACGACTCACTATAGGGAGACCACCATGGAGGCACA AGAGGAAGAGG | |
| | | | |
| 162 | FGF61 | TAGTCAGTGTGGAAAATCTCTAGCAGTG | |
| 163 | FGR94 | CTCGATGTCAGCAGTTCTTGAAGTACTC | |
| 164 | FGF60 | CAGACCCTTTTAGTCAGTGTGGAAAATC | |
| 165 | FGR53 | GTCTACTTGTGTGCTATATCTCTTTTTC | |
| 166 | FGF46 | GCATTCCCTACAATCCCCAAAG | |
| 167 | FGR95 | GGTCTAACCAGAGAGACCCAGTACAG | |
| | | | |
| 168 | AF2 | AGCTTGCCTTGAGTGCTTCAAGTAGTGTGTG | |
| 169 | AF6 | TGCCTTGAGTGCAAGTAGTGTGTGCCC | |
| 170 | F2018 | AAAAGGGCTGTTGGAAATGTGG | |
| 171 | F2042 | GGAAGGACACCAAATGAAAGATTGTACTGAGAG | |
| 172 | AR1539 | GCCTGTCTTTCAGTGCAATCTTTCATTTGGTGTCC | |
| 173 | AR1603 | TCTGTTCTGAGGAAAATTCCCTGGCCTCCC | |
| 174 | F4650 | ATTCCCTACAATCCCCAAAGTCAAG | |
| 175 | F4650.1 | ATTCCCTACAATCCCCAAAGTC | |
| 176 | F4956 | TGGAAAGGTGAAGGGGCAGTAGTAATACAAG | |

FIGURE 1F

| | | | |
|---|---|---|---|
| 177 | F4956.1 | TGGAAAGGTGAAGGGGCAGTAGTAATACA | |
| 178 | R5090 | CTCATCCTGTCTACTTGCCACACAATCATCAC | |
| 179 | R5220 | CCCTAGTGGGATGTGTACTTCTGAAC | |
| 180 | F7695 | TAGGAGTAGCACCCACCAAGGCAAAGAG | |
| 181 | R9173 | TGGTGTGTAGTTCTGCCAATCAGGGAAG | |
| 182 | R9626 | CTTGAAGCACTCAAGGCAAGCTTTATTG | |
| | | | |
| 183 | REV F 7750 | GGGATTTGGGGTTGCTCTGG | 64.5 |
| 184 | REV F 7750.1 | GGGATTTGGGGCTGCTCTGG | 66.5 |
| | | | |
| 185 | REV F 7830 | TGATAGTAGGAGGCTTGGTAGG | 63.4 |
| 186 | REV F 7830.1 | TGATAGTAGGAGGCTTAATAGG | 59.7 |
| 187 | REV F 7830.2 | TGATAGTAGGAGGCTTGATAGG | 61.5 |
| | | | |
| 188 | REV F 7911 | GTTAGGCAGGGATATTCACC | 60.4 |
| 189 | REV F 7911.1 | GTTAGGCAGGGATACTCACC | 62.4 |
| | | | |
| 190 | REV R 8300 | CCCTGTCTTATTCTTCTAGG | 58.4 |
| 191 | REV R 8300.1 | CCCTGTCTTATTCTTACAGG | 58.4 |
| 192 | REV R 8300.2 | CCCTGTCTTATTCTTGTAGG | 58.4 |
| | | | |
| 193 | REV R 8300 64T | TTTTTTTTTTTTTTTTTTTTTTTTTTTTTTTTTTTT<br>TTTTTTTTTTTTTTTTTTTTCCCTGTCTTATTCTTCTAGG | 58.4 |
| 194 | REV R 8300.1 64T | TTTTTTTTTTTTTTTTTTTTTTTTTTTTTTTTTTTT<br>TTTTTTTTTTTTTTTTTTTTCCCTGTCTTATTCTTACAGG | 58.4 |
| 195 | REV R 8300.2 64T | TTTTTTTTTTTTTTTTTTTTTTTTTTTTTTTTTTTT<br>TTTTTTTTTTTTTTTTTTTTCCCTGTCTTATTCTTGTAGG | 58.4 |
| | | | |
| 196 | VPR R 5507 | TTCTTCCTGCCATAGGAGATGC | 62 |
| 197 | VPR R 5507.1 | TTCTTCCTGCCATAGGAAATGC | 60 |
| | | | |
| 198 | VPR R 5419 | GCAGTTGTAGGCTGACTTCC | 62.4 |
| 199 | VPR R 5419.1 | GCAGTTGTAGGCTGACTCCC | 64.5 |
| 200 | VPR R 5419.2 | GCAGTTGTAGGCTGGCTTCC | 64.5 |
| | | | |
| 201 | VPR R 5419 64T | TTTTTTTTTTTTTTTTTTTTTTTTTTTTTTTTTTTT<br>TTTTTTTTTTTTTTTTTTTTGCAGTTGTAGGCTGACTTCC | |
| 202 | VPR R 5419.1 64T | TTTTTTTTTTTTTTTTTTTTTTTTTTTTTTTTTTTT<br>TTTTTTTTTTTTTTTTTTTTGCAGTTGTAGGCTGACTCCC | |

FIGURE 1G

| | | | |
|---|---|---|---|
| 203 | VPR R 5419.2 64T | TTTTTTTTTTTTTTTTTTTTTTTTTTTTTTTTTTTTTTTT TTTTTTTTTTTTTTTTTTTTTGCAGTTGTAGGCTGGCTTCC | |
| 204 | NEF F 8235.2 | TAGCTGGCTGGACAGATAG | 60.5 |
| 269 | VPR R 5294 64T (ARGOS PRIMER #231) | TTTTTTTTTTTTTTTTTTTTTTTTTTTTTTTTTTTTTTTT TTTTTTTTTTTTTTTTTTTTAGCGAACAAACAGTAGTTGT TGCAG | 59.6 |
| 270 | VPR R 5294.1 64T (ARGOS PRIMER #232) | TTTTTTTTTTTTTTTTTTTTTTTTTTTTTTTTTTTTTTTT TTTTTTTTTTTTTTTTTTTTAGCGAACAAACAGTAGTTGT TGCAA | 57.9 |
| 271 | VPR R 5294.2 64T (ARGOS PRIMER #233) | TTTTTTTTTTTTTTTTTTTTTTTTTTTTTTTTTTTTTTTT TTTTTTTTTTTTTTTTTTTTAGCGATCAAACAGCAGTTGT TGCAG | 61.5 |
| 272 | VPR R 5294.3 64T (ARGOS PRIMER #234) | TTTTTTTTTTTTTTTTTTTTTTTTTTTTTTTTTTTTTTTT TTTTTTTTTTTTTT TTTTTAGCGAACAAACAGTAGTTG TTGAAG | 57.8 |
| 273 | VPR R 5294.4 64T (ARGOS PRIMER #235) | TTTTTTTTTTTTTTTTTTTTTTTTTTTTTTTTTTTTTTTT TTTTTTTTTTTTTT TTTTTAGCGATCAAACAGTAGTTGTT GCAG | 59.7 |
| 274 | ENV F 5500 | GGCTTAGGCATCTCCTATGGCAG | |
| 275 | ENV F 5500.1 | GGCTTAGGCATTTCCTATGGCAG | |
| 276 | ENV F 5760 | AGACAGTGGCAATGAGAGTGATGG | |
| 277 | ENV F 5760.1 | AGACAGTGGCAATGAGAGTGAAGG | |
| 278 | ENV F 5760.2 | AGACAGTGGCAATGAGAGTGACGG | |
| 279 | ENV F 5760.3 | AGACAGTGGCAATGAGAGTGAGGG | |
| 280 | ENV R 8300 | TTACCCTGTCTTATTCTTCTAGG | |
| 281 | ENV R 8300.1 | TTACCCTGTCTTATTCTTGTAGG | |
| 282 | ENV R 8300.2 | TTACCCTGTCTTATTCGTGTGGG | |
| 283 | ENV R 8300.3 | TTACCCTGTCTTATTCTTACAGG | |
| 284 | ENV R 8618 | CCTTCCAGTCCCCCCTTTTCT | |
| 285 | ENV R 8618.1 | CCATCCAGTCCCCCCTTTTCT | |
| 286 | ENV R 8362 | TTTGACCACTTGCCACCCAT | |
| 287 | ENV R 8362.1 | TTTGACCACTTGCCCCCCAT | |
| 288 | ENV R 8362.2 | TTTGACCACTTGTTACCCAT | |

FIGURE 1H

| | | |
|---|---|---|
| 289 | ENV R 8362.3 | TTTGACCACTTGCCTCCCAT |
| 290 | T7 ENV F 5760 | TAATACGACTCACTATAGGGAGAAGACAGTGGCACCACCATGGAGAGTGATGG |
| 291 | T7 ENV F 5760.1 | TAATACGACTCACTATAGGGAGAAGACAGTGGCACCACCATGGAGAGTGAAGG |
| 292 | T7 ENV F 5760.2 | TAATACGACTCACTATAGGGAGAAGACAGTGGCACCACCATGGAGAGTGACGG |
| 293 | T7 ENV F 5760.3 | TAATACGACTCACTATAGGGAGAAGACAGTGGCACCACCATGGAGAGTGAGGG |
| 294 | ENV R 8618 64T | TTTTTTTTTTTTTTTTTTTTTTTTTTTTTTTTTTTTTTTTTTTTTTTTTTTTTTTTTTTTCCTTCCAGTCCCCCCTTTTCT |
| 295 | ENV R 8618.1 64T | TTTTTTTTTTTTTTTTTTTTTTTTTTTTTTTTTTTTTTTTTTTTTTTTTTTTTTTTTTTTCCATCCAGTCCCCCCTTTTCT |
| 296 | ENV R 8362 64T | TTTTTTTTTTTTTTTTTTTTTTTTTTTTTTTTTTTTTTTTTTTTTTTTTTTTTTTTTTTTGACCACTTGCCACCCAT |
| 297 | ENV R 8362.1 64T | TTTTTTTTTTTTTTTTTTTTTTTTTTTTTTTTTTTTTTTTTTTTTTTTTTTTTTTTTTTTGACCACTTGCCCCCCAT |
| 298 | ENV R 8362.2 64T | TTTTTTTTTTTTTTTTTTTTTTTTTTTTTTTTTTTTTTTTTTTTTTTTTTTTTTTTTTTTGACCACTTGTTACCCAT |
| 299 | ENV R 8362.3 64T | TTTTTTTTTTTTTTTTTTTTTTTTTTTTTTTTTTTTTTTTTTTTTTTTTTTTTTTTTTTTGACCACTTGCCTCCCAT |
| 300 | VIF F 4292 | AAGACAGCAGTACAAATGGCAG |
| 301 | VIF F 4292.1 | AAGACAGCAGTACAGATGGCAG |
| 302 | VIF F 4292.2 | AAGACAGCAGTGCAAATGGCAG |
| 303 | VIF F 4292.3 | AAGACAGCAGTACTAATGGCAG |
| 304 | VIF F 4502 | TGGAAAGGTGAAGGGGCAGTAG |
| 305 | VIF F 4502.1 | TGGAAAGGTGAAGGGGCAGTGG |
| 306 | VIF F 4502.2 | TGGAAAGGTGAAGGAGCAGTAG |
| 307 | VIF F 4502.3 | TGGAAAGGTGAAGGGGCGGTAG |
| 308 | T7 VIF F 4587 | TAATACGACTCACTATAGGGAGACCACCATGGAAAACAGATGGCAGGTG |
| 309 | T7 VIF F 4587.1 | TAATACGACTCACTATAGGGAGACCACCATGGAAAACAGATGGCAGGTA |
| 310 | T7 VIF F 4587.2 | TAATACGACTCACTATAGGGAGACCACCATGGAAAACAGATGGCAGGCG |
| 311 | T7 VIF F 4587.3 | TAATACGACTCACTATAGGGAGACCACCATGGAAAACAGATGGCAGGGG |
| | | USE VPR REVERSE AND 64T PRIMERS FOR VIF AMPLIFICATIONS |
| 312 | VPU F 5409 | GAAGCATCCAGGAAGTCAGC |
| 313 | VPU F 5409.1 | GAAGCATCCAGGAAGCCAGC |
| 314 | VPU F 5409.2 | GAAGCATCCAGGAAGTCGGC |
| 315 | VPU F 5409.3 | GAAGCATCCAGGAAGTCAAC |
| 316 | VPU F 5409.4 | GAAGCATCCAGGGAGTCAGC |
| 317 | VPU F 5507 | GCATCTCCTATGGCAGGAAGAA |
| 318 | VPU F 5507.1 | GCATTTCCTATGGCAGGAAGAA |

FIGURE 1I

| | | |
|---|---|---|
| 319 | VPU F 5507.2 | GCATCTCCTATGGCAGGAAGAG |
| 320 | VPU R 6002 | CTGTGGGTACACAGGCATGTGT |
| 321 | VPU R 6002.1 | CTGTGGGTACACAGGCATGCGT |
| 322 | VPU R 6002.2 | CTGTGGGTACACAAGCATGTGT |
| 323 | VPU R 6002.3 | CTGTGGGTACACAGGCTTGTGT |
| 324 | VPU R 6426 | GCACAATAATGTATGGGAATTGG |
| 325 | VPU R 6426.1 | GCACAATAATGTATAGGAATTGG |
| 326 | VPU R 6426.2 | GCACAATAATGTATGGGGATTGG |
| 327 | VPU R 6426.3 | GCACAATAATGTATGGGAATCGG |
| 328 | VPU R 6426.4 | GCACAATAATGTATGGGAATGGG |
| 329 | T7 VPU F 5577 | TAATACGACTCACTATAGGGAGATCCTCTATCAAAGCAGTAAG |
| 330 | T7 VPU F 5577.1 | TAATACGACTCACTATAGGGAGATCCTCTATCAAAGCAGTGAG |
| 331 | T7 VPU F 5577.2 | TAATACGACTCACTATAGGGAGATCCTCTATCAGAGCAGTAAG |
| 332 | T7 VPU F 5577.3 | TAATACGACTCACTATAGGGAGATCCTCTACCAAAGCAGTAAG |
| 333 | VPU R 6002 64T | TTTTTTTTTTTTTTTTTTTTTTTTTTTTTTTTTTTTTTTTTTTTTTTTTTTTTTTTCTGTGGGTACACAGGCATGTGT |
| 334 | VPU R 6002.1 64T | TTTTTTTTTTTTTTTTTTTTTTTTTTTTTTTTTTTTTTTTTTTTTTTTTTTTTTTTCTGTGGGTACACAGGCATGCGT |
| 335 | VPU R 6002.2 64T | TTTTTTTTTTTTTTTTTTTTTTTTTTTTTTTTTTTTTTTTTTTTTTTTTTTTTTTTCTGTGGGTACACAAGCATGTGT |
| 336 | VPU R 6002.3 64T | TTTTTTTTTTTTTTTTTTTTTTTTTTTTTTTTTTTTTTTTTTTTTTTTTTTTTTTTCTGTGGGTACACAGGCTTGTGT |
| 337 | POL F 1370 | AATGATGACAGCATGTC |
| 338 | POL F 1370.1 | AATGATGACAGCATGCC |
| 339 | POL F 1370.2 | AATGATGGTAGCCTGTC |
| 340 | POL F 1566 | AAGGGCTGTTGGAAATGTGG |
| 341 | POL F 1566.1 | AAGGGCTGTTGGAAATGTAG |
| 342 | POL F 1566.2 | AAGGGCTGTTGGAAATGTAA |
| 343 | POL F 1566.3 | AAGGGCTGTTGGAAGTGTGG |
| 344 | POL F 1566.4 | AAAGGTTGCTGGAAATGTGG |
| 345 | POL R 4765 | CCTAGTGGGATGTGTACTTCTGA |
| 346 | POL R 4765.1 | CCTAGTGGGATGTGTACTTCCGA |
| 347 | POL R 4765.2 | CCTAGTGGGATGTGTATTTCTGA |
| 348 | POL R 4765.3 | CCTAGTGGGATGTGCACTTCTGA |
| 349 | POL R 4765.4 | CCTAGTGGGATATGTACTTCTGA |
| 350 | POL R 4765.5 | CCTAGTGGGATGTATACACCTGA |

FIGURE 1J

| | | |
|---|---|---|
| 351 | POL R 5031 | CCAAGTATTGTAGAGATCCTACC |
| 352 | POL R 5031.1 | CCAAGTATTGTAGAGATCTTACC |
| 353 | POL R 5031.2 | CCAAGTATTGTAGAGACCCTACC |
| 354 | POL R 5031.3 | CCAAGTATTGTAGGGATCCTACC |
| 355 | POL R 5031.4 | CCAAGTATTGTAGTGTCCCTACC |
| | | |
| 356 | T7 POL F 1661 | TAATACGACTCACTATAGGGAGACCACCATGGGGAAGGCCAGGGAATTTCC |
| 357 | T7 POL F 1661.1 | TAATACGACTCACTATAGGGAGACCACCATGGGGAAGGCCAGGGAATTTTC |
| 358 | T7 POL F 1661.2 | TAATACGACTCACTATAGGGAGACCACCATGGGGAAGGCCAGGAAATTTCC |
| 359 | T7 POL F 1661.3 | TAATACGACTCACTATAGGGAGACCACCATGGGGAAGGCCAGGAAATTTTC |
| 360 | T7 POL F 1661.4 | TAATACGACTCACTATAGGGAGACCACCATGGGGAAGGCCAGGGAATTTCC |
| | | |
| 361 | POL R 4765 64T | TTTTTTTTTTTTTTTTTTTTTTTTTTTTTTTTTTTTTTTTTTTTTTTTTTTTTTTTTTTTTTTTCCTAGTGGGATGTGTACTTCTGA |
| 362 | POL R 4765.1 64T | TTTTTTTTTTTTTTTTTTTTTTTTTTTTTTTTTTTTTTTTTTTTTTTTTTTTTTTTTTTTTTTTCCTAGTGGGATGTGTACTTCCGA |
| 363 | POL R 4765.2 64T | TTTTTTTTTTTTTTTTTTTTTTTTTTTTTTTTTTTTTTTTTTTTTTTTTTTTTTTTTTTT TTTTCCTAGTGGGATGTGTATTTCTGA |
| 364 | POL R 4765.3 64T | TTTTTTTTTTTTTTTTTTTTTTTTTTTTTTTTTTTTTTTTTTTTTTTTTTTTTTTTTTTTTTTTCCTAGTGGGATGTGCACTTCTGA |
| 365 | POL R 4765.4 64T | TTTTTTTTTTTTTTTTTTTTTTTTTTTTTTTTTTTTTTTTTTTTTTTTTTTTTTTTTTTTTTTTCCTAGTGGGATATGTACTTCTGA |
| 366 | POL R 4765.5 64T | TTTTTTTTTTTTTTTTTTTTTTTTTTTTTTTTTTTTTTTTTTTTTTTTTTTTTTTTTTTTTTTTCCTAGTGGGATGTATACACCTGA |
| | | |
| 367 | NEF F 7974 | AAGAAGGTGGAGAGCAAGAC |
| 368 | NEF F 7974.1 | AAGAAGGTGGAGAGCAAGGC |
| 369 | NEF F 7974.2 | AAGAAGGTGGAGAGAGAGAC |
| 370 | NEF F 7974.3 | AAGAAGGTGGCGAGCAAGAC |
| 371 | NEF F 7974.4 | AAGAAGGTGGCGAGCAAGGC |

FIGURE 1K

GGTCTCTCTGGTTAGACCAGATCTGAGCCTGGGAGCTCTCTGGCTAACTAGGGAACCCACTGCTTAAGCCTCAA
CCAGAGAGACCAATCTGGTCTAGACTCGGACCCTCGAGAGACCGATTGATCCCTTGGGTGACGAATTCGGAGTT                    74

TAAAGCTTGCCTTGAGTGCTTCAAGTAGTGTGTGCCCGTCTGTTGTGTGACTCTGGTAACTAGAGATCCCTCAG
ATTTCGAACGGAACTCACGAAGTTCATCACACACGGGCAGACAACACACTGAGACCATTGATCTCTAGGGAGTC                    148

```
                ─────────────────AF2─────────────────▶           ──GAG F 124──▶   ┌──
                                                                  ──GAG F 124──▶   └FG
                    ──────────AF6──────────▶
```

ACCCTTTTAGTCAGTGTGGAAAATCTCTAGCAGTGGCGCCCGAACAGGGACCTGAAAGCGAAAGGGAAACCAGA
TGGGAAAATCAGTCACACCTTTTAGAGATCGTCACCGCGGGCTTGTCCCTGGACTTTCGCTTTCCCTTTGGTCT                    222

```
  ────────FGF60────────▶          ────MMy1────▶
        ──────FGF61──────▶
```

GGAGCTCTCTCGACGCAGGACTCGGCTTGCTGAAGCGCGCACGGCAAGAGGCGAGGGGCGGCGACTGGTGAGTA
CCTCGAGAGAGCTGCGTCCTGAGCCGAACGACTTCGCGCGTGCCGTTCTCCGCTCCCCGCCGCTGACCACTCAT                    296

CGCCAAAAATTTTGACTAGCGGAGGCTAGAAGGAGAGAGATGGGTGCGAGAGCGTCAGTATTAAGCGGGGGAGA
GCGGTTTTTAAAACTGATCGCCTCCGATCTTCCTCTCTCTACCCACGCTCTCGCAGTCATAATTCGCCCCCTCT                    370

```
  ──GAG F 304──▶          ──GAG F 334──▶
  ──GAG F 304──           ──GAG F 334──
                             M  G  A  R  A  S  V  L  S  G  G  E
                             ──────────gag──────────
```

FIGURE 2-A

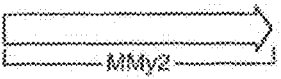
FIGURE 2-B

```
AGAGAAGGCTTTCAGCCCAGAAGTGATACCCATGTTTTCAGCATTATCAGAAGGAGCCACCCCACAAGATTTAA
----+----+----+----+----+----+----+----+----+----+----+----+----+----+---- 888
TCTCTTCCGAAAGTCGGGTCTTCACTATGGGTACAAAAGTCGTAATAGTCTTCCTCGGTGGGGTGTTCTAAATT

E  K  A  F  S  P  E  V  I  P  M  F  S  A  L  S  E  G  A  T  P  Q  D  L
                                     GAG

ACACCATGCTAAACACAGTGGGGGGACATCAAGCAGCCATGCAAATGTTAAAAGAGACCATCAATGAGGAAGCT
----+----+----+----+----+----+----+----+----+----+----+----+----+----+---- 962
TGTGGTACGATTTGTGTCACCCCCCTGTAGTTCGTCGGTACGTTTACAATTTTCTCTGGTAGTTACTCCTTCGA

⟵─ MMy4 ─⟶

N  T  M  L  N  T  V  G  G  H  Q  A  A  M  Q  M  L  K  E  T  I  N  E  E  A
                                     GAG

GCAGAATGGGATAGAGTGCATCCAGTGCATGCAGGGCCTATTGCACCAGGCCAGATGAGAGAACCAAGGGGAAG
----+----+----+----+----+----+----+----+----+----+----+----+----+----+---- 1036
CGTCTTACCCTATCTCACGTAGGTCACGTACGTCCCGGATAACGTGGTCCGGTCTACTCTCTTGGTTCCCCTTC

A  E  W  D  R  V  H  P  V  H  A  G  P  I  A  P  G  Q  M  R  E  P  R  G  S
                                     GAG

TGACATAGCAGGAACTACTAGTACCCTTCAGGAACAAATAGGATGGATGACAAATAATCCACCTATCCCAGTAG
----+----+----+----+----+----+----+----+----+----+----+----+----+----+---- 1110
ACTGTATCGTCCTTGATGATCATGGGAAGTCCTTGTTTATCCTACCTACTGTTTATTAGGTGGATAGGGTCATC

D  I  A  G  T  T  S  T  L  Q  E  Q  I  G  W  M  T  N  N  P  P  I  P  V
                                     GAG

GAGAAATTTATAAAAGATGGATAATCCTGGGATTAAATAAAATAGTAAGAATGTATAGCCCTACCAGCATTCTG
----+----+----+----+----+----+----+----+----+----+----+----+----+----+---- 1184
CTCTTTAAATATTTTCTACCTATTAGGACCCTAATTTATTTTATCATTCTTACATATCGGGATGGTCGTAAGAC

G  E  I  Y  K  R  W  I  I  L  G  L  N  K  I  V  R  M  Y  S  P  T  S  I  L
                                     GAG

GACATAAGACAAGGACCAAAGGAACCCTTTAGAGACTATGTAGACCGGTTCTATAAAACTCTAAGAGCCGAGCA
----+----+----+----+----+----+----+----+----+----+----+----+----+----+---- 1258
CTGTATTCTGTTCCTGGTTTCCTTGGGAAATCTCTGATACATCTGGCCAAGATATTTTGAGATTCTCGGCTCGT

D  I  R  Q  G  P  K  E  P  F  R  D  Y  V  D  R  F  Y  K  T  L  R  A  E  Q
                                     GAG
```

FIGURE 2-C

```
AGCTTCACAGGAGGTAAAAAATTGGATGACAGAAACCTTGTTGGTCCAAAATGCGAACCCAGATTGTAAGACTA
+---+---+---+---+---+---+---+---+---+---+---+---+---+---+---+ 1332
TCGAAGTGTCCTCCATTTTTTAACCTACTGTCTTTGGAACAACCAGGTTTTACGCTTGGGTCTAACATTCTGAT

A  S  Q  E  V  K  N  W  M  T  E  T  L  L  V  Q  N  A  N  P  D  C  K  T
   ─────────────────────────────── GAG ───────────────────────────────────

TTTTAAAAGCATTGGGACCAGCGGCTACACTAGAAGAAATGATGACAGCATGTCAGGGAGTAGGAGGACCCGGC
+---+---+---+---+---+---+---+---+---+---+---+---+---+---+---+ 1406
AAAATTTTCGTAACCCTGGTCGCCGATGTGATCTTCTTTACTACTGTCGTACAGTCCCTCATCCTCCTGGGCCG
                                       ┌──── POL F 1370 ────>
   I  L  K  A  L  G  P  A  A  T  L  E  E  M  M  T  A  C  Q  G  V  G  G  P  G
   ─────────────────────────────── GAG ───────────────────────────────────

CATAAGGCAAGAGTTTTGGCTGAAGCAATGAGCCAAGTAACAAATTCAGCTACCATAATGATGCAGAGAGGCAA
+---+---+---+---+---+---+---+---+---+---+---+---+---+---+---+ 1480
GTATTCCGTTCTCAAAACCGACTTCGTTACTCGGTTCATTGTTTAAGTCGATGGTATTACTACGTCTCTCCGTT

H  K  A  R  V  L  A  E  A  M  S  Q  V  T  N  S  A  T  I  M  M  Q  R  G  N
   ─────────────────────────────── GAG ───────────────────────────────────

TTTTAGGAACCAAAGAAAGATTGTTAAGTGTTTCAATTGTGGCAAAGAAGGGCACACAGCCAGAAATTGCAGGG
+---+---+---+---+---+---+---+---+---+---+---+---+---+---+---+ 1554
AAAATCCTTGGTTTCTTTCTAACAATTCACAAAGTTAACACCGTTTCTTCCCGTGTGTCGGTCTTTAACGTCCC

F  R  N  Q  R  K  I  V  K  C  F  N  C  G  K  E  G  H  T  A  R  N  C  R
   ─────────────────────────────── GAG ───────────────────────────────────

CCCCTAGGAAAAAGGGCTGTTGGAAATGTGGAAAGGAAGGACACCAAATGAAAGATTGTACTGAGAGACAGGCT
+---+---+---+---+---+---+---+---+---+---+---+---+---+---+---+ 1628
GGGGATCCTTTTTCCCGACAACCTTTACACCTTTCCTTCCTGTGGTTTACTTTCTAACATGACTCTCTGTCCGA
     ┌──── F2018 ────>           ┌──────── F2042 ────────>
   A  P  R  K  K  G  C  W  K  C  G  K  E  G  H  Q  M  K  D  C  T  E  R  Q  A
   ─────────────────────────────── GAG ───────────────────────────────────
     ┌──── POL F 1566 ────>         ┌──────── AR1539 ────────┐
          ┌──── MMy28 ────>
```

```
ACAGTACTAAATGGAGAAAATTAGTAGATTTCAGAGAACTTAATAAGAGAACTCAAGACTTCTGGGAAGTTCAA
                                                                            2368
TGTCATGATTTACCTCTTTTAATCATCTAAAGTCTCTTGAATTATTCTCTTGAGTTCTGAAGACCCTTCAAGTT

D  S  T  K  W  R  K  L  V  D  F  R  E  L  N  K  R  T  Q  D  F  W  E  V  Q
                      POL 1655 to 4693

TTAGGAATACCACATCCCGCAGGGTTAAAAAAGAAAAAATCAGTAACAGTACTGGATGTGGGTGATGCATATTT
                                                                            2442
AATCCTTATGGTGTAGGGCGTCCCAATTTTTTCTTTTTAGTCATTGTCATGACCTACACCCACTACGTATAAA

L  G  I  P  H  P  A  G  L  K  K  K  K  S  V  T  V  L  D  V  G  D  A  Y  F
                      POL 1655 to 4693

TTCAGTTCCCTTAGATGAAGACTTCAGGAAGTATACTGCATTTACCATACCTAGTATAAACAATGAGACACCAG
                                                                            2516
AAGTCAAGGGAATCTACTTCTGAAGTCCTTCATATGACGTAAATGGTATGGATCATATTTGTTACTCTGTGGTC

S  V  P  L  D  E  D  F  R  K  Y  T  A  F  T  I  P  S  I  N  N  E  T  P
                      POL 1655 to 4693

GGATTAGATATCAGTACAATGTGCTTCCACAGGGGATGGAAAGGATCACCAGCAATATTCCAAAGTAGCATGACA
                                                                            2590
CCTAATCTATAGTCATGTTACACGAAGGTGTCCCTACCTTTCCTAGTGGTCGTTATAAGGTTTCATCGTACTGT

G  L  D  I  S  Y  Q  N  V  L  P  Q  G  W  K  G  S  P  A  I  F  Q  S  S  M  T
                      POL 1655 to 4693

AAAATCTTAGAGCCTTTTAGAAAACAAAATCCAGACATAGTTATCTATCAATACATGGATGATTTGTATGTAGG
                                                                            2664
TTTTAGAATCTCGGAAAATCTTTTGTTTTAGGTCTGTATCAATAGATAGTTATGTACCTACTAAACATACATCC

K  I  L  E  P  F  R  K  Q  N  P  D  I  V  I  Y  Q  Y  M  D  D  L  Y  V  G
                      POL 1655 to 4693

ATCTGACTTAGAAATAGGGCAGCATAGAACAAAAATAGAGGAGCTGAGACAACATCTGTTGAGGTGGGGACTTA
                                                                            2738
TAGACTGAATCTTTATCCCGTCGTATCTTGTTTTTATCTCCTCGACTCTGTTGTAGACAACTCCACCCCTGAAT

S  D  L  E  I  G  Q  H  R  T  K  I  E  E  L  R  Q  H  L  L  R  W  G  L
                      POL 1655 to 4693

CCACACCAGACAAAAAACATCAGAAAGAACCTCCATTCCTTTGGATGGGTTATGAACTCCATCCTGATAAATGG
                                                                            2812
GGTGTGGTCTGTTTTTTGTAGTCTTTCTTGGAGGTAAGGAAACCTACCCAATACTTGAGGTAGGACTATTTACC

T  T  P  D  K  K  H  Q  K  E  P  P  F  L  W  M  G  Y  E  L  H  P  D  K  W
                      POL 1655 to 4693
```

FIGURE 2-G

ACAGTACAGCCTATAGTGCTGCCAGAAAAAGACAGCTGGACTGTCAATGACATACAGAAGTTAGTGGGAAATT
TGTCATGTCGGATATCACGACGGTCTTTTCTGTCGACCTGACAGTTACTGTATGTCTTCAATCACCCTTTAA 2886

T V Q P I V L P E K D S W T V N D I Q K L V G K L
——— POL 1855 to 4693 ———

<——— MMy30 ———>
<——— MMy30a ———>

GAATTGGGCAAGTCAGATTTACCCAGGGATTAAAGTAAGGCAATTATGTAAACTCCTTAGAGGAACCAAAGCAC
CTTAACCCGTTCAGTCTAAATGGGTCCCTAATTTCATTCCGTTAATACATTTGAGGAATCTCCTTGGTTTCGTG 2960

N W A S Q I Y P G I K V R Q L C K L L R G T K A
——— POL 1855 to 4693 ———

TAACAGAAGTAATACCACTAACAGAAGAAGCAGAGCTAGAACTGGCAGAAAACAGAGAGATTCTAAAAGAACCA
ATTGTCTTCATTATGGTGATTGTCTTCTTCGTCTCGATCTTGACCGTCTTTTGTCTCTCTAAGATTTTCTTGGT 3034

L T E V I P L T E E A E L E L A E N R E I L K E P
——— POL 1855 to 4693 ———

GTACATGCAGTGTATTATGACCCATCAAAAGACTTAATAGCAGAAATACAGAAGCAGGGGCAAGGCCAATGGAC
CATGTACCTCACATAATACTGGGTAGTTTTCTGAATTATCGTCTTTATGTCTTCGTCCCCGTTCCGGTTACCTG 3108

V H S V Y Y D P S K D L I A E I Q K Q G Q G Q W T
——— POL 1855 to 4693 ———

ATATCAAATTTATCAAGAGCCATTTAAAAATCTGAAAACAGGAAAATATGCAAGAATGAGGGGTGCCCACACTA
TATAGTTTAAATAGTTCTCGGTAAATTTTTAGACTTTTGTCCTTTTATACGTTCTTACTCCCCACGGGTGTGAT 3182

Y Q I Y Q E P F K N L K T G K Y A R M R G A H T
——— POL 1855 to 4693 ———

ATGATGTAAAACAATTAACAGAGGCAGTGCAAAAAATAACCACAGAAAGCATAGTAATATGGGGAAAGACTCCT
TACTACATTTTGTTAATTGTCTCCGTCACGTTTTTTATTGGTGTCTTTCGTATCATTATACCCCTTTCTGAGGA 3256

N D V K Q L T E A V Q K I T T E S I V I W G K T P
——— POL 1855 to 4693 ———

FIGURE 2-H

```
AAATTTAAACTGCCCATACAAAAGGAAACATGGGAAACATGGTGGACAGAGTATTGGAAGCCACCTGGATTCC
TTTAAATTTGACGGGTATGTTTTCCTTTGTACCCTTTGTACCACCTGTCTCATAACCGTTCGGTGGACCTAAGG    3330

K  F  K  L  P  I  Q  K  E  T  W  E  T  W  W  T  E  Y  W  Q  A  T  W  I  P
  ──────────────── POL 1655 to 4693 ────────────────

TGAGTGGGAGTTTGTTAATACCCCTCCCTTAGTGAAATTATGGTACCAGTTAGAGAAAGAACCCATAGTAGGAG
ACTCACCCTCAAACAATTATGGGGAGGGAATCACTTTAATACCATGGTCAATCTCTTTCTTGGGTATCATCCTC    3404

E  W  E  F  V  N  T  P  P  L  V  K  L  W  Y  Q  L  E  K  E  P  I  V  G
  ──────────────── POL 1655 to 4693 ────────────────

CAGAAACCTTCTATGTAGATGGGGCAGCTAACAGGGAGACTAAATTAGGAAAAGCAGGATATGTTACTAATAGA
GTCTTTGGAAGATACATCTACCCCGTCGATTGTCCCTCTGATTTAATCCTTTTCGTCCTATACAATGATTATCT    3478

A  E  T  F  Y  V  D  G  A  A  N  R  E  T  K  L  G  K  A  G  Y  V  T  N  R
  ──────────────── POL 1655 to 4693 ────────────────

GGAAGACAAAAAGTTGTCACCCTAACTGACACAACAAATCAGAAGACTGAGTTACAAGCAATTTATCTAGCTTT
CCTTCTGTTTTTCAACAGTGGGATTGACTGTGTTGTTTAGTCTTCTGACTCAATGTTCGTTAAATAGATCGAAA    3552

G  R  Q  K  V  V  T  L  T  D  T  T  N  Q  K  T  E  L  Q  A  I  Y  L  A  L
  ──────────────── POL 1655 to 4693 ────────────────

GCAGGATTCGGGATTAGAAGTAAACATAGTAACAGACTCACAATATGCATTAGGAATCATTCAAGCACAACCAG
CGTCCTAAGCCCTAATCTTCATTTGTATCATTGTCTGAGTGTTATACGTAATCCTTAGTAAGTTCGTGTTGGTC    3626

Q  D  S  G  L  E  V  N  I  V  T  D  S  Q  Y  A  L  G  I  I  Q  A  Q  P
  ──────────────── POL 1655 to 4693 ────────────────

ATCAAAGTGAATCAGAGTTAGTCAATCAAATAATAGAGCAGTTAATAAAAAAGGAAAAGGTCTATCTGGCATGG
TAGTTTCACTTAGTCTCAATCAGTTAGTTTATTATCTCGTCAATTATTTTTCCTTTTCCAGATAGACCGTACC    3700

D  Q  S  E  S  E  L  V  N  Q  I  I  E  Q  L  I  K  K  E  K  V  Y  L  A  W
  ──────────────── POL 1655 to 4693 ────────────────
                                                                    ← MMy
```

FIGURE 2-I

```
GTACCAGCACACAAAGGAATTGGAGGAAATGAACAAGTAGATAAATTAGTCAGTGCTGGAATCAGGAAAGTACT
                                                                          3774
CATGGTCGTGTGTTCCTTAACCTCCTTTACTTGTTCATCTATTTAATCAGTCACGACCTTAGTCCTTTCATGA

V  P  A  H  K  G  I  G  G  N  E  Q  V  D  K  L  V  S  A  G  I  R  K  V  L
                        ──── POL 1655 to 4693 ────
  ═══════════════════╗
  ──── MMy31a ───────╝

ATTTTTAGATGGAATAGATAAGGCCCAAGATGAACATGAGAAATATCACAGTAATTGGAGAGCAATGGCTAGTG
                                                                          3848
TAAAAATCTACCTTATCTATTCCGGGTTCTACTTGTACTCTTTATAGTGTCATTAACCTCTCGTTACCGATCAC

F  L  D  G  I  D  K  A  Q  D  E  H  E  K  Y  H  S  N  W  R  A  M  A  S
                        ──── POL 1655 to 4693 ────

ATTTTAACCTGCCACCTGTAGTAGCAAAAGAAATAGTAGCCAGCTGTGATAAATGTCAGCTAAAAGGAGAAGCC
                                                                          3922
TAAAATTGGACGGTGGACATCATCGTTTTCTTTATCATCGGTCGACACTATTTACAGTCGATTTTCCTCTTCGG

D  F  N  L  P  P  V  V  A  K  E  I  V  A  S  C  D  K  C  Q  L  K  G  E  A
                        ──── POL 1655 to 4693 ────

ATGCATGGACAAGTAGACTGTAGTCCAGGAATATGGCAACTAGATTGTACACATTTAGAAGGAAAAGTTATCCT
                                                                          3996
TACGTACCTGTTCATCTGACATCAGGTCCTTATACCGTTGATCTAACATGTGTAAATCTTCCTTTTCAATAGGA

M  H  G  Q  V  D  C  S  P  G  I  W  Q  L  D  C  T  H  L  E  G  K  V  I  L
                        ──── POL 1655 to 4693 ────

GGTAGCAGTTCATGTAGCCAGTGGATATATAGAAGCAGAAGTTATTCCAGCAGAAACAGGGCAGGAAACAGCAT
                                                                          4070
CCATCGTCAAGTACATCGGTCACCTATATATCTTCGTCTTCAATAAGGTCGTCTTTGTCCCGTCCTTTGTCGTA

V  A  V  H  V  A  S  G  Y  I  E  A  E  V  I  P  A  E  T  G  Q  E  T  A
                        ──── POL 1655 to 4693 ────

ATTTTCTTTTAAAATTAGCAGGAAGATGGCCAGTAAAAACAATACATACTGACAATGGCAGCAATTTCACCGGT
                                                                          4144
TAAAAGAAAATTTTAATCGTCCTTCTACCGGTCATTTTTGTTATGTATGACTGTTACCGTCGTTAAAGTGGCCA

Y  F  L  L  K  L  A  G  R  W  P  V  K  T  I  H  T  D  N  G  S  N  F  T  G
                        ──── POL 1655 to 4693 ────
```

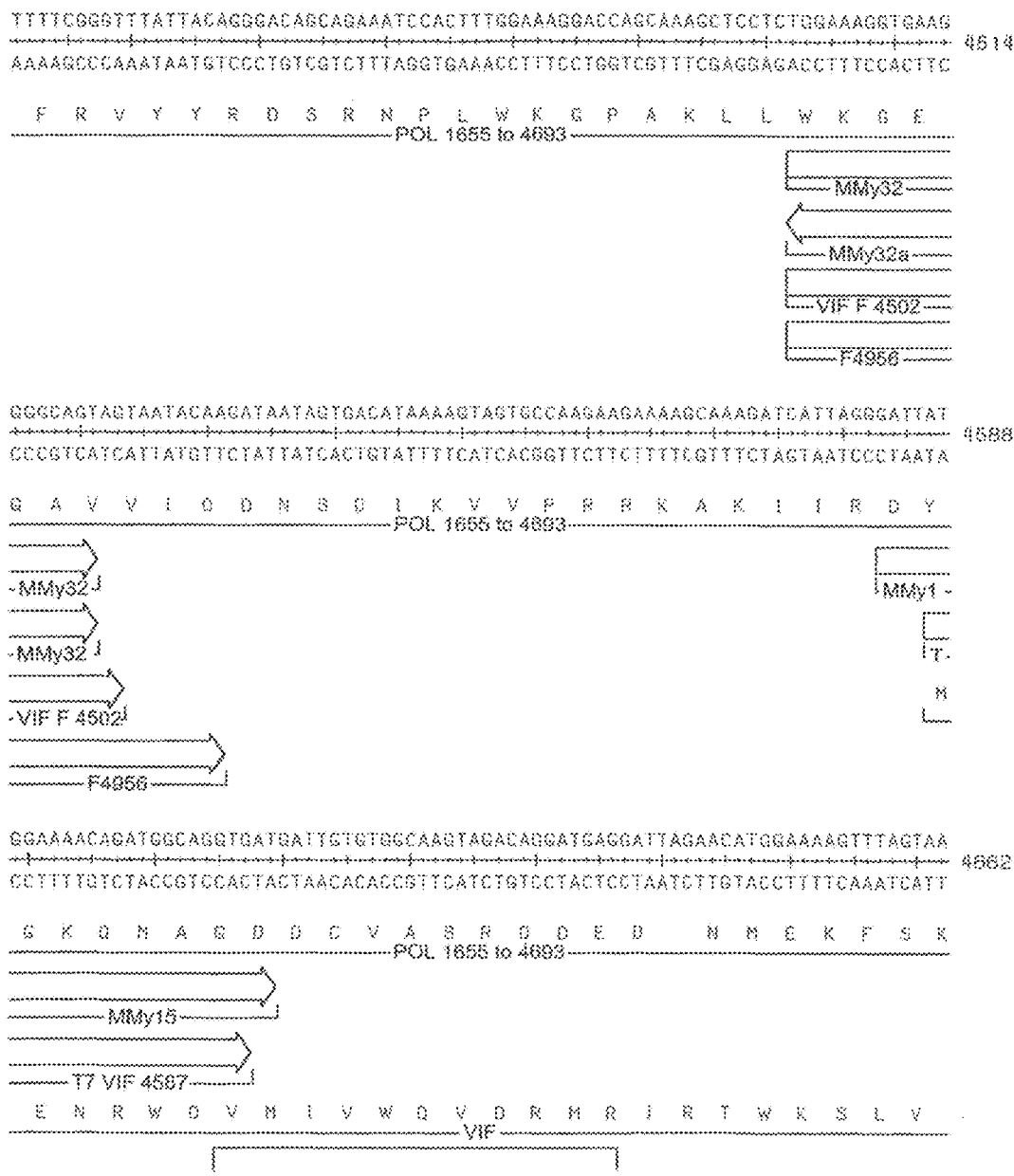
FIGURE 2-L

```
                    |_____R5090_____|

AACACCATATGTATGTTTCAGGGAAAGCTAGGGGATGGTTTTATAGACATCACTATCAAAGCCCTCATCCAAGA
----+----+----+----+----+----+----+----+----+----+----+----+----+----+----  4736
TTGTGGTATACATACAAAGTCCCTTTCGATCCCCTACCAAAATATCTGTAGTGATACTTCGGGAGTAGGTTCT

T  F  Y  V  C  F  R  E  S  .
|_____POL 1656 to 4693_____|
   K  H  H  Y  V  S  G  K  A  R  G  W  F  Y  R  H  H  Y  E  S  P  H  P  R
                                    |_____VIF_____

ATAAGTTCAGAAGTACACATCCCACTAGGGGATGCTAGATTGGTAATAACAACATATTGGGGTCTGCATACAGG
----+----+----+----+----+----+----+----+----+----+----+----+----+----+----  4810
TATTCAAGTCTTCATGTGTAGGGTGATCCCCTACGATCTAACCATTATTGTTGTATAACCCCAGACGTATGTCC

|_____R5220_____|
   |_____POL R 4765_____|
   I  S  S  E  V  H  I  P  L  G  D  A  R  L  V  I  T  T  Y  W  G  L  R  T  G
_____VIF_____

AGAAAGAGACTGGCATTTGGGTCAGGGAGTCTCCATAGAATGGAGGAAAAAGAGATATAGCACACAAGTAGACC
----+----+----+----+----+----+----+----+----+----+----+----+----+----+----  4884
TCTTTCTCTGACCGTAAACCCAGTCCCTCAGAGGTATCTTACCTCCTTTTTCTCTATATCGTGTGTTCATCTGG

|_____FGR53_____|
   E  R  D  W  H  L  G  Q  G  V  S  I  E  W  R  K  K  R  Y  S  T  Q  V  D
_____VIF_____

CTGAACTAGCAGACCAACTAATTCATCTGTATTACTTTGACTGTTTTTCAGACTCTGCTATAAGAAAGGCCTTA
----+----+----+----+----+----+----+----+----+----+----+----+----+----+----  4958
GACTTGATCGTCTGGTTGATTAAGTAGACATAATGAAACTGACAAAAAGTCTGAGACGATATTCTTTCCGGAAT

<=================MMy16a=================>
   |_____MMy16_____|
   P  E  L  A  D  Q  L  I  H  L  Y  Y  F  D  C  F  S  D  S  A  I  R  K  A  L
_____VIF_____
```

```
TTAAGAATGAAGCTGTTAGACATTTTCCTAGGATTTGGCTCCATGGCTTAGGGCAACATATCTATGAAACTTAT
----+----+----+----+----+----+----+----+----+----+----+----+----+----+---- 5264
AATTCTTACTTCGACAATCTGTAAAAGGATCCTAAACCGAGGTACCGAATCCCGTTGTATAGATACTTTGAATA
```

⇒
⊢MMy⟩
  L  K  N  E  A  V  R  H  F  P  R  I  W  L  H  G  L  G  Q  H  I  Y  E  T  Y
  ─────────────────────────────VPR─────────────────────────────

```
GGGATACTTGGGCAGGAGTGGAAGCCATAATAAGAATTCTGCAACAACTGCTGTTTATCCATTTTCAGAATTG
----+----+----+----+----+----+----+----+----+----+----+----+----+----+---- 5328
CCCTATGAACCCGTCCTCACCTTCGGTATTATTCTTAAGACGTTGTTGACGACAAATAGGTAAAAGTCTTAAC
```

┌──── VPR 5294 R 64T ────┐
                                      ┌──── VPR R 5296 ────┐
                                        └──── VPR R 5296 ──┘

G  D  T  W  A  G  V  E  A  I  I  R  I  L  Q  Q  L  L  F  I  H  F  Q  N  W
  ─────────────────────────────VPR─────────────────────────────

```
GGTGTCGACATAGCAGAATAGGCGTTACTCGACAGAGGAGAGCAAGAAATGGAGCCAGTAGATCCTAGACTAGA
----+----+----+----+----+----+----+----+----+----+----+----+----+----+---- 5402
CCACAGCTGTATCGTCTTATCCGCAATGAGCTGTCTCCTCTCGTTCTTTACCTCGGTCATCTAGGATCTGATCT
```

┌── VPR R 5328 ──┐              ⟨═════════⟩                  ┌─ VPR R 5393 ─┐
└── VPR R 5328 ──┘               └── MMy19 ──┘
                                ┌── VPR R 5363 ──┐
                                └── VPR R 5363 ──┘
  V  S  T  ·                                       M  E  P  V  D  P  R  L  E
  ─VPR─                                             ── TAT 5377 to 5591 ──

```
GCCCTGGAAGCATCCAGGAAGTCAGCCTAAAACTGCTTGTACCAATTGCTATTGTAAAAGTGTTGCTTTCATT
----+----+----+----+----+----+----+----+----+----+----+----+----+----+---- 5476
CGGGACCTTCGTAGGTCCTTCAGTCGGATTTTGACGAACATGGTTAACGATAACATTTTCACAACGAAAGTAA
```

┌─ VPR R 5393 ─┐  ┌──── VPR R 5419 ────┐
                  ┌──── VPU F 5409 ────┐
  P  W  K  H  P  G  S  Q  P  K  T  A  C  T  N  C  Y  C  K  K  C  C  F  H
  ──────────────────── TAT 5377 to 5591 ────────────────────

FIGURE 2-O

```
GCCAAGTTTGTTTCATAACAAAAGCCTTAGGCATCTCCTATGGCAGGAAGAAGCGGAGACAGCGACGAAGAGCT
++++++++++|++++++++++|++++++++++|++++++++++|++++++++++|++++++++++|++++++++++|++ 5550
CGGTTCAAACAAAGTATTGTTTTCGGAATCCGTAGAGGATACCGTCCTTCTTCGCCTCTGTCGCTGCTTCTCGA
```

```
            ┌─────────────────────────┐
            └──── ENV F 5500 ─────────┘
                ┌───────────────────┐
                └──── VPR R 5507 ───┘
 C  Q  V  C  F  I  T  K  A  L  G  I  S  Y  G  R  K  K  R  R  Q  R  R  R  A
                    ─────── TAT 5377 to 5591 ───────
                ┌───────────────────┐
                └──── VPU F 5507 ───┘
                          M  A  G  R  S  G  D  S  D  E  E  L
                          ──────── REV 5516 to 5591 ────────
```

```
CATCAGAACAGTCAGACTCATCAAGCTTCTCTATCAAAGCAGTAAGTAGTACATGTAATGCAACCTATACCAAT
++++++++++|++++++++++|++++++++++|++++++++++|++++++++++|++++++++++|++++++++ 5624
GTAGTCTTGTCAGTCTGAGTAGTTCGAAGAGATAGTTTCGTCATTCATCATGTACATTACGTTGGATATGGTTA
```

```
                ┌───────────────────┐                    M  Q  P  I  P  I
                └──── T7 VPU F 5577 ─┘                   └─ VPU 5608 to 5856 ─
                        ┌───────────────────┐
                        └──────  MMy25  ────┘
 H  Q  N  S  Q  T  H  Q  A  S  L  S  K
 ──────────── TAT 5377 to 5591 ────────
    I  R  T  V  R  L  I  K  L  L  Y  Q  S
    ────────── REV 5516 to 5591 ─────────
```

```
AGTAGCAATAGTAGCATTAGTAGTAGCAATAATAATAGCAATAGTTGTGTGGTCCATAGTAATCATAGAATATA
++++++++++|++++++++++|++++++++++|++++++++++|++++++++++|++++++++++|++++++++ 5698
TCATCGTTATCATCGTAATCATCATCGTTATTATTATCGTTATCAACACACCAGGTATCATTAGTATCTTATAT
```

```
   V  A  I  V  A  L  V  V  A  I  I  I  A  I  V  V  W  S  I  V  I  I  E  Y
   ───────────────────── VPU 5608 to 5856 ─────────────────────
```

```
ACCCACAGACCCCAACCCACAAGAAGTAGTATTGGTAAATGTGACAGAAAATTTTAACATGTGGAAAAATGACA
                                                                              6068
TGGGTGTCTGGGGTTGGGTGTTCTTCATCATAACCATTTACACTGTCTTTTAAAATTGTACACCTTTTTACTGT
```

```
VPU R 6
     P  T  D  P  N  P  Q  E  V  V  L  V  R  V  I  E  N  F  N  N  W  K  N  D
                               ENV 5771 to 8341
```

```
TGGTAGAACAGATGCATGAGGATATAATCAGTTTATGGGATCAAAGCCTAAAGCCATGTGTAAAATTAACCCCA
                                                                              6142
ACCATCTTGTCTACGTACTCCTATATTAGTCAAATACCCTAGTTTCGGATTTCGGTACACATTTTAATTGGGGT
```

```
  M  V  E  Q  M  H  E  D  I  I  S  L  W  D  Q  S  L  K  P  C  V  K  L  T  P
                               ENV 5771 to 8341
```

```
CTCTGTGTTAGTTTAAAGTGCACTGATTTGAAGAATGATACTAATACCAATAGTAGTAGCGGGAGAATGATAAT
                                                                              6216
GAGACACAATCAAATTTCACGTGACTAAACTTCTTACTATGATTATGGTTATCATCATCGCCCTCTTACTATTA
```

```
  L  C  V  S  L  K  C  T  D  L  K  N  D  T  N  T  N  S  S  S  G  R  M  I  M
                               ENV 5771 to 8341
```

```
GGAGAAAGGAGAGATAAAAAACTGCTCTTTCAATATCAGCACAAGCATAAGAGGTAAGGTGCAGAAAGAATATG
                                                                              6290
CCTCTTTCCTCTCTATTTTTTGACGAGAAAGTTATAGTCGTGTTCGTATTCTCCATTCCACGTCTTTCTTATAC
```

```
   E  K  G  E  I  K  N  C  S  F  N  I  S  T  S  I  R  G  K  V  Q  K  E  Y
                               ENV 5771 to 8341
```

```
CATTTTTTTATAAACTTGATATAATACCAATAGATAATGATACTACCAGCTATAAGTTGACAAGTTGTAACACC
                                                                              6364
GTAAAAAAATATTTGAACTATATTATGGTTATCTATTACTATGATGGTCGATATTCAACTGTTCAACATTGTGG
```

```
  A  F  F  Y  K  L  D  I  I  P  L  Q  N  D  T  T  S  Y  K  L  T  S  C  N  T
                               ENV 5771 to 8341
```

FIGURE 2-U

```
ACAGTCTGGGGCATCAAGCAGCTCCAGGCAAGAATCCTGGCTGTGGAAAGATACCTAAAGGATCAACAGCTCCT
----+----+----+----+----+----+----+----+----+----+----+----+----+----+---- 7548
TGTCAGACCCCGTAGTTCGTCGAGGTCCGTTCTTAGGACCGACACCTTTCTATGGATTTCCTAGTTGTCGAGGA

T  V  W  G  I  K  Q  L  Q  A  R  I  L  A  V  E  R  Y  L  K  D  Q  Q  L  L
                              ENV 5771 to 8341

GGGGATTTGGGGTTCCTCTGGAAAACTCATTTGCACCACTGCTGTGCCTTGGAATGCTAGTTGGAGTAATAAAT
----+----+----+----+----+----+----+----+----+----+----+----+----+----+---- 7622
CCCCTAAACCCCAACGAGACCTTTTGAGTAAACGTGGTGACGACACGGAACCTTACGATCAACCTCATTATTTA

|---- REV F 7550 ----->
   G  I  W  G  C  S  G  K  L  I  C  T  T  A  V  P  W  N  A  S  W  S  N  K
                              ENV 5771 to 8341
```

```
CTCTGGAACAGATTTGGAATCACACGACCTGGATGGAGTGGGACAGAGAAATTAACAATTACACAAGCTTAATA
----+----+----+----+----+----+----+----+----+----+----+----+----+----+---- 7696
GAGACCTTGTCTAAACCTTAGTGTGCTGGACCTACCTCACCCTGTCTCTTTAATTGTTAATGTGTTCGAATTAT

S  L  E  Q  I  W  N  H  T  T  W  M  E  W  D  R  E  I  N  N  Y  T  S  L  I
                              ENV 5771 to 8341

CACTCCTTAATTGAAGAATCGCAAAACCAGCAAGAAAAGAATGAACAAGAATTATTGGAATTAGATAAATGGGC
----+----+----+----+----+----+----+----+----+----+----+----+----+----+---- 7770
GTGAGGAATTAACTTCTTAGCGTTTTGGTCGTTCTTTTCTTACTTGTTCTTAATAACCTTAATCTATTTACCCG

<---- MMy89a ---->
                 |---- MMy89 ----->
   H  S  L  I  E  E  S  Q  N  Q  E  K  N  E  Q  E  L  L  E  L  D  K  W  A
                              ENV 5771 to 8341

AAGTTTGTGGAATTGGTTTAACATAACAAATTGGCTGTGGTATATAAAATTATTCATAATGATAGTAGGAGGCT
----+----+----+----+----+----+----+----+----+----+----+----+----+----+---- 7844
TTCAAACACCTTAACCAAATTGTATTGTTTAACCGACACCATATATTTTAATAAGTATTACTATCATCCTCCGA

|---- REV F 7791 ----->              |---- REV F 7830 ----
          |---- REV F 7791 ----|                   REV F 7832
                                                   REV F 7832

S  L  W  N  W  F  N  I  T  N  W  L  W  Y  I  K  L  F  I  M  I  V  G  G
                              ENV 5771 to 8341
```

```
AAGTAGTGTGATTGGATGGCCTACTGTAAGGGAAAGAATGAGACGACCTGAGCCAGCAGCAGATAGGGTGGGAG
----+----+----+----+----+----+----+----+----+----+----+----+----+----+---- 8436
TTCATCACACTAACCTACCGGATGACATTCCCTTTCTTACTCTGCTGGACTCGGTCGTCGTCTATCCCACCCTC
```

→ Nef
→ MMy9
→ MMy9

S S V I G W P T V R E R M R R A E P A A D R V G
————————— NEF 8343 to 8963 —————————

```
CAGCATCTCGAGACCTGGAAAAACATGGAGCAATCACAAGTAGCAATACAGCAGCTACCAATGCTGCTTGTGCC
----+----+----+----+----+----+----+----+----+----+----+----+----+----+---- 8510
GTCGTAGAGCTCTGGACCTTTTTGTACCTCGTTAGTGTTCATCGTTATGTCGTCGATGGTTACGACGAACACGG
```

A A S R D L E K H G A I T S S N T A A T N A A C A
————————— NEF 8343 to 8963 —————————

```
TGGCTAGAAGCACAAGAGGAGGAGGAGGTGGGTTTTCCAGTCACACCTCAGGTACCTTTAAGACCAATGACTTA
----+----+----+----+----+----+----+----+----+----+----+----+----+----+---- 8584
ACCGATCTTCGTGTTCTCCTCCTCCTCCACCCAAAAGGTCAGTGTGGAGTCCATGGAAATTCTGGTTACTGAAT
```

W L E A Q E E E E V G F P V T P Q V P L R P M T Y
————————— NEF 8343 to 8963 —————————

```
CAAGGCAGCTGTAGATCTTAGCCACTTTTTAAAAGAAAAGGGGGGACTGGAAGGGCTAATTCACTCCCAAAGAA
----+----+----+----+----+----+----+----+----+----+----+----+----+----+---- 8658
GTTCCGTCGACATCTAGAATCGGTGAAAAATTTTCTTTTCCCCCCTGACCTTCCCGATTAAGTGAGGGTTTCTT
```

← MMy10a →
← MMy10 →
ENV R 8618

K A A V D L S H F L K E K G G L E G L I H S Q R
————————— NEF 8343 to 8963 —————————

```
TGGGAGTGGCGAGCCCTCAGATCCTGCATATAAGCAGCTGCTTTTTGCCTGTACTGGGTCTCTCTGGTTAGAC
----+----+----+----+----+----+----+----+----+----+----+----+----+----+--  9102
ACCCCTCACCGCTCGGGAGTCTAGGACGTATATTCGTCGACGAAAAACGGACATGACCCAGAGAGACCAATCTG
```

NEF R 9089

FGR95

```
CAGATCTGAGCCTGGGAGCTCTCTGGCTAACTAGGGAACCCACTGCTTAAGCCTCAATAAAGCTTGCCTTGAGT
----+----+----+----+----+----+----+----+----+----+----+----+----+----+--  9176
GTCTAGACTCGGACCCTCGAGAGACCGATTGATCCCTTGGGTGACGAATTCGGAGTTATTTCGAACGGAACTCA
```

R9626

```
GCTTC
-----> 9181
CGAAG
```

| PRIMER NUMBER | | REVERSE PRIMER GROUP NUMBER | Tm |
|---|---|---|---|
| 32 | GCTCTATTAGATACAGGAGC | 2 | 58 |
| 33 | GCTTTATTAGATACAGGAGC | 1 | 56 |
| 34 | GCTCTGTTAGATACAGGAGC | 3 | 60 |

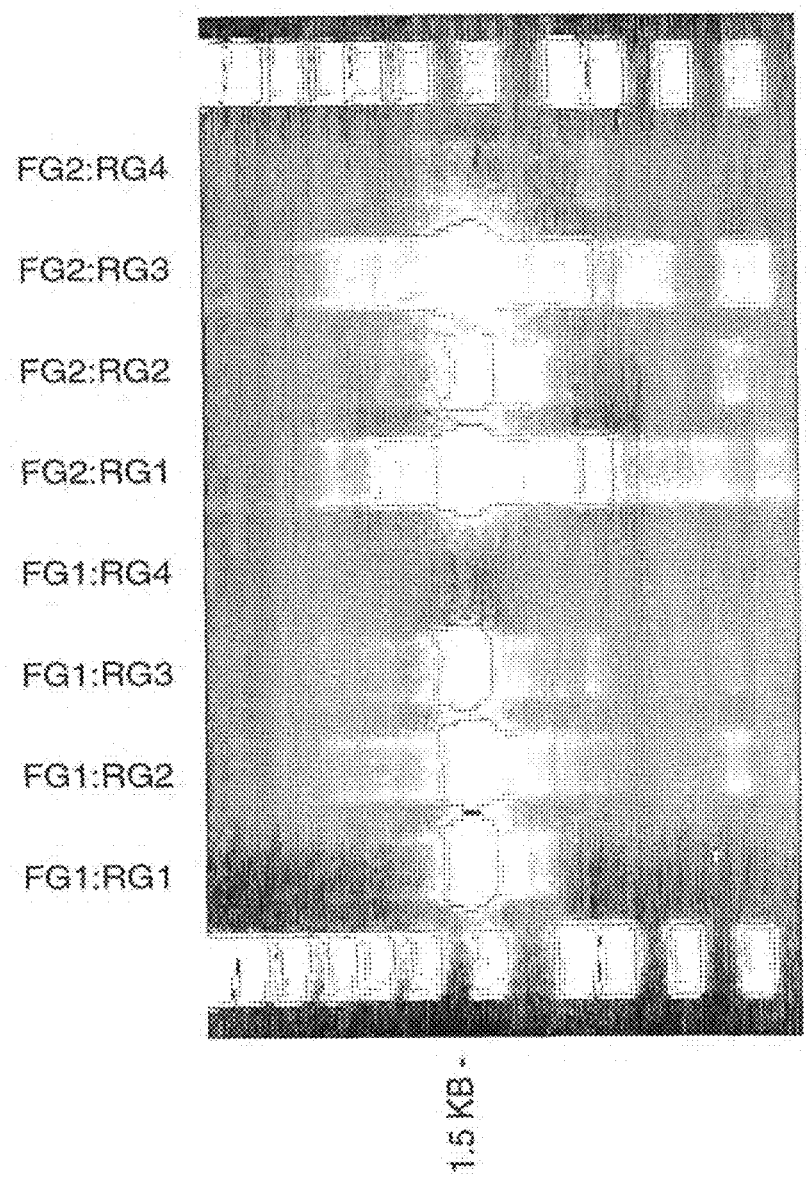

```
        B8
    ┌────────┐
   ┌─┴────────────┐
KIRLRPGGKKKYKLKHIVWAS (SEQ ID NO:403)
        ↓
KIRLRPGGRKKYKLKHIVWAS (SEQ ID NO:404)

B8
   ┌────────┐
TGSEELRSLYNTVATLYC (SEQ ID NO:405)
      ↓
TGSEEFRSLYNTVATLYC (SEQ ID NO:406)
```

*FIG. 18B*

STRAIN-INDEPENDENT AMPLIFICATION OF PATHOGENS AND VACCINES THERETO

FIELD OF THE INVENTION

The invention relates to methods for strain-independent amplification of pathogens and to patient-specific vaccines and related compositions. Preferred embodiments of the invention relate to patient-specific vaccines against retroviruses, such as HIV and HCV.

BACKGROUND OF THE INVENTION

Many pathogens rapidly mutate and recombine, making it difficult to produce effective vaccines. This problem is most prevalent with viral pathogens, and in particular with RNA viruses, such as HIV. HIV infected individuals can harbor multiple HIV strains and typically harbor multiple HIV quasispecies. Therapeutic strategies aimed at treating individuals infected with pathogens such as HIV-1 face enormous difficulties ranging from the development of viral strains which are resistant to the anti-virals to the numerous side effects of these drugs, making continuous administration of these therapies extremely difficult and expensive.

Several therapeutic HIV vaccines have been developed, however clinical trials of these vaccines have shown little efficacy. One explanation for the lack of success of these vaccines is the use of viral vectors as immunogens which encompass consensus sequences of the HIV viral genome. The presence of consensus sequences does not necessarily argue for the efficacy of the sequences in eliciting immune responses against a heterologous virus. Because of the still high and growing level of divergence between the consensus sequence and the autologous infecting HIV strain, vaccines or anti-viral reagents based on the HIV-1 subtype B consensus sequence are unable to adequately treat HIV infection. Moreover, it is likely that those viral vector-based vaccines do not target the most efficient cells of the immune system in terms of antigen processing and presentation, namely dendritic cells.

A number of publications have suggested the use of antigen presenting cells loaded with HIV nucleic acids or peptides as a vaccine for HIV. For example, Huang et al. (J Infect. Dis. 2003 187:315-319) disclose dendritic cells loaded with liposome-complexed HIV proteins and the possible use of such loaded cells as a vaccine. Weissman et al. (J Immunol 2000 165:4710-4717) disclose transfection of dendritic cells with mRNA encoding a single cloned HIV gag sequence, resulting in the delivery of antigenic gag peptides to MHC class I and II molecules and the induction of CD4+ and CD8+ T cells responses in vitro. U.S. Pat. Nos. 5,853,719 and 6,670,186 (Nair et al.) describe the use of RNA derived from a tumor or pathogen isolated from a patient for in vitro loading of autologous antigen presenting cells, and their use as a vaccine. However, vaccinating patients with antigen presenting cells loaded with total pathogen RNA could increase the pathogen load in the patient.

The difficulty in selecting primers capable of amplifying the nucleic acids from all variants of a given pathogen, and in particular, all variants of HIV, has long been recognized. Amplification of specific regions of the HIV genome is complicated by the high mutation rate of the HIV genome caused by the low fidelity reverse transcriptase of the virus and immune selection in vivo. Nevertheless, primers have been developed that can amplify certain regions of the HIV genome from multiple HIV variants. For example, Abravaya et al. (J Clinical Microbio 2000 38:716-723) disclose HIV-1-specific and HIV-2-specific primers and probes targeted to conserved sequences in the pol gene for use in multiplex PCR assays to detect HIV-1 group M subtypes A, B, C, D, E, F and G, and group O and HIV-2 RNA in plasma, and the use of such assays to improve the safety of the blood supply.

Christopherson et al. (Nucleic Acids Res 1997 25:654-658) discuss the effect of internal primer-HIV-1 template mismatches on RT-PCR to amplify a 142 base pair region of gag. Five to six mismatches, but not two to four mismatches, between the HIV-1 template and primers 28-30 bases length significantly decreased the yield of RT-PCR. The primers were designed to be longer than is typically used in order to accommodate mismatches. Reduced efficiency of amplification of the more divergent HIV-1 subtypes A and E could be improved 4-fold to 10-fold by lowering the annealing temperature to 50° C. and implementing a reverse transcription step that gradually increases in temperature. Also, substitution of 5-methylcytosine for cytosine, or of inosine at positions of variable bases resulted in less than 4-fold difference in product yield between the homologous and most divergent HIV-1 templates. Primers that terminated in a T allowed amplification when matched or mismatched with C, G or T.

Michael et al. (J Clin Microbiol 1999 37:2557-2563) disclose primers for the amplification of a 155 nucleotide sequence of the HIV-1 gag gene. The primers were selected to maximize homology to 30 HIV-1 isolates of subtypes A through G, and to minimize HIV-1 to primer mismatches near the 3' end of the primer. The annealing temperature during amplification was lowered to increase mismatch tolerance. The optimized primers and amplification conditions increased the quantity of HIV-1 RNA detected in comparison to previously available tests, but underrepresented subtypes A, D, F and G, and contained no members of subtypes H and J.

U.S. Pat. No. 6,001,558 discloses the use of multiple primers to amplify short fragments (<200 base pairs) of the LTR and pol regions from multiple HIV-1 isolates and the LTR, pol and env regions from multiple HIV-2 isolates. Multiple probes were then used to detect the amplification products. The primer/probe combinations were able to detect five HIV-1 isolates from groups M and O, and two HIV-2 isolates. Primers corresponding to highly conserved sequences of HIV-1 were selected by the following criteria: 1) the lengths of amplified PCR products could not exceed 200 base pairs, as smaller products are more efficiently amplified than larger products, and are less sensitive to other reaction conditions; 2) primer sets must amplify a functional probe region for detection of the amplified product; 3) mismatch near the 3' end of the primer would be far less preferable than mismatches near the 5' end; and 4) other criteria for 3' end stability, length (about 23-31 nucleotides), GC content and interactions with other primers and probes.

U.S. Pat. No. 6,194,142 discloses methods for in vitro diagnosis HIV-1, HIV-2 and SIV infection using primer pairs corresponding to sequences that are conserved between the gag, pol and env genes of HIV-1 Bru, HIV-1 Mal and HIV-1 Eli, HIV-2 ROD and SIV MAC strains, and between the nef2, vif2 and vpx genes of HIV-2 ROD and SIV MAC, or the env, nef1, vif1 and vpr genes of HIV-1 Bru, HIV-1 Mal and HIV-1 Eli. Mixtures of primers with variant nucleotides corresponding to HIV variants and SIV were used simultaneously in a PCR reaction.

U.S. Pat. No. 6,232,455 discloses primer/probe sets derived from consensus sequences of 31 HIV-1 group M (subtypes (A, B and D) and group O isolates and 14 isolates of the HIV-2 A and B subtypes. HIV-1 consensus primer/probe sets are specific for the detection of HIV-1, while HIV-2 consensus primer/probe sets are specific for the detection of HIV-2.

U.S. Pat. No. 6,531,588 discloses primers for amplification of 0.7 kB, 1.57 kb or 2.1 kb regions of pol from multiple HIV quasispecies in a patent, followed by sequencing to determine patient-specific HIV genotype information for use in determining the appropriate therapy and monitoring drug resistance.

U.S. 2003/0148280 disclose primer sets and probes for the detection of purportedly all HIV-1 group M, N and O strains including circulating recombinant forms (CRF, which refers to recombinants between subtypes), and intergroup recombinants. The primers are targeted to HIV-1 gag p24 (399 by amplicon), pol integrase (864 bp amplicon), and env gp41 immunodominant region (IDR; 369 bp amplicon).

None of these publications suggest the possibility of using amplified autologous pathogen nucleic acids encoding specific polypeptides from multiple species of a pathogen present in an individual for the preparation of antigen presenting cell vaccines or nucleic acid vaccines. The present invention addresses the long felt need to develop patient specific vaccines to treat autologous infecting pathogens and offers additional advantages as well.

SUMMARY OF THE INVENTION

Applicants have discovered methods for the nucleic acid amplification of multiple variants (strains) of any pathogen present in a sample, and preferably in a sample from a pathogen infected individual. In preferred embodiments, the pathogen is a retrovirus, such as HIV. The amplified pathogen nucleic acid can be used to identify the pathogen variants present in a sample, to quantitate the pathogen present in a sample, and as a nucleic acid vaccine, or in the preparation of antigen presenting cell vaccines. Nucleic acids produced by the methods of the invention can be used to transfect (load) antigen presenting cells. The loaded antigen presenting cells can then be used as a vaccine for the treatment of pathogen infection. In another embodiment, nucleic acids produced by the methods of the invention can be used directly as nucleic acid vaccines without prior loading into antigen presenting cells.

The invention further provides methods of selecting primers suitable for amplification of multiple variants of a pathogen, comprising:

a. choosing a first region for forward primer annealing and a second region for reverse primer annealing, wherein said first and second regions flank an open reading frame and/or an epitope of a pathogen; and b. choosing candidate forward and reverse primers for said first and second regions, wherein at least one of said primers is designed to compensate for sequence variability between multiple variants of a pathogen.

Preferably, the candidate forward and reverese primers are chosen to produce an amplification product over 200 nucleotides in length, more preferably at least 225, 250, 300 or more nucleotides in length.

In preferred embodiments, the amplified nucleic acid contains transcription and translation signals for efficient in vivo or in vitro transcription to produce an mRNA which can then be translated in vitro or in vivo. The applicants further provide methods of loading antigen presenting cells, preferably dendritic cells, using nucleic acids, preferably mRNA produced by the methods of the invention. The loaded antigen presenting cells are useful as vaccines for the treatment of pathogen infection.

Thus, in another aspect, the invention provides a composition comprising: an antigen presenting cell transfected with a plurality of nucleic acids encoding one or more antigens from multiple strains (variants) of a pathogen present in a mammal. The nucleic acids can be derived from nucleic acid amplification of pathogen polynucleotides using a plurality of primer pairs designed to compensate for variability between said variants of pathogen, and said antigen presenting cell and said pathogen nucleic acids are from or derived from said mammal. The invention further provides methods of making antigen presenting cells loaded with nucleic acids representative of multiple variants of a pathogen infecting an individual, and methods of treating pathogen infected individuals using the vaccines of the invention. Preferred antigen presenting cells are dendritic cells.

In one aspect, the invention provides a nucleic acid vaccine, comprising a plurality of nucleic acids encoding one or more antigens from multiple variants of a pathogen present in a mammal and a pharmaceutically acceptable carrier, wherein said nucleic acids are derived by nucleic acid amplification of pathogen polynucleotides using a plurality of primer pairs that compensate for nucleotide sequence variability between said variants of pathogen.

In another aspect, the invention provides a method of producing pathogen amplicons representing one or more polypeptides from at least two strains of a pathogen, comprising: (a) combining polynucleotides from a first and a second strain of a pathogen to form a mixture; and (b) amplifying said polynucleotides to produce a first amplicon and a second amplicon; wherein said first amplicon encodes a polypeptide from said first strain and said second amplicon encodes the corresponding polypeptide form said second strain. Such amplicons can be used as nucleic vaccines, for the transfection of antigen presenting cells, and for the production of in vitro translated pathogen polypeptides.

The ability to amplify targeted pathogen genes and fragments thereof from multiple strains of a pathogen circumvents the need to purify or amplify total pathogen nucleic acids, such as a pathogen DNA or RNA genome, a full-length cDNA copy of an RNA virus, etc. For example, providing a full HIV genome as a nucleic acid vaccine or for loading into APCs, whether the genes are present in the form of nucleic acid fragments or as a contiguous pathogen genome, could result in the reconstitution infectious virus. In addition, certain pathogen nucleic acids or polypeptides (e.g., HIV nef or vpr) can have deleterious effects, particularly with respect to antigen presenting cells. Polypeptides or nucleic acids encoding polypeptides having deleterious effects can be eliminated or present in lower molar ratios with respect to nucleic acids encoding other pathogen polypeptides. Accordingly, by providing vaccines comprising nucleic acids that represent pathogen polypeptides from multiple pathogen strains, but which represent less than the full pathogen genome or encode less than all of the pathogen proteins, the negative effects of pathogen infection can be avoided, such as persistent infection, constitutive expression of viral genes or proteins. Deleterious pathogen polynucleotides and proteins can be avoided as well. Thus, the invention provides compositions comprising nucleic acids encoding one or more polypeptides from multiple strains of a pathogen present, wherein one or more pathogen polypeptides are not represented from any strain. The nucleic acids can represent polypeptides from multiple pathogen strains present in one or more individuals. The amplified pathogen nucleic acids can be produced directly from pathogen nucleic acids present in a biological sample from one or more pathogen infected individuals, or can be produced from cloned isolates of a pathogen. Thus, in one aspect, the invention provides an isolated antigen presenting cell (APC) comprising nucleic acids encoding one or more polypeptides from multiple strains of a pathogen present in an individual subject, wherein one or more pathogen polypeptides are not represented from any strain.

In another embodiment of the invention, the amplified pathogen nucleic acids are translated in vitro, and used to vaccinate patients directly, or to load APCs. The pathogen polypeptides or APCs loaded with such peptides together with a pharmaceutically acceptable carrier can be administered as a vaccine. Accordingly, the invention provides a composition comprising pathogen polypeptides from multiple strains of a pathogen, wherein one or more pathogen polypeptides are not represented from any strain. The invention also provides an isolated APC comprising pathogen polypeptides from multiple strains of a pathogen present in an individual subject, wherein one or more pathogen polypeptides are not represented from any strain.

In one embodiment, the invention provides a method of preparing an autologous vaccine, comprising: transfection antigen presenting cells obtained or derived from a pathogen-infected individual with nucleic acids encoding one or more pathogen polypeptides from multiple strains of a pathogen present in said individual or in one or more other individuals, wherein one or more pathogen polypeptides are not represented from any strain.

In another aspect, the invention provides a method of preparing an autologous vaccine, comprising: transfecting antigen presenting cells obtained or derived from a pathogen-infected mammal with nucleic acids encoding one or more antigens from multiple variants of a pathogen present in said mammal, wherein said nucleic acids are derived by nucleic acid amplification of pathogen polynucleotides using a plurality of primer pairs that can compensate for variability between said variants of pathogen.

In yet another aspect, the invention provides a method of treating a pathogen infected mammal, comprising:

a. amplifying nucleic acids of multiple variants of a pathogen present in a mammal using a plurality of primer pairs that can amplify multiple variants of said pathogen to produce amplified pathogen DNA;

b. optionally transcribing said amplified pathogen DNA to produce pathogen RNAs; and c. administering said pathogen DNA or said pathogen RNA to said mammal. The methods of the invention can be used to amplify the nucleic acid of any pathogen. In addition, the amplified product can be quantitated to determine pathogen load (e.g., viral load) and can be sequenced to determine pathogen evolution within an individual. In a preferred embodiment, the pathogen is HIV of HCV. The invention provides primers for the amplification of multiple variants of HIV, consisting essentially of SEQ ID NO: 1-58, 60-161 and 172-371; primers consisting essentially of an oligonucleotide having at least 75% sequence identity to nucleic acid selected from the group consisting of SEQ ID NO: 1-58, 60-161 and 172-371; and primer pairs comprising combinations of primers selected from the group consisting of SEQ ID NO:1-58 and 60-371 and nucleic acids having at least 75% sequence identity to SEQ ID NOs:1-58 and 60-371; as well as kits containing such primer pairs. The kits may additionally contain one or more reagents, including, but not limited to a thermostable DNA polymerase, reverse transcriptase, deoxyribonucleotide triphosphates and CD40L mRNA. In one aspect, the invention provides a strain-independent method of amplifying HIV sequences, comprising: amplifying multiple variants of HIV DNA with a forward primer and a reverse primer of the invention.

In another aspect, the invention provides an autologous vaccine against HIV that elicits a therapeutic immune response directed at multiple defined HIV protein variants expressed by an infected patient's unique virus specie(s). In a preferred embodiment, the invention provides a patient-specific vaccine composed of autologous ex vivo generated mature dendritic cells transfected with RNA encoding multiple HIV antigens derived from autologous virus.

BRIEF DESCRIPTION OF THE DRAWINGS

FIGS. 1A, 1B, 1C, 1D, 1E, 1F, 1G, 1H, 1I, 1J, and 1K show a list of primers, 5' to 3' sequence, length and Tm. The numbers in the primer names correspond to their position with respect to the HIV genome having accession number NC_001802 in the HIV Sequence Database provided by the Los Alamos National Laboratory and available on the word wide web at the following http address: //hiv-web.lanl.gov/content/index.

Figure 2:
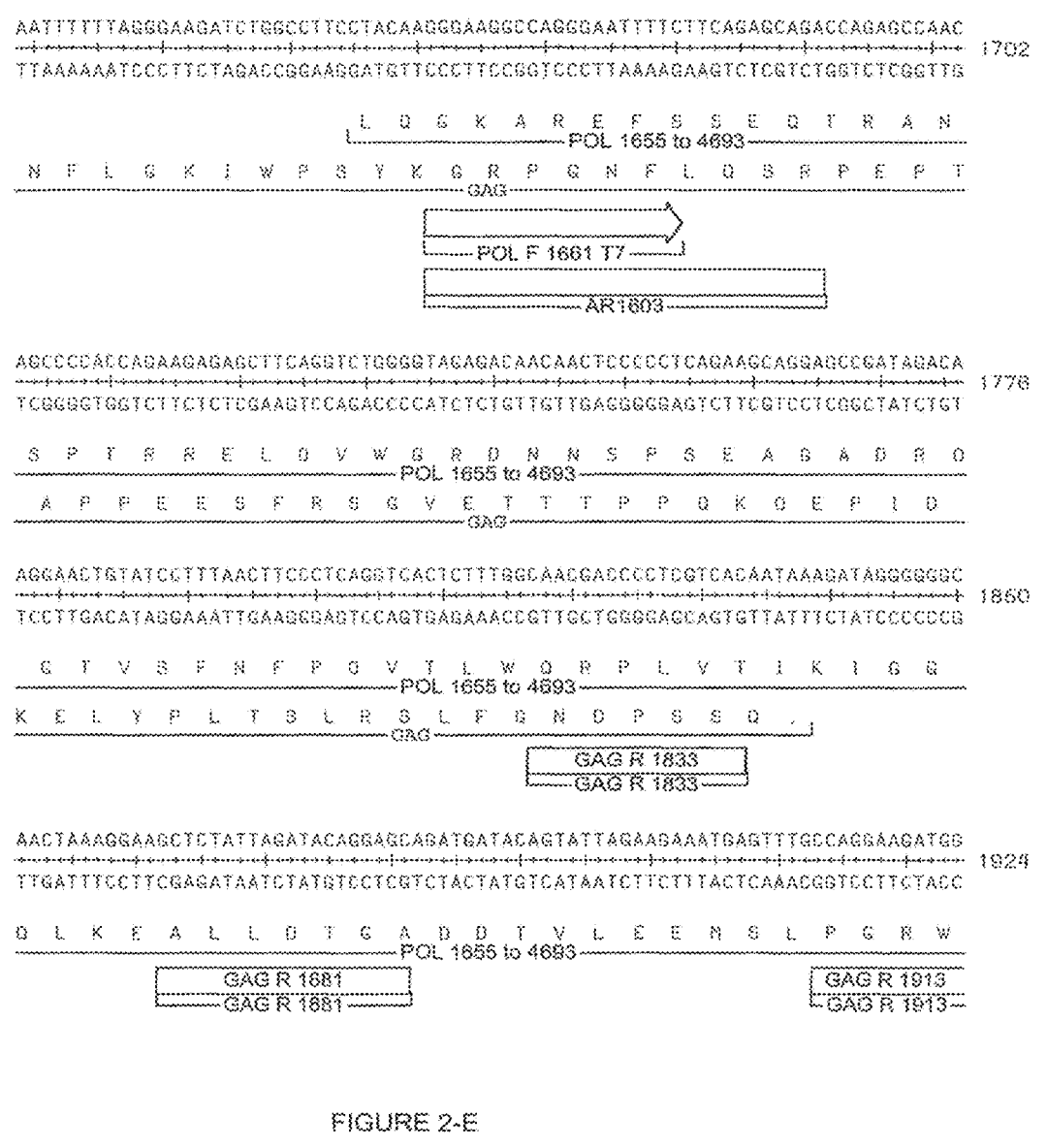
Figure 2:
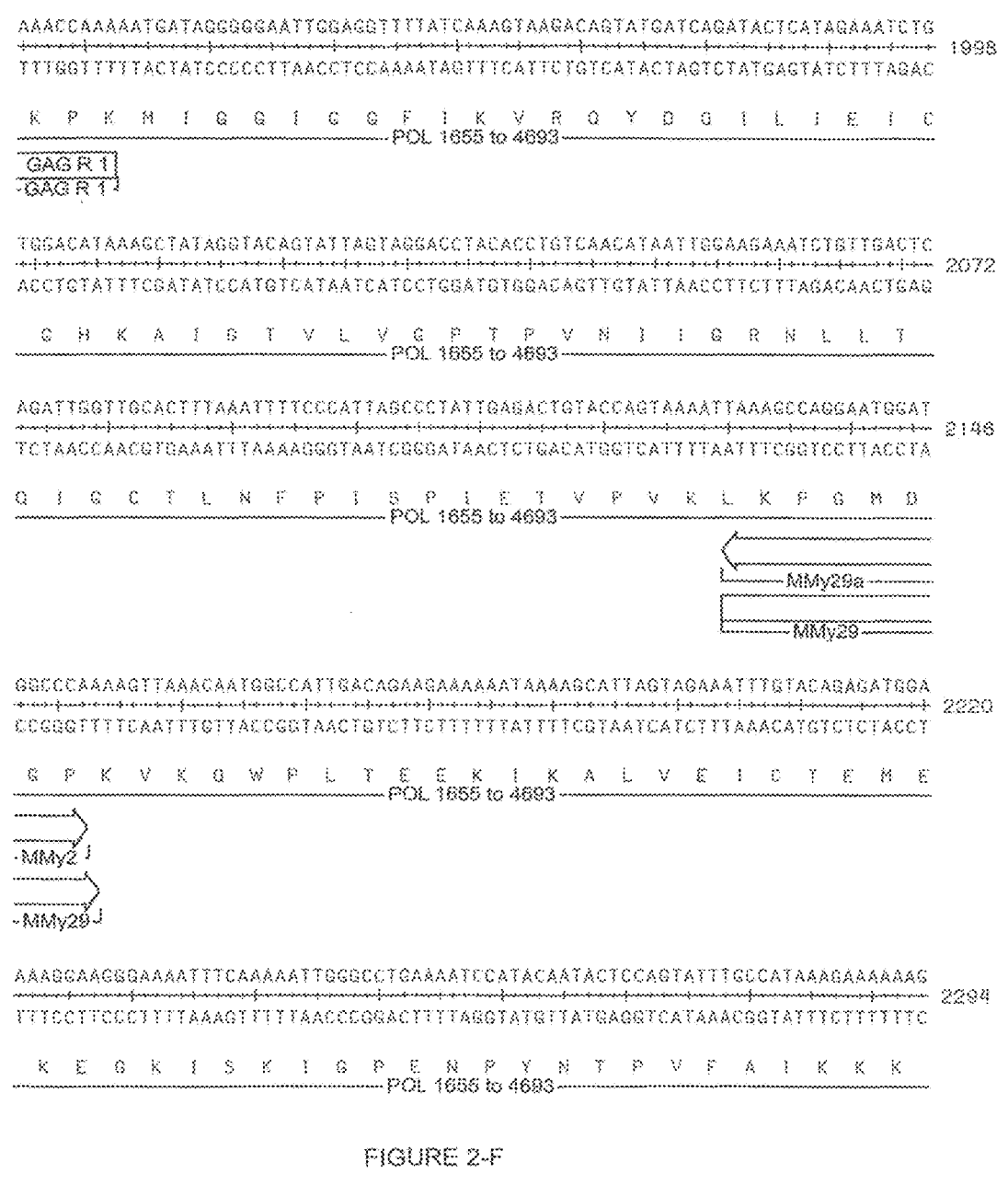
Figure 2:
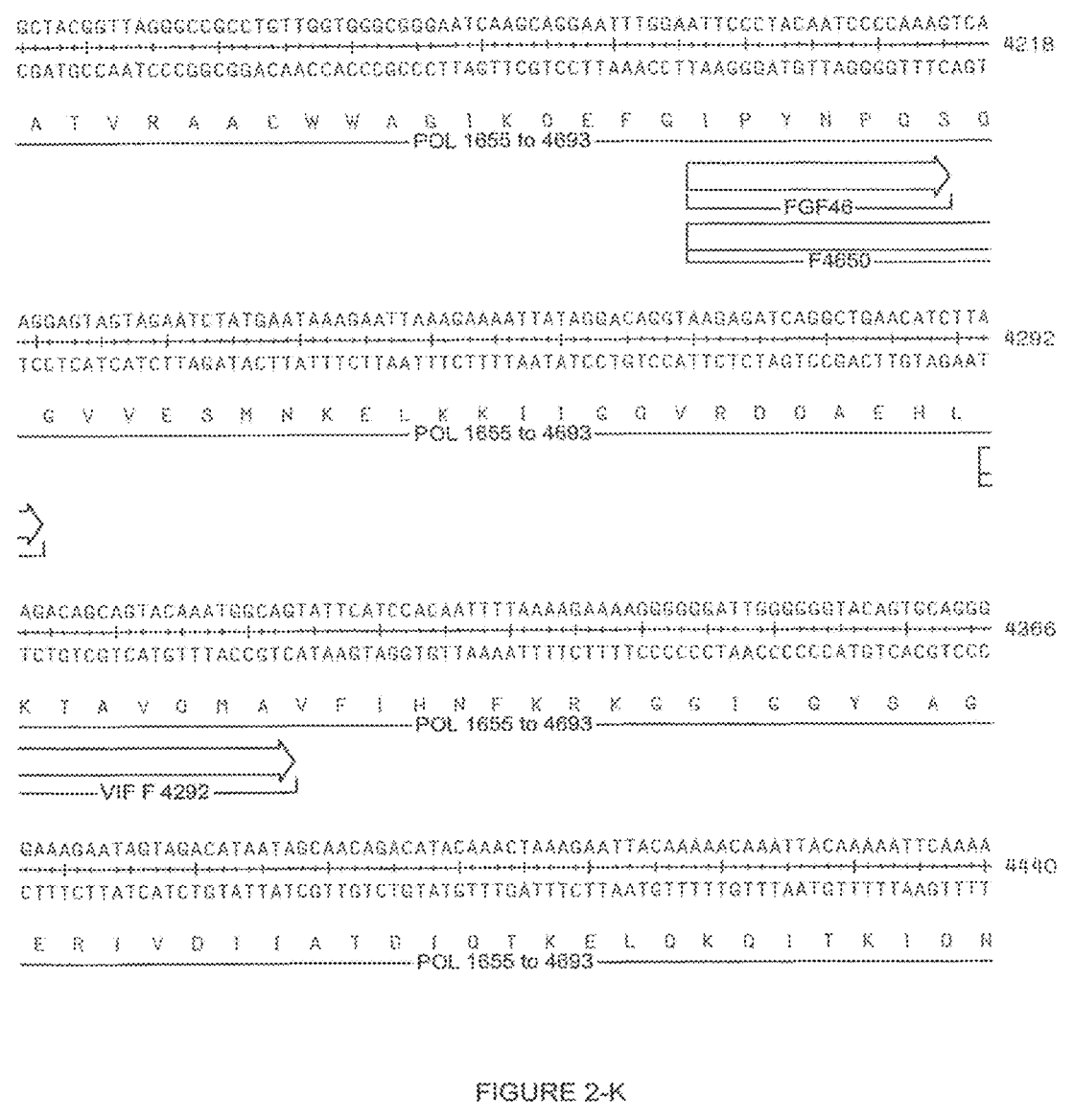
Figure 2:
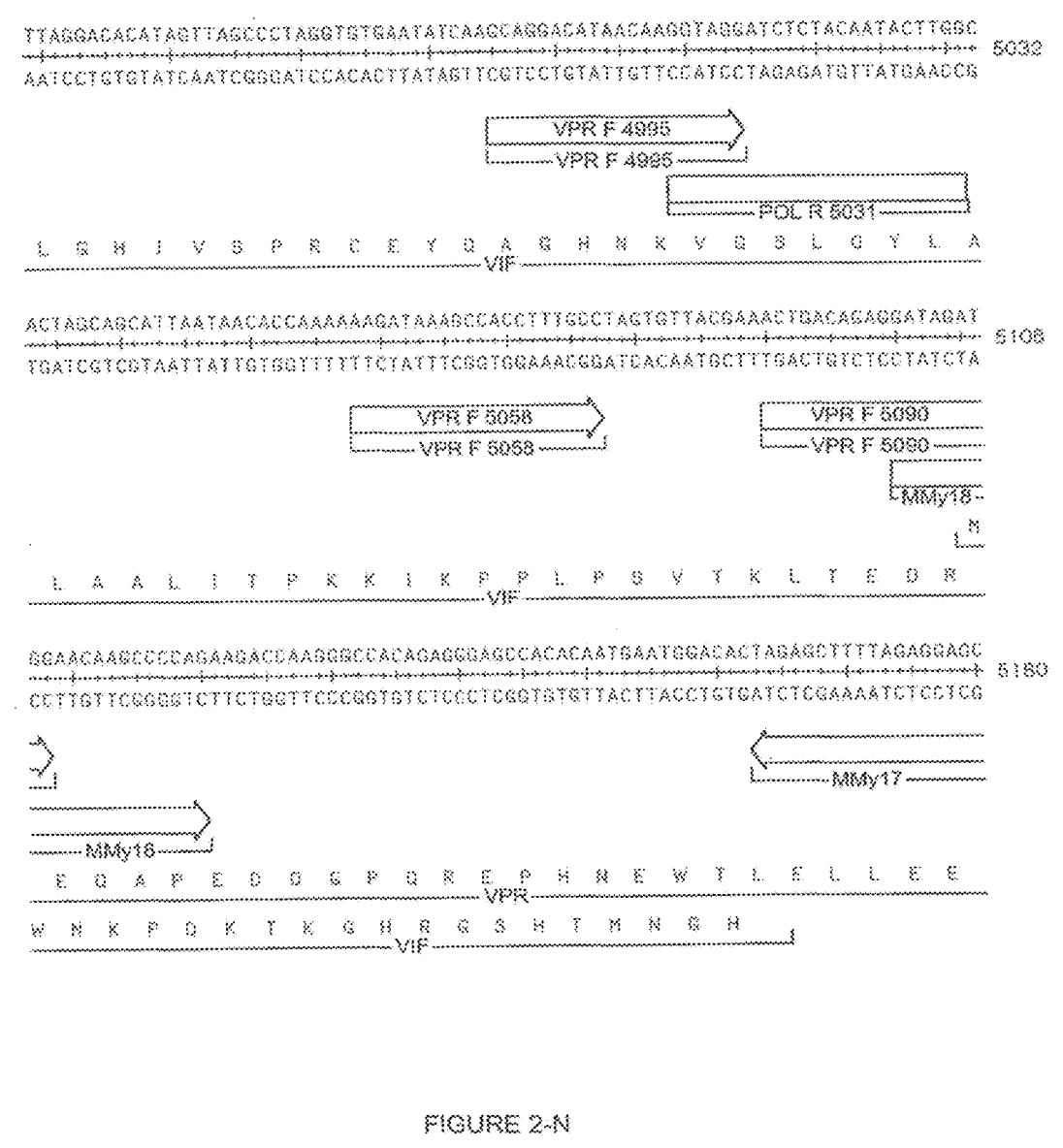
Figure 2:
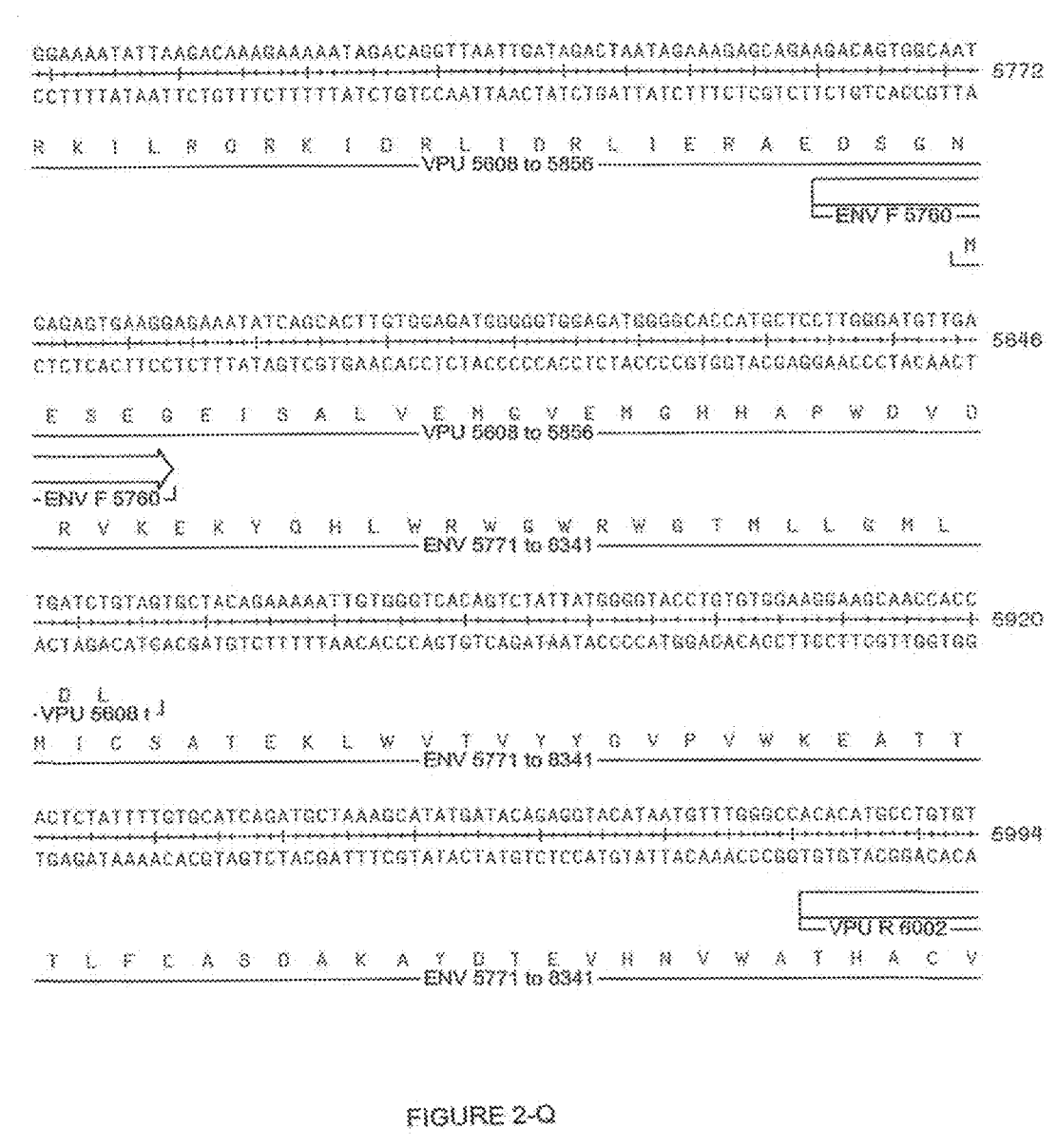
Figure 2:
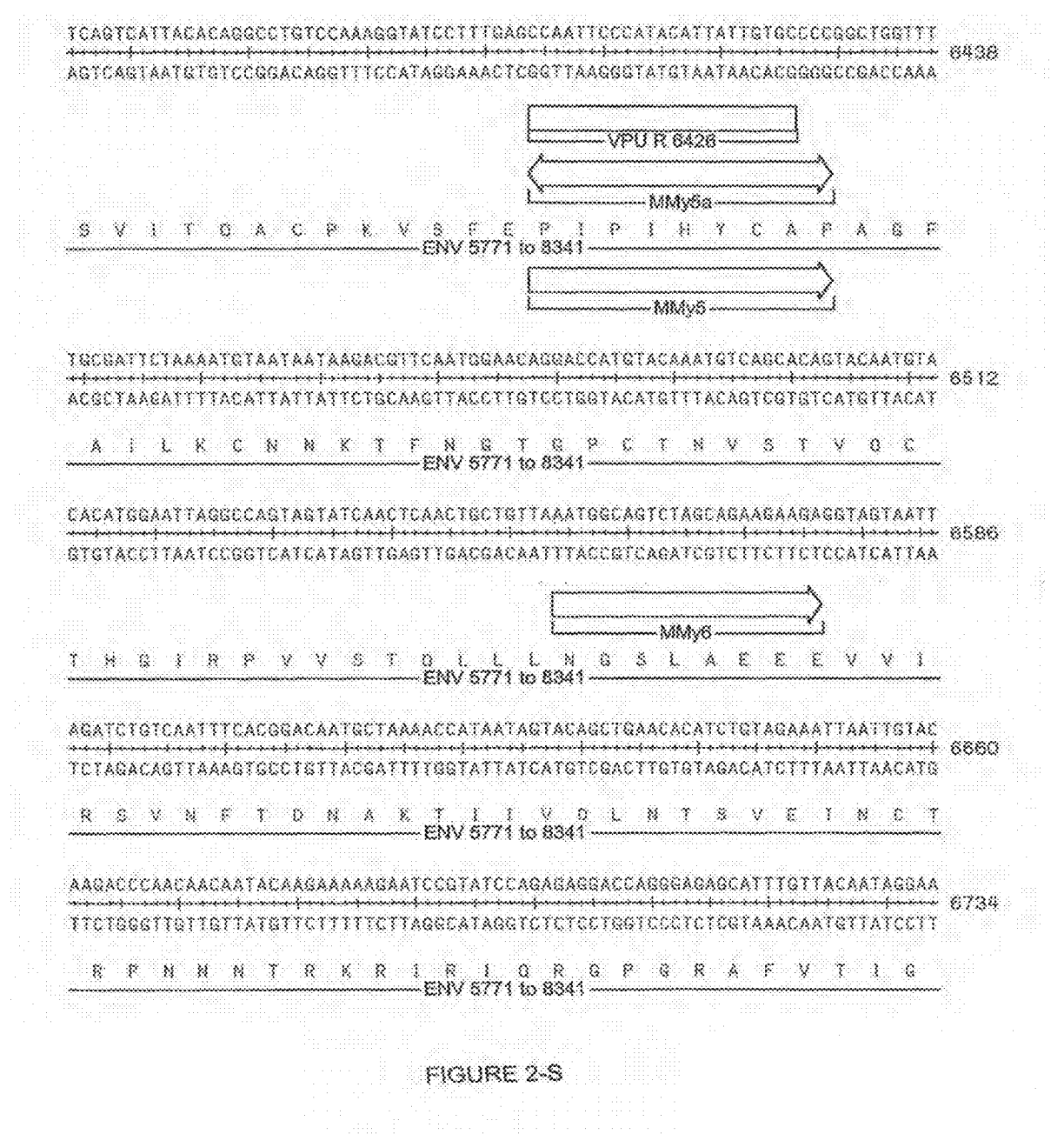
Figure 2:
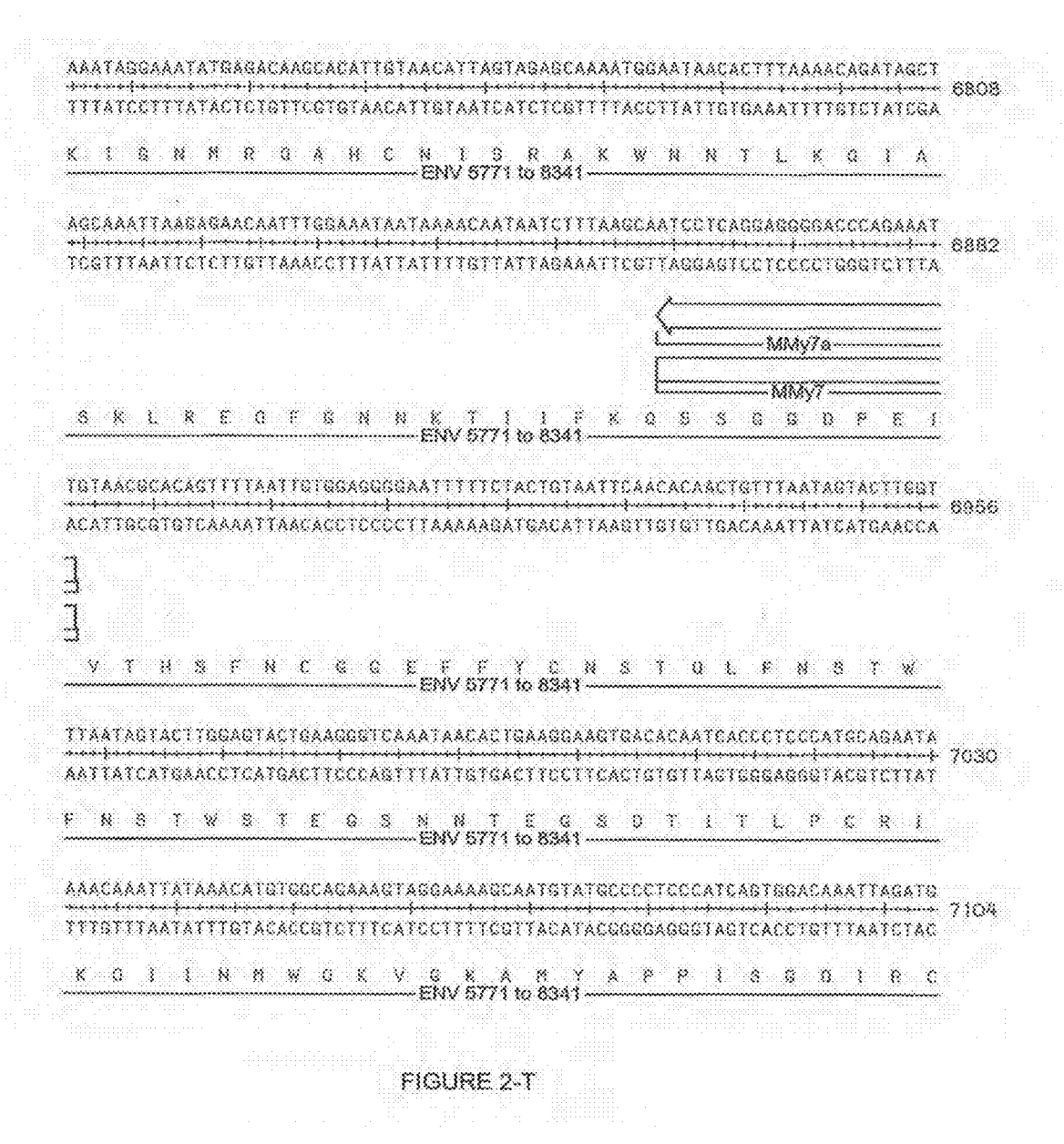
Figure 2:
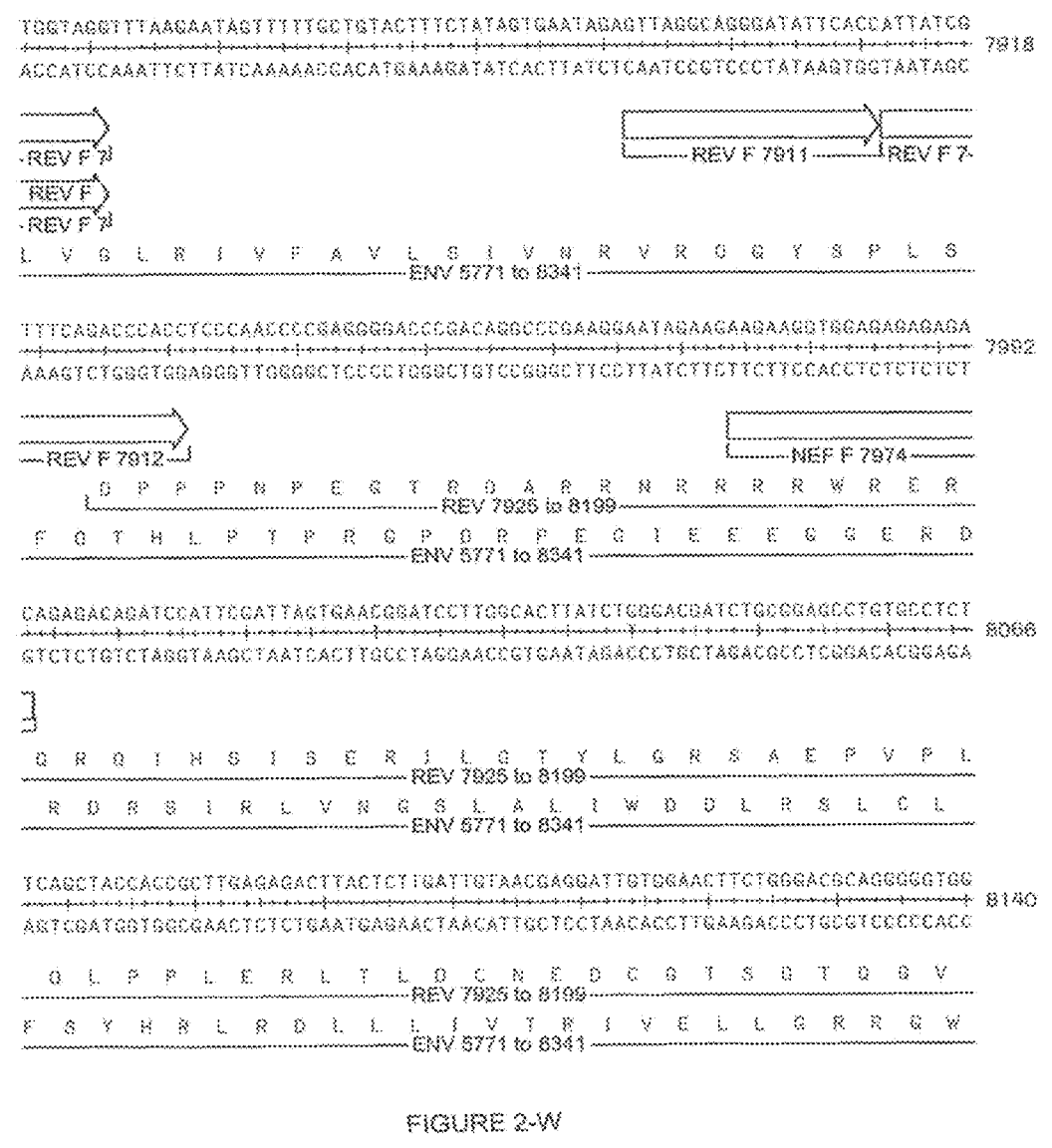
Figure 2:
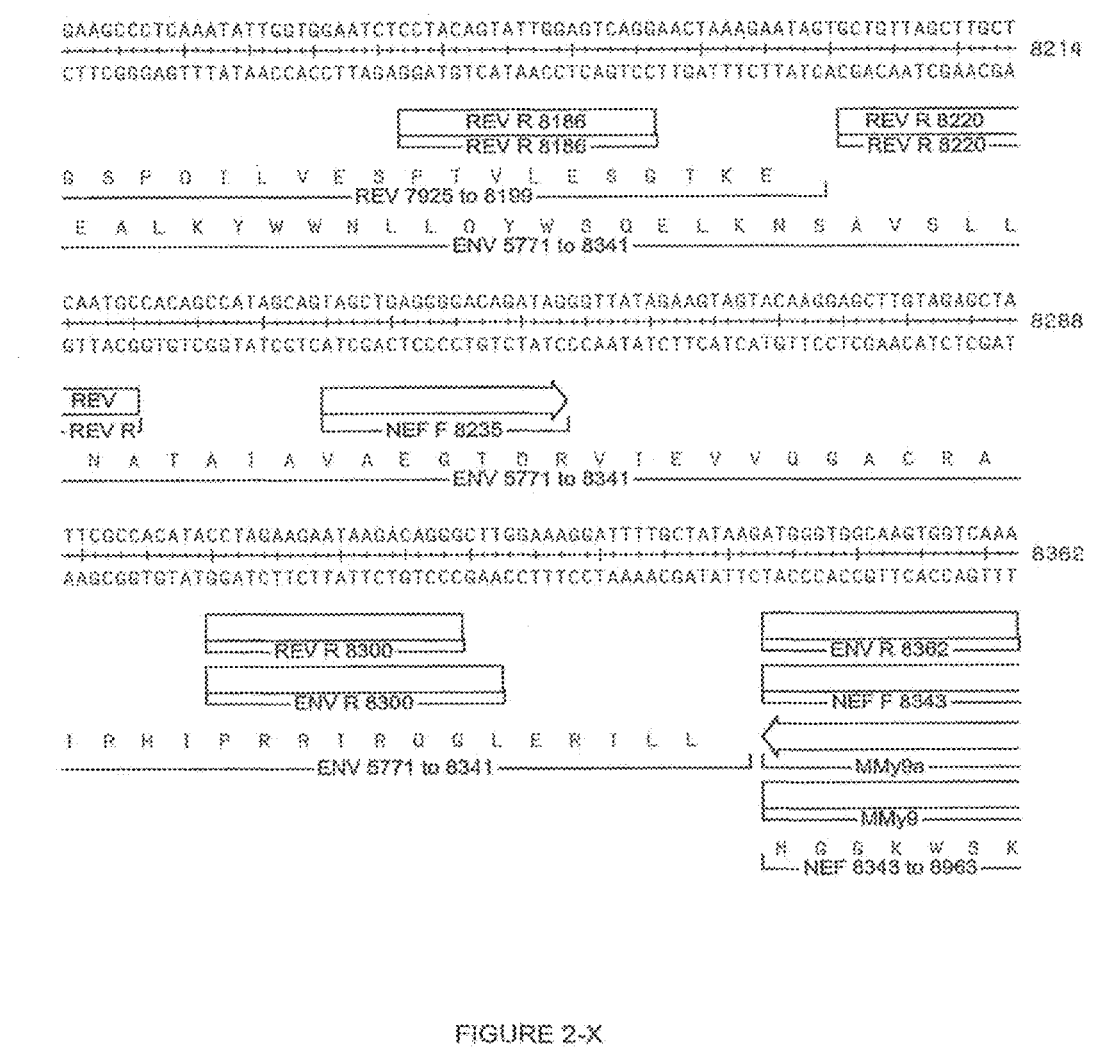
Figure 2:
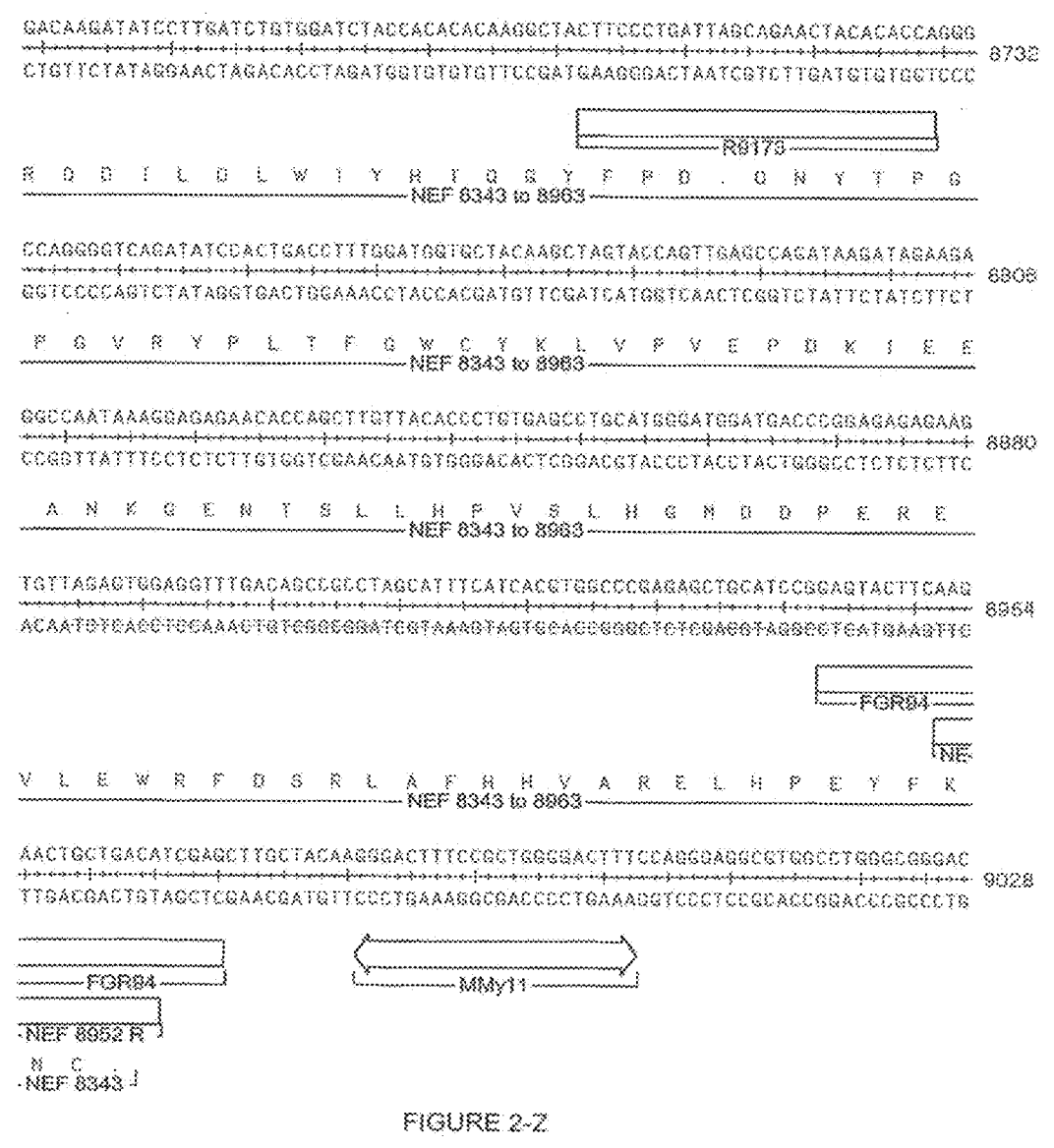

FIGS. 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, and 2AA show the sequence of the HIV genome having accession number NC_001802, open reading frames and protein sequences of gag, env, rev, vpr and nef, and position and orientation of primers. Sense strand (SEQ ID NO:388) and complementary strand (SEQ ID NO:389) are provided.

FIG. 4A: agarose gel resolution of PCR reactions performed at 60° C., 62° C. and 65° C. The primer groups in each lane are the same as described in FIG. 3. FIG. 4B: Inverse complement of primers 32, 33 and 34, reverse primer group number and Tm. FIG. 4C: Alignment of pBKBH10S, p93TH253.3, p90CF402.1 and p93BR029.4 HIV plasmid templates in region corresponding to primers 32-34. The underlined "A" corresponds to position 6 in the inverse complement of the primers shown in FIG. 4B.

FIG. 5. Amplification of GAG region from noninfectious HIV RNA template using multiplex RT-PCR. The primary PCR product was amplified using nested primers in a secondary PCR reaction. The primer groups used for amplification are indicated above each lane.

FIG. 6. Aligned sequences of multiple HIV quazispecies amplified pBKBH10S, p93TH253.3, p90CF402.1 and p93BR029.4 HIV plasmid templates. Four unique variants, A, B, C and D were amplified in the PCR reaction described in Example 4.

FIG. 7A shows an agarose gel resolution of an RT-PCR amplification of HIV VPR, REV, and NEF coding regions from non infectious HIV RNA. The primary PCR product was amplified in a secondary PCR reaction using nested primers. The primer groups used for amplification are indicated above the lanes. FIG. 7B shows an agarose gel resolution of amplified gag regions using individual primer pairs indicated by SEQ ID NOs above each lane. FIG. 7C shows an agarose gel resolution of amplified nef regions.

FIGS. 10A, 10B, and 10C show the sequence alignment of quasi-species detected in the GAG (FIG. 10A; SEQ ID NO:398), REV (FIG. 10B; SEQ ID NO:399) and VPR (FIG. 10C; SEQ ID NO:400) regions amplified from RNA isolated from the plasma of an infected HIV patient. Dots indicate sequence identity.

FIG. 18B shows amino acid substitutions in gag p17 amplified from HIV quasispecies isolated from Patient 1.

DETAILED DESCRIPTION

Figure 3:
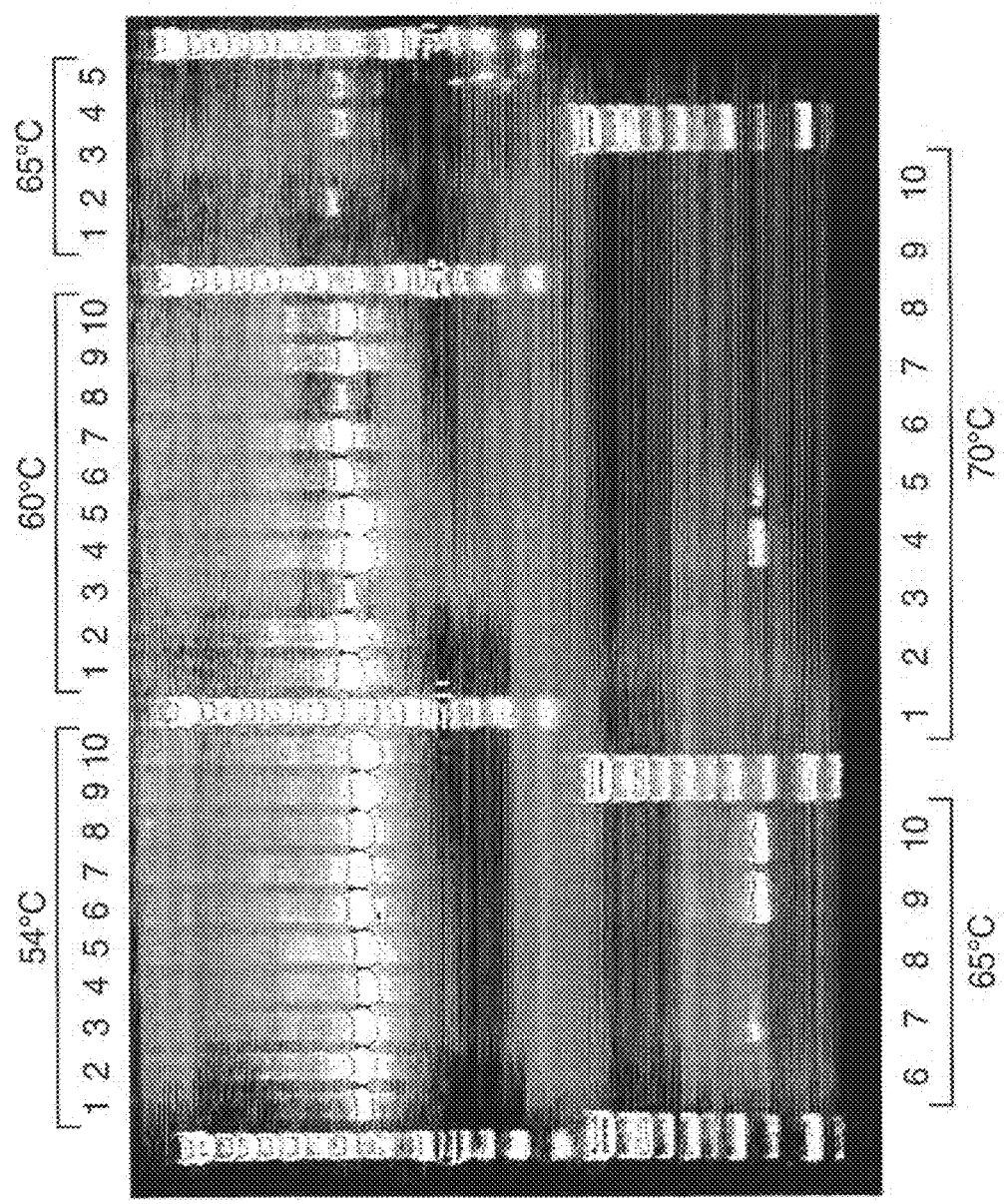
FIG. 3. Amplification of gag regions from pBKBH10S plasmid template using groups of designed primers. The following primer groups were used: Lane 1: FG1:RG1; Lane 2: FG1:RG2; Lane 3: FG1:RG3; Lane 4: FG1:RG4; Lane 5: FG1:RG5; Lane 6: FG2:RG1; Lane 7: FG2:RG2; Lane 8: FG2:RG3; Lane 9: FG2:RG4; Lane 10: FG2:RG5.

The invention relates to methods of amplifying nucleic acids from most or all of the variants of a pathogen present in a sample. The primer compositions, amplified product, and derivatives thereof, have use in identification and quantization of pathogen variants present in an individual, and as nucleic acid vaccines and cell based vaccines for treatment or prevention of pathogen infection.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains. However, in the event of an otherwise irreconcilable conflict, the present specification shall control.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. These methods are described in the following publications. See, e.g., Sambrook et al. MOLECULAR CLONING: A LABORATORY MANUAL, 2nd edition (1989); CURRENT PROTOCOLS IN MOLECULAR BIOLOGY (F. M. Ausubel et al. eds. (1987)); the series METHODS IN ENZYMOLOGY (Academic Press, Inc.); PCR: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1988)); USING ANTIBODIES, A LABORATORY MANUAL (Harlow and Lane eds. (1999)); and ANIMAL CELL CULTURE (R. I. Freshney ed. (1987)).

Definitions

As used herein, certain terms may have the following defined meanings As used in the specification and claims, the singular form "a," "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

"Amplification" refers to nucleic acid amplification procedures using primers and nucleic acid polymerase that generate multiple copies of a target nucleic acid sequence. Such amplification reactions are known to those of skill in the art, and include, but are not limited to, the polymerase chain reaction (PCR, see U.S. Pat. Nos. 4,682,195, 4,683,202 and 4,965,188), RT-PCR (see U.S. Pat. Nos. 5,322,770 and 5,310,652) the ligase chain reaction (LCR, see EP 0 320 308), NASBA or similar reactions such as TMA described in U.S. Pat. No. 5,399,491 and gap LCR (GLCR, see U.S. Pat. No. 5,427,202). If the nucleic acid target is RNA, RNA may first be copied into a complementary DNA strand using a reverse transcriptase (see U.S. Pat. Nos. 5,322,770 and 5,310,652). An "amplicon" refers to nucleic acids that were synthesized using amplification procedures.

The term "antigen" is well understood in the art and includes substances which are immunogenic, i.e., immunogen, and includes any of a variety of different formulations of immunogen or antigen.

The term "antigen presenting cells (APC)" refers to a class of cells capable of presenting one or more antigens in the form of antigen-MHC complex recognizable by specific effector T cells of the immune system. APCs include, but are not limited to, macrophages, B-cells and dendritic cells, such as immature dendritic cells, mature dendritic cells, plasmacytoid dendritic cells and Langerhans cells.

As used herein, the term "consisting essentially of" shall mean excluding other elements of any essential significance to the combination. Thus, a composition consisting essentially of the elements as defined herein would not exclude trace contaminants from the isolation and purification method, biological buffers and pharmaceutically acceptable carriers, such as phosphate buffered saline, preservatives, and the like. When used in the context of a primer and a reference oligonucleotide, the term "consisting essentially of" means the primer shall not have more than 10 additional nucleotide residues at the 5' end of a reference nucleotide, nor more than 10 additional nucleotide residues at the 3' end of a reference oligonucleotide. For example, a primer consisting essentially of an oligonucleotide of SEQ ID NO:X may have from 0 to 10 additional nucleotides at the 5' end of SEQ ID NO:X, and from 1 to 10 additional nucleotides at the 3' end of SEQ ID NO:X. Preferably, a primer consisting essentially of a reference oligonucleotide has no more than 5, 6, 7, 8 or 9 additional nucleotides at each of the 5' and 3' ends of the reference oligonucleotide. Most preferably, a primer consisting essentially of a reference oligonucleotide has no more than 1, 2, 3 or 4 additional nucleotides at each of the 5' and 3' ends of the reference oligonucleotide.

As used herein, a composition comprising a primer consisting essentially of an oligonucleotide selected from the group consisting of: SEQ ID NO:X, SEQ ID NO:Y and SEQ ID NO:Z, may contain one or any combination of the oligonucleotides of SEQ ID NO:X, SEQ ID NO:Y and SEQ ID NO:Z, with from 0 to 10 additional nucleotides on either 5' and/or 3' end of each oligonucleotide. The composition itself comprises such primers, and so may contain additional element as well.

"Corresponding polypeptides", as used herein, are polypeptides encoded by different alleles of a pathogen gene or fragment thereof. As a hypothetical example, strain X of a virus has four genes, a, b, c and d, which encode polypeptides A, B, C and D, respectively. Strain Y of the virus encodes different alleles of the same four genes, designated as a', b', c' and d', which encode polypeptides A', B', C' and D', respectively. Thus, A and A' are corresponding polypeptides, B and B' are corresponding polypeptides, etc. The term polypeptide refers to both a full-length protein, as well as a fragment thereof.

As used herein, "expression" refers to the process by which polynucleotides are transcribed into mRNA and translated into peptides, polypeptides, or proteins. If the polynucleotide is derived from genomic DNA of a eukaryote, expression may include splicing of the mRNA. Regulatory elements required for expression include promoter sequences to bind RNA polymerase and translation initiation sequences for ribosome binding. For example, a bacterial expression vector may include a promoter such as the lac promoter and for transcription initiation, a Shine-Dalgarno sequence for ribosome binding and the start codon AUG for initiation of translation (Sambrook et al. (1989) supra). Similarly, a eukaryotic expression vector may include a heterologous or homologous promoter for RNA polymerase II, a downstream polyadenylation signal, the start codon AUG, and a termination codon for detachment of the ribosome. Such vectors can be obtained commercially or assembled by the sequences described in methods known in the art, for example, the methods herein below for constructing vectors in general.

The term "genetically modified" means containing and/or expressing a foreign gene or nucleic acid sequence which in turn, modifies the genotype or phenotype of the cell or its progeny. In other words, it refers to any addition, deletion or disruption to a cell's endogenous nucleotides.

"HIV RNA" means genomic HIV RNA and HIV mRNA, as well as RNA produced by transcription of HIV amplicons prepared by the methods of the invention.

"HIV variants" or "variants of HIV" or "HIV strain" refers to any existing or new varieties of HIV, and includes, but is not limited to, HIV-1 and HIV-2, HIV-1 Groups M, N and O, all HIV subtypes (clades), including HIV-1 subtypes A1, A2, B, C, C, F1, F2, G, H, J and K, variants of clades, all quasi-species thereof and circulating recombinant forms. As the term "strain" is used herein, two HIV isolates that differ by a single nucleotide would be considered two different "strains" of HIV. The term groups is commonly used to refer to the HIV-1 lineages M, N and O. The term subtypes is used to refer to the major clades within a group. There is further sequence variability within subtypes. Circulating Recombinant Form (CRF) describes a recombinant lineage, that plays an important role in the HIV pandemic. The CRF members commonly share a similar or identical mosaic structure i.e., they descend from the same recombination event(s). Circulating recombinant forms of HIV include, but are not limited to:

| Name | Reference strain | Subtypes |
|---|---|---|
| CRF01_AE | CM240 | A, E |
| CRF02_AG | IbNG | A, G |
| CRF03_AB | Kal153 | A, B |
| CRF04_cpx | 94CY032 | A, G, H, K, U |
| CRF05_DF | VI1310 | D, F |
| CRF06_cpx | BFP90 | A, G, J, K |
| CRF07_BC | CN54 | B', C |
| CRF08_BC | GX-6F | B', C |
| CRF09_cpx | 96GH2911 | not yet published |
| CRF10_CD | TZBF061 | C, D |
| CRF11_cpx | GR17 | A, CRF01_AE, G, J |
| CRF12_BF | ARMA159 | B, F |
| CRF13_cpx | 96CM-1849 | A, CRF01_AE, G, J, U |
| CRF14_BG | X397 | B, G |
| CRF15_01B | 99TH.MU2079 | CRF01_AE, B |
| CRF16_A2D | KISII5009 | A2, D |

Descriptions and maps of the above CRFs and links to HIV sequences can be found at hiv.lanl.gov/content/hiv-db/CRFs/CRF.html.

Similarly, "pathogen variants" or "variants of a pathogen" or "pathogen strains" or "strains of a pathogen" refer to all variants of a pathogen, and includes variants, mutants and recombinants of a pathogen that may be present in a patient. As used herein, two variants of a pathogen that differ by a single nucleotide are considered two different strains of the pathogen.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to an organism in vivo.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated", "separated" or "diluted" polynucleotide, peptide, polypeptide, protein, antibody, or fragment(s) thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragment(s) thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as its glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature. An isolated mammalian cell, such as an antigen presenting cell is separated or removed from its normal location in the mammal.

"Loading of antigen presenting cells (APCs)" refers to the uptake by the APC of an antigen, epitope thereof, peptide, protein, or of a nucleic acid encoding the foregoing. APCs can be loaded in vitro or in situ.

"mRNA" means a translatable RNA. The mRNA will contain a ribosome binding site and start codon. Preferably, the mRNA will also contain a 5' cap, stop codon and polyA tail.

"Multiplex polymerase chain reaction (PCR)" is a variant of PCR in which two or more target sequences are simultaneously amplified in a single amplification reaction using multiple pairs of primers. As non-limiting examples, multiplex amplification includes amplification reactions of different genes, different alleles of a single gene and different fragments of a single gene. Methods for optimizing multiplex PCR conditions are disclosed in Abravaya et al. J Clinical Microbiol 2000 38:716-723; Kremer at al. J Clin Microbiol 2004 42:3017-3022; Garcia-Canas et al. Electrophoresis 2004 25:2219-2226; and Markoulatos et al. J Clin Lab Anal 2003 17:108-12, the contents of which are incorporated by reference.

"Pathogen", as used herein, refers to any disease causing organism or virus, and also to attenuated derivatives thereof.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. SCI., 18th Ed. (Mack Publ. Co., Easton (1990)).

An "effective amount" is an amount sufficient to effect beneficial or desired results. An effective amount can be administered in one or more administrations, applications or dosages.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In addition to a native nucleic acid molecule, a nucleic acid molecule of the present invention may also comprise modified nucleic acid molecules.

By "primer" is meant an oligonucleotide of 9 to 150 nucleotides in length that can be used in an amplification reaction. A primer consisting essentially of SEQ ID NO:X will not have more than additional nucleotides on the 5' end of SEQ ID NO:X, nor more than 10 additional nucleotides on the 3' end of SEQ ID NO:X. By "forward primer" is meant a primer that can be extended by a RNA polymerase or DNA polymerase into a nucleic acid that corresponds to the sequence of a sense strand or translated mRNA. By "reverse primer" is meant a primer that can be extended by a RNA polymerase or DNA polymerase into a nucleic acid that is complementary to the sense strand or translated mRNA. "Primer pair" refers to forward and reverse primers that can be used in amplification reactions to produce an amplicon.

The term "RNA" refers to polymeric forms of ribonucleotides of any length, wherein the ribonucleotides or ribonucleotide analogs are joined together by phosphodiester bonds. The term "RNA" includes, for example, single-stranded, double-stranded and triple helical molecules, primary transcripts, mRNA, tRNA, rRNA, in vitro transcripts, in vitro synthesized RNA, branched polyribonucleotides, isolated RNA of any sequence, and the like.

Calculations of homology or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). When aligning two primers or candidate primers of different lengths, the length of the shorter primer should be at least 60%, and even more preferably at least 70%, 80%, 90%, 100% of the length of the longer sequence. For the purpose of comparing the percent identity between promoter primers (e.g, T7 promoter primers) and poly dT primers, the noncoding regions are omitted from the comparison. By noncoding is meant regions outside of an open reading frame. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (1970) 48:444-453) algorithm which has been incorporated into the GAP program in the GCG software package (available on the world-wide web at gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available on the world-wide web at gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol., 215: 403-10. BLAST nucleotide searches can be performed with the NBLAST program, score=100, wordlength=12 to obtain nucleotide sequences homologous to pathogen nucleic acid molecules and primers of the invention. BLAST protein searches can be performed with the XBLAST program, score=50, wordlength=3 to obtain amino acid sequences homologous to EPLIN protein molecules of the invention. To obtain gapped alignments for comparison purposes, Gapped BLAST can be utilized as described in Altschul et al., (1997) Nucleic Acids Res., 25(17):3389-3402. When utilizing BLAST and Gapped BLAST programs, the default parameters of the respective programs (e.g., XBLAST and NBLAST) can be used. See ncbi.nlm.nih.gov.

Rapidly mutating pathogens, such as HIV, present a difficult target for vaccination. Previous vaccination strategies against pathogens have been directed against common strains or consensus sequences. However, these strategies have failed to provide protection or therapeutic effect against rapidly mutating or recombining pathogens, where the pathogen target can be highly variable. Development of an autologous pathogen vaccine, such an autologous HIV vaccine, particularly one that can simultaneously target all variants infecting the patient, represents a new paradigm in therapeutics. The ability to treat a pathogen infected individual with a vaccine that directs the immune response against specific pathogen antigens present in that individual should prove to be more efficacious than vaccines directed against consensus antigens, such as prior HIV vaccines, which have so far shown little or no ability to mediate viral clearance or suppress viral loads.

It is an object of the invention to provide a patient-specific vaccination strategy for treatment of pathogens using personalized cellular or nucleic acid vaccines that compensate for pathogen variability present within an individual. This strategy relies on the amplification of pathogen nucleic acid from an infected subject, and use of such amplified pathogen material, or derivatives thereof, in a patient-specific vaccine. The amplified pathogen nucleic acids, or derivatives thereof (e.g., in vitro transcription products, in vitro transcription/translation products, or vectors containing such amplified nucleic acids), can be used as an autologous or allogenic nucleic acid vaccine, or loaded into autologous antigen presenting cells (APCs), such as dendritic cells (DCs), which are then administered to the patient. In addition, the amplified products can be used to identify pathogen variants present in an infected individual and to monitor the effects of therapeutic intervention.

Polymerase Chain Reaction (PCR) and other nucleic acid amplification techniques offer a convenient and efficient way to obtain DNA encoding the specific pathogen antigens of interest. However, owing to the high mutation frequency of some pathogens, particularly of retroviral pathogens, such as HIV, prior to the instant invention it was a significant challenge to design PCR primers which could reliably amplify targeted regions of pathogen variants that may be present in an individual patient. For example, even though there is considerably less heterogeneity in HIV sequences that flank coding regions, absolutely conserved regions do not exist to enable the design of single universal primer pair for each gene of interest. Therefore, the methods of the invention employ pools of forward and reverse antigen-specific primers for nucleic acid amplification of pathogen genes of interest, or portions thereof, such that most or all strains of a pathogen present in an infected individual will react with at least one forward and one reverse primer to allow amplification of diverse target sequences.

The invention provides methods for the strain-independent nucleic acid amplification of pathogen nucleic acids using multiple primer pairs and amplification conditions that compensate for variability among pathogen nucleic acids at the primer annealing sites. Using these methods, it is possible to amplify all or targeted portions from essentially all of the variants of a pathogen present in an infected individual. Amplification of all or most of the pathogen variants present in an individual produces amplicons that can be used to identify and quantitate the variants present in an infected individual. Such amplicons or derivatives thereof can be used in cell-based vaccines or nucleic acid vaccines to treat pathogen infection and/or to identify the pathogen variants present in an infected individual. These amplified products (amplicons) can be used directly, or can be converted to translatable RNAs, for loading into APCs, preferably autologous APCs, either in situ or in vitro. The amplicons and in vitro transcripts prepared from the transcript can be used as nucleic acid vaccines. In vitro translated polypeptides prepared from such in vitro transcripts can be used as polypeptide vaccines and for loading APCs.

An important aspect to strain-independent amplification of pathogen nucleic acids is the selection of primers and amplification conditions. The applicants have discovered methods for selecting primer pairs capable of amplifying divergent regions of pathogen nucleic acids. In order to amplify selected target antigens from a variable pathogen, such as HIV, in a strain-independent manner, pools of PCR primers can be strategically selected to ensure reliable amplification of intended targets and simultaneous co-amplification of existing variants.

The number and choice of which autologous antigens to target for amplification can be predicated on two main factors: (1) substantial regions of the target gene should be amenable to nucleic acid amplification using pools of primers with manageable complexities, and (2) preferably, expression of the target antigen does not adversely affect the biology of the target APCs, such as DCs. By amplifying specific regions of pathogen nucleic acids, rather than total pathogen nucleic acids, it is possible to select regions encoding the most immunogenic fragments, and to avoid regions that may have negative effects on the immune system. For example, portions of HIV nef gene involved in the inhibition of dendritic cells can be avoided by choosing primers that do not amplify the region of nef responsible for inhibition.

Multiple primers which correspond to known variants of a pathogen can be designed for hybridization at a target locus. However, in order to manage primer complexity, it is useful to first determine the conserved nucleotide sequences between known pathogen variants. Selection of primers that hybridize to conserved regions of pathogen nucleic acid reduces the number of primers needed to ensure amplification of all or most variants of pathogen present in an individual. Another important consideration in primer selection is that mismatch in the 3' half of a primer sequence to known variant annealing sites should be avoided or minimized, however a 3' terminal mismatched T will typically not have an adverse effect on amplification. Remaining 3' mismatches can be compensated for by lowering the annealing temperature. Mismatch at the 5' half of primer sequence is tolerated and can be compensated for by lowering the annealing temperature. Amplification reaction conditions can be optimized to allow for amplification of all pathogen variants present in an infected individual while avoiding non-specific amplification. Accordingly, amplification using the primers and/or methods of the invention allows for identification and quantitation of all variants of a pathogen present in an individual. In contrast, prior art methods typically underestimated the amount of pathogen present, as only a single pathogen variants was identified.

The methods described above and in the examples below for the selection of primer pairs capable of amplifying multiple variants of HIV are applicable to selecting primer pairs capable of amplifying multiple variants of any pathogen. The primer selection process described herein comprises the steps of choosing a first region for forward primer annealing and a second region for reverse primer annealing, wherein said first and second regions flank an open reading frame and/or an epitope of a pathogen; and choosing candidate forward and reverse primers for said first and second regions, wherein at least one of said primer is designed to compensate for sequence variability between multiple variants of a pathogen.

In one embodiment of the invention, primers are designed by the above method to amplify nucleic acids from multiple variants of a pathogen present in an infected mammal. The amplified nucleic acids can then be used in an autologous nucleic acid vaccine to treat the same pathogen infected mammal. Alternatively, the amplified nucleic acid can be used as an allogenic nucleic acid vaccine to treat a different mammal infected by the pathogen, or as a prophylactic vaccine to prevent infection. For prophylactic uses, nucleic acid vaccines or nucleic acid loaded APCs can be prepared using amplicons made from pathogen nucleic acids isolated or derived from one or more individuals.

Thus, in one embodiment, the invention provides a method of producing pathogen amplicons representing one or more polypeptides from at least two strains of a pathogen, comprising: (a) combining polynucleotides from a first and second strain of a pathogen to form a mixture; and (b) amplifying said polynucleotides to produce a first amplicon and a second amplicon; wherein said first amplicon encodes a polypeptide from said first strain and said second amplicon encodes the corresponding polypeptide from said second strain. For example, the polynucleotides from the first and second strain can be obtained from biological samples from one or more pathogen infected individuals, from one or more pathogen cultures, from cloned pathogens or cloned pathogen nucleic acids. The amplicons and RNA produced by in vitro transcription of such amplicons are useful as nucleic acid vaccines and for loading antigen presenting cells.

In a further embodiment, the invention provides a nucleic acid vaccine, comprising a plurality of nucleic acids encoding one or more antigens from multiple variants of a pathogen present in a mammal and a pharmaceutically acceptable carrier, wherein said nucleic acids are derived by nucleic acid amplification of pathogen polynucleotides using a plurality of primer pairs that can compensate for variability between said variants of pathogen.

In another embodiment, the invention provides a method of treating infection, comprising administering the above nucleic acid vaccine to said pathogen-infected mammal.

Similarly, the invention provides a method of preparing a nucleic acid vaccine, comprising: combining a plurality of nucleic acids encoding one or more antigens from multiple variants of a pathogen present in a mammal with a pharmaceutically acceptable carrier, wherein said nucleic acids are derived by nucleic acid amplification of pathogen polynucleotides using a plurality of primer pairs that can compensate for variability between said variants of pathogen.

In yet another embodiment, the invention provides an isolated antigen presenting cell (APC) comprising nuclei acids encoding one or more polypeptides from multiple strains of a pathogen present in an individual subject, wherein one or more pathogen polypeptides are not represented from any strain. As a hypothetical example, assume a virus has a total of three genes, a, b, and c, which encode polypeptides A, B and C. This virus is rapidly mutating and two strains of the virus are isolated from an infected patient, strains X and Y. Strain X has alleles a', b', and c', which encode polypeptides A', B' and C'. Strain Y has different alleles of the same genes, which are designated a*, b* and c*, and encode variant polypeptides A*, B* and C*. As specified above, the above antigen present cell, comprises nucleic acids encoding one or more pathogen polypeptides from multiple strains of a pathogen (e.g, strains X and Y of the virus), but at least one pathogen polypeptide is not represented from any strain. This means that the APC could contain polynucleotides representing each allele of one or two of the three genes. For example, the APC could contain polynucleotides encoding A', A*, B' and B*, but not C' or C*. Here the pathogen polypeptide not represented from any strain is polypeptide C, where neither C' nor C* is represented. The term polypeptide, as used herein, refers to both full-length proteins and fragments thereof. Thus, The APC could contain nucleic acids encoding A', A*, B', B*, and corresponding fragments of C' and C*. but not all of C' and C*. The advantage of this approach over using nucleic acids encoding all of the pathogen polypeptides is that it avoids reconstituting infectious pathogen. An additional advantage is that nucleic acids encoding polypeptides that may be harmful to a patient or to an antigen presenting cell can be specifically avoided.

The nucleic acid vaccines of the invention are suitable for administration to a mammal. In preferred embodiments, the mammal is a primate, and most preferably a human. Most preferably the nucleic acid vaccines of the invention are administered to the specific mammal from which the pathogen polynucleotides were derived. For example, in a preferred embodiment, the pathogen polynucleotides are isolated from an infected patient, and the nucleic acid vaccine is administered to that patient.

The vaccines of the invention comprise a plurality of nucleic acids encoding one or more antigens from multiple variants of a pathogen. The nucleic acid can be single or double stranded RNA or DNA. In a preferred embodiment, the nucleic acid is a RNA, most preferably the nucleic acid is an mRNA. The nucleic acid vaccines of the invention should be capable of being expressed in one or more cell type in the mammal to which they are administered. By expressed is meant that the nucleic acid can be translated directly (e.g., a translatable RNA), or can be transcribed to produce a translatable mRNA (e.g., a DNA comprising a promoter and a start codon followed by an open reading frame) and/or can be transcribed once integrated into the genome of the mammalian cell to which it is introduced (e.g., linear DNA, DNA vectors, RNA viral vectors and DNA viral vectors. A translatable mRNA may be produced by transcription in vivo (either as a primary or processed transcript), or by in vitro transcription. In preferred embodiments, the nucleic acid used in the vaccines of the invention is a RNA, most preferably, an mRNA.

The term pathogen refers to any virus or organism which is involved in the etiology of a disease and also to attenuated derivatives thereof. Such pathogens include, but are not limited to, bacterial, protozoan, fungal and viral pathogens such as *Helicobacter*, such as *Helicobacter pylori, Salmonella, Shigella, Enterobacter, Campylobacter*, various mycobacteria, such as *Mycobacterium leprae, Bacillus anthracis, Yersinia pestis, Francisella tularensis, Brucella* species, *Leptospira interrogans, Staphylococcus*, such as *S. aureus, Streptococcus, Clostridum, Candida albicans, Plasmodium, Leishmania, Trypanosoma*, human immunodeficiency virus (HIV), HCV, HPV, CMV, HTLV, herpes virus (e.g., herpes simplex virus type 1, herpes simplex virus type 2, coronavirus, varicella-zoster virus, and Epstein-Barr virus), papilloma virus, influenza virus, hepatitis B virus, poliomyelitis virus, measles virus, mumps virus, and rubella virus. The methods of the invention are particularly useful for amplification of nucleic acids from highly variable pathogens, such as viral pathogens, preferably retroviral pathogens, and most preferably HIV and HCV.

Variants or strains of a pathogen refers to any derivatives of a pathogen. Such derivatives may occur (or may have occurred) by mutation or recombination or recombinant manipulation of a pathogen. For example, variants of HIV encompass known and unidentified HIV variants, and include, but are not limited to, HIV-1 Groups M, N and O, all HIV subtypes or clades, including HIV-1 clades A1, A2, B, C, C, F1, F2, G, H, J and K, variants of clades, all variants of HIV-2, and all recombinants and quasi-species thereof.

"Multiple variants of a pathogen" or "multiple strains of a pathogen" is intended to include variants of a pathogen that are present in an infected individual. Multiple variants of a pathogen may have been introduced into an individual, either concomitantly or separately. Alternatively, multiple pathogen variants can arise within an individual through mutation and/or recombination. For example, in a preferred embodiment, the pathogen is a retrovirus, preferably HIV. Multiple variants of a pathogen (HIV) present in one infected individual could include any HIV that may be present in that individual. In such cases, the multiple variants of HIV could include HIV-1, including any or all of the HIV-1 groups M, N and O, and subtypes, clades and quasi-variants thereof, as well HIV-2 and variants thereof, and classes of HIV not yet identified.

By antigen is meant a polypeptide comprising one or more immunogenic epitopes. For example, the amplified nucleic acids of the invention can encode one or more open reading frames, or portions of one or more open reading frames. For example, in a preferred embodiment, the pathogen is HIV and the amplified nucleic acids encode one or more open reading frames, or portions thereof, of one or more HIV polypeptides from each or at least most variants of HIV present in the infected individual. Preferred HIV polypeptides are gag, rev, nef, vpr and env and fragments or epitopes thereof. Preferred fragments of vpr (using NC_001802 as a reference sequence) are encoded by nucleotides 5105-5320 (encoding vpr amino acid residues 1-72); 5138-5320 (encoding vpr amino acid residues 12-72); 5105-5165 (encoding vpr amino acid residues 1-20) and 5138-5165 (encoding vpr amino acid residues 12-20); and corresponding fragments of other HIV variants. Additional preferred vpr fragments are residues 25-40, 29-37, 30-38, 31-39, 31-50, 34-42, 41-49, 52-62, 53-63, 55-70, 59-67, and 62-70. Additional fragments and epitopes can be found at the HIV Molecular Immunology Database available on the internet http site: (//hiv.lanl.gov/content/immunology/), the contents of which are incorporated by reference.

Pathogen polynucleotides are the template or are the source of the template for amplification of the nucleic acids encoding one or more pathogen antigens or epitopes. The pathogen polynucleotide may be either DNA or RNA. As non-limiting examples, the pathogen polynucleotide could be a DNA, such as a pathogen genome, a DNA vector or fragment, or a pathogen DNA integrated into genome of the pathogen's host. When the pathogen polynucleotide is a DNA, it can be used directly as a template for amplification according to the methods of the invention.

The pathogen polynucleotide could also be a RNA in the form of a pathogen genome (e.g., retroviral genomes) or pathogen mRNA, which may be spliced or unspliced. For example, in the case of HIV, the nucleic acid could be DNA corresponding to the integrated viral DNA in the host genome, or corresponding to HIV cDNA present in a cell prior to viral integration into the host genome. HIV RNA could be in the form of a viral RNA genome, isolated from viral particles or from host cells during viral replication, and could also be in the form of HIV mRNA, spliced or unspliced. In a preferred embodiment, the pathogen RNA is HIV genomic RNA isolated from HIV virions. In cases where the pathogen polynucleotide is a RNA, it can be reversed transcribed to produce a cDNA, which can then serve as a template for nucleic acid amplification.

Preferably, the pathogen polynucleotide is from, or is derived from, multiple pathogen variants present in an infected individual. In this context, by "derived from" is meant that the nucleic acid is at least partially purified from the pathogen or cell(s) containing pathogen nucleic acid, or that the nucleic acid is amplified from pathogen nucleic acid. By deriving the nucleic acid from multiple pathogen variants present in an individual, the resulting vaccine can elicit an immune response to potentially all of the variants of pathogen present in an individual.

The primary amplicon produced by nucleic acid amplification using primers selected according to the methods of the invention will comprise a DNA encoding a pathogen antigen or epitope thereof. The primary amplicons can be used in a nucleic acid vaccine without further modifications. Alternatively, the primary amplicon can be inserted into an expression cassette or expression vector for use in a nucleic acid vaccine, viral vaccine or for loading into APCs. In a preferred embodiment, the primary DNA amplicon is modified to function as a template for in vitro transcription.

In order to transcribe a template DNA sequence (e.g., a PCR product), the template should contain a RNA polymerase binding site or promoter. Furthermore, for efficient translation in eukaryotic cells, the transcribed RNA preferably contains a 5' Cap, a Kozak sequence including an ATG translational initiation codon, and a polyadenylated sequence at it 3' end. Preferably, the transcribed RNA will also contain a translational stop codon (UAA, UAG or UGA). Some of these transcriptional and translational signals, such as the promoter, Kozak sequence, start and stop codons may be present in the template of the of the target pathogen nucleic acid, and could be amplified during PCR or other amplification reaction. Alternatively, these sequences can be included in forward and reverse primers used at any stage of amplification.

If the intended vaccine is an mRNA vaccine for in situ administration, or for loading into APCs, then the promoter sequence contained in the 5' nested primer should be suitable for in vitro transcription. Promoters suitable for in vitro transcription and methods of in vitro transcription are known to those skilled in the art. As a non-limiting example, preferred promoters are those corresponding to commercially available RNA polymerases, such as the T7 promoter and the SP6 promoter. Other useful promoters are known to those skilled in the art. If the intended vaccine contains a nucleic acid intended for transcription with in a target cell, the promoter contained in the 5' primer sequence is should be one that is active in the intended target cell. Also, in cases where the vaccine contains a nucleic acid intended for transcription within the target cell, the promoter and translational initiation signals can be amplified from the template, incorporated into a forward primer, or by inserting the amplicon into an expression cassette. Preferably, the promoter allows for efficient transcription using commercially available in vitro transcription kits. Methods of in vitro transcription and translation are known to those skilled in the art (see, for example, U.S. 2003/0194759). In typical in vitro transcription reactions, a DNA template is transcribed using a bacteriophage RNA polymerase in the presence of all four ribonucleoside triphosphates and a cap dinucleotide such as m$^7$G(5')ppp(5')G or a cap analog, such as ARCA.

The promoter and translational initiation signals can be included in a primer used during primary amplification or in a nested primer used in a subsequent round. The annealing target for the primers used in an optional secondary round of amplification can be the same as that used in the primary amplification reaction, or it can be a site internal ("nested") to the primary amplicon. In a preferred embodiment, the forward primer used in the primary or secondary (preferably secondary) round of amplification will comprise a 5' non-hybridizing region (an "overhang") encoding a promoter (e.g., T7 promoter), and a 3' region complimentary to the antisense strand of the primary amplicon. Typically, the forward primer will also contain a Kozak sequence, preferably an optimized Kozak sequence, e.g., bases 5' CCAC-CATGG (SEQ ID NO:59), wherein the underlined ATG is the translational initiation codon. The Kozak sequence including ATG start codon may either be in the 5' overhang region of the forward primer, or in the 3' annealing region of the primer, depending upon whether such sequences are present in the primary amplicon. In addition, if the primary amplicon contains a less than optimal Kozak sequence, it can be optimized by using a forward primer with an optimal, although not completely complementary, Kozak sequence. Preferably, the 3' portion of forward primer will be essentially complimentary to the sequence immediately downstream of initiator ATG codon or the most 5' coding sequence amplified during primary amplification. The reverse primer preferably contains a 5' polyT overhang at its 5' end which will serve as a template for polyadenylation during in vitro transcription. The 3' half of the reverse primer will be complimentary to the sense sequence isolated in the primary amplification reaction. If an appropriate translational stop codon is not present in the primary amplicon, it can be included in the 5' overhang portion of the reverse primer. The secondary amplicon obtained by amplification using primers such as those described above can then serve as a template in an in vitro transcription reaction in the presence of m$^7$G cap or an analogue thereof, such as ARCA (see U.S. 2003/0194759).

Thus, in another embodiment, the invention provides a method of treating a pathogen infected mammal, comprising:
a. amplifying nucleic acids of multiple variants of a pathogen present in a mammal using a plurality of primer pairs that can amplify multiple variants of said pathogen to produce amplified pathogen DNA;
b. optionally transcribing said amplified pathogen DNA to produce pathogen RNAs; and
c. administering said pathogen DNA or said pathogen RNA to said mammal.

Methods for formulating and delivering nucleic acid vaccines to a subject are known to those of skill in the art. See, for example, Scheel et al. Eur J Immunol (2204) 34:537-547; Hoerr et al. (2000) Eur J Immunol 30:1-7; Liu et al (2002) Vaccine 20:42-48; Riedl et al. (2002) J Immunol 168:4951; Riedel et al. (2004) J Mol Med 82:144; U.S. 5,783.567; U.S. Pat. No. 6,603,998; EP0880360; EP1083232; the contents of which are incorporated by reference. Routes of administration include, but are not limited to, topical delivery, electroporation of the skin, as well as cutaneous, subcutaneous, intradermal, mucosal and intramuscular administration, and the like.

As an alternative to using the primary or secondary amplicon or an in vitro transcribed RNA as a nucleic acid vaccine, such nucleic acids can be loaded into antigen presenting cells in vitro. The loaded antigen presenting cells are then suitable for use as a vaccine.

Thus, in another embodiment, the invention provides a composition comprising: an antigen presenting cell transfected with a plurality of nucleic acids encoding one or more antigens from multiple variants of a pathogen present in a mammal, wherein said nucleic acids are derived from nucleic acid amplification of pathogen polynucleotides using a plurality of primer pairs that can compensate for variability between said variants of pathogen, and said antigen presenting cell and said pathogen nucleic acids are from or derived from said mammal.

Antigen presenting cells (APC) include, but are not limited to, macrophages, B-cells and dendritic cells, such as immature dendritic cells, mature dendritic cells and Langerhans cells. Professional antigen-presenting cells, in particular dendritic cells (DCs), provide a powerful vehicle for stimulation of cell-mediated immunity through effects on both CD4$^+$ and CD8$^+$ T-cells (Banchereau 1998, Banchereau 2000). Intrinsic to their function, they efficiently process antigens for presentation on both MHC class I and II products to CD4$^+$ and CD8$^+$ T cells. Dendritic cells, isolated from peripheral blood or bone marrow through surface antigen enrichment techniques or harvested from cultures of PBMCs, can be loaded with specific candidate antigens and are then capable of presenting the relevant antigen(s) to naïve or resting T-cells (Heiser 2000, Mitchell 2000). Preferably, the antigen presenting cells are autologous to the individual to be vaccinated, and the pathogen nucleic acid is isolated or derived from the patient as well.

The antigen presenting cells are either made by and in the mammalian subject, or are derived from cells isolated from the mammalian subject. In a preferred embodiment, the antigen presenting cell is a dendritic cell. The term "dendritic cells (DC)" refers to a diverse population of morphologically similar cell types found in a variety of lymphoid and non-lymphoid tissues (Steinman (1991) Ann. Rev. Immunol. 9:271-296) or derived from dendritic cell precursors in vitro. Dendritic cells are the most potent of the APCs, and provide the signals necessary for T cell activation and proliferation. Dendritic cells are derived from bone marrow progenitor cells, circulate in small numbers in the peripheral blood and appear either as immature Langerhans' cells or terminally differentiated mature cells. In preferred embodiments, dendritic cells are differentiated from monocytes. Methods for the isolation of antigen presenting cells (APCs), and for producing dendritic cell precursors and mature dendritic cells are known to those skilled. See, for example, Berger et al. J Immunol Methods 2002 268:131-40, U.S. Patent Applications 20030199673, 20020164346 and 60/522,512, and WO 93/20185 the contents of which are incorporated by reference. In a preferred embodiment, dendritic cells are prepared from CD14+ peripheral blood monocytic cells (PBMCs) by methods described in Romani et al. (J Exp Med 1994 180:83-93) or Sallusto et al. (J Exp Med 1994 179:1109-1118), the contents of which are incorporated by reference. Alternatively, dendritic cells can be prepared from CD34+ cells by the method of Caux et al. (J Exp Med 1996 184:695-706).

Methods for loading antigen presenting cells are known to those of skill in the art, and include, but are not limited to, electroporation, passive uptake, lipofection, cationic reagents, viral transduction, $CaPO_4$ and the like. See, for example, PCT/US05/22705 and U.S. Ser. No. 60/583,579; U.S. Pub. No. 2003/0143743; U.S. Pub. No. 20050008622; U.S. Pub. No. 20040235175; and U.S. Pub. No. 20040214333; the contents of which are incorporated by reference. In preferred embodiments, the antigen presenting cells are loaded with both CD40L mRNA and RNA encoding multiple strains of pathogen polypeptides. The human CD40L cDNA, CD40L protein and a preferred CD40L mRNA useful for transfection of antigen presenting cells are shown is SEQ ID NO:407 and 408, respectively. In preferred embodiments an mRNA corresponding to nucleotides 38-877 of SEQ ID NO:410. Preferably, the mRNA is 5' capped and polyadenylated. In preferred embodiments, the cap is ARCA. Preferred polyA tail lengths are in the range of 50-1000 nucleotides, more preferably 64-900 nucleotides, and most preferably 101-600 nucleotides. In a further embodiment, antigen presenting cells are loaded with polypeptides made by in vitro translation of the RNAs encoding pathogen polypeptides from multiple strains of a pathogen. The pathogen polypeptides may be loaded into antigen presenting cells with CD40L mRNA. Dendritic cells can be loaded in vitro when mature or immature. Loaded immature dendritic cells can be matured in vitro prior to vaccination or in vivo (with or without an exogenous maturation stimulus) following vaccination. Alternatively, nucleic acids can be delivered to antigen presenting cells in situ. See, for example Liu et al. (Vaccine 2002 20:42-48), Lisziewics et al. (Vaccine 2003 21:620-623) and O'Hagen (Curr Drug Targets Infect Disord 2001 1:273-286), the contents of which are incorporated by reference.

Preferably, the antigen presenting cell in the above composition is a dendritic cell. The loaded dendritic cell can then be used as a vaccine to treat the pathogen infection in a patient. Preferably, the pathogen and antigen presenting cell (e.g., dendritic cell) are autologous to the treated patient.

In another embodiment, the invention provides a method of preparing an autologous vaccine, comprising: transfecting antigen presenting cells obtained or derived from a pathogen-infected mammal with nucleic acids encoding one or more antigens from multiple variants of a pathogen present in said mammal, wherein said nucleic acids are derived by nucleic acid amplification of pathogen polynucleotides using a plurality of primer pairs designed to compensate for variability between said variants of pathogen.

The invention further provides a vaccine comprising the loaded antigen presenting cells described above. In such vaccines, the loaded antigen presenting cells will be in a buffer suitable for therapeutic administration to a patient. The vaccine may further comprise an adjuvant for factors for the stimulation of antigen presenting cells or T cells. Methods of formulating pharmaceutical compositions are known to those skilled in the art. See, for example, the latest version of Remington's Pharmaceutical Science.

The optimal immunization interval for dendritic cell vaccines can be determined by one of skill in the art. In a preferred embodiment, patients will be vaccinated 5 times with between $1 \times 10^6$ to $1 \times 10^7$ viable RNA-loaded DCs per dose. The dose level selected for vaccination is expected to be safe and well-tolerated.

Methods of isolating, preparing, transfecting, formulating and administering antigen presenting cells to patients is known in the art. See, for example, Fay et al. Blood 2000 96:3487; Fong et al. J Immunol 200 1b 166:4254-4259; Ribas et al. Proc Am Soc Clin Onc 2001 20:1069; Schuler-Thurner et al. J Exp Med. 2002 195:1279-88. Erratum in: J Exp Med. 2003197:395; and Stift et al. J Clin Oncol 2003 21: 135-142, the contents of which are incorporated by reference.

Routes of APC administration employed clinically include, but are not limited to, intravenous (IV), subcutaneous (SC), intradermal (ID), and intralymphatic. Objective clinical responses have been reported following IV, SC, and ID dosing of other APC vaccines. Currently, there is a developing preference for ID administration since the dermis is a normal residence for dendritic cells from which they are known to migrate to draining lymph nodes. In murine models, SC-injected dendritic cells are later found in T-cell areas of draining lymph nodes and trigger protective antitumor immunity that is superior to that following IV immunization. There is murine evidence that dendritic cell injection directly into a lymph node is superior to other routes of delivery in generating protective antitumor immunity or cytotoxic T-lymphocytes (CTLs) (Lambert et al. Cancer Res 2001 61:641-646, the contents of which are incorporated by reference). This suggests that an entire dendritic cell dose should be delivered so that it impacts on a single draining lymph node or basin (rather than dividing the dose among multiple sites to engage as many nodes as possible).

To assess the immunogenicity of the vaccine, immune responses in vaccinated individuals can be monitored by following the maturation profiles of CD4+ and CD8+ T cells. For example, restoration of HIV-specific effector cell function can be determined by the presence of cells expressing the phenotype of effector T-cells, CD45 RA$^+$ CCR7$^-$ and secreting elevated levels of IFN-γ and granzyme B. Restoration of HIV-specific proliferative responses can be determined by the capacity of cells to produce IL-2 and to become CFSE low following stimulation with dendritic cells transfected with HIV-RNAs Restoration HIV-specific memory T cell compartment.

Maturation of specific T cells induced by the vaccine can be measured using surface and intracellular markers using flow cytometry assay. CD8+ T cells will be monitored by staining for surface markers including αβTCR, CD45RA, CCR7 and CD107 or intracellular molecules such as granzyme B or γ-IFN. CD3, CD4, CCR7 and IL-2 can be used to monitor CD4+ T cells. Such assays can be used to monitor immune response following incubation with peptides encompassing the autologous HIV sequences from the patient. Comparison of the cellular immune responses at baseline and monthly prior to each new vaccination allows determination the impact of the vaccine on the breadth of the cellular immune response. The breadth of the immune response can also be measured using the CFSE proliferation assay.

While hundreds of CTL epitopes encoded by HIV antigens have been described, consideration of the above factors for an autologous HIV vaccine led the applicants to the selection of gag (p55), rev, nef and vpr as the primary targets for the vaccine. However, other HIV antigens could also be targeted using the methods of the invention. The method described above was used to select primers capable of amplifying multiple strains of HIV from an HIV infected individual. In particular, the applicants have discovered primers capable of amplifying the gag, nef, rev and vpr genes from multiple HIV strains. The primers sequences, primer numbers and names, Tm and length are shown in FIG. 1. The positions of these primers with respect to a reference HIV genome (Accession number NC001802) is shown in FIG. 2.

Thus, in one aspect, the invention provides a composition comprising an HIV gag forward primer consisting essentially of an oligonucleotide selected from the group consisting of: SEQ ID NOs:1-20, 206 and 207 and oligonucleotides having at least 75% sequence identity to SEQ ID NO:1-20, 206 and 207. Preferably the sequence identity is at least 80%, 85%, 90%, or at least 95%.

Preferred gag forward primers are SEQ ID NOs:1, 4, 16, 17, 19 and 20, which can be used as a sole forward primer or in any combination. A preferred combination of gag forward primers is SEQ ID NOs:16 and 17; and 19 and 20.

The invention further provides a composition comprising an HIV gag reverse primer consisting essentially of an oligonucleotide selected from the group consisting of: SEQ ID NOs:21-43, 102-113 and 220-232 and oligonucleotides having at least 75% sequence identity to SEQ ID NOs:21-43, 102-113 and 220-232. Preferably the sequence identity is at least 80%, 85%, 90%, or at least 95%.

Preferred gag reverse primers are SEQ ID NOs:21, 22, 26, 27, 32-34, 36-38, 40-41 and 106-108. Preferred combinations of gag reverse primers are SEQ ID NOs:33 and 41; SEQ ID NOs:32, 36, 37 and 40; SEQ ID NOs: 21, 26 and 38; SEQ ID NOs:22 and 27; SEQ ID NOs:32, 33 and 34; SEQ ID NOs:36, 37, 38, 40 and 41; and SEQ ID NOs:106, 107 and 108.

The invention also provides a composition comprising an HIV vpr forward primer consisting essentially of an oligonucleotide selected from the group consisting of SEQ ID NOs:44-58, 208 and 209 and oligonucleotides having at least 75% sequence identity to SEQ ID NOs:44-58, 208 and 209. Preferably the sequence identity is at least 80%, 85%, 90%, or at least 95%.

Preferred vpr forward primers are SEQ ID NOs:44-52. Preferred combinations of vpr forward primers are SEQ ID NOs:44 and 48; and SEQ ID NOs:57 and 58.

The invention further provides a composition comprising an HIV vpr reverse primer consisting essentially of an oligonucleotide selected from the group consisting of: SEQ ID NOs:60-73, 114-122, 196-203, 233-241 and 261-273 and oligonucleotides having at least 75% sequence identity to SEQ ID NOs:60-73, 114-122, 196-203, 233-241 and 261-273. Preferably the sequence identity is at least 80%, 85%, 90%, or at least 95%.

Preferred vpr reverse primers are SEQ ID NOs:196-203 and 269-273. Preferred combinations of vpr reverse primers are SEQ ID NOs:196 and 197; SEQ ID NOs:198, 199 and 200; SEQ ID NOs:201-203; and SEQ ID NOs:269-273.

The invention also provides a composition comprising an HIV rev forward primer consisting essentially of an oligonucleotide selected from the group consisting of: SEQ ID NOs:74-88, 183-189, 210 and 211 and oligonucleotides having at least 75% sequence identity to SEQ ID NOs:74-88, 183-189, 210 and 211. Preferably the sequence identity is at least 80%, 85%, 90%, or at least 95%.

Preferred combinations of rev forward primers are SEQ ID NOs:87 and 88; SEQ ID NOs:183 and 184; SEQ ID NOs: 185, 186 and 187; and SEQ ID NOs: 188 and 189.

The invention further provides a composition comprising an HIV rev reverse primer consisting essentially of an oligonucleotide selected from the group consisting of: SEQ ID NOs:89-101, 123-129, 190-195, 242-248 and 258-260 and oligonucleotides having at least 75% sequence identity with SEQ ID NOs:89-101, 123-129, 190-195, 242-248 and 258-260. Preferably the sequence identity is at least 80%, 85%, 90%, or at least 95%.

Preferred combinations of rev reverse primers are SEQ ID NOs:190, 191 and 192; and SEQ ID NOs:193, 194 and 195.

The invention also provides a composition comprising an HIV env forward primer consisting essentially of an oligonucleotide selected from the group consisting of: SEQ ID NOs:130-132, 134-136 and 212-214 and oligonucleotides having at least 75% sequence identity to SEQ ID NOs:130-132, 134-136 and 212-214. Preferably the sequence identity is at least 80%, 85%, 90%, or at least 95%.

The invention further provides a composition comprising an HIV env reverse primer consisting essentially of an oligonucleotide selected from the group consisting of: SEQ ID NOs:133, 154-159, 249 and 255-258 and oligonucleotides having at least 75% sequence identity to SEQ ID NO:133, 154-159, 249 and 255-258.

The invention additionally provides a composition comprising an HIV env reverse primer consisting of the oligonucleotide of SEQ ID NO:133 or oligonucleotide having at least 75% sequence identity to SEQ ID NO:133. Preferably the sequence identity is at least 80%, 85%, 90%, or at least 95%.

The invention also provides a composition comprising an HIV nef forward primer consisting essentially of an oligonucleotide selected from the group consisting of: SEQ ID NOs:138-139, 147, 148, 204 and 215-218 and oligonucleotide having at least 75% sequence identity to SEQ ID NOs:138-139, 147, 148, 204 and 215-218. Preferably the sequence identity is at least 80%, 85%, 90%, or at least 95%.

In addition, the invention provides a composition comprising an HIV nef forward primer consisting of an oligonucleotide selected from the group consisting of: SEQ ID NOs:140-143 and oligonucleotides having at least 75% sequence identity to SEQ ID NOs:140-143. Preferably the sequence identity is at least 80%, 85%, 90%, or at least 95%.

Preferred combinations of nef forward primers are SEQ ID NOs:138, 139 and 204; SEQ ID NOs:140-143; SEQ ID NOs: 147-148; and SEQ ID NOs:138 and 139.

The invention further provides a composition comprising an HIV nef reverse primer consisting essentially of an oligonucleotide selected from the group consisting of: SEQ ID NOs:144-146, 149-153 and 250-254 and oligonucleotides having at least 75% sequence identity to SEQ ID NOs:144-146, 149-153 and 250-254. Preferably the sequence identity is at least 80%, 85%, 90%, or at least 95%.

Preferred combinations of nef reverse primers are SEQ ID NOs:144-146; and SEQ ID NOs: 149-151.

In order to amplify an HIV sequence, one or more forward primers are combined with one or more reverse primers. Thus, the invention provides primer pair combinations useful for the amplification of multiple variants of HIV. These primer pair combinations can contain one forward primer and one reverse primer (each primer will typically be present in more than one copy). However, to ensure amplification of multiple variants of HIV, the most useful primer pair combinations will contain a plurality of forward primers and a plurality of reverse primers.

Thus, the invention provides a composition comprising:
a. a gag forward primer comprising an oligonucleotide selected from the group consisting of SEQ ID NOs:1-20, 162, 164, 168, 169, 206 and 207 and oligonucleotides having at least 75% sequence identity to SEQ ID NO:1-20, 162, 164, 168, 169, 206 and 207; and
b. a gag reverse primer comprising an oligonucleotide selected from the group consisting of SEQ ID NOs: 21-43, 102-113, 172, 173 and 220-232 and oligonucleotide having at least 75% sequence identity to SEQ ID NOs: 21-43, 102-113, 172, 173 and 220-232.

Preferably the sequence identity is at least 80%, 85%, 90%, or at least 95%.

Preferred combinations of gag forward primers with gag reverse primers are SEQ ID NOs:1, 32, 33 and 34; SEQ ID NOs: 4, 32, 33 and 34; SEQ ID NOs:16, 17, 32, 33 and 34; SEQ ID NOs: 1, 36, 37, 38, 40 and 41; SEQ ID NOs: 4, 36, 37, 38, 40 and 41 and SEQ ID NOs: 16, 17, 36, 37, 38, 40 and 41.

In another aspect, the invention provides a composition comprising:
a. a vpr forward primer comprising an oligonucleotide selected from the group consisting of SEQ ID NOs: 44-58, 176, 177, 208 and 209 and oligonucleotides having at least 75% sequence identity to SEQ ID NOs:44-58, 176, 177, 208 and 209; and
b. a vpr reverse primer comprising an oligonucleotide selected from the group consisting of SEQ ID NOs: 60-73, 114-122, 196-200, 233-241 261-273 and oligonucleotides having at least 75% sequence identity to SEQ ID NOs: 60-73, 114-122, 196-200, 233-241 and 261-273.

Preferably the sequence identity is at least 80%, 85%, 90%, or at least 95%.

Preferred combinations of forward and reverse vpr primers are: SEQ ID NOs: 44, 48, 196 and 197, or SEQ ID NOs: 44, 48, 198, 199 and 200, or SEQ ID NOs: 49, 196 and 197, or SEQ ID NOs:49, 198, 199 and 200.

In yet another aspect, the invention provides a composition comprising:
a. a nef forward primer comprising an oligonucleotide selected from the group consisting of SEQ ID NOs: 138-143, 147, 148, 204 and 215-218 and oligonucleotide having at least 75% sequence identity to SEQ ID NOs:138-143, 147, 148, 204 and 215-218; and
b. a nef reverse primers comprising an oligonucleotide selected from the group consisting of SEQ ID NOs: 144-146, 149-153 and 250-254 and oligonucleotides having at least 75% sequence identity to SEQ ID NOs:144-146, 149-153 and 250-254. Preferably the sequence identity is at least 80%, 85%, 90%, or at least 95%.

Preferred combinations of nef forward and reverse primers are: SEQ ID NOs: 138, 139, 144, 145, 146 and 204, or SEQ ID NOs: 140-146, or SEQ ID NOs:138, 139, 144, 145 and 146.

In yet another aspect, the invention provides a composition comprising:
a. an env forward primer comprising an oligonucleotide selected from the group consisting of SEQ ID NOs:

130-132, 134-136 and 212-214 and oligonucleotides having at least 75% sequence identity to SEQ ID NOs:130-132, 134-136 and 212-214; and
b. an env reverse primer comprising an oligonucleotide selected from the group consisting of SEQ ID NOs: 133, 154-159, 249 and 255-258 and oligonucleotides having at least 75% sequence identity to SEQ ID NO:133, 154-159, 249 and 255-258.

Preferably the sequence identity is at least 80%, 85%, 90%, or at least 95%.

In practicing the methods of the invention, it is possible to isolate any of the following for use as a template in the primary nucleic acid amplification: integrated HIV provirus, genomic HIV RNA (from virions or cells replicating HIV virions), HIV primary transcripts and HIV processed mRNA. However, in a preferred embodiment of the invention, HIV RNA genomes are isolated from virions present in the blood. The open reading frames of env and rev partially overlap in the HIV genome, and in the normal course of HIV expression, the first and second rev exons in the rev primary RNA transcript are spliced to result in a processed rev mRNA. Because the preferred HIV template is HIV genomic RNA, it is most practical to amplify the first or second rev exon, rather than the entire rev gene, which is only in-frame after splicing. Accordingly, in preferred embodiments, the invention provides combinations of rev forward and reverse primers suitable for amplification of the second rev exon.

Thus, in yet another aspect, the invention provides a composition comprising:
a. a rev forward primer comprising an oligonucleotide selected from the group consisting of SEQ ID NOs: 74-88, 183-189, 210 and 211 and oligonucleotides having at least 75% sequence identity to SEQ ID NOs:74-88, 183-189, 210 and 211; and
b. a rev reverse primer comprising an oligonucleotide selected from the group consisting of SEQ ID NOs: 89-101, 123-129, 190-195, 242-248 and 258-260 and oligonucleotides having at least 75% sequence identity with SEQ ID NOs:89-101, 123-129, 190-195, 242-248 and 258-260.

Preferably the sequence identity is at least 80%, 85%, 90%, or at least 95%.

Preferred combinations of rev forward and reverse primers are SEQ ID NOs: 183, 184, 190, 191 and 192; and SEQ ID NOs:185, 186, 187, 190, 191 and 192; and SEQ ID NOs:188-192.

In one embodiment of the invention, rev forward primers can be combined with nef reverse primers to produce a single amplicon encoding nef and the second exon of rev. Nested PCR would then be used to produce separate secondary nef and rev amplicons.

Accordingly, the invention provides a composition comprising:
a. a rev forward primer comprising an oligonucleotide selected from the group consisting of SEQ ID NOs: 74-88, 183-189, 210 and 211 and oligonucleotides having at least 75% sequence identity to SEQ ID NOs:74-88, 183-189, 210 and 211; and
b. a nef reverse primer comprising an oligonucleotide selected from the group consisting of and SEQ ID NOs:144-146, 149-153 and 250-254 and oligonucleotides having at least 75% sequence identity to SEQ ID NOs:144-146, 149-153 and 250-254.

Preferably the sequence identity is at least 80%, 85%, 90%, or at least 95%.

Similarly, it is possible to produce other primary amplicons of one or more consecutive combinations of HIV genes of interest. For example, a gag forward primer could be combined with a nef reverse primer to amplify most of the HIV genome. Other non-limiting examples are the combination of a vpr forward primer with a nef reverse primer, a vpr forward primer with a rev reverse primer and env forward primer with a nef reverse primer.

Thus, the invention further provides a composition comprising:
a. a forward primer comprising an oligonucleotide selected from the group consisting of SEQ ID NOs:1-20, 44-58, 74-88, 130-132, 134-136, 162-188 and 189 and oligonucleotides having at least 75% sequence identity to SEQ ID NOs:1-20, 44-58, 74-88, 130-132, 134-136, 162-188 and 189; and
b. a reverse primer comprising an oligonucleotide selected from the group consisting of and SEQ ID NOs:60-73, 89-101, 114-122, 133, 144-146, 190-192, 196-203 and 269-273 and oligonucleotides having at least 75% sequence identity to SEQ ID NOs:60-73, 89-101, 114-122, 133, 144-146, 190-192, 196-203 and 269-273.

Preferably the sequence identity is at least 80%, 85%, 90%, or at least 95%.

The primers and primer pairs described above are useful for the amplification of HIV nucleic acids to produce primary DNA amplicons encoding targeted antigens.

Based on these guidelines, forward and reverse nested primers suitable for amplification of the gag, vpr, env, rev and nef antigens from multiple variants of HIV are provided. These primers can be used in a primary amplification reaction or, preferably, in a second round of nucleic amplification following primary amplification. In preferred embodiments, the primary amplification is performed with the HIV forward and reverse gag, vpr, rev, env and/or nef primers described above, followed by a secondary amplification using the nested primer pairs described below.

Thus, the invention provides a forward primer comprising a 5' portion and a 3' portion, wherein the 5' portion comprises a promoter and an optimized Kozak sequence and the 3' portion comprises a sequence selected from the group consisting of GTGCGAGAGCGT (SEQ ID NO: 206, for gag amplification), GTGCGAGACCGT (SEQ ID NO: 207, for gag amplification), AACAAGCCCCAG (SEQ ID NO:208, for vpr amplification), AACAAGCCCCGG (SEQ ID NO:209, for vpr amplification), ACCCACCTCCC (SEQ ID NO:210, for rev amplification), ACCCGCCTCCC (SEQ ID NO:211, for rev amplification), GAGTGATGG (SEQ ID NO:212, for env amplification), GAGTGAAGG (SEQ ID NO:213, for env amplification), GAGTGAGGG (SEQ ID NO:214, for env amplification), GTGGCAAGTGGT-CAAAAAG (SEQ ID NO:215 for nef amplification), GTG-GCAAGTGGTCAAAACG (SEQ ID NO:216, for nef amplification), TGGGAGCAGTGTCTCA (SEQ ID NO:217, for nef amplification) and AGGCACAAGAG-GAAGAGG (SEQ ID NO:218, for nef amplification), AGAGTGATGG (SEQ ID NO:372, for env amplification), AGAGTGAAGG (SEQ ID NO:373, for env amplification), AGAGTGACG (SEQ ID NO:374, for env amplification), AGAGTGAGGG (SEQ ID NO:375, for env amplification), AAACAGATGGCAGGTG (SEQ ID NO:376, for vif amplification), AAACAGATGGCAGGTA (SEQ ID NO:377, for vif amplification), AAACAGATGGCAGGCG (SEQ ID NO:378, for vif amplification), AAACAGATGGCAGGGG (SEQ ID NO:379, for vif amplification), TCTAT-CAAAGCAGTAAG (SEQ ID NO:380; for vpu amplification); TCTATCAAAGCAGTGAG (SEQ ID NO:381; for vpu amplification); TCTATCAGAGCAGTAAG (SEQ ID NO:382; for vpu amplification); TCTACCAAAGCAG-TAAG (SEQ ID NO:383; for vpu amplification); GGAAGGCCAGGGAATTTCC (SEQ ID NO:384, for pol amplification), GGAAGGCCAGGGAATTTTC (SEQ ID NO:385, for pol amplification), GGAAGGCCA-GGGAATTTCC (SEQ ID NO:386, for pol amplification), and GGAAGGCCAGGAAATTTTC (SEQ ID NO:387, for pol amplification). Preferably, the promoter is the T7 promoter. In preferred embodiments of the above primers, the 5' portion of the oligonucleotide comprises a T7 promoter and an optimized Kozak sequence, together having the sequence TAATACGACTCACTATAGGGAGACCAC-CATGG (SEQ ID NO:219), wherein the T7 promoter sequence is shown in regular font and the optimized Kozak sequence is shown in italic font. In preferred T7 promoter/primer embodiments, the combined 5' and 3' portions together comprise a sequence selected from the group consisting of SEQ ID NO:19, 20, 57, 58, 87, 88, 134, 135, 136, 147, 148, 160, 161, 290-293, 308-311, 329-332 and 356-360.

The invention also provides reverse primers comprising a 5' portion and a 3' portion, wherein the 5' portion comprises a polyT oligonucleotide having approximately 30-100 T nucleotides, and the 3' portion comprises a sequence selected from the group consisting of: 5'GTGAC-GAGGGGTCGTTG (SEQ ID NO:220), 5'GTGAC-GAGGGGTCGCTG (SEQ ID NO:221), 5'GTAAC-GAGGGGTCGTTG (SEQ ID NO:222), 5'GTGTCGAGGGGGCGTTG (SEQ ID NO:223), 5'GCTC-CTGTATCTAATAGAGC (SEQ ID NO:224), 5'GCTCCT-GTATCTAATAAAGC (SEQ ID NO:225), 5'GCTCCTG-TATCTAACAGAGC (SEQ ID NO:226), 5'GGTTTCCATCTTCCTGG (SEQ ID NO:227), 5'GGTTTCCATCTTCCTGC (SEQ ID NO:228), 5'GGCT-TCCATCTCCCTGG (SEQ ID NO:229), 5'GGTTTC-CATTTCCCTGG (SEQ ID NO:230), 5'GGTTTC-CATTTTCCTGG (SEQ ID NO:232), 5'GGATAAACAGCAGTTGTTGC (SEQ ID NO:233), 5'GAATAAACAGCAGTTGTTGT (SEQ ID NO:234), 5'GAATAAACAGCAGCTGTTGC (SEQ ID NO:235), 5'ATTCTGCTATGTCGACACCC (SEQ ID NO:236), 5'ATTCTGCTATGTCGGCGCCC (SEQ ID NO:237), 5'ATTCTGCTATGTCGGCACCC (SEQ ID NO:238), 5'ATTCTGCTATGTTGACACCC (SEQ ID NO:239), 5'CTCCATTTCTTGCTCTCCTC (SEQ ID NO:240), 5'CTCCATTTCTTGCTCTTCTC (SEQ ID NO:241), 5'CCTGACTCCAATACTGTAGG (SEQ ID NO:242), 5'CCTGACTCCAATACTGCAGG (SEQ ID NO:243), 5'CCTGACTCCAATATTGTAGG (SEQ ID NO:244), 5'GCATTGAGCAAGCTAACAGC (SEQ ID NO:245), 5'GCATTGAGCAAGCTAACTGC (SEQ ID NO:246), 5'GCATTGAGCAAGTTAACAGC (SEQ ID NO:247), 5'GCATTAAGCAAACTAACAGC (SEQ ID NO:248), 5'ATAGCAAAGCCCTTTC (SEQ ID NO:249), 5'CCAG-TACAGGCAAAAAGC (SEQ ID NO:250), 5'CAGTACA-GGCGAAAAGC (SEQ ID NO:251), 5'CCAGTACAG-GCAAGAAGC (SEQ ID NO:252), 5'GTCAGCAGTCTTT (SEQ ID NO:253), 5'GTCAGCAGTCTCA (SEQ ID NO:254), 5'GACCACTTGCCACCC (SEQ ID NO:255), 5'GACCACTTGCCACTC (SEQ ID NO:256), 5'GAC-CACTTGCCCCCC (SEQ ID NO:257), 5'CCCTGTCTTAT-TCTTCTAGG (SEQ ID NO:258), 5'CCCTGTCTTATTCT-TACAGG (SEQ ID NO:259), 5'CCCTGTCTTATTCTTGTAGG (SEQ ID NO:260), 5'GCAGTTGTAGGCTGACTTCC (SEQ ID NO:261), 5'GCAGTTGTAGGCTGACTCC (SEQ ID NO:262), 5'GCAGTTGTAGGCTGGCTTCC (SEQ ID NO:263), 5'AGCGAACAAACAGTAGTTGTTGCAG (SEQ ID NO:264), 5'AGCGAACAAACAGTAGTTGTTGCAA (SEQ ID NO:265), and 5'AGCGATCAAACAGCAGTTGT-TGCAG (SEQ ID NO:266), AGCGAACAAACAGTAGT-TGTTGAAG (SEQ ID NO:267), AGCGATCAAACAG-TAGTTGTTGCAG (SEQ ID NO:268).

Preferably, the 5' polyT portion is 64 T nucleotides in length. In preferred embodiments the reverse nested primer composition comprises one or more oligonucleotides selected from the group consisting of SEQ ID NOs: 102-129, 137, 149-153, 157-159, 193-195, 201-203 and 269-273.

In yet another embodiment, the invention provides a kit for the amplification of multiple variants of HIV, comprising:
  a) a forward primer comprising an oligonucleotide selected from the group consisting of SEQ ID NOs: 1-20, 44-58, 74-88, 130-132, 134-136, 138-143, 147-148, 160-162, 164, 168, 169, 176, 177, 180, 183-189 and 204; and
  b) a reverse primer comprising an oligonucleotide selected from the group consisting of 21-43, 60-73, 89-129, 133, 137, 144-146, 149-159, 163, 167, 172, 173, 178, 179, 181, 182, 190-203, and 220-273.

Preferably, the kit additionally contains a thermostable DNA polymerase, dNTPs, and a buffer (1× or concentrated) suitable for amplification reactions. In addition, the kit may also contain a reverse transcriptase and/or non-infectious HIV control templates for amplification. Also, the kit will preferably contain at least one pair of forward and reverse nested primers for secondary amplification of the primary amplicon. The forward nested primer will contain a 5' promoter, and optionally a Kozak sequence containing a translation initiation codon, as well as a 3' sequence targeting a primary amplicon of interest. The reverse nested primer will contain a 5' polyT sequence and a 3'sequence complimentary to a primary amplicon of interest, and optionally, a translation stop codon. The kits are useful for the identification and quantitation of pathogen variants and for preparation of vaccines.

In another aspect, the invention provides a strain-independent method of amplifying HIV sequences, comprising: amplifying multiple variants of HIV DNA with one or more forward primers comprising an oligonucleotide selected from the group consisting of SEQ ID NO:1-18, 44-56, 74-86, 130-136, 138-143 and 204 and with one or more reverse primers comprising an oligonucleotide selected from the group consisting of SEQ ID NO:21-43, 60-73, 89-101, 133, 144-146, 154-156, 190-102, 196-199 and 200.

The HIV DNA can comprise HIV DNA integrated into a host cell genome. However in preferred embodiments, the HIV DNA is a cDNA prepared by reverse transcription of HIV genomic RNA or HIV mRNA. Methods for isolating integrated HIV DNA, HIV genomic RNA and HIV mRNA from an infected individual are known to those skilled in the art. Similar methods can be used to isolate nucleic acids of other pathogens of interest.

Preferably the HIV nucleic acid is isolated or derived from a biological sample from an individual infected with HIV who will be treated with a vaccine of the invention. "Biological sample" as used herein, refers to any biological sample that may contain a pathogen, pathogen-infected cells or pathogen nucleic acid, and includes, but is not limited to, blood, plasma, serum, peripheral blood mononuclear cells (PBMC), seminal fluid, vaginal secretions, ocular lens fluid, cerebral spinal fluid, saliva, milk, ascites fluid, synovial fluid, peritoneal fluid, amniotic fluid, tissue, tissue culture and the like.

Most preferably, virions containing HIV genomic RNA are isolated from blood or serum. The genomic RNA obtained from the virions can be subjected to reverse transcription to produce an HIV cDNA. Methods of isolating HIV virions from infected patients, as well as methods of making cDNA are known to those skilled in the art. Reverse transcription of HIV RNA can be primed using random hexamers or specific oligonucleotide primers. The HIV cDNA can then be used as a template in the above method of strain-independent amplification of HIV sequences. These same methods can be used to prepare a cDNA from the mRNA or genomic RNA of other pathogens.

The DNA amplified by the methods of the invention can be used in a nucleic acid vaccine or may be loaded into antigen presenting cells which can then be used as a vaccine. In addition, the DNA can be sequenced in order to identify the variants of HIV present in a sample or infecting a patient. DNA amplified from a pathogen template or cDNA copy thereof is referred to as a "primary amplicon". The primary amplicon can be modified by inserting it into an expression cassette, expression vector and/or delivery vector, which can then be used as a nucleic acid vaccine, a viral vector vaccine, etc., or such vectors can be loaded into antigen presenting cells which can be used as a vaccine.

In a preferred embodiment, the primary amplicon is subjected to a second round of amplification using nested primers containing transcription and translation signals suitable for either expression in vitro and/or expression in vitro. Preferably, the DNA is subjected to a second round of amplification using a forward nested primer containing: 1) a promoter suitable for in vitro transcription, such as the T7 or SP6 promoter, 2) an optimized Kozak sequence including an ATG codon; in combination with a reverse nested primer containing a the complement of a translational stop codon and a polyT tail. The secondary amplicon resulting from the nested round of amplification can be used as a template for in vitro transcription and 5' capping. The resulting mRNA can then be used in a nucleic acid vaccine, or to load antigen presenting cells, which can then be used as a vaccine.

As a non-limiting example, pathogen RNA is reverse transcribed into single-stranded cDNA using a reverse transcriptase, appropriate reaction buffers, and random hexamers. The single-stranded cDNA is then amplified by PCR into double-stranded DNA in a primary PCR reaction using multiplex primers. Product from a primary PCR reaction is taken into a second round or nested PCR amplification. In this round amplification 5' primer(s) contains overhang with T7 RNA polymerase binding sequences and 3' primer contains overhang with poly T stretches. The modifications introduced by overhanging regions in a nested round of PCR enable transcription of the PCR product in vitro and successful translation upon delivery into the DCs. The process can be interrupted after either step of PCR amplification and PCR products, can be stored frozen for further processing. Purification of cDNA material is performed using the QIAquick® PCR Purification Kit components (QIAquick® Columns, PB buffer, PE buffer, and EB buffer). The double-stranded DNA is used as a template in a standard transcription reaction. Clean-up of the in vitro-transcribed RNA is performed using components in the RNeasy® Kit (RNeasy® Column, RLT buffer, and RPE buffer). The RNA is eluted in nuclease-free water. If necessary, ethanol precipitation is performed to concentrate the RNA. The RNA is re-suspended in nuclease-free water and passed through a 0.8/0.2 µm polyethersulfone (PES) filter, then dispensed into 0.5 mL safe-lock polypropylene tubes, and cryopreserved at ≤−150° C. for long-term storage.

Accordingly, the invention provides a strain-independent method of making HIV RNA, comprising:
a) producing a primary amplicon by amplifying multiple variants of HIV DNA using a forward primer and a reverse primer, wherein said forward primer comprises an oligonucleotide selected from the group consisting of: SEQ ID NOs:1-18, 44-56, 74-86, 130-132, 162-188 and 189; and said reverse primer comprises an oligonucleotide selected from the group consisting of SEQ ID NOs:60-73, 89-101, 133, 144-146, 190-192, and 196-200;
b) amplifying said primary amplicon using a forward promoter primer and a reverse primer comprising a 5' polyT tail to produce an amplified expression cassette; and
c) transcribing said expression cassette to produce an HIV RNA.

Preferably, the HIV DNA is a cDNA prepared by reverse transcription of HIV genomic RNA or HIV mRNA. In a preferred embodiment, the forward promoter primer comprises a T7 or SP6 promoter. Preferably, the forward primer further comprises an optimized Kozak sequence 3' to the promoter.

Capped and polyadenylated RNAs can be tested in an in vitro translation reaction and/or followed by transfection into dendritic cells or other antigen presenting cells. The identity of the translated proteins can be tested in Western blot analysis using specific antibodies. Lack of negative impact of expressed individual antigens as well as their combination on the maturation of APCs can be tested by analysis of extra-cellular markers. For example, the ability of DC to mature can be established by phenotypic analysis using flow cytometry markers (e.g., HLA DR, CD86, CD83, CD14). To eliminate the possibility that newly expressed proteins affect function of DC, individual RNAs encoding antigens or their combination can be co-transfected in combination with Flu RNA followed by testing of the co-transfected DCs in CTL assays. Such methods are known to those of skill in the art.

Capped and polyadenylated RNAs made according to the methods of the invention can be transfected into dendritic cells or other antigen presenting cells, either in vitro or in situ. Such in vitro transfected antigen presenting cells can then be used as a vaccine. Alternatively, capped and polyadenylated RNA can be translated in vitro and then loaded into antigen presenting cells in vitro, or used directly in a vaccine. Thus, in another embodiment, the invention provides a method of loading an antigen presenting cell, comprising contacting an antigen presenting cell with an RNA produced by the method of the invention.

The following examples are intended as non-limiting embodiments of the invention.

EXAMPLES

Example 1

Selection of Primers for Amplification of Multiple Variants of HIV

Analysis of the 49 full length HIV isolates deposited in Los Alamos National Database revealed highly variable regions in the HIV genomes as well as regions outside of coding sequences of selected antigens with lower variability.

Those relatively conserved regions, mostly outside of the open reading frames of gag, vpr and rev served as a template for design of oligonucleotides to be used in PCR amplification. Since mutations additional to those present in identified sequences listed in Los Alamos Database could occur in individual patient, multiple regions for primer annealing were determined. Primers complimentary to these isolates were analyzed. Nucleotide regions with relative sequence conservation among isolates were preferred for primer selection. The following parameters were applied to primer design: primers were to have a Tm of 55° C.-62° C., a length of about 17-20 bp, were not predicted to form homodimers, were to lack of secondary structure and homology to sequences other than HIV in a BLAST analysis. To minimize the number of primers used, a mismatch at the 5' half of a primer sequence was tolerated, while a mismatch in the 3' half was not allowed. To assure no-fail amplification of any chosen antigen several regions outside of open reading frames of interest were chosen as well. FIG. 1 outlines schematic representation of the regions selected for primer design. The number in the name of the primer corresponds to the position within sequence with accession number NC_001802 chosen as a reference. This reference sequence contains a mutation which truncates VPR, which is not present in most HIV sequences.

Primers annealing to the selected regions upstream and downstream of gag (outside of NC_001802 225-1838 will allow for amplification of the entire open reading frame of gag. After regions for primers had been identified, the primers for each chosen location complimentary to each known HIV sequence were determined. An example for reverse primer group gag 1883 encoding all complimentary sequences to the 49 analyzed isolated is shown Table 1.

TABLE 1

| 5' | g | t | G | a c g a G | g g g T | c g t | t G 3' | SEQ ID NO: 21 |
|---|---|---|---|---|---|---|---|---|
| | g | t | G | a c g a G | g g g T | c g *C* | t G | SEQ ID NO: 22 |
| | g | t | G | a c g a *T* | g g g T | c g t | t G | SEQ ID NO: 23 |
| | g | *a* | G | a c g a G | g g g T | c g t | t G | SEQ ID NO: 24 |
| | *t* | t | G | a c g a G | g g *G* | c g t | t G | SEQ ID NO: 25 |
| | g | t | *A* | a c g a G | g g *G* | c g t | t G | SEQ ID NO: 26 |
| | g | t | G | *t* c g a G | g g *G* | c g t | t G | SEQ ID NO: 27 |
| | g | t | G | a c *a a* G | g g g T | c g t | t G | SEQ ID NO: 28 |
| | g | t | *A* | a c g a G | g g g T | c g t | t G | SEQ ID NO: 29 |
| | g | *c* | *A* | a c g a G | g g g T | c g t | t G | SEQ ID NO: 30 |
| | g | *c* | G | a c g a G | g g g T | c g t | t G | SEQ ID NO: 31 |

Reverse primer group for location 1833 of NC_001802 selected to amplify gag. Since this is a reverse group of primers inverse compliment sequences is shown here. Variable bases complimentary to all analyzed HIV sequences are shown in italics, wherein the non-consensus variant is in bold italics.

To minimize number of primers used we applied further selection criteria: mismatch in the 3' half of a primer sequence is avoided where possible, however mismatch at the 5' half of primer sequence is tolerated. Such mismatch could be compensated by lowering of PCR amplification stringency. When those selection criteria were applied the list of primers for that group was shortened considerably as shown in Table 2, which shows primers divergent in their 3' half.

TABLE 2

| 5' | g t | *G* | a | c g A g g g g t | c g t | t g 3' | SEQ ID NO: 21 |
|---|---|---|---|---|---|---|---|
| | g t | *G* | a | c g A g g g g t | c g *C* | t g | SEQ ID NO: 22 |
| | g t | *A* | a | c g A g g g g *G* | c g t | t g | SEQ ID NO: 26 |
| | g t | *G* | *T* | c g A g g g g *G* | c g t | t g | SEQ ID NO: 27 |

Sequence of reverse primers selected for the region gag 1833. The sequence complimentary to reference sequence NC_001802 is shown in the top row. Mutations in the region found in distinct HIV isolates are indicated in upper case bold italics. The reverse compliment sequence to that of reference sequence is shown here.

Table 3, below, details the primer design for on group of forward primers for Rev. Sequence alignment of multiple HIV isolates from the most common HIV clades, as well as less common isolates, revealed a region of relative conservation with variable residues in positions 7847 and 7848. Therefore, in order to design a primer that was perfectly complimentary to the consensus B sequence (Rev F7830), but could also accommodate this frequent sequence transition, additional alternative primers were designed. These alternative primers contain compensatory mutations to the frequently found mutations in positions 7847 and 7848 (Rev F 7830.1 and Rev F 7830.2). Only the 3' half of the primers was designed to carry compensatory mutation, whereas mismatch at the 5' half of residues 7830-7840 was allowed. In order to assure the "no-fail" amplification of various strains, more than one region outside an open reading frame of interest was analyzed. For example, isolate 01A1.CM.CM53122 would fail to amplify using primers designed for region Rev F7830 due to the deletion of the target region. In order to compensate for this, therefore, sequences at positions 7550 and 7911 were also used to design forward Rev primers.

TABLE 3

| REV F 7830 | 5'-TGATAGTAGG AGGCTTGGTA GG-3' | SEQ ID NO: 185 |
|---|---|---|
| REV F 7830.1 | 5'-TGATAGTAGG AGGCTTAATA GG-3' | SEQ ID NO: 186 |
| REV F 7830.2 | 5'-TGATAGTAGG AGGCTTGATA GG-3' | SEQ ID NO: 187 |
| CONSENSUS A1 | ---------- ------aa-- -- | |
| A1.KE.KER2008 | ---------- ---T--AA-- -- | |
| A1.KE.KER2009 | --G------- ---T--AA-- -- | |
| A1.KE.KNH1207 | ---------- ------AA-- -- | |
| A1.KE.KNH1211 | -A-------- ------AA-- -- | |

TABLE 3-continued

| | | | |
|---|---|---|---|
| CONSENSUS_B | ---------- | ---------- | -- |
| B.AR.ARMA173 | ---------- | -------A-- | -- |
| B.AR.ARM8008 | ---------- | ---------- | -- |
| B.GB.CAM1 | -----A---- | ---T--AA-- | -- |
| CONSENSUS_C | ---------- | -------A-- | -- |
| C.BR.98BR004 | --------A- | -------A-- | -- |
| C.BR.92BR025 | A--------- | -------A-- | -- |
| C.BW.00BW38428 | --G------- | -------A-- | -- |
| C.BW.96BWM032 | ---------- | -------A-- | -- |
| CONSENSUS_D | ---------- | -------a-- | -- |
| D.UG.94UG114 | ---------- | -------A-- | -- |
| D.UG.99UGB21875 | ---------- | ---------- | -- |
| D.UG.99UGB25647 | ---------C | -------A-- | -- |
| D.UG.99UGD23550 | -A---A---- | -------A-- | -- |
| CONSENSUS_F1 | ---------- | -------A-- | -- |
| F1.BE.VI850 | -------G-- | -------A-- | -- |
| F2.CM.MP255 | ---------- | -------A-- | -- |
| CONSENSUS_G | ---------- | ---t--AA-- | -- |
| G.BE.DRCBL | ---------- | ------AA-- | -- |
| G.NG.92NG083 | ---------- | ---T--AA-- | -- |
| CONSENSUS_H | ---------- | ---T--aA-- | -- |
| H.BE.VI991 | ---------- | ---TA-AA-- | -- |
| H.BE.VI997 | -A-------- | --CT---A-- | -- |
| H.CF.90CF056 | ---------- | ---T--AA-- | -- |
| J.SE.SE7022 | -----A---- | ------AA-- | -- |
| CONSENSUS_01_AE | ---------- | ---T--AA-- | -- |
| 01_AE.CF.90CF402 | -A-------- | ---T--AA-- | -- |
| 01_AE.CF.90CF11697 | --G------- | ---T--AA-- | -- |
| 01_AE.CF.90CF4071 | ---------- | ---T--AA-- | -- |
| CONSENSUS_02_AG | ---------- | ---t--aA-- | -- |
| 02_AG.NG.IBNG | ---------- | ---T--AA-- | -- |
| 02_AG.CM.97CM-MP807 | --C------- | ---T---A-- | -- |
| 03_AB.RU.KAL153-2 | ---------- | ---------- | -- |
| CONSENSUS_04_CPX | ---------- | -------A-- | -- |
| 04_CPX.GR.97PVMY | ---------- | -------A-- | -- |
| CONSENSUS_06_CPX | ---------- | ------Aa-- | -- |
| CONSENSUS_07_BC | -A-------- | -------A-- | -- |
| CONSENSUS_08_BC | ---------- | -------A-- | -- |
| CONSENSUS_10_CD | ---------- | ------aA-- | -- |
| CONSENSUS_11_CPX | ---------- | ------Aa-- | -- |
| CONSENSUS_12_BF | ---------- | -------A-- | -- |
| 12_BF.AR.ARMA159 | ---------- | -------A-- | -- |
| CONSENSUS_14_BG | -----a---- | ---T--AA-- | -- |
| 01A1.CM.CM53122 | .......... | .......... | .. |
| A1C.IN.95IN21301 | ---------- | ---A--AA-- | -- |
| BF.AR.ARMA038 | ---------- | ---------- | -- |

To enable transcription of a PCR fragment in vitro, the fragment was modified to insert a T7 RNA polymerase binding site at the 5' end. Further, successful initiation of translation required the addition, at its 3' end, of both the translation initiator ATG codon optimized to contain a Kozak sequence and a poly(T)64 tail. Modification of primary PCR sequences was achieved by subjecting PCR fragments obtained in the primary PCR reaction to an additional nested round of PCR in which modified forward and reverse primers were used. The forward primer contained an overhang encoding the sequence of a T7 RNA promoter, as well as the bases ACC in a −3, −2 and −1 position of the initiator ATG codon for the antigen. In addition, for HIV genes such as Rev, where the ATG codon had not been amplified during the first round of PCR amplification, the ATG codon was also added during the nested PCR reaction. The 3' half of the nested forward primer was complimentary to the sequence immediately downstream of either the initiator ATG codon or the most 5' coding sequence amplified during the primary PCR amplification. The reverse primer also contained a poly(T)64 overhang at its 5 'end, which served as a template for a polyadenylation (polyA) sequence at the 3' end of the RNA molecule during transcription. The 3' half of the reverse primer was complementary to the sequence isolated in a primary PCR reaction.

Example 2

Determination of Amplification Conditions for Gag Primers

Further reduction of the PCR reaction number was achieved by multiplexing PCR primers for each antigen. PCR primers were grouped in basis of their Tm. Then permutations containing each group of forward primers with each group of reverse primers were tested in a PCR reactions at different temperatures. In order to reduce risk of working with infectious material during initial selection of primers, divergent non-infectious near full-length HIV clones obtained from NIH AIDS Research and Reference Reagent Program were used to test the primer designs and optimize reaction conditions.

10 ng of noninfectious HIV clone pBKBH10S plasmid template (NIH AIDS Research & Reference Reagent program Cat #194) was used in a 25 µL PCR reaction containing 1×Pfu buffer, 0.2 mM each dNTP final concentration, 0.4 µM final concentration of each primer and 1 unit of PFU Hot start (Stratagene) polymerase. The reaction was heated at 95° C. for 45 seconds and then taken through 25 rounds of amplifications at 95° C. for 45 sec, annealing temperature as indicated in FIG. 3 for 45 sec and 72° C. for 3 min. The final extension was at 72° C. for 10 min. Primer groups were as follows: forward group 1 (FG1): primers having SEQ ID NOs:1 and 4; forward group 2 (FG2): primers having SEQ ID NOs:16 and 17; reverse group 1 (RG1): primers having SEQ ID NOs:33 and 41, reverse group 2 (RG2): primers having SEQ ID NOs:32, 36, 37 and 40; reverse group 3 (RG3): primer have SEQ ID NO:34; reverse group 4 (RG4): primers having SEQ ID NOs:21, 26, 38; reverse group 5 (RG5): primers having SEQ ID NOs:22 and 27. The results are shown in FIG. 3. Lanes 1-10 for each annealing temperature contained PCR reactions performed with groups of primers as indicated in the figure legend. While amplification using all of these primer groups was successful at permissive temperatures, 54° C. and 60° C., some primer combinations failed to produce amplicons at higher temperatures, 65° C. and 70° C.

Example 3

Multiplex PCR Amplification of Multiple Variants of HIV Per Reaction

There is evidence that HIV is present in a single individual in a few forms or quazispecies which arise due to a mechanism of mutational escape from any pressure present in this individual (CTL or small molecule). Evidence also exists that patients may be superinfected and host various HIV strains at the same time. The power of current technology is in its ability to amplify all HIV variants present in the patient using conditions stringent enough to amplify a specific product yet promiscuous enough to allow for a single base pair nucleotide mismatch between primer and target sequence.

To experimentally test our ability to amplify multiple HIV variants in the same reaction different HIV templates were mixed in a single PCR reaction. Molecular clones encoding sequences coding for various HIV isolates used in this experiment are listed below.

| Clone name | Country of origin | HIV clade | Accession number |
|---|---|---|---|
| pBKBH10S | France | B | M15654 |
| P93TH253.3 | Thailand | A/E | U51189 |
| P90CF402.1 | Central Africa | A/E | U51188 |
| P93BR029.4 | Brazil | B/F | AF005495 |

Figures 4A, 4B, 4C:
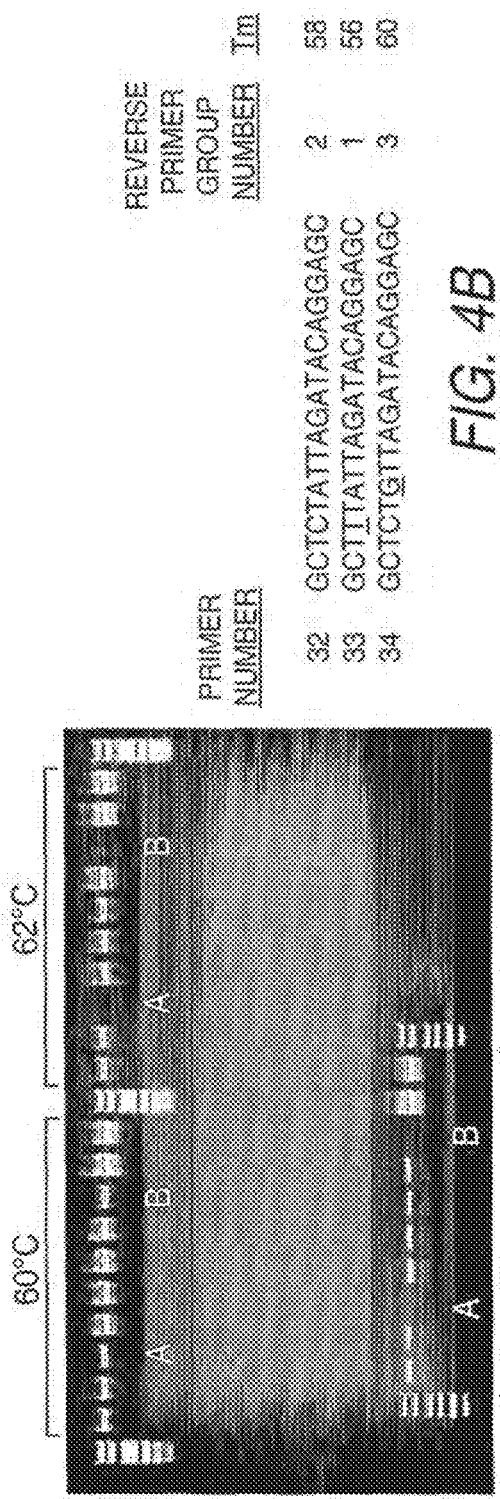
FIGS. 4A, 4B, and 4C show the multiplex PCR amplification of four HIV subtypes per reaction.

Thus, once the reaction conditions for PCR amplification was determined as in Example 2, complexity of a PCR reaction was increased by supplying templates encoding HIV genomes of four distinct isolates into one PCR reaction. Specifically, 2.5 ng of each plasmid template pBKBH10S, p90CF204.1, p93BR029.4 and p93TH253.3, each corresponding to different HIV templates (obtained from HIV AIDS research and reference reagent program Cat #194, 3284, 4009, and 3283 respectively), were mixed in a 25 µL PCR reaction. Reaction conditions and primer mixes were the same as described in Example 2 and FIG. 3. In this experiment annealing temperatures were 60° C., 62° C. and 65° C. as indicated. The results are shown in FIG. 4A. Failed PCR reactions (lanes A and B) at 62° C. and 65° C. have reverse primer 34 as a common denominator, which is the only primer in reverse primer group 3. Primer-template mismatches can be compensated for by lowering the Tm to 60° C.

4B shows the 5' to 3' sequences of the inverse complement of reverse primers 32, 33 and 34 used in reverse primer groups 2, 1 and 3, respectively, as well as the calculated Tm for each primer. FIG. 4C shows an alignment of the four plasmid template sequences in the target region corresponding to these primers. Sequence analysis reveals that position 6 from 5' end of the target primer sequence contains adenine (a) in all molecular clones used in the reaction. Primer 34 however contains guanine (g) in this position and the lack of complimentarity between primer 34 and target sequence did not allow for successful amplification at stringent temperatures. BLAST analysis of primer 34 reveals complimentarity to the HIV isolated from Japan, accession number AB078005 included in our initial analysis of 49 full length HIV isolates. It is important to note that although the mismatch between primer and target did not amplify at stringent conditions, lowering stringency of PCR amplification annealing temperature to 60° C. resulted in a successful amplification event. Demonstration that mismatch in primer:target sequences could be compensated by promiscuous PCR condition serves as the first indication that chosen strategy for HIV amplification will be successful. Primer 33 also contains a mismatch at the position 4 relative to the target sequence; however this primer is a member of group RG2 containing 3 other members one or more of which was successfully annealing to the target sequence resulting in a PCR product.

In summary, combination of multiplex PCR primers that correspond to different regions outside coding sequences and contain multiple sequence variation in their sequence if they targeted to the same region together with altered stringency for PCR reaction by varying Tm will assure no-fail amplification of coding sequence in the primary PCR.

Example 4

Amplification of GAG Region from Noninfectious HIV RNA Template Using Multiplex PCR pBKBH10S plasmid DNA containing a noninfectious near full length HIV genome (NIH AIDS Research & Reference Reagent program Cat #194) was digested with XbaI and in vitro transcribed using T7 RNA polymerase. Briefly, 1 µg of plasmid DNA template was transcribed for 3 to 4 hours in a final reaction volume of 20 µl, followed by a 30 minute digestion with DNase Turbo to remove the DNA template. The RNA was purified on a RNeasy™ column (QIAGEN®), eluted in RNase-free water, aliquoted and stored in liquid nitrogen freezer.

100,000 copies of the resulting 9.2 kb in vitro transcribed RNA was used as a template for first strand cDNA synthesis reaction containing 1× Sensiscript™ buffer (QIAGEN®), 0.5 mM of each dNTP final concentration, 10 µM of random hexamers final concentration, 10 units of RNAse inhibitor (Ambion®) and Sensiscript™ RT (QIAGEN®). The 20 µL reaction was incubated at 37° C. for 1 hour. 10,000 copies of cDNA was taken into each primary PCR reaction containing 1×PFU ultra reaction buffer (Stratagene™), 0.2 mM of each dNTP (Stratagene™), 2.5 Units of Hot Start PfuUltra™ polymerase (Stratagene™), 0.4 µM each forward and reverse primers in primer groups FG1, FG2, RG1, RG2, RG3 and RG4 as described in Example 2 and in the forward and reverse primer groups indicated in FIG. 5. The final volume of the reaction was 25 µL. The reaction was denatured at 95° C. for 2 min and then taken through 40 cycles as follows: 95° C. for 30 sec, 54° C. for 30 sec, 72° C. for 3 min. A secondary PCR amplification was performed using the template from the primary amplification with nested Gag forward T7 primer group (GAG F T7; primers 19 and 20) and Gag reverse 64T primer group (GAG R 64T; primers 106, 107 and 108). After the final cycle, the reaction was allowed to complete at 72° C. for 10 min and then chilled to 4° C. 4 µL of each sample was loaded on nondenaturing 1% agarose gel. The results shown in FIG. 5 indicate that multiplex PCR using primer group combinations FG1:RG1, FG1:RG2, FG1:RG3, FG2:RG1, FG2:RG2 and FG2:RG3 allowed amplification of the gag coding sequence from the HIV sequence contained in pBKBH10S.

Example 5

Figure 6:
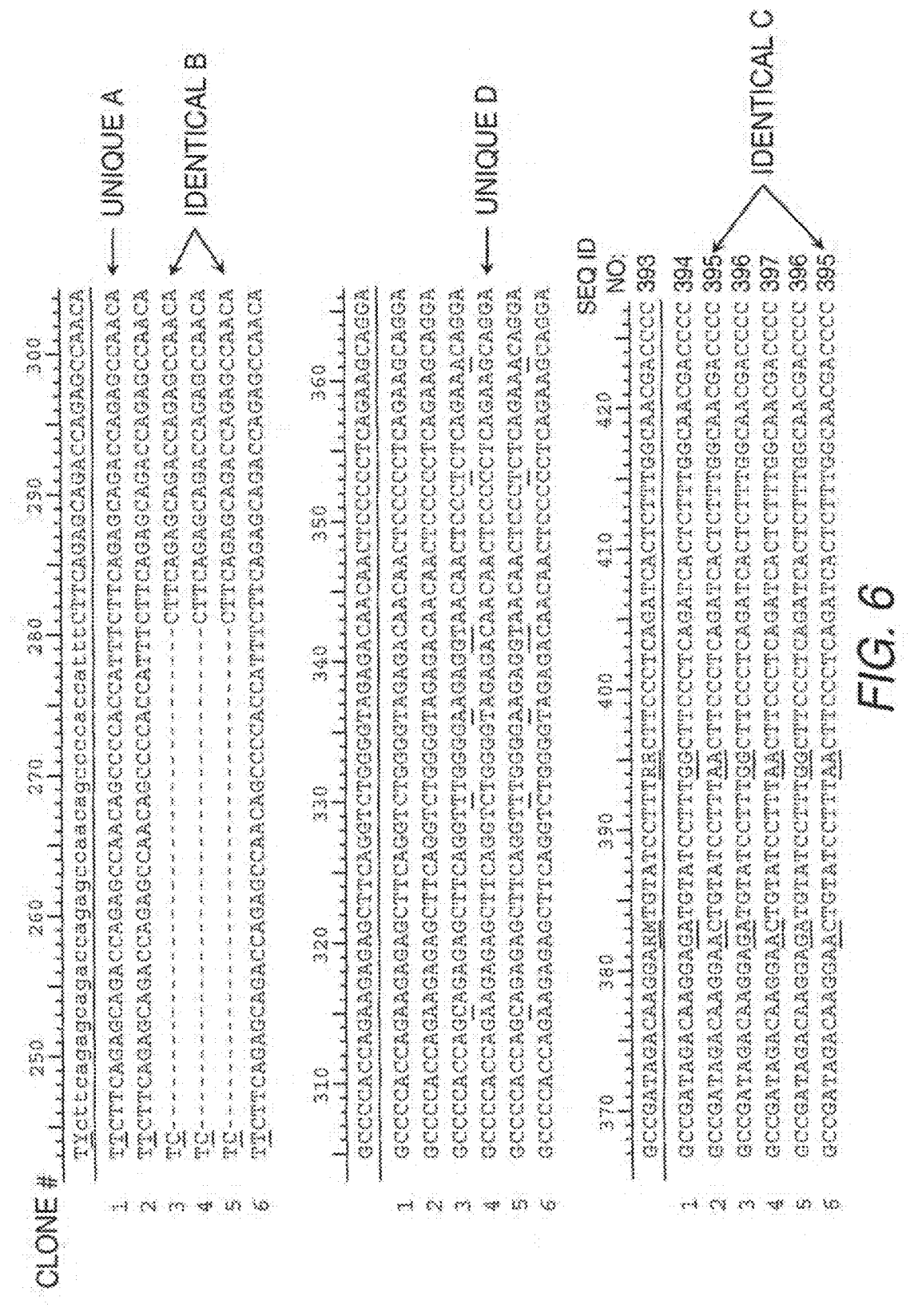

Multiple HIV Quasi-species can be Amplified Using the Primers of the Invention 2.5 ng of each pBKBH10S, p90CF402.1, p93BR029.4, and p93TH253.3 representing four HIV quasi-species were mixed in the primary PCR reaction containing 1×Pfu buffer, 0.2 mM of each dNTP, primer group FG2 and RG2 at 0.4 µM each final concentration and 1 unit of Pfu Hot start polymerase (Stratagene). The PCR reaction was commenced as described in Example 2. Upon completion, 1 µL of the primary PCR reaction was taken into a secondary 25 µL reaction containing 1×Pfu buffer, 0.2 mM of each dNTP, 0.4 µM final concentration of primer 19, 0.4 µM final concentration of primer 36 and 1 unit of Pfu hot start polymerase (Stratagene™). 2 µL of a secondary PCR product was subcloned using the Zero Blunt® TOPO® PCR cloning kit (Invitrogen™). Individual colonies were used to inoculate bacterial cultures. Plasmid DNA from those cultures was isolated using a QIAquick mini column (QIAGEN®) and analyzed via restriction digest using the EcoRI site present in regions of the cloning vector flanking the insert. Clones which contained an insert of approximately 1.65 kb were selected for further sequencing. Partial sequences obtained from this analysis were aligned using Lasergene software (DNAStar). The results of that alignment are shown in FIG. 6. Sequence analysis indicates that final mixture is composed of four distinct clones (A, B, C and D), indicating that the invention enables isolation of multiple HIV variants or quasi-species which may be present in a patient.

Example 6

Amplification of VPR, REV, and NEF Coding Regions from Non Infectious HIV RNA

First strand cDNA of near full length non-infectious HIV RNA was synthesized by RT-PCR of in vitro transcribed RNA from pBKBH10S as described in Example 4. The cDNA material synthesized from 10,000 copies of HIV RNA was taken into each primary PCR reaction containing multiplex primers for nef, vpr or rev. A secondary PCR reaction using the nested T7 and 64T primer groups shown below was performed using the product of the primary PCR reaction as the template. (VPR 64 T primers 231 through 235 correspond to SEQ ID NOs:269-273.) The reaction conditions were the same as described above except that the final primer concentration was 0.4 µM for nef, 0.2 µM rev and 0.6 µM for vpr. Primer groups consisted of the following primers:

VPR F 4995: Primer 44 and Primer 48; VPR F 5058: Primer 49; VPR R 5507: Primer 196 and Primer 197; VPR R 5419: Primer 198, Primer 199, and Primer 200; VPR F T7: Primer 57 and Primer 58; VPR R 64T (Full length): Primer 201, Primer 202, and Primer 203; VPR R 64T (Truncated): Primer 231, Primer 232, Primer 233, Primer 234, and Primer 235; REV F 7750: Primer 183 and Primer 184; REV F 7830: Primer 185, Primer 186, and Primer 187; REV F 5507: Primer 188 and Primer 189; REV R 8300: Primer 190, Primer 191, and Primer 192; REV F T7: Primer 87 and Primer 88; REV R 64T: Primer 193, Primer 194, and Primer 195; NEF F 8235: Primer 138, Primer 139, and Primer 204; NEF F 8343: Primer 140, Primer 141, Primer 142, and Primer 143; NEF R 9069: Primer 144, Primer 145, and Primer 146; NEF F T7: Primer 147 and Primer 148; NEF R 64T: Primer 149, Primer 150, and Primer 151.

Figure 7A:
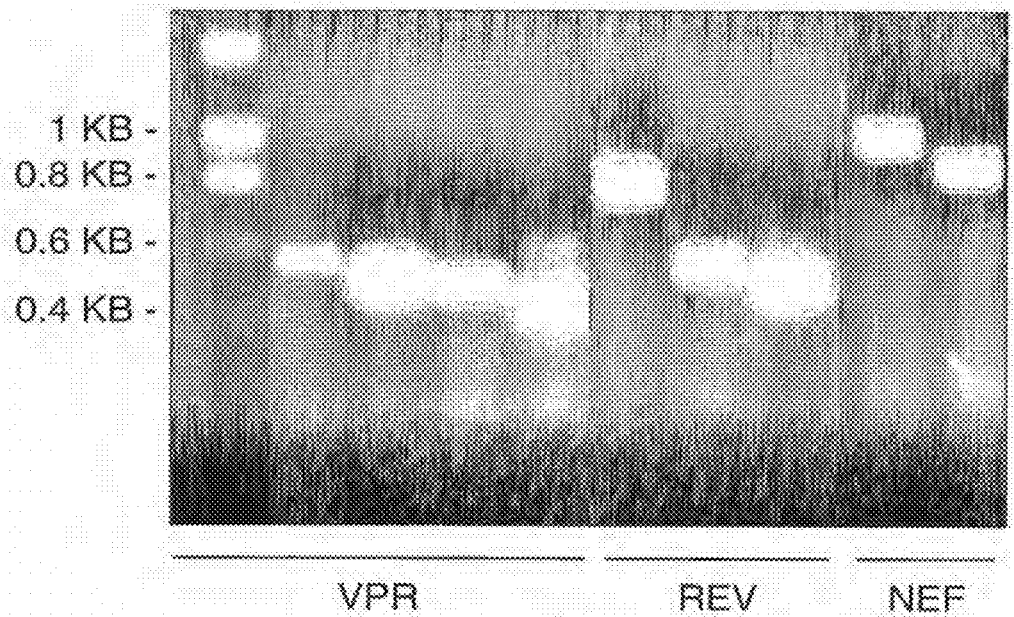
FIGS. 7A, 7B, and 7C show agarose gels resolving various RT-PCR products.

The forward and reverse primer combinations are shown in FIG. 7a. Each combination resulted in amplification.

Figure 7B:
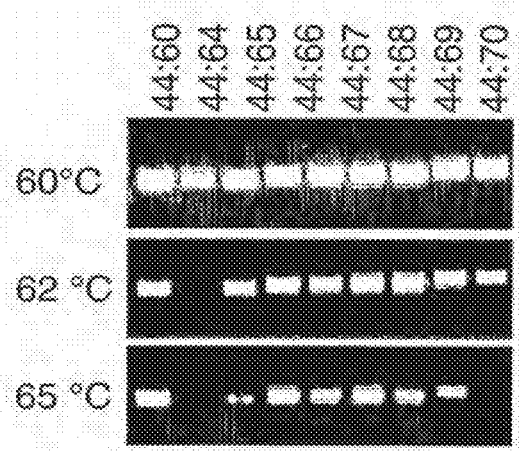

FIG. 7b demonstrates amplification of the vpr coding region from in vitro transcribed pBKBH10S RNA using forward vpr primer 44 combined in separate amplification reactions at various stringencies (annealing temperatures) with vpr reverse primers 60, 61, 64, 65, 66, 67, 68, 69 and 70. As expected, product yield was reduced with increased annealing temperature, and some primers failed to amplify at higher temperatures. Thus, lowering the PCR stringency conditions compensates for primer mismatch with the template.

Figure 7C:
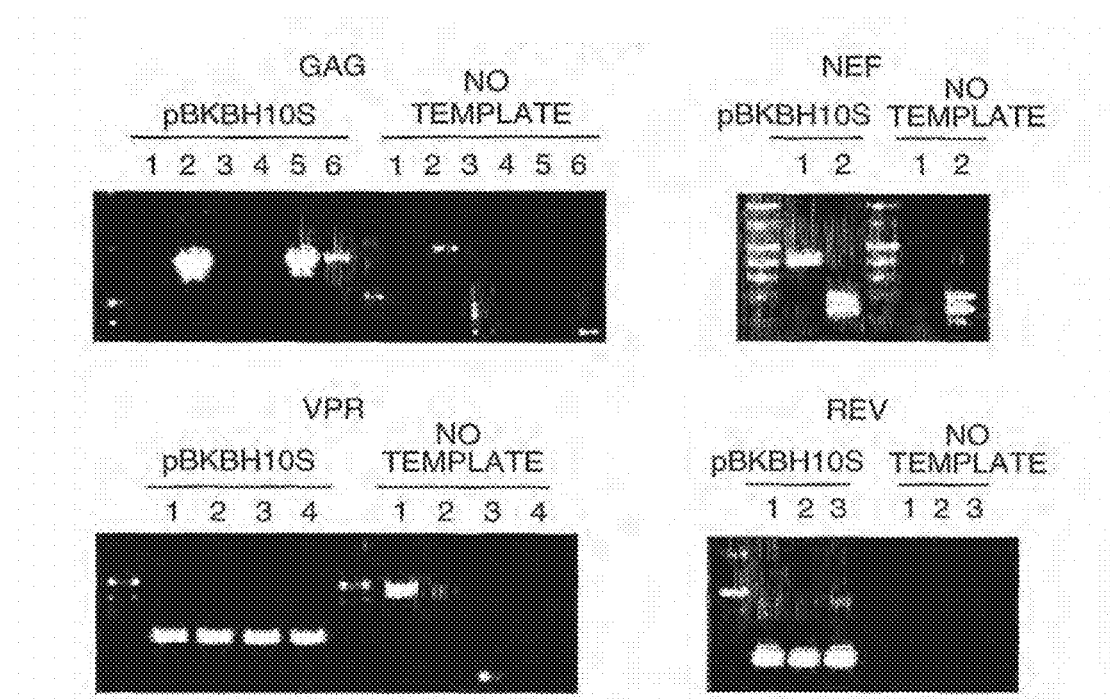

FIG. 7c demonstrates the amplification of nef from in vitro transcribed pBKBH10S RNA. The in vitro transcribed RNA was used as a template for first strand cDNA synthesis in a reaction containing oligo dT(20) primer, 10 units of Superscript™ III (Invitrogen™), 2 units RNAseout™ (Invitrogen™), 0.5 mM of each dNTP (Clontech™), 5 mM DTT and Superscript™ first strand buffer. The reaction was incubated at 55° C. for 1 hour.

A total volume of 2.5 µL of the first strand cDNA reaction was then taken into a primary PCR reaction containing 5 units of PFUultra™ HS, PFU buffer (Stratagene™), 0.8 mM of each dNTP (Clontech™), and 0.4 mM of Nef primer groups NEF F 8235 and NEF R 9069 (lane 1) or Nef primer groups NEF F 8343 and NEF R 9069 (lane 2), in a final reaction volume of 50 4. The PCR reaction was denatured at 95° C. for 2 minutes and then run for 40 cycles as follows: 95° C. for 30 seconds, 54° C. for 30 seconds, and 72° C. for 3 minutes. After the last cycle, extension was performed at 72° C. for 10 minutes and the reaction was stopped by chilling to 4° C. The PCR products were analyzed by agarose gel electrophoresis (FIG. 7c). The composition of the nef primer groups for the PCR reaction was as follows:

| NEF forward primer groups | NEF reverse primer group |
|---|---|
| NEF F 8235 (primers 138, 139 and 204) | NEF R 9069 (primers 144, 145 and 146) |
| NEF F 8343 (primers 140, 141, 142 and 143) | |

Example 7

The GAG Coding Region can be Amplified from HIV RNA Isolated from an Infected Patient's Plasma An HIV infected patient's plasma was used to isolate HIV RNA. After low speed centrifugation to clarify the plasma material it was diluted in lysis buffer and purified on a Nucleospin® purification column according to the manufacturer's instructions (Macherey-Nagel). RNA was eluted in nuclease free water and stored at −86° C. until further use. The RNA was taken into a 20 µL first strand cDNA synthesis reaction containing 1×Superscript™ first strand synthesis buffer (Invitrogen™), 5 mM DTT, 40 units of RNAse inhibitor, 0.5 mM of each dNTP, final 1 µM of primer GAG R1913 group and 400 units of Superscript III™ (Invitrogen). The reaction was incubated at 55° C. for 1 hour and then at 70° C. for 15 minutes to inactivate the enzyme. 2.5 ul of the RT reaction was taken into each PCR reaction using the same conditions as described above except the primers were used at 0.4 µM final concentration and elongation time during PCR cycles was 2 min. Composition of the primer groups for each PCR reaction was as follows:

GAG F 124: Primer 1; GAG F 304: Primer 4; GAG F 334: Primer 16 and Primer 17; GAG R 1881: Primer 32, Primer 33, and Primer 34; GAG R 1913: Primer 36, Primer 37, Primer 38, Primer 40, and Primer 41; GAG F T7: Primer 19 and Primer 20; GAG R 64T: Primer 106, Primer 107, and Primer 108.

Figure 8:
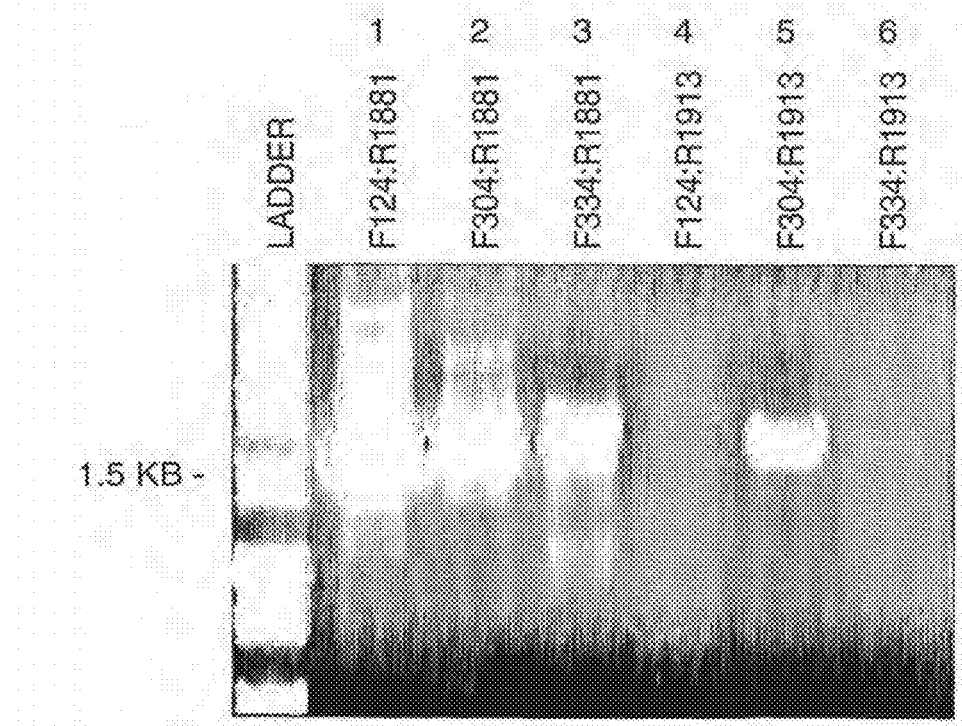
FIG. 8. Agarose gel resolution of the GAG coding region was amplified by RT-PCR from HIV RNA isolated from the plasma of an infected HIV patient. The primary PCR product was amplified in a secondary PCR reaction using nested primers. The primer groups used for amplification are indicated above each lane.

1 µL of the primary PCR amplicon was taken into a secondary PCR reaction containing 1× Pfu buffer, 0.2 mM each dNTP, 2.5 units of Pfu Hot Start Polymerase (Stratagene™) and 0.2 µM of each nested forward T7 promoter primer GAG F 334 (SEQ ID NO:19) and reverse 64T primer GAG R 1881 (SEQ ID NO:106). The results are shown in FIG. 8. Each of primer combinations F124:R1881, F304: R1881, F334:R1881, F304:R1913 and F334:R1913 amplified the gag coding region using a template HIV RNA isolated from the plasma of a chronically infected HIV patient.

Example 8

VPR and REV Coding Regions can be Amplified from HIV RNA Isolated from the Plasma of an Infected HIV Patient The HIV RNA was isolated from plasma as described in the example above. The RNA was taken into a 20 µL first strand cDNA synthesis reaction containing 1× first strand synthesis buffer (Invitrogen™), 5 mM DTT, 40 units of RNAse inhibitor, 0.5 mM of each dNTP, 1 µM of primer VPR R5507 or Rev R8300 groups (as indicated below) and 400 units of Superscript™ III. The reaction was incubated at 55° C. for 1 hour and then at 70° C. for 15 minutes to inactivate the enzyme. 2.5 ul of RT reaction was taken into each PCR reaction using the same conditions as described above except primers used at 0.6 µM final concentration for VPR and 0.2 µM for REV, and elongation time during PCR cycles was 2 min. Composition of the primer groups for each PCR reaction was as follows:

| VPR forward primers | VPR reverse primers |
| --- | --- |
| VPR F 4995 (primers 44 and 48) | VPR R 5507 (primers 196 and 197) |
| VPR F 5058 (primer 49) | VPR R 5419 (primers 198, 199 and 200) |
| VPR F T7 (primers 57 and 58) | VPR R 64T full length (primers 201, 202 and 203) |
| REV forward primers | REV reverse primers |
| REV F 7750 (primers 183 and 184) | REV R 8300 (primers 190, 191 and 192) |
| REV F 7830 (primers 185, 186 and 187) | |
| REV F 7911 (primers 188 and 189) | |
| REV F T7 (primers 87 and 88) | REV R 64T (primers 193, 194 and 195) |

Figure 9:
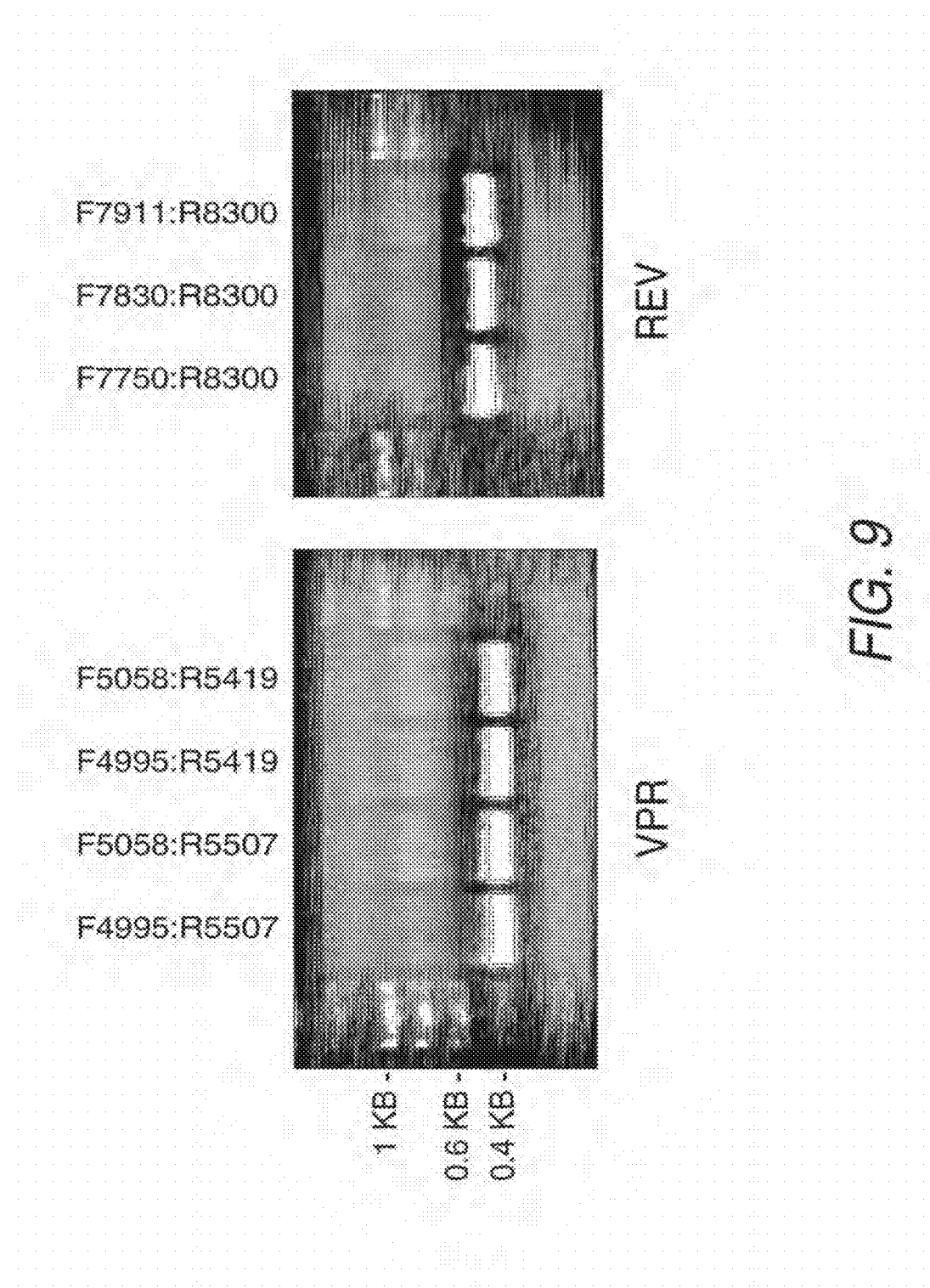
FIG. 9. Agarose gel resolution of VPR and REV coding regions amplified by RT-PCR from RNA isolated from the plasma of an infected HIV patient. The primary PCR product was amplified in a secondary PCR reaction using nested primers. The primer groups used for amplification are indicated above each lane.

1 µL of the primary PCR was taken into a secondary PCR containing 1× Pfu buffer, 0.2 mM each dNTP, 2.5 units of Pfu Hot Start Polymerase (Stratagene™) and primers containing 64T and T7 RNA polymerase binding sites as follows: 0.4 µM VPR primers VPR F 5090 and VPR R 5419 and 0.6 µM Rev primers REV F 7912 and REV R 8300. The results shown in FIG. 9 demonstrate that each of the following forward and reverse primer groups VPR F 4995: VPR R 5507, VPR F 5058:VPR R 5507, VPR F 4995:VPR R 5419 and VPR F 5058:VPR R 5419 can amplify vpr from HIV RNA obtained from a chronically infected patient. Similarly, each of the following forward and reverse primer groups REV F 7750:REV R 8300, REV F 7830:REV R 8300 and REV F 7911:REV R 8300 can amplify rev from HIV RNA obtained from a chronically infected patient.

Example 9

Amplification of the NEF Coding Region of HIV RNA from the Plasma of a Chronically Infected HIV Patient HIV RNA is isolated from plasma material as described above. The RNA is taken in the first strand cDNA synthesis 20 µL reaction containing 1× first strand synthesis buffer (Invitrogen™), 5 mM DTT, 40 units of RNAse inhibitor, 0.5 mM of each dNTP, 1 µM of primer NEF R 9069 and 400 units of Superscript™ III. The reaction is incubated at 55° C. for 1 hour and then at 70° C. for 15 minutes to inactivate the enzyme. 2.5 ul of RT reaction is taken into each PCR reaction using the same conditions as described above except primers used at 0.4 µM final concentration and elongation time during PCR cycles is 2 min. Composition of the nef primer groups for each PCR reaction are as follows:

| NEF forward primer groups | NEF reverse primer group |
| --- | --- |
| NEF F 8235 (primers 138, 139 and 204) | NEF R 9069 (primers 144, 145 and 146) |
| NEF F 8343 (primers 140, 141, 142 and 143) | |

1 µL of primary PCR is taken into secondary PCR containing 1× Pfu buffer, 0.2 mM each dNTP, 2.5 units of Pfu Hot Start Polymerase (Stratagene™) and 0.2 µM of each primer containing 64T and T7 RNA polymerase binding sites: primers NEF F 8343 and NEF R 9069.

Example 10

Figure 10A:
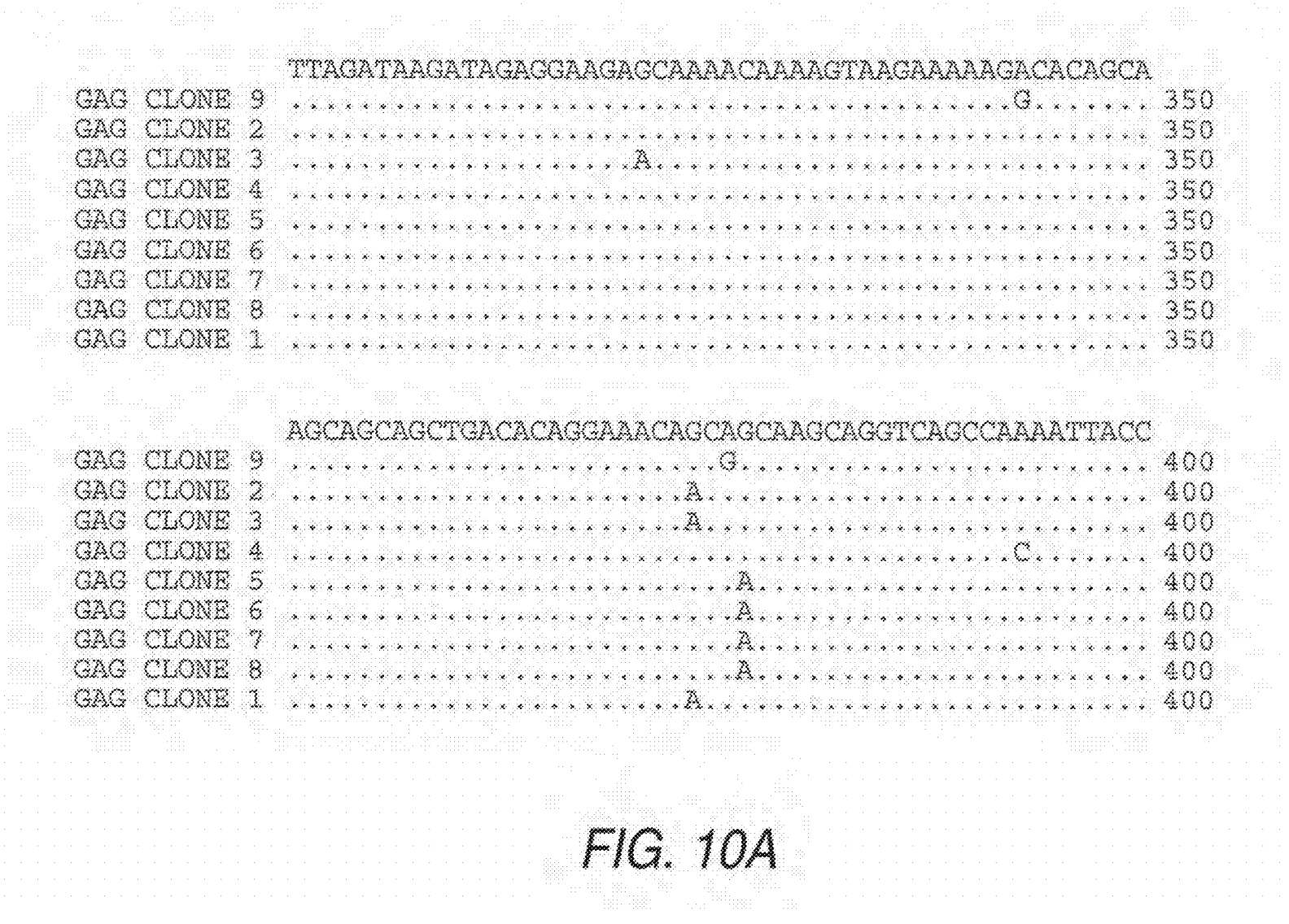
Figure 10B:
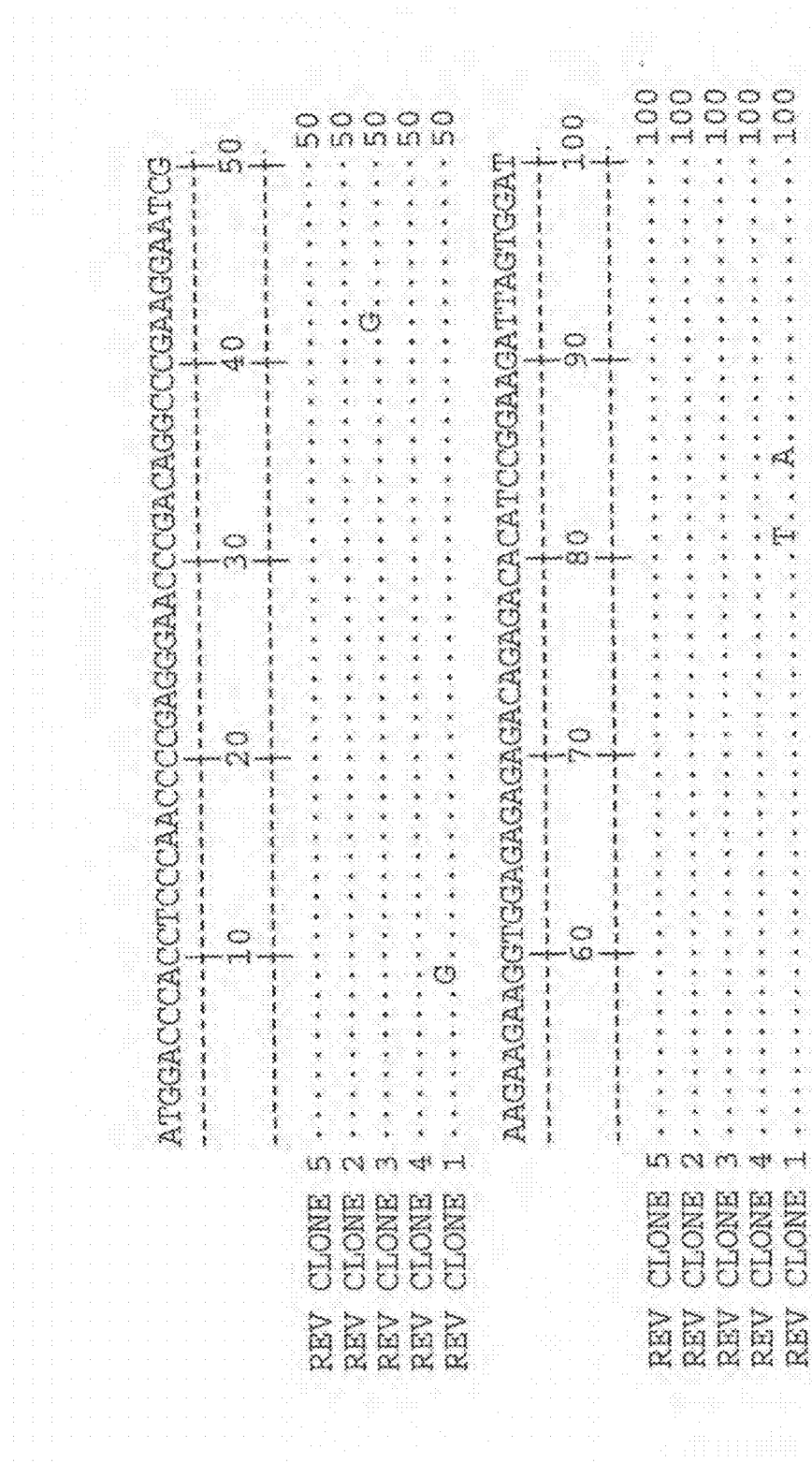
Figure 10C:
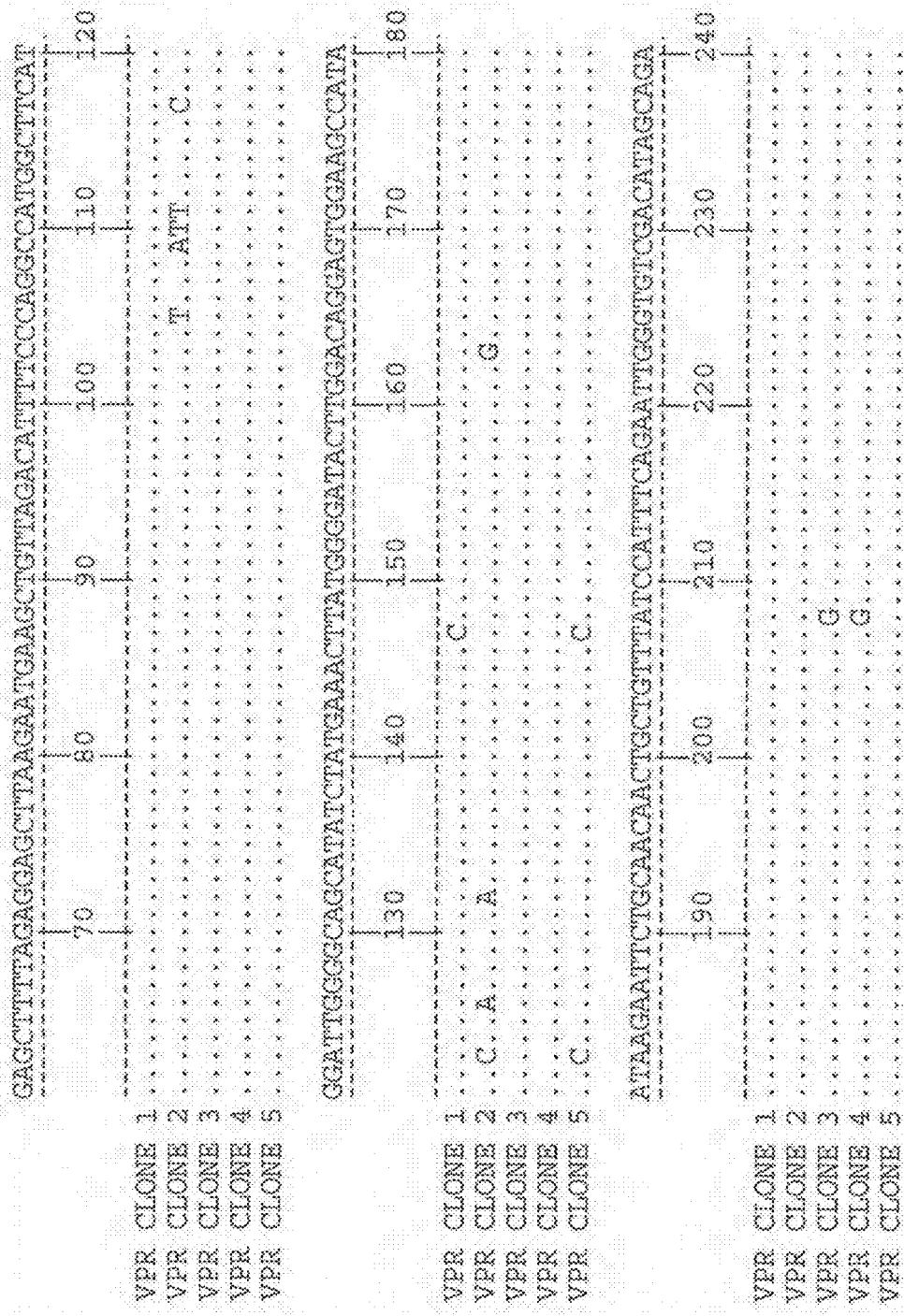

Multiple HIV Quasi-species can be Detected by Analysis of Gag, Rev and Vpr Coding Sequences Amplified from a Chronically Infected HIV Patient Gag coding regions were amplified from patient material as described above. The PCR fragments obtained in a secondary nested PCR using multiple primer combinations (lanes GAG F 124:GAG R 1881, GAG F 304:GAG R 1881, GAG F 334:GAG R 1881, GAG F 304:GAG R 1913 FIG. 8) were subcloned and sequenced as described above. Alignment of partial sequences is shown in FIG. 10C. Analysis indicates that at least 7 distinct GAG clones were recovered from this patient's plasma.

Alignment of coding sequences for Rev and VPR respectively. PCR products from secondary nested PCR reactions for Rev and VPR were subcloned and analyzed as described for GAG. Sequence analysis of rev clones (FIG. 10B) and vpr clones (FIG. 10C) demonstrate the amplification of multiple HIV quasi-species.

Example 11

Figure 11:
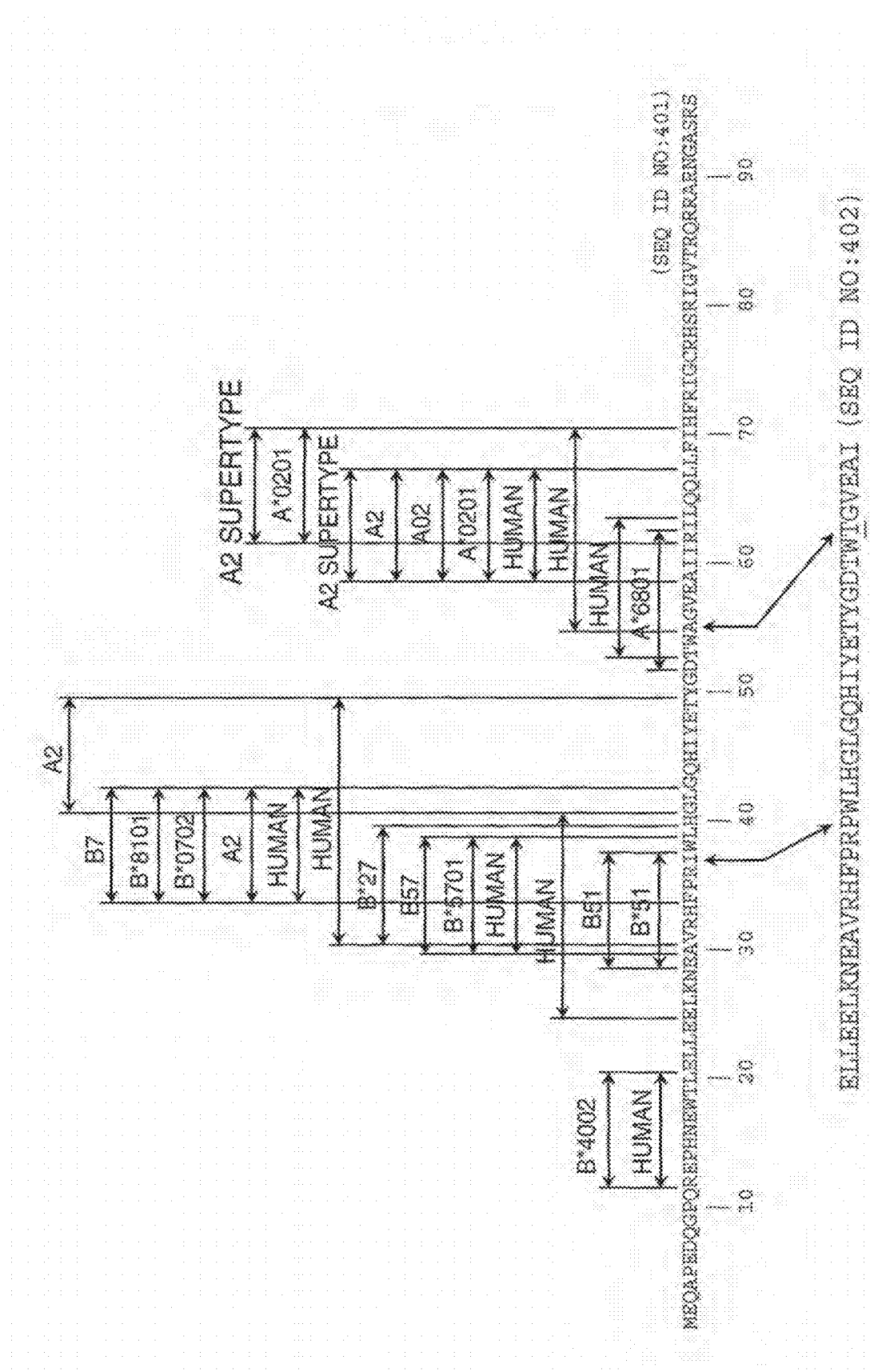
FIG. 11. Isolated mutations in VPR coding region affect protein sequence in HLA epitopes.

Isolated Quasi-species of VPR Contain Amino Acid Changes in Protein Sequence Regions of HLA Epitopes The predicted HLA epitope map for the VPR coding sequence (Los Alamos National Laboratory HIV Sequence Database) was compared to the deduced protein sequence of isolated VPR clones obtained by amplification of HIV RNA from the same chronically infected HIV patient. Two of identified amino acid substitutions affect protein composition in a CTL epitopes (FIG. 11).

Example 12

RNA Encoded GAG Expression in Dendritic Cells

Isolation of Human Dendritic Cells

A leukapheresis sample from a healthy volunteer was collected on a COBE Spectra (Gambro BCT) using the AutoPBSC procedure described by Lifeblood (Memphis, Tenn.). Peripheral blood mononuclear cells (PBMCs) were isolated for the leukapheresis sample using a Ficoll™ density gradient (Histopaque®-1007 Hybri-Max®, Sigma) and cultured for 1 to 2 hours in a plastic flask to provide for adherence monocytes (CD14$^+$). Non-adherent cells were discarded and the remaining monocytes were cultured in X-VIVO-15™ medium (Cambrex) for six days in the presence of granulocyte macrophage-colony stimulating factor (GM-CSF) and interleukin-4 (IL-4). The monocyte-derived cells progressively lost expression of CD14 and acquired CD80 expression consistent with phenotype of dendritic cells in an immature state.

Figure 12:
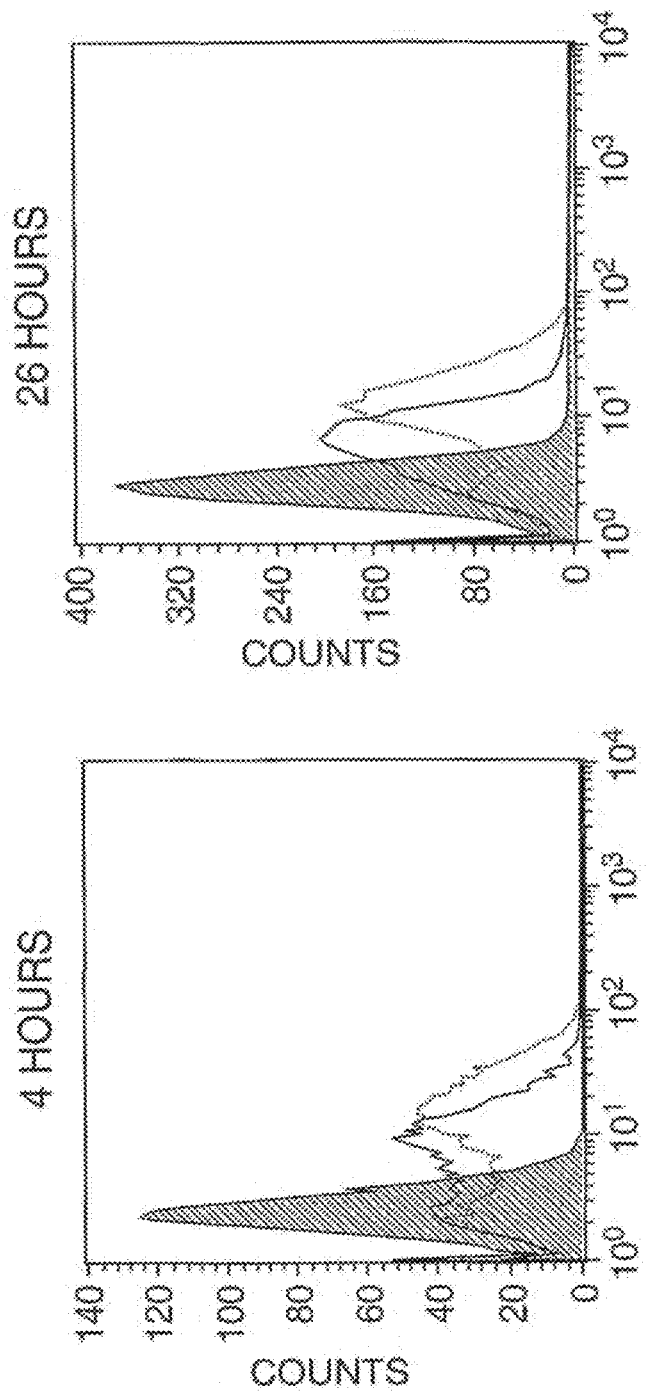
FIG. 12. Detection of gag expression in mature RNA transfected dendritic cells. FACS analysis of binding of an anti-gag monoclonal antibody on control (MART) cells (dashed line), gag transfected (solid line) or ARCA-gag transfected (grey line).

On day 7 the immature DC's were transfected by electroporation with 5 μg RNA/10$^6$ cells of either gag RNA modified with conventional m7G Cap analogue and (A)$_{64}$ tail or ARCA and (A)$_{64}$ tail. Specifically, immature dendritic cells are washed with phosphate buffered saline (PBS) to exchange buffer conditions and re-suspended in buffer. Dendritic cells are transfected with amplified pathogen RNA by electroporation. Electroporation is performed in 4 mm gap cuvettes containing 500 μL of the cell suspension containing 4×10$^7$ cells/mL at a pulse of 300V, 100Ω, and 150 μF. The cells are then cultured in medium containing the maturation cytokines, IL-1β, IL-6, tumor necrosis factor alpha (TNF-α), and dinoprostone (prostaglandin E$_2$), as well as GM-CSF and Interleukin-4 (IL-4) for 4 hours or 26 hours. Following the incubation to allow for protein expression, cells were harvested, fixed, permeabilized and stained with anti-GAG mouse monoclonal antibodies (NIH #4121) at 1:20 dilution. Antibody binding was detected with a donkey anti-mouse IgG-PE secondary antibody (Research Diagnostics, Inc., Flanders, N.J.). The cells were analyzed on Becton Dickinson FACSCalibur™ flow cytometer using the Cellquest™ analysis program. The results shown in FIG. 12 indicate that gag mRNA made according to the methods of the invention can is expressed in transfected DC at 4 and 26 hours post transfection.

Example 13

Time Course of GAG Protein Expression in HeLa Cells

Figure 13:
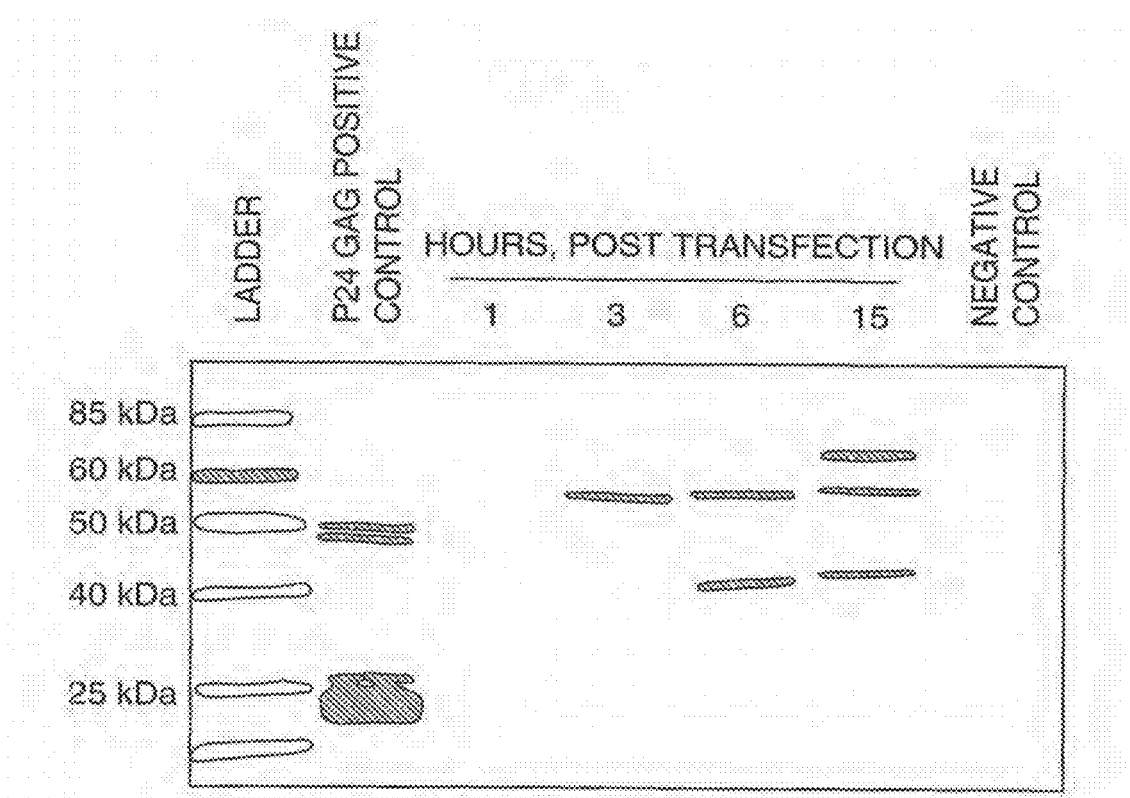
FIG. 13. Time course of GAG protein expression in HeLa Cells. Western Blot analysis of GAG protein expression in HeLa cells. Lysates from untransfected (negative Control Lane) or HeLa Cells were transfected with ARCA (A)64 tail RNA and harvested for analysis at indicated periods of time. P24 positive control lane contains 25 μg of p24 recombinant purified gag protein.

5×10$^5$ HeLa cells were transfected using Transmessenger™ (QIAGEN®) reagent with 2 μg of ARCA and (A)$_{64}$ tail modified RNA for GAG amplified from plasmid pBKBH10S. Negative control cells were treated the same way but no RNA was added during transfection. Following transfection cells were placed back into media for indicated periods of time and harvested for western blot analysis. Cells were lysed in an isotonic protein extraction buffer (0.01% triton X-100, 150 mM NaCl, 100 mM Tris pH 7.6, 5 mM EDTA). 25 μg of protein lysate from each condition was resolved using SDS-PAGE gel and transferred onto PVDF membrane followed by incubation with mouse monoclonal anti-GAG antibodies (NIH AIDS Research & Reference Reagent program Cat #4121) at a 1:40 dilution. Binding of antibodies was visualized by incubation with secondary goat anti-mouse antibodies (Santa Cruz Cat #sc-2055) and ECL™ plus reagent (Amersham) following manufacturer's recommendations. 200 ng recombinant purified GAG p24 (Immunodiagnostic) was used as a positive control. The results shown in FIG. 13 indicate that maximum protein expression in HeLa cells is observed between 6 and 15 hrs post-transfection.

Example 14

REV Expression in Dendritic Cells

Figure 14:
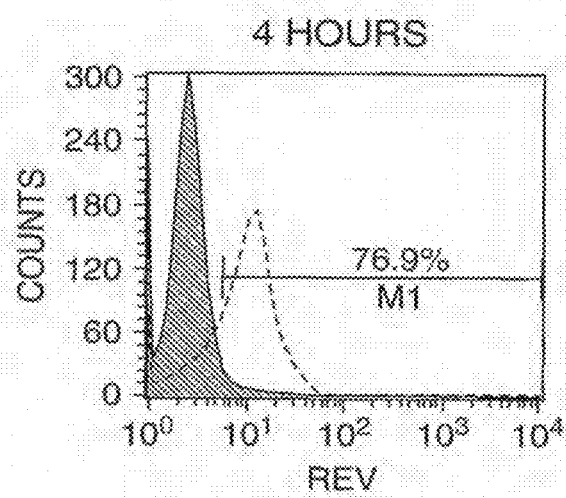
FIG. 14. Detection of REV expression in mature RNA transfected dendritic cells. FACS analysis of binding of an anti-rev polyclonal antibody on control (MART) cells (filled), rev-transfected (dashed line) dendritic cells.

Dendritic cells were harvested on day 6 and transfected with 5 μg RNA/10$^6$ cells of MART or ARCA (A)$_{64}$ tail REV RNA and placed back in culture with fresh cytokines and maturation cocktail. At 4 hours transfected cells were fixed, permeabilized and stained with an anti-REV sheep polyclonal antibody at (Novus Biologicals, cat.# ab9513) at a 1/1000 dilution. Antibody binding was detected with a donkey anti-sheep IgG-PE secondary antibody (United States Biologicals, Swampscott, Mass.). The cells were analyzed on a Becton-Dickinson FACSCalibur™ flow cytometer using the Cellquest™ analysis program. FIG. 14 shows expression of rev mRNA in DC at 4 hours post-transfection.

Example 15

REV Protein Expression Time Course in HeLa Cells

Figure 15:
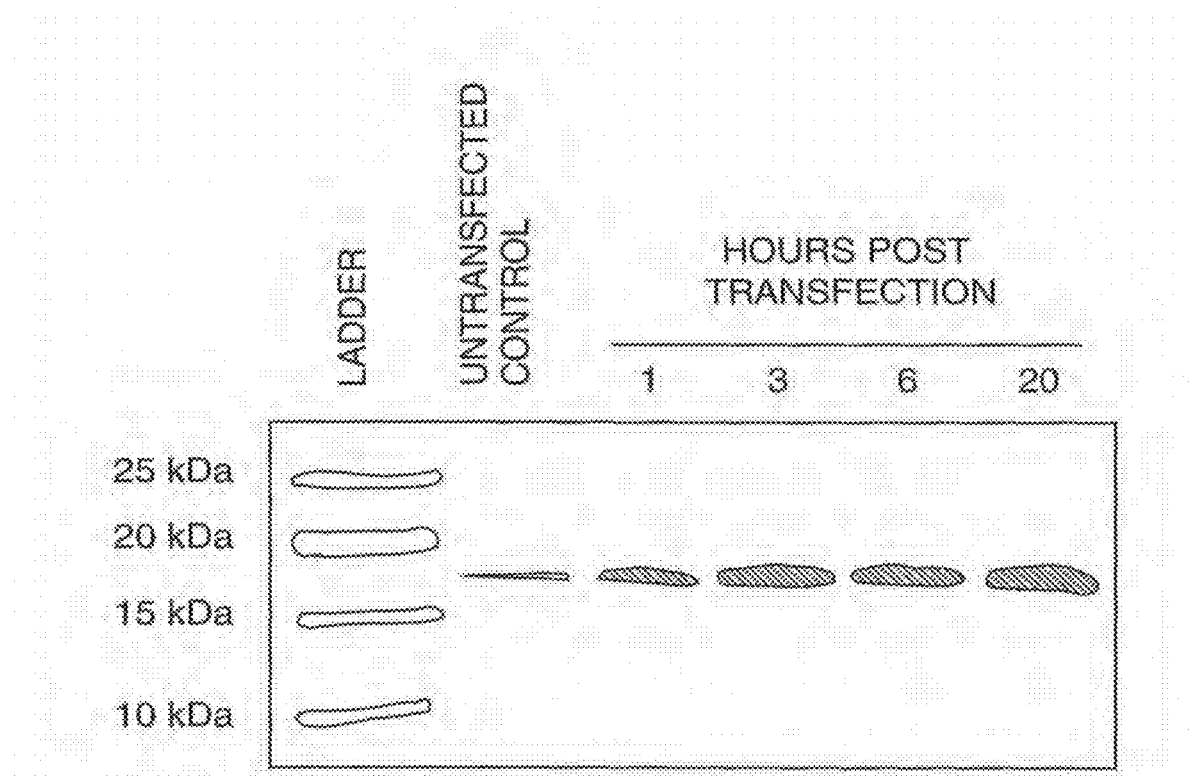
FIG. 15. REV protein expression time course in HeLa Cells. Western Blot analysis of lysates from untransfected or transfected HELA cells transfected with ARCA $A_{64}$ tail REV. The time of harvest is indicated above the lanes.

HeLa cells were transfected with ARCA and (A)$_{64}$ tail modified RNA as described above for western blot analysis. 40 μg of protein lysates were resolved on SDS gel electrophoresis and transferred to a PVDF membrane. Protein was detected by incubation with polyclonal sheep anti-REV antibodies (Novus Biologicals Cat # ab9513) at a 1:1500 dilution. Binding of antibodies was visualized by incubation with secondary anti-sheep antibodies (Santa Cruz Cat #sc-2701) followed by developing with ECL plus kit (Amersham). The results of shown in FIG. 15 and from another independent experiment indicate that maximum level of expression of REV protein is between 6 and 20 hours post-transfection.

Example 16

Nef Expression in Dendritic Cells

Figure 16:
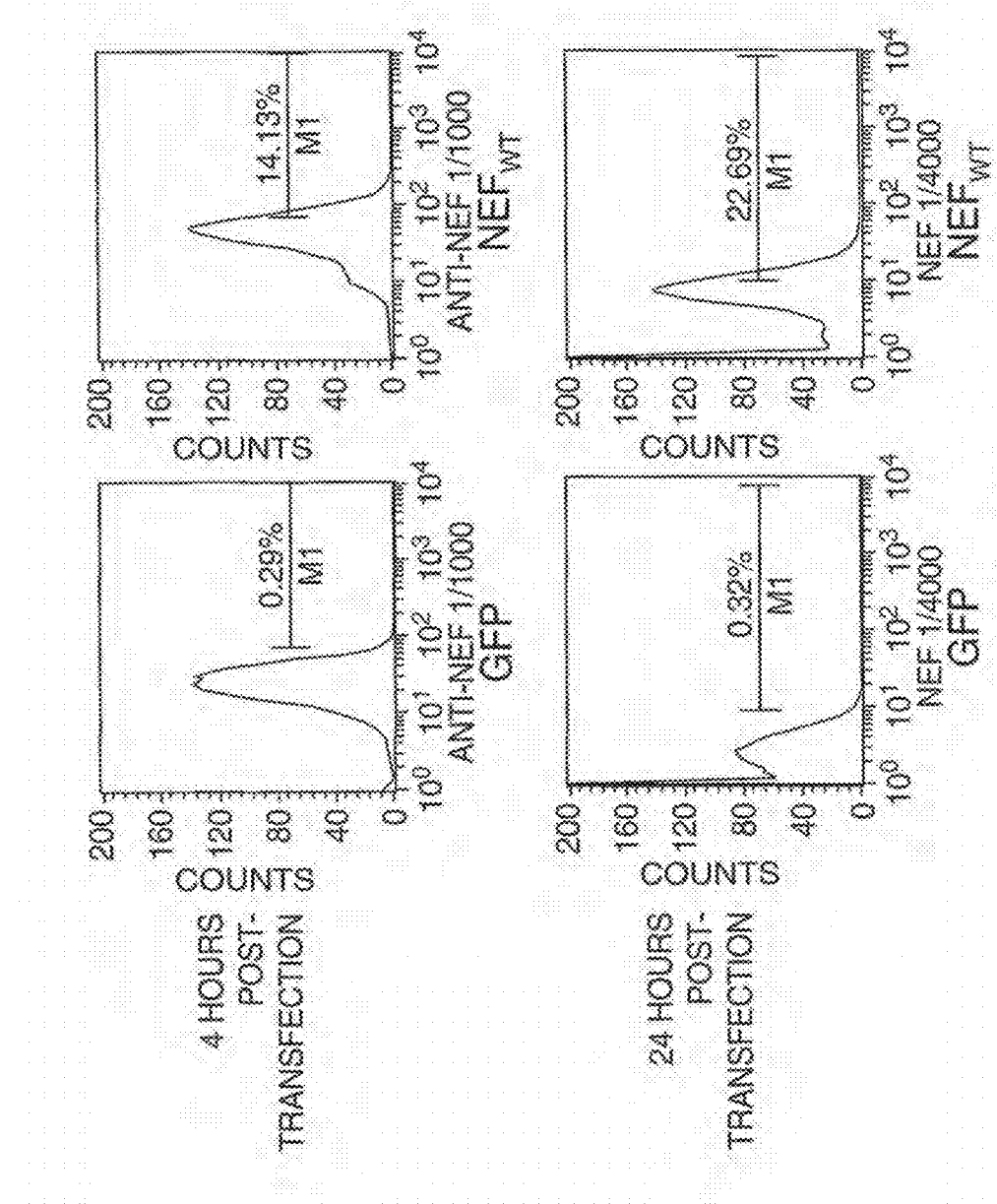
FIG. 16. FACS analysis of NEF expression in mature RNA transfected dendritic cells.

Dendritic cells were harvested on day 6 and electroporated with 4 μg RNA/10$^6$ cells of GFP or ARCA (A)$_{64}$ tail NEF RNA and placed back in culture with fresh cytokines and maturation cocktail. At 4 or 24 hours transfected cells were fixed, permeabilized and stained with an anti-Nef Rabbit polyclonal antibody at (courtesy of Dr. R. Sekaly) at a 1/1000 (4 hrs.) or 1/4000 (24 hrs.) dilution. Antibody binding was detected with a goat anti-rabbit secondary antibody (Southern Biotechnology Associates, Birmingham, Ala.). The cells were analyzed on a Becton-Dickinson FACSCalibur™ flow cytometer using the Cellquest™ analysis program. The results shown in FIG. 16 indicate that nef is expressed at both 4 and 24 hours post-transfection.

Example 17

Successful Amplification of Multiple HIV RNA Antigen Quasispecies from Patients with HIV Infection and Expression in Dendritic Cells To validate our novel multiplex RT-PCR procedure we amplified the four antigens from plasma of patients with HIV infection. RNA extracted from the archived frozen plasma of three patients with HIV titers of 250,000, 146,148, and 3,221,835 copies/mL, respectively, was used in RT-PCR for each antigen. The following T7 promoter and 64 dT primer groups were used for nested PCR.

| GAG forward T7 primer group | GAG reverse 64 dT primer group |
|---|---|
| Primers 19 and 20 | Primers 106, 107 and 108 |
| VPR forward T7 primer group | VPR reverse 64 dT primer group |
| Primers 57 and 58 | Primers 201, 202 and 203 |
| REV forward T7primer group | REV reverse 64 dT primer group |
| Primers 87 and 88 | Primers 193, 194 and 195 |
| NEF forward T7 primer group | NEF reverse 64 dT primer group |
| Primers 147 and 148 | Primers 149, 150 and 151 |

Figures 17A, 17B:
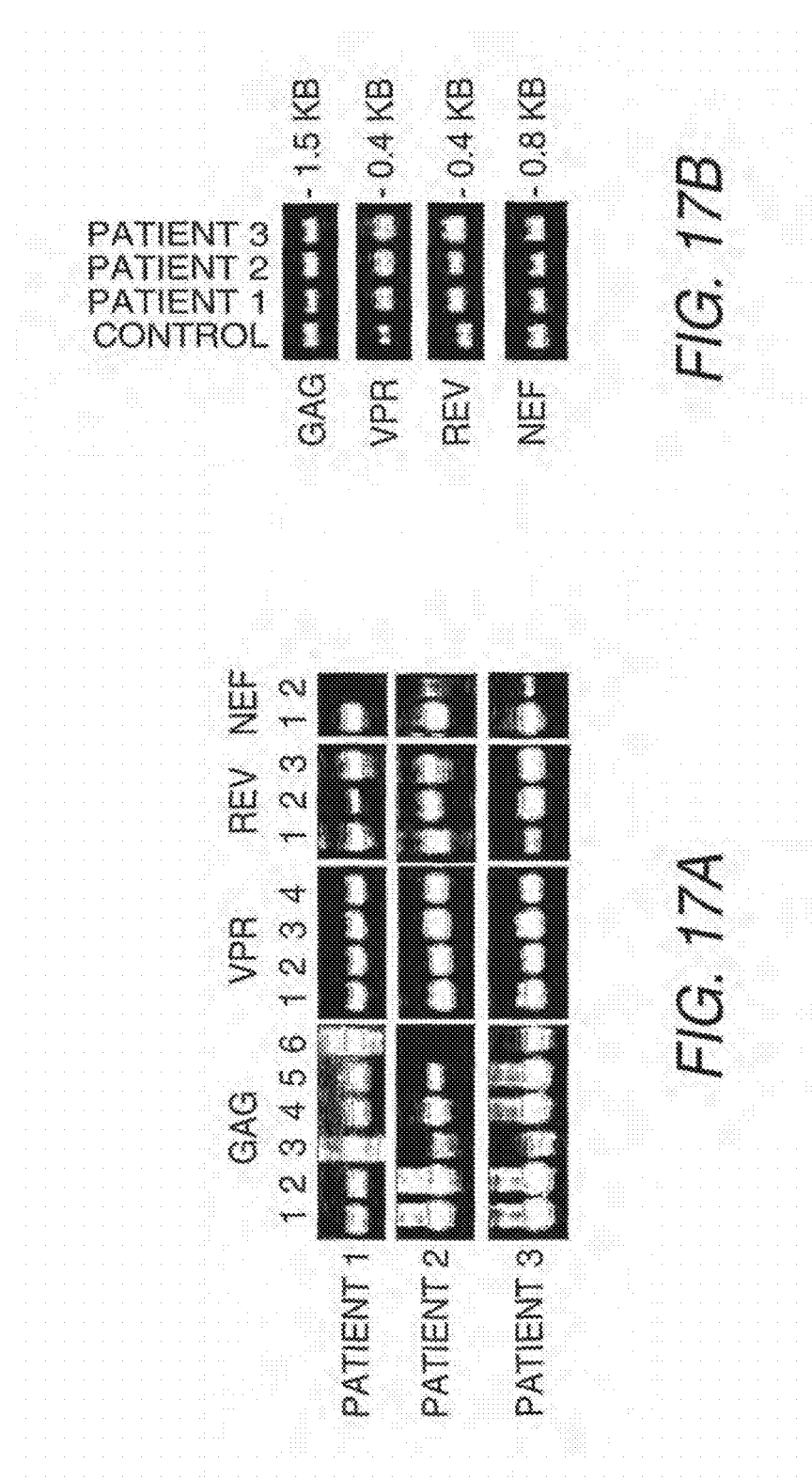
FIG. 17A shows an agarose gel resolution of gag, vpr, rev and nef regions from 3 HIV patients. The primer groups used in each lane are as follows:
Gag: lane 1 F124:R1881; Lane 2 F304:R1881; Lane 3 F334:R1881; Lane 4 F124:R1913;
Lane 5 F304:R1913; Lane 6 F334:R1913.
Vpr Lane 1 F4995:R5507, Lane 2 F5058:R5507; Lane 3 F4995:R5419; Lane 4 F5058:R5419.
Rev Lane 1 F7750:R8300; Lane 2 F7830:R8300; lane 3 F7911:R8300.
Nef Lane 1 F8235:R9069; Lane 2 F8343:R9069. See Examples 6, 7 and 8 for the composition of each primer group.
FIG. 17B shows an agarose gel resolution of gag, vpr, rev and nef in vitro transcripts prepared from amplified HIV RNA.

FIG. 17A demonstrates the successful amplification of all four antigens in all three patients with HIV infection.

Products from the nested round of PCR were transcribed in vitro to generate RNA, and all four antigens were transcribed successfully (FIG. 17b). This indicated that all PCR fragments were modified successfully with the T7 promoter during the nested round of PCR. Independent confirmation of successful modification with the T7 RNA polymerase binding site, together with the polyT 64 stretch, as well as confirmation of sequence identity, was provided by analysis of sequence data obtained from subcloned secondary PCR fragments.

Our strategy of using groups of forward and reverse primers was designed to amplify multiple HIV quasispecies unique to each patient with HIV infection. Because of the variation of HIV antigen quasispecies between individual patients, it is to be expected that different primer groups would anneal to different quasispecies sequences, such that amplification would occur in a pattern that is unique to each patient. This is demonstrated in FIG. 17a for amplification of Gag in three patients with HIV infection: the primer group in lane 3 did not produce any PCR product for Patient 1 but resulted in a clean product for Patient 2, whereas the group of primers in lane 6 failed to amplify material from Patient 2, but successfully amplified the RNA of Patient 1 and Patient 3.

Figure 18A:
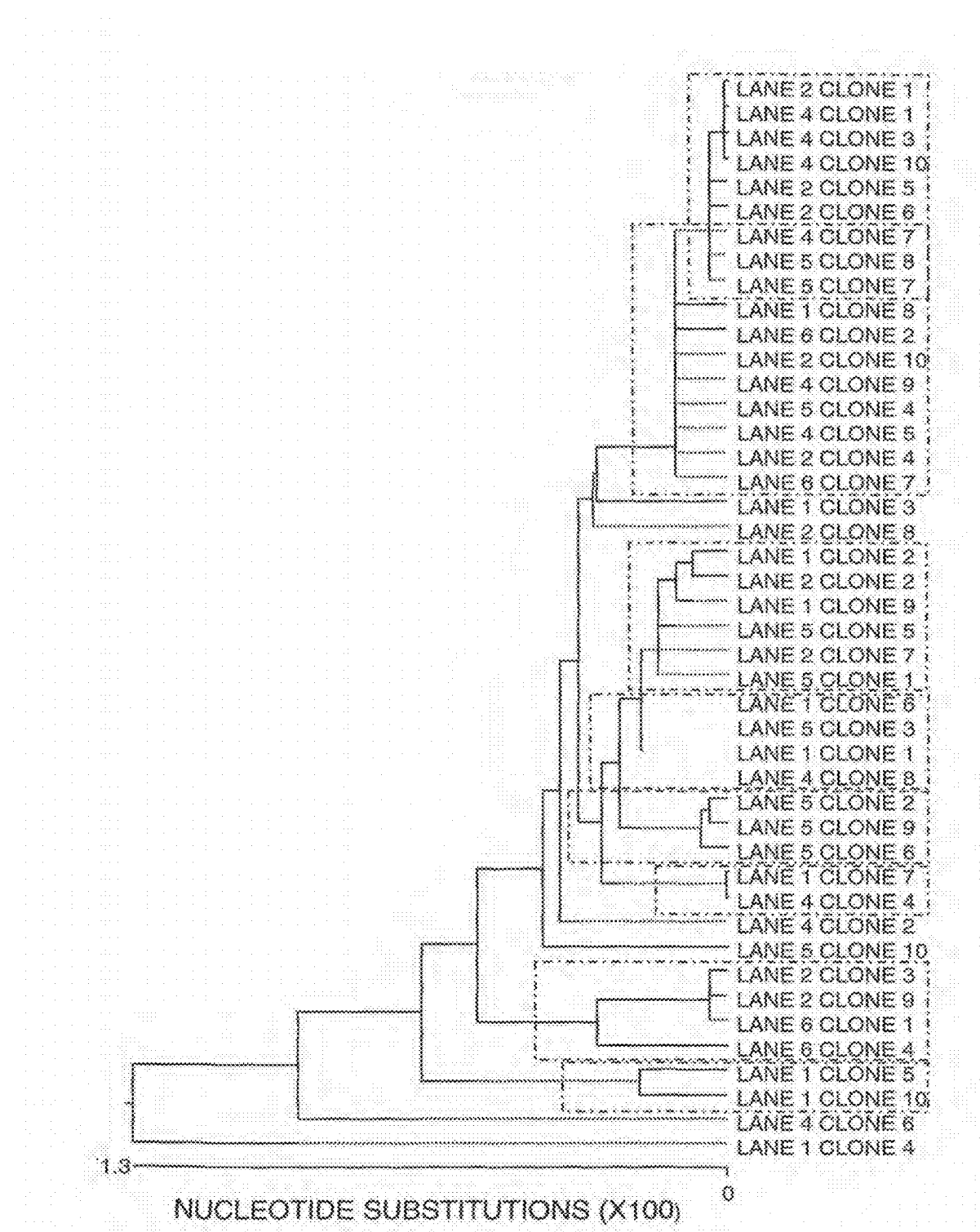
FIG. 18A shows a phylogenetic tree of HIV gag quasispecies amplified from Patient 3.

To confirm that distinct primer groups capture distinct HIV quasispecies, we sequenced and analyzed full length PCR Gag clones obtained from Patient 3, who was highly viremic (HIV titer of 3,221,835 copies/mL). In this experiment distinct bands of expected size for Gag were obtained in lanes 1, 2, 4, 5, and 6 (FIG. 17a). The secondary PCR fragments were cloned, screened for the presence of an insert and sequenced. PCR products amplified by distinct primer groups combination were cloned separately, with a total of 10 positive clones per group of primers. Nucleotide sequence analysis was performed using Lasergene software (DNAStar), the Los Alamos HIV Sequence Database, and BLAST analysis. Phylogenetic relationships of newly amplified nucleotide sequences were estimated by comparison with corresponding sequences with those previously reported. Consensus sequences of common HIV clades were obtained from the Los Alamos HIV Sequence Database and used as a reference. Nucleotide sequences were aligned using Clustal V software. Phylogenetic trees were constructed using the MegAlign module of the Lasergene software. Analysis of the phylogenetic relationship of distinct Gag clones from patient 3 revealed a broad diversity of captured quasispecies (FIG. 18A). More important, and as predicted, some quasispecies were captured by amplification using certain groups of primers and some were not.

Figure 18C:
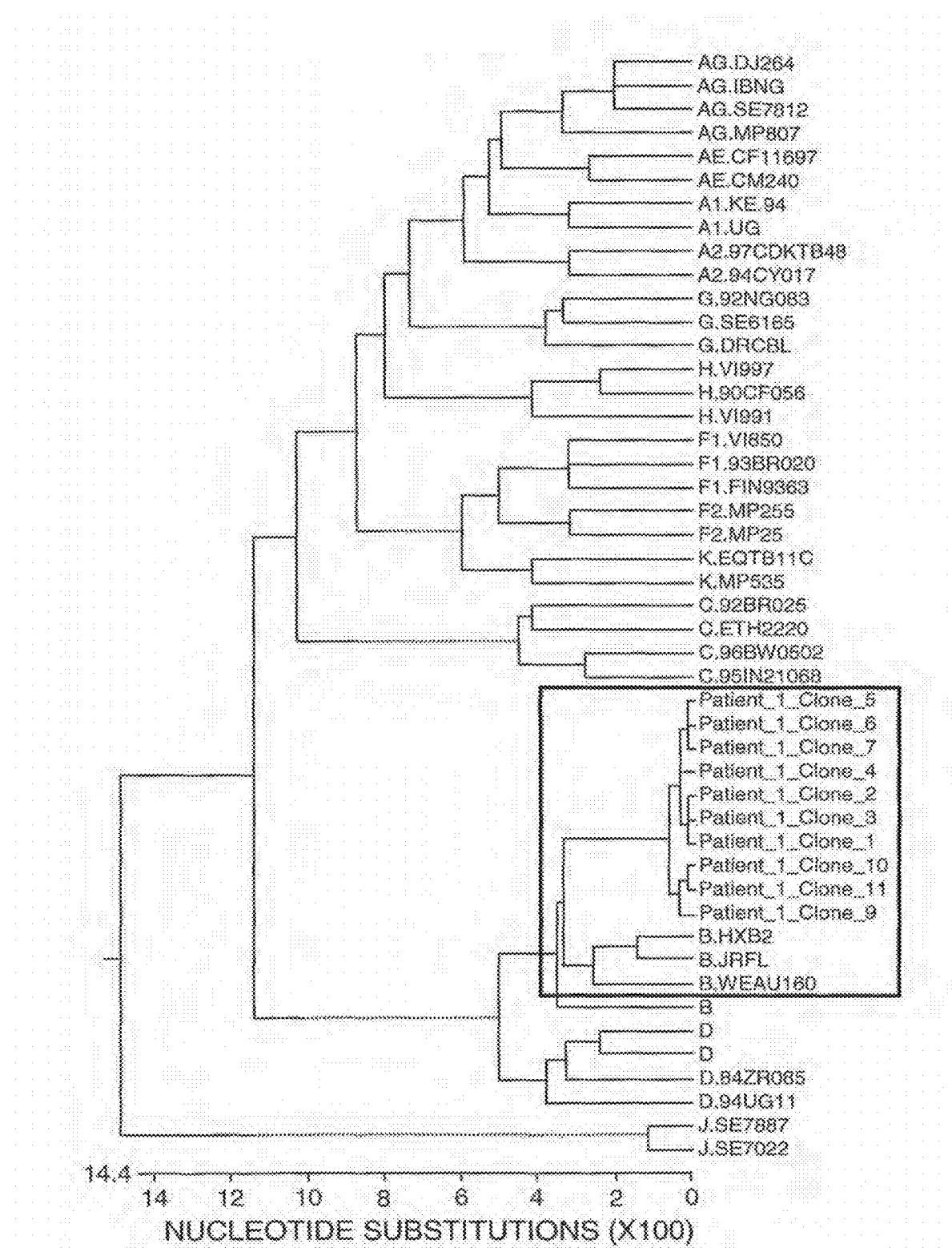
FIG. 18C shows a phylogenetic tree of HIV gag quasispecies amplified from Patient 1.
Figure 18D:
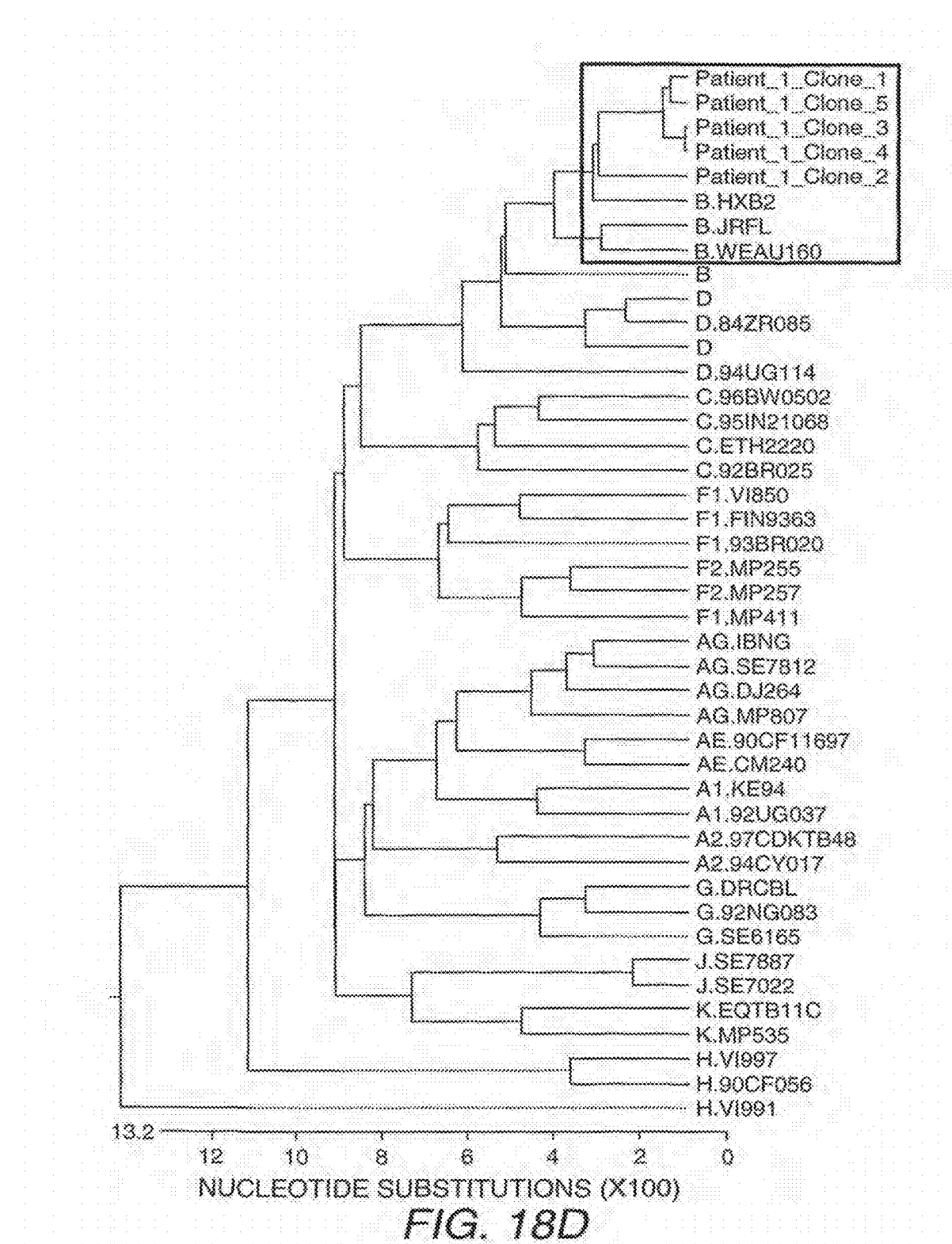
FIG. 18D shows a phylogenetic tree of HIV rev quasispecies amplified from Patient 1.
Figure 18E:
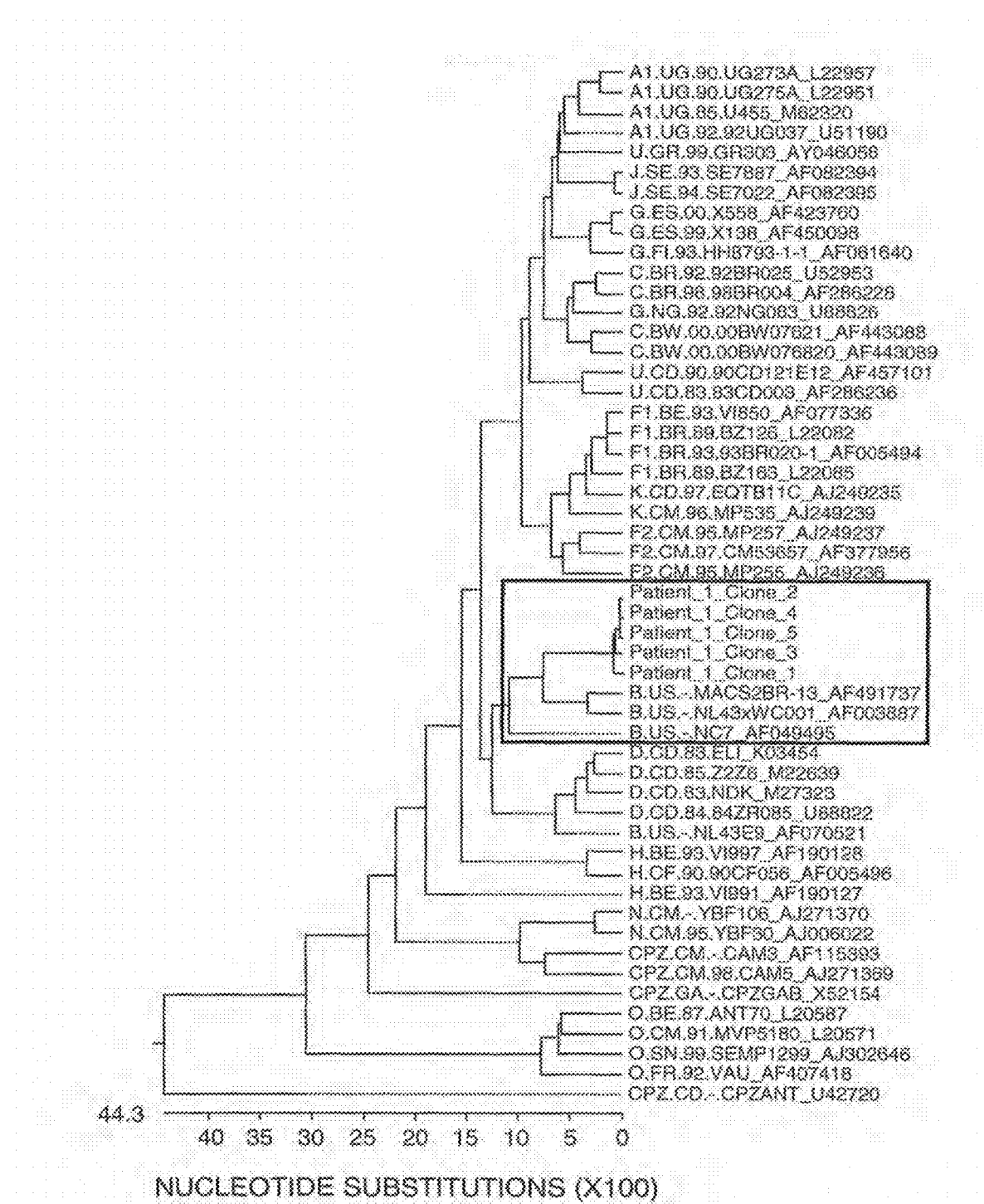
FIG. 18E shows a phylogenetic tree of HIV vpr quasispecies amplified from Patient 1.
Figure 19:
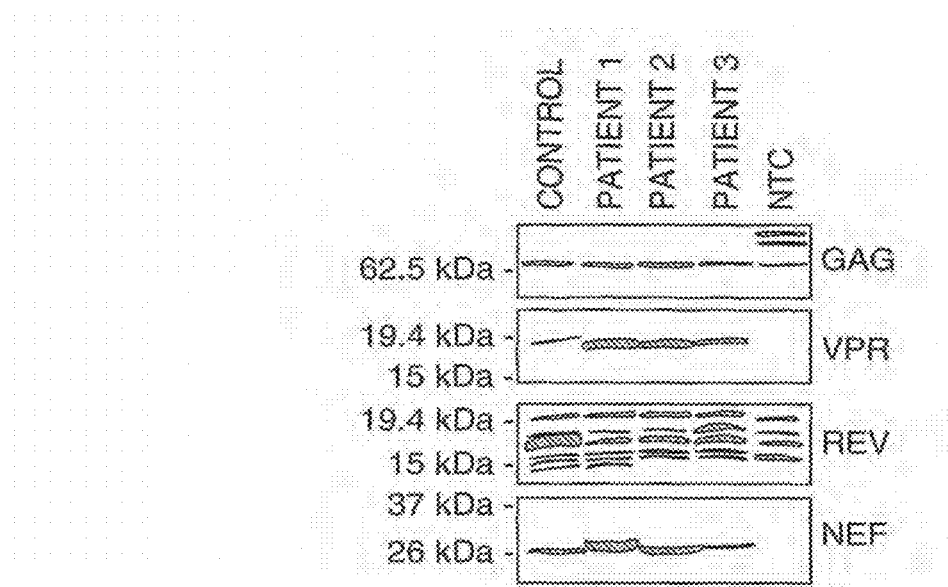
FIG. 19. Polyacrylamide gel resolution of gag, vpr, rev and nef proteins prepared by in vitro translation of HIV RNA amplified from three patients. The control lane shows the gag protein prepared by in vitro translation of the Gag RNA amplified from control plasmid pBKBH10S.

A potentially pivotal advantage of our vaccine technology antigens would be the amplification and antigen presentation of quasispecies antigens representing HIV escape mutations which evolve under host CTL to induce resistance to the initial immune response. In Patient 1, we identified sequence mutations in the Gag quasispecies that might result in amino acid substitutions in the Gag p17 protein, then compared these mutated amino acid sequences to predicted HLA epitopes of using the Los Alamos Molecular Immunology database. These data, summarized in FIG. 18b, indicated that some captured mutations resulted in amino acid transitions located in the relevant position of an HLA epitope associated with antigen presentation. This could reflect the evolution of HIV quasispecies that are resistant to CTL pressure. By contrast, new and relevant immunogenic epitopes that arise as a result of HIV mutations would also be captured using our newly developed amplification protocol. The phylogenetic relationships of full length gag, rev and vpr clones amplified for the plasma of HIV infected Patient 1 are shown in FIGS. 18C, 18D and 18E We have confirmed the translation of RNA and expression of HIV Gag, Vpr, Rev and Nef antigen proteins in transfected eukaryotic cells, using RNA isolated and amplified from at least three patients with HIV infection. Capped and polyadenylated RNA amplified from patients with HIV infection for Gag was translated in vitro in the presence of $^{35}S$ methionine. Proteins were resolved by electrophoresis using a denaturing gel, transferred to PVDF and exposed. Amplified RNA for Vpr was transfected into HeLa cells, and amplified RNA for Rev and Nef was transfected into dendritic cells. Twelve to fifteen hours after transfection, cells were harvested and lysed. Whole cell lysates were resolved on SDS-PAGE gels, transferred onto PVDF and probed using specific antibodies for each antigen. Rev protein was detected using polyclonal sheep anti-Rev antibody (Novus Biologicals), Vpr protein was detected using anti anti-HIV-$1_{NL4-3}$Vpr antiserum (1-46) (NIH AIDS Research & Reference Reagent program) and Nef protein was detected using anti-Nef Rabbit polyclonal antibody (courtesy of Dr. R. Sekaly). These results are summarized in FIG. 19, which shows that proteins with the appropriate molecular weight (56 kDa) were detected in an in vitro translation reaction using Gag RNA as a template. The control lane contains lysates obtained from cells transfected with the corresponding antigen RNA amplified from non-infectious HIV clones. The NTC lane contained lysates obtained from transfected cells or the in vitro translation mix, in the absence of any RNA. Molecular weights of the molecular markers are indicated on the left. The identity of the expressed Gag protein was confirmed by Western Blot using Gag RNA amplified form the control plasmid pBKBH10S. Gag RNA from Patient 1 and Patient 3 was translated in HeLa cell extracts. Other antigens were detected in cell lysates from dendritic or HeLa cells transfected with RNA encoding Vpr (10.5 kDa), Rev (11.4 kDa), and Nef (23.6 kDa). In Patient 1, the specific band recognized with anti-Nef antibody was diffuse, with some material migrating at higher molecular weight. One possible explanation is that more than one quasispecies of Nef, or a mutation of Nef with a post-translational modification was present, which gave rise to different proteins migrating according to variations in molecular weight. A similar observation was made in lysates obtained from DCs transfected with Rev RNA from Patient 3. The identity of the expressed Gag protein was confirmed by FACS analysis of DCs transfected with Gag RNA from Patient 1 using anti-Gag monoclonal antibody (Beckman Coulter). Intracellular FACS staining of DCs harvested 4 hours post-electroporation positively stained cells. Binding of antibodies in cell transfected with RNA modified with ARCA analogue was higher than those transfected with RNA modified with conventional m7G cap analogue. Equal mass of either m7G capped RNA or ARCA modified RNA were used, indicating that ARCA-capped mRNA yields higher protein expression compared to that of m7G capped gag mRNA. Vpr amplified from HIV strains isolated form a patient have been expressed in Dendritic cells (data not shown) as well as in HeLa cells.

The results in the foregoing examples demonstrate that: (1) primer pools of limited complexity can be strategically designed to reliably amplify the intended products from a diverse group of templates spanning different Clades, (2) nested PCR can be performed to add the T7 promoter to the 5' end and an oligo-dT tail to the 3' end, (3) multiple HIV quasispecies present in patient serum can be amplified by this method, (4) the nested PCR products can be transcribed into capped, polyadenylated RNA, (5) dendritic cells can be transfected with antigen-specific RNA and express the expected protein as shown by FACs analysis, and (6) The protein produced is of the correct molecular weight as shown by Western blot analysis of transfected cells. Together, these observations provide substantial evidence that our vaccine design strategy provides for the amplification of multiple HIV quasispecies for antigen presentation by dendritic cells. Further, by combining groups of primers, it is possible to provide for the presentation of the entire breadth of HIV quasispecies and CTL repertoire unique to an individual patient with HIV infection, representing a significant development in AIDS vaccine technology.

Example 18

Dendritic Cells Transfected with HIV mRNA Amplified from Patient Plasma Stimulate Autologous Peripheral Blood Mononuclear Cells (PBMCs)

Figure 20:
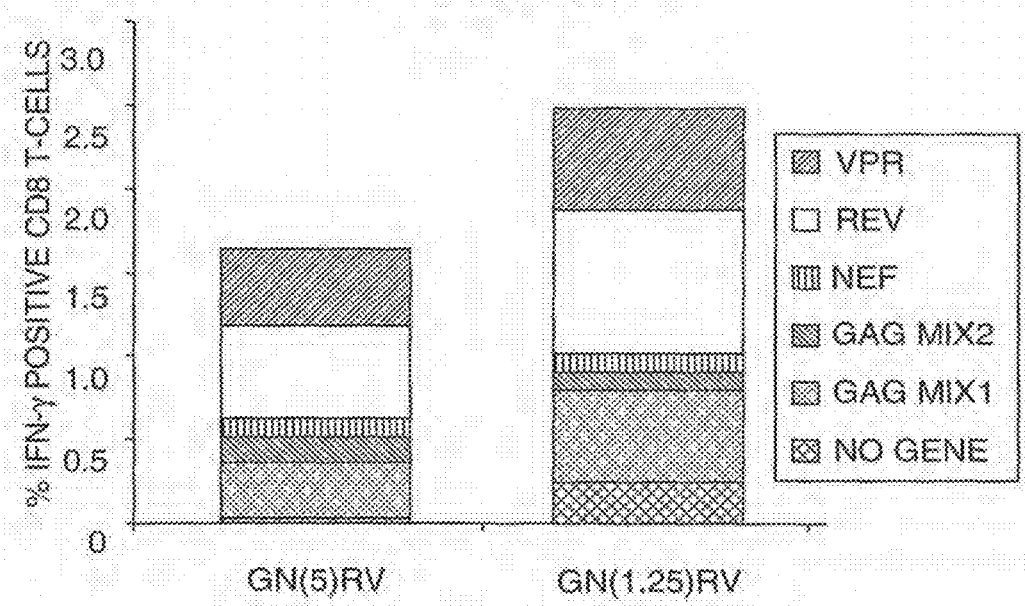
FIG. 20. Immature DCs were co-transfected with four autologous HIV genes (Vpr, Rev, Nef, and Gag) along with RNA encoding CD40L, and subsequently cultured in the presence of IFN-gamma to achieve full DC maturation. The antigen loaded mature DC were used to stimulate autologous HIV patient PBMCs. After 6 days in culture, PBMCs were recovered, and restimulated with four individual overlapping peptide libraries corresponding to consensus sequences for Vpr, Rev, Nef and gag (two pools). The frequency of IFN-g positive cells was determined by ICS in response to the recognition of each individual HIV gene. DC preparations were loaded with 1 μg RNA/million DC with each of the four HIV genes, and in a parallel experiment, the NEF RNA payload was reduced to 0.25 μg/million DC, whereas the other three genes were each transfected at 1 μg RNA/million DC.

Autologous HIV RNA was prepared by amplifying HIV strains in patient plasma using the primers of the invention to produce an HIV DNA, which was then transcribed in vitro to produce HIV mRNA encoding vpr, rev, nef and gag polypeptides. Immature DCs were co-transfected with four autologous HIV genes (Vpr, Rev, Nef, and Gag) along with RNA encoding CD40L, and subsequently cultured in the presence of IFN-g to achieve full DC maturation. The antigen loaded mature DC were used to stimulate autologous HIV patient PBMCs. After 6 days in culture, PBMCs were recovered, and restimulated with four individual overlapping peptide libraries corresponding to consensus sequences for Vpr, Rev, Nef and gag (two pools). The frequency of IFN-gamma positive CD8+ T cells was determined by ICS in response to the recognition of each individual HIV gene. DC preparations were loaded with 1 μg RNA/million DC with each of the four HIV genes (FIG. 20, left column), and in a parallel experiment, the Nef RNA payload was reduced to 0.25 μg/million DC, whereas the other three genes were each transfected at 1 μg RNA/million DC (FIG. 20, right column). The results show that reducing the Nef mRNA payload with respect to the Vpr, Rev and Gag mRNAs enhances overall immunity without comprising the immune response to the Nef antigen.

Example 19

Figure 21:
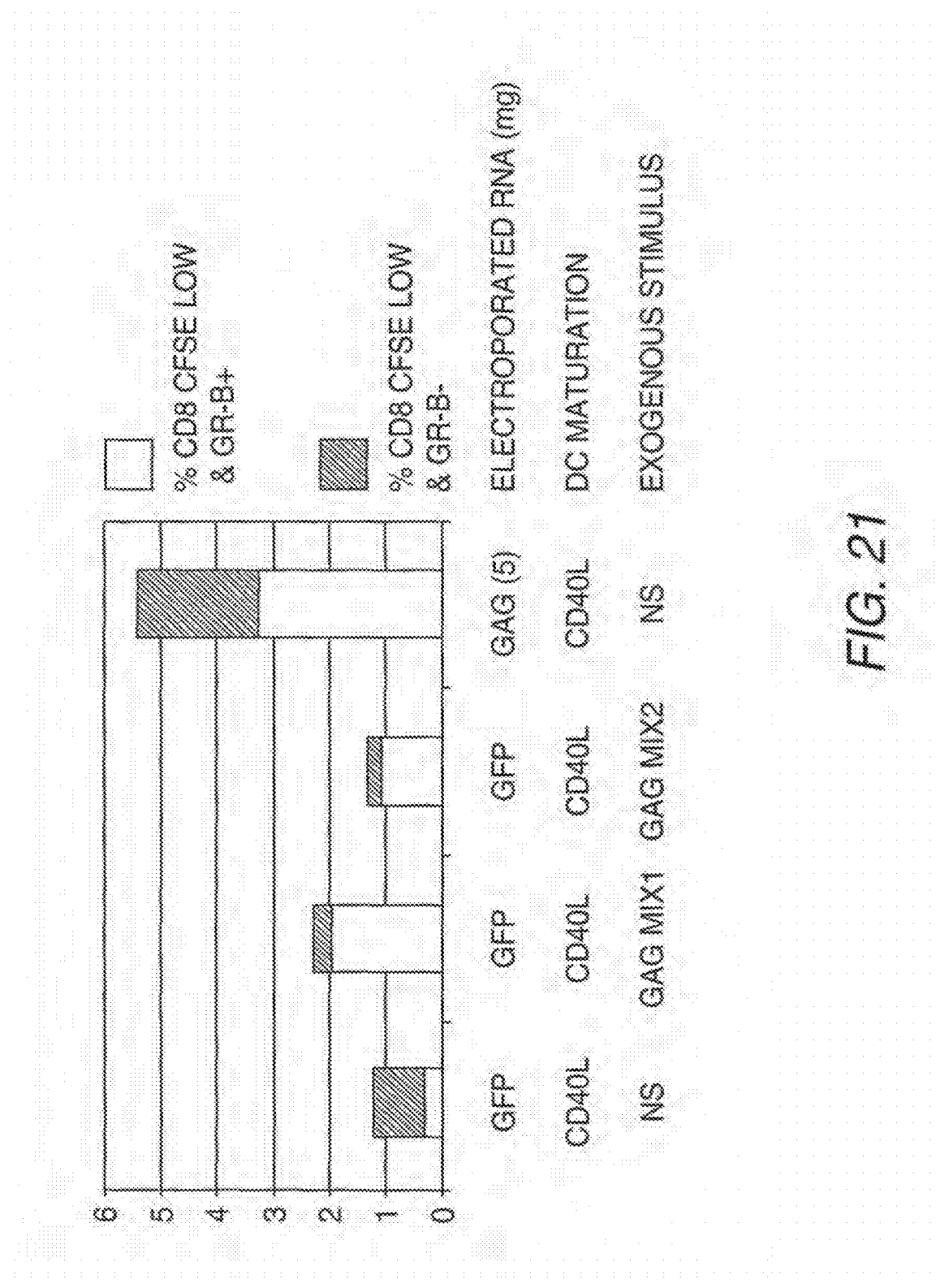
FIG. 21. Immature DC were transfected with either 5 μg eGFP RNA/million DC only (negative control), or eGFP transfected DCs subsequently pulsed with gag consensus peptides as two pools. Alternatively, DCs were transfected with autologous Gag RNA (5 ug RNA/million DC). In all cases, DCs were co-transfected with CD40L RNA, and subsequently cultured in medium comprising IFN-gamma to achieve full maturation. Antigen-loaded DCs were co-cultured with PBMCs previously labeled with CFSE. After 6 days, PBMCs were recovered and the frequency of antigen-reactive (CFSE low) cells was determined. In addition, CFSE low cells were stained by ICS for Granzyme B as a marker of CTL effector function.

Mature Dendritic Cells Transfected with Autologus HIC RNA Induce Stronger Recall Responses than Mature DCs Pulsed with Consensus Peptides Immature DC were transfected with either 5 μg eGFP RNA/million DC only (negative control), or eGFP transfected DCs subsequently pulsed with gag consensus peptides as two pools. Alternatively, DCs were transfected with autologous Gag RNA (5 μg RNA/million DC). In all cases, DCs were co-transfected with CD40L RNA, and subsequently cultured in IFN-gamma to achieve full maturation. Antigen-loaded DCs were co-cultured with PBMCs previously labeled with CFSE. After 6 days, PBMCs were recovered and the frequency of antigen-reactive (CFSE low) cells was determined. In addition, CFSE low cells were stained by ICS for Granzyme B as a marker of CTL effector function. The results shown in FIG. 21 demonstrate the superior immune response induced by DCs loaded with autologous HIV gag RNA as compared to DCs pulsed with gag consensus peptide.

Example 19

Clinical Trial of Autologous Dendritic Cell Vaccine Loaded with RNA Encoding Polypeptides from Multiple Strains of HIV in a Patient The purpose of this trial is to examine the safety, and immunological response of administering a dendritic cell vaccine to HIV-infected patients undergoing HAART therapy. Primary objectives for this study are:
  To examine the safety of multiple administrations of RNA-loaded DCs in HIV-infected patients undergoing HAART therapy.
  To assess the T-cell response to RNA-loaded DC vaccination by using the Intracellular Cytokine Staining (ICS) and CSFE T cell proliferation assays on blood samples collected 8 times during the course of the study at Visit 1 (screening), Visit 2 (baseline prior to vaccination), prior to each of the 5 vaccinations at weeks 4, 8, 20, 32, and at week 36 and/or at the end of study/discontinuation visit.

Trial Design

The Pre-treatment Phase will be conducted on an outpatient basis prior to the start of the Treatment Phase. Patient eligibility will be assessed via screening assessments and confirmed at the Baseline Evaluation. This phase consists of:

Screening Visit.
Blood draw
Leukapheresis Visit [occurs after the managing physician determines the patient is suitable for leukapheresis].
Immunological monitoring (samples will be collected at Visit 2 (screening) and Visit 3 (baseline prior to vaccination).
Baseline Evaluation (will be performed on the first day of dosing but prior to initial administration of the vaccine).

During the Treatment Phase, patients will receive intradermal vaccinations at Study Weeks 0, 4, 8, 20, and 32. Patients randomized to arm 1 of the study will receive $1.2 \times 10^7$ transfected DCs in a volume of 0.6 mL, and patients randomized to arm 2 of the study will receive $1.2 \times 10^6$ transfected DCs in a volume of 0.6 mL. Safety assessments will be performed at each visit. Immunological monitoring will be performed at Visit 2 (screening), Visit 3 (baseline prior to vaccination), after each subsequent administration on study weeks —4, 0, 4, 8, 20, 32, and/or at the end of study/discontinuation visit (a minimum of two weeks following the administration of the last vaccine.

Safety
  Treatment-emergent changes in vital signs (blood pressure, heart rate, respiratory rate, and body temperature) from baseline values obtained prior to each vaccination.
  Incidence of treatment-emergent AEs
  Treatment-emergent changes in localized vaccine injection site reactions following each vaccination.
  Treatment-emergent adenopathy, tenderness, or inflammation (inguinal and axillary) assessed before and after each vaccination.
  Treatment-emergent changes from baseline values (including grading by CTC) in clinical laboratory tests obtained prior to each vaccination.
  Treatment-emergent changes in physical examinations and electrocardiograms (ECGs) at periodic intervals during the Treatment Phase.
  Treatment-emergent changes in autoimmunity evaluations as measured by clinical signs and symptoms (e.g., rash, cytopenias, arthralgias) and laboratory assessments (ANA, RF, anti-dsDNA antibody, $CH_{50}$, anti-thyroid antibody, Indirect Coombs test) at periodic intervals during the Treatment Phase.

Selection and Enrollment of Subject
  Screening and evaluations to determine eligibility must be completed within 2 weeks prior to study entry.

Inclusion Criteria
  HIV-1 infection as documented by any licensed ELISA test kit and confirmed by Western blot at any time prior to study entry. A positive HIV-1 culture, HIV-1 antigen, plasma HIV-1 RNA, or a second antibody test by a method other than ELISA is acceptable as an alternative confirmatory test.
  Subjects currently receiving their first potent ART regimen, defined as a combination of three or more antiretroviral drugs, for a period of ≥6 months prior to study entry. If the subject is currently receiving a potent ART regimen that is not their first potent ART regimen, then the subject must have been receiving the current potent ART regimen for at least 4 weeks prior to the date the screening HIV-1 RNA level was obtained and must have changed to the current potent ART regimen for reasons other than virologic failure.
  NOTE: Ritonavir in combination with another protease inhibitor will be counted as one antiretroviral agent.
  Documentation of current, persistent HIV-1 RNA levels ≤400 copies/mL for a period of at least 6 months before study entry, in which 1 month equals 30 days, documented by at least three measurements separated from each other by at least 1 month, with the first measurement performed at least 6 months before study entry, and the other measurements performed within 6 months of study entry.
  Documentation of current, persistent CD4+ T-cell counts ≥350 cells/mm³ for a period of at least 3 months before study entry, in which 1 month equals 30 days, documented by at least two measurements, with the first measurement performed at least 3 months before study entry and the second measurement performed within 1 month of study entry.
  CD4+ cell count ≥350 cells/mm³ obtained at screening at any AACTG-certified flow laboratory.
  At study screening, HIV-1 RNA level ≤200 copies/mL by the Roche Amplicor HIV-1 Monitor™ UltraSensitive assay.
  Men and women age ≥18 years.
  Laboratory values obtained within 30 days prior to study entry:
    Creatinine ≤3×ULN.
    AST (SGOT), ALT (SGPT), and alkaline phosphatase ≤5×ULN.
  Laboratory values obtained within 30 days prior to study entry and again within 72 hours of study entry. These values must be obtained at two separate time points:
    Absolute neutrophil count (ANC) ≥750/mm³.
    Hemoglobin >8 g/dL.
    Platelet count ≥75,000/mm³.
  Negative pregnancy test for all female subjects with reproductive potential.

Exclusion Criteria
  Any acute infection or serious medical illness within 14 days prior to study entry. Subject will be excluded from this study for a serious illness (requiring systemic treatment and/or hospitalization) until the subject either completes therapy or is clinically stable on therapy, in the opinion of the investigator, for at least 14 days prior to study entry.
  Any HIV-1 RNA value obtained within 6 months of study entry >400 copies/mL.
  Any CD4 T-cell count obtained within 3 months of study entry <350 cells/mm³.
  History of lymph node irradiation
  Prior use of any HIV vaccine.
  Use of hydroxyurea within 45 days before study entry.
  Pregnancy and breast-feeding.
  Receipt of any immune modulators or suppressors within 30 days prior to study entry, including, but not limited to drugs such as systemic corticosteroids; interferons; interleukins; thalidomide; sargramostim (granulocyte-macrophage colony-stimulating factor [GM-CSF]); dinitrochlorobenzene (DNCB); thymosin alpha, thymopentin, inosiplex; polyribonucleoside; ditocarb sodium.
  Allergy/sensitivity to study drug(s) or their formulations.
  Active drug or alcohol use or dependence that, in the opinion of the investigator, would interfere with adherence to study requirements.
  Known HIV-1 seroconversion within one year prior to study entry.
  Any investigational antiretroviral agents that are not obtained through expanded access.

Treatment of Patients
Study Medication and Dose
  The vaccine consists of aseptically processed, mature, autologous dendritic cells electroporated with autologous, selected HIV RNAs. Each dose will be provided in a cryovial containing 0.6cc cryopreserved cells suspended at a concentration of $1.2 \times 10^7$ cells/mL (arm 1) or $1.2 \times 10^6$ (arm 2) to provide autologous, amplified HIV RNA-loaded, mature DCs suspended in 10% DMSO and 5% glucose in heat-inactivated autologous plasma.

Dose Rationale

Selection of the upper dose level was driven by the anticipated maximum number of RNA transduced dendritic cells that could be produced from a single leukapheresis and that could provide at least six vaccines (five for administration and one for quality control). The immunization interval was selected to achieve multiple immunizations, which are often required to demonstrate immunological responses, within a reasonable time frame.

Dosage and Dosing

Preparation of the Vaccine for Administration

The vaccine will be removed from cryogenic storage immediately prior to administration to the patient, and thawed by rolling the vial between open palms or holding the vial in a closed fist. The product will be completely thawed within three to five minutes. Caution should be taken in this procedure, as the vial is extremely cold when first removed from the dry-shipper.

The vaccine should be administered immediately after thawing to minimize the thawed cells' exposure to DMSO.

Prior to use, the thawed cells should be gently mixed by tapping the vial. Inversion of the vial must be avoided. After mixing, the vaccine will be drawn into three 1 mL allergy syringes (0.2 mL will be drawn into each syringe) with an integral 26-gauge needle (supplied by manufacturer).

Vaccine Administration

The vaccine should be administered immediately after the syringe has been filled to prevent unequal dose delivery due to cells settling in the syringe.

The vaccine will be administered intradermally. The administration will occur at Study Weeks 0, 4, 8, 20, and 32.

At each vaccine injection day, the entire dose will be targeted to a single lymph node basin starting with the right axilla and then rotating clockwise among the four anatomic sites (right axilla, left axilla, left inguinal, and right inguinal). Injections should be made in the anteromedial aspect of the limb as near to the joint as possible. For the arm, the anterior surface of the upper arm distal to the elbow can be used.

Administration of the vaccine must be delivered by three intradermal injections delivering 0.2 mL of vaccine, for a total dose of 0.6 mL. Each injection site must be approximately 5 cm from each other. Care must be taken to withdraw the needle slowly as to minimize leak back. The percentage of leak back must be averaged and rounded to the nearest quarter over the three injections and recorded in the patient's CRF. No dose modifications of the study medication are permitted during the study.

Study Treatment Assignment

After a patient signs the Informed Consent form, the site personnel will register the patient with the Sponsor. The site personnel will assign a site specific screen number that is unique to each patient at the screen visit.

After confirming that all pre-treatment evaluations are acceptable, patients will be given an ID Number and enrolled. A maximum of twenty evaluable patients will be enrolled. Patients with insufficient cells, after the leukapheresis, to produce at least six doses of vaccine (five for administration and one for quality control) will be withdrawn from the study. These patients will constitute manufacturing failures and will not be replaced in the study. Patients who are removed or remove themselves from the study for reasons unrelated to disease progression or vaccine treatment before completing at least five vaccinations (e.g. accidental death, lost to follow-up) are inevaluable and will be replaced. If, in the opinion of the Investigator, disease progression requires other therapy before the first vaccine injection is available, the patient will be discontinued from the study for disease progression and will not be replaced.

Concomitant Medication(s)/Treatment(s) Permitted

Patients may take any concomitant medications with the exception of concomitant ART, other immunosuppressive agents, or any other form of immunotherapy. All concomitant prescription and prohibited concomitant over-the-counter (OTC) medications (e.g., topical steroid, etc.) taken during the study will be recorded in the CRF. Non-prohibited concomitant OTC medications will not be recorded in the CRF.

Study Medication Handling

Collection and Shipping of Vaccine Components

Blood/plasma Specimen Collection

Leukapheresis

Patients will undergo leukapheresis at the clinical site's leukapheresis donor center using a COBE Spectra Leukapheresis System. If peripheral vein access is inadequate, a rigid double lumen catheter may be placed in the jugular or subclavian vein. It is recommended that the apheresis nurse visually asseses venous access during the screening visit.

Approximately 180 mL of leukapheresis product will be collected during the leukapheresis visit.

A separate approximate 150 mL of autologous plasma will be collected during to the leukapheresis collection.

The patient will have their blood pressure recorded and blood drawn for complete blood cell count (CBC) with differential prior to and immediately following the leukapheresis. CBC with differential will also be performed on the leukapheresis product.

PBMCs will be collected in a sterile, disposable, single-use cytapheresis bag in accordance with standard clinical practices and directions supplied in the Study Reference Manual.

Leukapheresis specimen and autologous plasma specimen will be transported to the manufacturing laboratory facility without further processing in a special shipping container provided by the manufacturer. These products will be maintained in a controlled, monitored, insulated container, and transported by overnight commercial carrier.

Leukapheresis product must be shipped to the manufacturer on the day of the procedure according to the instructions in the Study Reference Manual.

At the manufacturing facility, leukapheresis product will be inspected to determine if it is acceptable for vaccine manufacturing. If the product is not adequate to produce at least six vaccines, the patient will be discontinued from the study.

Storage Conditions for the Vaccine

Each dose of vaccine will be approximately $1.2 \times 10^7$ cells in a total volume of 0.6 mL (arm 1) or $1.2 \times 10^6$ cells in a total volume of 0.6 mL (arm 2). Each dose of vaccine will be provided in a cryovial containing cryopreserved cells suspended at a concentration of $1.2 \times 10^7$ cells/mL to provide autologous, amplified tumor total RNA-loaded, mature DCs suspended in 10% DMSO and 5% glucose in heat-inactivated autologous plasma. Each treatment day's vaccine will be shipped individually. A stock of the study medication will NOT be maintained at the clinical site. The cryovial will be transported in a liquid nitrogen dry-shipper under controlled conditions at temperatures equal to or lower than −150° C.

The cryovial will be stored in this dry shipper at the site until use. The shipper must be returned immediately to the manufacturer in order to ship subsequent doses.

Time and Events Schedule

Figure 22:
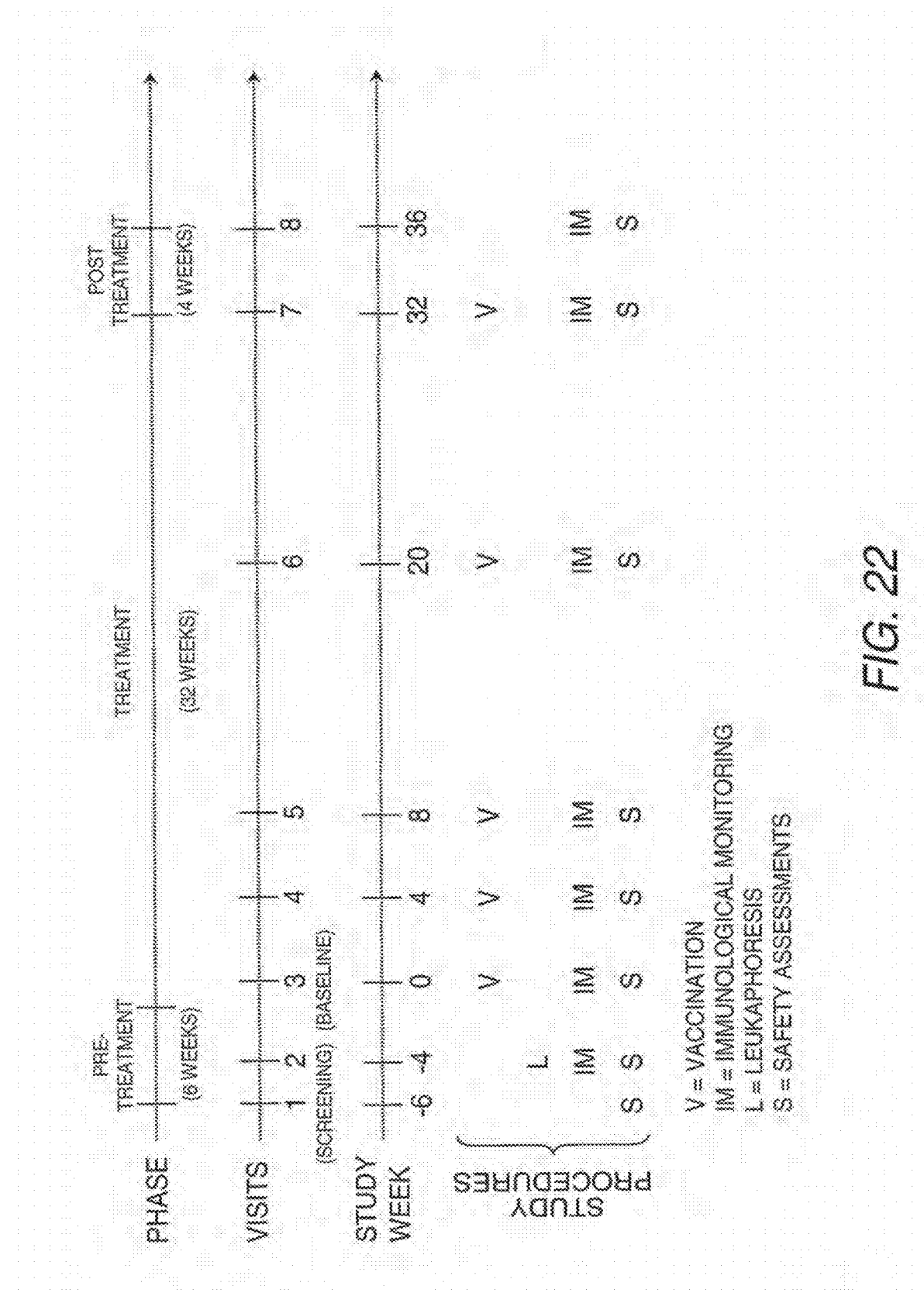
FIG. 22. Time and events schedule for clinical trial procedures.

The Pre-treatment Phase will be conducted on an outpatient basis prior to the start of the Treatment Phase. A time line is shown in FIG. 22. The total duration of the Pre-treatment Phase will be 6 weeks. The Pre-treatment Phase consists of the following visits:
Screen Visit (Visit 1)
Leukapheresis Visit (Visit 2)
Baseline Evaluation Visit (Visit 3)

Treatment Phase

The following study evaluations should be performed during the Treatment Phase:

Immunological Monitoring

In addition to the clinical safety endpoints, immunologic responses will be assessed. Immunological monitoring will be performed at Visit 1 (screening visit), at Visit 3 (baseline prior to vaccination), prior to the administration of each subsequent vaccines on study weeks 4, 8, 20, 32, and on week 36 (Visit8) or at the end of study/discontinuation visit (a minimum of two weeks following the administration of the last vaccine).

Blood samples will be collected at seven time points and assayed for the presence of T-cells responding to vaccination by ICS (measuring IFN-γ and IL-2) and by CFSE T cell proliferation according to the following methods:

Preparation of PBMC for Immunomonitoring Analyses:

Equipment/Supplies
1. Sterile 50 ml polypropylene tubes
2. 37° C. water bath
3. 10 and 25 ml pipets, individually wrapped
4. 2 ml cryogenic vials
5. −80° C. freezer
6. Freezing containers (Nalgene)
7. Liquid Nitrogen freezer
8. Hemacytometer Reagents
1. Human AB Serum (Gemini BioProducts)
2. DMSO (Cat# D2650, endotoxin tested, Sigma), DMSO expires 6 months after opening.
3. RPMI 1640 (Life Technologies)
4. Human Serum Albumin (5 grams, cat# A5843, low endotoxin, Sigma; or Serologicals Corp.)
To make 12.5% HSA solution, add 40 mls RPMI 1640 in the 5 gram bottle. Mix gently by inversion. Do not vortex as HSA will foam up. Filter sterilize and store at 4° C. for up to 6 months.
5. Assay Media: MATIS+10% Human AB serum
Pipet into a sterile 500 ml bottle:
250 mls RPMI 1640
250 mls EHAA
10 ml Pen/Strep solution
25 mls of 200 mM L-Glutamine
50 ul of 0.5 M 2-Mercaptoethanol solution
50 mls heat inactivated human AB serum
Label the bottle with date and initials. Store at 4° C.
6. Trypan Blue (0.4% in PBS, cat# T8154Sigma)

Procedure

Freezing PBMC
1. Place Nalgene freezing containers at 4° C.
2. Label cryovials with:
Patient ID
$10 \times 10^6$ PBMC
Blood draw date and Tech initials
3. Place labeled cryovials in −20° C. freezer.
4. For each cryovial, 1 ml of total volume is added per $10 \times 10^6$ PMBC.
5. Prepare 2× freezing media: for 20 cryovials
10 mls 12.5% HSA solution
2.5 mls DMSO
Mix and place on ice for a minimum of 30 minutes.
6. Resuspend ficolled PBMC at $2 \times 10^7$ viable lymphocytes/ml in cooled 12.5% HSA solution
7. Add the chilled 2× freezing media to the cell suspension drop wise, while gently swirling the tube.
8. Remove chilled cryovial from −20° C. and aliquot 1 ml per cryovial.
9. Place cryovial on ice once PBMC is aliquoted.
10. Transfer cryovials into Nalgene freezing container and place in a −80° C. freezer.
11. For long-term storage, transfer the cyrovials into liquid nitrogen freezer after 24 hours of freezing at −80° C. Never store cells at −20° C., even temporarily.
12. Record the vial location (box number and slot number) on both the specimen database and freezer binder.

Thawing PBMC
1. Place the cell culture media at 37° C. water bath for about 30 minutes.
2. Label a 50 ml centrifuge tube per sample and add 8 mls of warm (22° C. to 37° C.) assay media.
3. Remove cryovials from liquid nitrogen freezer and place directly on dry ice.
4. Thaw no more than 2 cryovials at a time. Place cryovials in a 37° C. water bath until cell suspension is almost completely melted or a small bit of ice remains.
5. Dry off the outside of the cryovials and wipe with 70% ethanol.
6. Add 1 ml of warm (22° C. to 37° C.) cell culture media to the thawed cells slowly.
7. Transfer the cell suspension to the 50 ml polypropylene tubes containing 8 mls of media.
8. Balance tubes and centrifuge at 1200 rpm for 10 minutes.
9. Aspirate supernatant and resuspend cells in 2 ml assay medium.
10. Perform manual cell count using Trypan Blue to determine PBMC viability.

ICS Protocol

Equipment/Supplies
Sterile 50 ml polypropylene tubes
Sterile 15 ml polypropylene tubes
1 ml, 96 well round bottom plate Reagents
Human AB Serum (Gemini BioProducts)
RPMI 1640 (Life Technologies)
PBS
PBS 2% FCS
15 mer HIV and Control peptide
Brefeldin A
Antibodies: CD4 APC-Cy7, CD27-PE, IL-2 FITC, IFN-γ APC, CCR7-PE Cy7, CD28
CyChrome (BD) and CD45 RA ECD (Coulter)
PBMCs from HIV infected individuals Procedure
1. Thawing PBMC (see related Protocol)
2. ICS
Distribute $2.10^6$ cells/1ml/well (96 well Deep round bottom plate). We prepare 5 well for each peptide for the 6 color staining
Anti-CD28 antibody and CD49d (Becton Dickinson, San Jose, Calif.) was added to each sample (1 μg/mL) as costimulators.

Activate the cells with
SEA (200 ng/ml)
Or NS (Negative Control)
Or peptide(s) (5 μg/ml)
Incubate all samples at 37° C. Total incubation will be approximately for 12 hours.
After 1-1.5 hours of incubation at 37° C., add brefeldin A to a final concentration of 10 μg/ml.
Transfer the cells in 96 well round bottom plate when a total of 12 hours of incubation is done.
Wash twice with PBS 2% FCS.
Stain for cell surface markers. (CD4 APC-Cy7 (5 μl), CD27 PE (10 μl), CD28 CyChrome (20 μl), CCR7-PE Cy7 (10 μl), CD45 RA CyChrome (10 μl) in 100 μl of PBS 2% FCS.
Incubate at 4° C. for 30 minutes.
Wash twice with PBS 2% FCS.
Add 100 μl PBS and 100 μl 4% paraformaldehyde.
Incubate at RT for 30 minutes.
Wash twice with permeabilization buffer (0.5% saponin in PBS. Every time freshly prepared).
Add 50 μl permeabilization buffer.
Incubate at RT for 30 minutes.
Stain for intracellular cytokines IL-2 FITC (1 μl), IFN-γ APC (10 μl) in 50 μl of permeabilization buffer
Incubate at room temperature for 30 minutes.
Wash twice in PBS 2% FCS.
Add 100 μl PBS and 100 p14% paraformaldehyde.
Analysis the cells on FACS next days.
Controls:
Unstained cells as negative control.
Isotype control for surface staining
Isotype control for intracellular staining
Positive control.
Permeabilization control (Perm-a-sure=recognize a constitutively expressed human cell protein): one sample will be permeabilized, one will not.
Activation control: one sample will remain unstimulated as no activation background controls.
CSFE T cell proliferation assay
Reagents:
SEB or SEA stock 1 mg/mL
5-6-Carboxyfluorescein diacetate succinimidyl ester (CFSE)(Molecular Probes, cat# C-1157)
Cell surface markers: FL2 (PE), FL3 (PerCP or Cychrome) and FL4 (APC)-conjugated antibodies
PBS
Staining wash buffer: PBS 2% FCS
RPMI-10 Human AB serum (Sigma).
Procedure:
Titration
CFSE is dissolved in anhydrous reagent grade DMSO and stored at −80° C. New preparation of CFSE must be titrated to obtain optimal staining results. For titration, an equal volume of concentrations between 0.5-5 μM CFSE is added to PBMCs (1×10$^7$/mL) and incubated in dark with gentle mixing at room temperature for 8 minutes. The reaction is quenched by addition of an equal volume of HS for 1 minute. Cells are washed with PBS and cultured at 37° C. at 5% $CO_2$ at 1×10$^6$/mL in RPMI containing 10% HS overnight and the fluorescence intensity of cells treated with various concentrations is determined by FACS analysis. The optimal CFSE concentration is defined to be the one at which all cells are stained at a fluorescence intensity between 10$^3$ and 10$^4$ log units in flow cytometry (FL1 channel). We observed that the fluorescence intensity decreases significantly between the time of staining and the next day, so all titration results and experimental data are collected only after 24 hours of incubation at the above mentioned conditions. FL2 (PE) and FL3 (PerCP or Cychrome)-conjugated surface markers should be added to set the voltage and compensation at all CFSE concentration tested (if the CFSE fluorescence is too high, it is nearly impossible to compensate for FL2 and FL3). In our experiments, the final CFSE concentration used usually varies between 0.5 and 1.25 μM.
Staining
1) Resuspend PBMCs at 10 millions/mL in PBS.
2) Prepare 2×CFSE solution. (If the final working solution is 1.5 uM then prepare a 3 uM solution)
3) Add 1 volume of 2×CFSE to PBMCs.
4) Incubate 8-10 min with gentle mixing under the hood with no light.
5) Quench by completing the tube volume with of RPMI 10% HS.
6) Collect the cells (7 min, 1400PRM) and resuspend at 1 million per ml with complete media.
7) Distribute the cells in 96 Deep-well plates (1 to 2 millions/well) and stimulate with SEB (1 μl/ml or SEA 50-100 ng/mL) as a positive control for proliferation, 10 ug/ml of single peptide, 2 ug/ml/peptide when using a peptide pool, 2 ug/ml of recombinant protein. 8) Incubate at 37° C. for 4 to 7 days.
9) Take out 800 ul of the supernatant and leave the cells in the bottom. Transfer cells into 96 V bottom plates using a mutltichannel pipetman.
10) Wash with PBS 2% FCS (100 ul).
11) Stain for surface markers in 50 μl of PBS 2% FCS.
12) Incubate 20 min at RT in the dark.
13) Wash with PBS 2% FCS (150 μl).
14) Resuspend in 400 μl of 2% formaldehyde in PBS 2% FCS.
15) Acquire data on flow cytometer.
Safety Assessments
Patient safety will be evaluated by physical examinations, including medical history, clinical laboratory tests, ECGs, vital sign measurements, and AE assessments. Safety variables will include grading of the incidence and severity of side effects associated with the administration of dendritic cells including hematologic and blood chemistry parameters. These variables will also include autoimmunity evaluations, adenopathy evaluations, and evaluations for localized vaccine injection site reactions. Results of all safety procedures and evaluations will be monitored throughout the study.
Physical Examination and Medical History
During the Screen Visit, a medical history will be taken with particular attention to 1) a review of the body systems and 2) use of prescription medications, including ART. It is recommended that at the screening visit the apheresis nurse visually assesses the patient's venous access.
A physical examination will be conducted at the Screen Visit, Baseline Evaluation Visit, and each of the subsequent visits during the Treatment Phase. A physical exam will also be conducted at study discontinuation. Physical findings within the following categories will be assessed: neurological, cardiovascular, respiratory, lymphatic, skin, abdomen, head, ears, eyes, nose, throat, and allergies.
Clinical Laboratory Assessments
Blood and urine specimens for the measurement and evaluation of clinical chemistry, hematology, and urinalysis parameters will be collected at various time points during the study. Values for the following parameters will be obtained:

Clinical Chemistry Assessment
Sodium
Potassium
Chloride
Creatinine
Calcium
SGOT (AST) (serum glutamic oxaloacetic transaminase)
SGPT (ALT) (serum glutamic pyruvic transaminase)
Alkaline Phosphatase
Bilirubin (total)
LDH (screen only) (lactic dehydrogenase)
Serum Albumin
Hematology Assessment
Complete Blood Cell Count with differential
Platelet Count
Hemoglobin (Hgb)
Hematocrit
Prothrombin Time (PT) (screen only)
Partial Thromboplastin Time (PTT) (screen only)
Urinalysis Dipstick only (including protein, glucose, hemoglobin, pH, and ketone), and microscopic if clinically indicated.

The results of clinical laboratory tests conducted during the study must be assessed by the Investigator to determine each patient's continuing eligibility for participation in the study. If values are outside the normal reference range, the Investigator must assign a toxicity grade per the CTC and assess whether or not the value is clinically significant within the context of the study. All abnormal laboratory values deemed clinically significant by the Investigator must be represented on the AE page in the CRF. If the laboratory abnormality is clearly related to a medically-defined diagnosis or syndrome, the diagnosis or syndrome will be recorded on the AE page, not the individual laboratory values. If the abnormal value is not related to a diagnosis or syndrome, the laboratory value will be recorded on the AE page.

Vital Signs and Weight

Vital signs include systolic and diastolic blood pressure, heart rate, respiratory rate, and body temperature. These measurements, along with the patient's weight, will be measured at the Screen Visit, Leukapheresis Visit (pre- and post-leukapheresis blood pressures only), Baseline Evaluation Visit, at all dosing visits (prior to vaccination and every fifteen minutes for the first hour post-vaccination, and every thirty minutes for the second hour post-vaccination for vital signs) and at study discontinuation. Vital sign measurements will be conducted after five minutes in the sitting position. No other measurements or procedures will be performed during this five-minute period.

Autoimmunity Evaluations

Autoimmunity evaluations will be measured by clinical signs and symptoms (e.g., rash, cytopenias, arthralgias) and by laboratory assessments of ANA, RF, anti-dsDNA antibody, $CH_{50}$, anti-thyroid antibody, and Indirect Coombs test. Evaluations will occur at the Screen Visit, and each subsequent visit. These measurements will also be repeated at study discontinuation.

Adenopathy Evaluations

The draining lymph nodes (axillary and inguinal) will be evaluated for changes in size, tenderness, or inflammation. Evaluations will be performed at the Baseline Evaluation Visit, and each subsequent visit. In addition, patients will record nodal discomfort at home between visits.

Vaccine Injection Site Reaction Evaluations

Vaccine injection site reaction evaluations will be performed every fifteen minutes for the first hour post-vaccination, every thirty minutes for the second hour post-vaccination, and at home by patients forty-eight hours post-vaccination. Patients will be given a card on which to record their forty-eight hour observations. The site personnel will telephone the patient to retrieve this information within two to six days following each vaccination. For patients who report a ≥Grade 2 site injection reaction AE, the principal investigator or designee will request that the patient return to the clinic for evaluation of the site injection reaction by trained personnel. The reactions will be graded according to the CTC and they will be recorded with the AEs in the CRF.

What is claimed is:

1. An isolated dendritic cell obtained or derived from an HIV-infected subject and comprising HIV polypeptides that:
   a) correspond to multiple allelic variants of at least one polypeptide from multiple strains of HIV present in said subject
   b) include less than all of the polypeptides from any of said HIV strains; and
   c) comprise nef polypeptides encoded by nucleic acids amplified from said subject using a nef forward primer comprising the sequence set forth in SEQ ID NO: 138, 139, 204, 367, 368, 369, 370, and/or 371 and a nef reverse primer comprising the sequence set forth in SEQ ID NO: 144, 145, and/or 146.

2. The dendritic cell of claim 1, wherein said nucleic acids are derived from nucleic acid amplification of pathogen polynucleotides.

3. The dendritic cell of claim 2, wherein said nucleic acids are RNAs.

4. The dendritic cell of claim 3, wherein said RNAs are in vitro transcribed RNAs.

5. The dendritic cell of claim 1 that is from or is derived from said subject.

6. The dendritic cell of claim 1, further comprising in vitro transcribed CD40L mRNA.

7. A vaccine comprising the dendritic cell of claim 1 and a pharmaceutically acceptable carrier.

8. A method of treating a pathogen-infected patient, comprising administering the vaccine of claim 7 to said patient.

9. A method of preparing an autologous dendritic cell vaccine that elicits an immune response, comprising: transfecting dendritic cells obtained or derived from an HIV-infected subject with nucleic acids that:
   a) encode multiple allelic variants of at least one polypeptide from multiple strains of HIV present in said subject;
   b) encode less than all of the polypeptides from any of said HIV strains; and
   c) comprise nucleic acids amplified from said subject using a nef forward primer comprising the sequence set forth in SEQ ID NO: 138, 139, 204, 367, 368, 369, 370, and/or 371 and a nef reverse primer comprising the sequence set forth in SEQ ID NO: 144 145, and/or 146.

10. The method of claim 9, wherein said nucleic acids are derived by nucleic acid amplification of pathogen polynucleotides using a plurality of primer pairs designed to compensate for variability between multiple strains of said pathogen.

11. The method of claim 10, wherein said nucleic acids further comprise an mRNA encoding CD40L.

* * * * *

```
                         SEQUENCE LISTING

<160> NUMBER OF SEQ ID NOS: 408

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
actctggtaa ctagagatcc                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
actctgataa ctagagatcc                                               20

<210> SEQ ID NO 3
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 3
actctggtag ctagagatcc                                              20

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 4
aattttgact agcggaggc                                               19

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
aaattttgac tagcggaggc                                              20

<210> SEQ ID NO 6
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 6 aaattttga ctagcggagg c                                             21

<210> SEQ ID NO 7
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 7
tattttgact agcggaggc                                               19

<210> SEQ ID NO 8
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 8 attttgact agcggaggc                                                19

<210> SEQ ID NO 9
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 9
```
actttgacta gcggaggc                                                18

<210> SEQ ID NO 10
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 10 tttttgact agcggaggc                                                 19

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11 aattttgac tagcggaggc                                                20

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 12
attttgacta gcggaggc                                                 18

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
aaattttgac tagcggaggc                                               20

<210> SEQ ID NO 14
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 14
cattttgact agcggaggc                                                19

<210> SEQ ID NO 15
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 15
attttgacta gcggaggc                                                 18

<210> SEQ ID NO 16
<211> LENGTH: 18
<212> TYPE: DNA
<213> ORGANISM: Artificial Sequence

```
<220> FEATURE:
<223> OTHER INFORMATION: Synthetic Oligonucleotide

<400> SEQUENCE: 16
agatgggtgc gagagcgt                                              18

<210> SEQ ID NO 17
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 17
agatgggtgc gagaccgt                                              18

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 18
agagagggtg cgagagcgt                                             19

<210> SEQ ID NO 19
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 19
taatacgact cactataggg agaccaccat gggtgcgaga gcgt                 44

<210> SEQ ID NO 20
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 20
taatacgact cactataggg agaccaccat gggtgcgaga ccgt                 44

<210> SEQ ID NO 21
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 21
gtgacgaggg gtcgttg                                               17

<210> SEQ ID NO 22
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 22
gtgacgaggg gtcgctg                                               17
```

<210> SEQ ID NO 23
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 23
gtgacgatgg gtcgttg                                                    17

<210> SEQ ID NO 24
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 24
gagacgaggg gtcgttg                                                    17

<210> SEQ ID NO 25
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 25
ttgacgaggg gtcgttg                                                    17

<210> SEQ ID NO 26
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 26
gtaacgaggg ggcgttg                                                    17

<210> SEQ ID NO 27
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 27
gtgtcgaggg ggcgttg                                                    17

<210> SEQ ID NO 28
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 28
gtgacaaggg gtcgttg                                                    17

<210> SEQ ID NO 29
<211> LENGTH: 17
<212> TYPE: DNA
<213> ORGANISM: Artificial Sequence
<220> FEATURE:
<223> OTHER INFORMATION: Synthetic Oligonucleotide

```
<400> SEQUENCE: 29
gtaacgaggg gtcgttg                                              17

<210> SEQ ID NO 30
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 30
gcaacgaggg gtcgttg                                              17

<210> SEQ ID NO 31
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 31
gcgacgaggg gtcgttg                                              17

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
gctcctgtat ctaatagagc                                           20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
gctcctgtat ctaataaagc                                           20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
gctcctgtat ctaacagagc                                           20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
gctcctgtgt ctaatagagc                                           20

<210> SEQ ID NO 36
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
tttggtttcc atcttcctgg                                                 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
tttggtttcc atcttcctgc                                                 20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
tttggcttcc atctccctgg                                                 20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
tttggcttcc atcttcctgg                                                 20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
tttggtttcc atttccctgg                                                 20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
tttggtttcc attttcctgg                                                 20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
```

-continued

```
tttggcttcc atcttcctgg                                       20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
ttcggtttcc atcttcctgg                                       20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 44
gcaggacata acaaggtagg                                       20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 45
gcaggacata gcaaggtagg                                       20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
gcaggacata acaaagtagg                                       20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
gcaggacata acaagatagg                                       20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
gcaggacata acaaagtaga                                       20

<210> SEQ ID NO 49
<211> LENGTH: 20
<212> TYPE: DNA
```

```
<213> ORGANISM: Artificial Sequence
<220> FEATURE:
<223> OTHER INFORMATION: Synthetic Oligonucleotide

<400> SEQUENCE: 49
aagataaagc cacctttgcc                                                   20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
cagataaagc cacctttgcc                                                   20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
aaggtaaagc cacctttgcc                                                   20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
aagataaggc cacctttgcc                                                   20

<210> SEQ ID NO 53
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 53
actgacagag gatagatgg                                                    19

<210> SEQ ID NO 54
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 54
actgatagag gatagatgg                                                    19

<210> SEQ ID NO 55
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 55
actaacagag gatagatgg                                                    19
```

<210> SEQ ID NO 56
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 56
actgacagag gacagatgg                                                  19

<210> SEQ ID NO 57
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 57
taatacgact cactataggg agaccaccat ggaacaagcc ccag                      44

<210> SEQ ID NO 58
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 58
taatacgact cactataggg agaccaccat ggaacaagcc ccgg                      44

<210> SEQ ID NO 59
<211> LENGTH: 9
<212> TYPE: DNA
<213> ORGANISM: Artificial Sequence
<220> FEATURE:
<223> OTHER INFORMATION: Kozak sequence

<400> SEQUENCE: 59 ccaccatgg                                                              9

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
ggataaacag cagttgttgc                                                 20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
gaataaacag cagttgttgt                                                 20

<210> SEQ ID NO 62
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 62
ggataaacgg cagttgttgc                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
gaataaacaa cagttgttgc                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
gaataaacag cagctgttgc                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 65
attctgctat gtcgacaccc                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 66
attctgctat gtcggcgccc                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 67
attctgctat gtcggcaccc                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
attctgctat gttgacaccc                                              20

```
<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
ctccatttct tgctctcctc                                           20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 70
ctccatttct tgctcttctc                                           20

<210> SEQ ID NO 71
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 71
ctccattcct tgctctcctc                                           20

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
ctctatttct tgctctcctc                                           20

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
ttccatttct tgctctcctc                                           20

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74
acataacaaa ttggctgtgg                                           20

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 75
acatatcaag ttggctgtgg                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
acataacaaa atggctgtgg                                               20

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77
acataacaaa ctggctgtgg                                               20

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
acataacaga ttggctgtgg                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
atagtaggag gcttggtagg                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
atagtaggag gcttagtagg                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
atagtaggag gcttgatagg                                               20

<210> SEQ ID NO 82
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 82
attatcgttt cagacccacc                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
attatcgttt cagacccgcc                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
attatcgttt cagaccctcc                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
attgtcgttt cagacccacc                                              20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
attgtcgttt cagacccgcc                                              20

<210> SEQ ID NO 87
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 87
taatacgact cactataggg agaccaccat ggacccacct ccc                    43

<210> SEQ ID NO 88
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 88
```

```
taatacgact cactataggg agaccaccat ggacccgcct ccc                    43
```

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 89

```
cctgactcca atactgtagg                                              20
```

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90

```
cctgactcca atactgcagg                                              20
```

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 91

```
cctgactcca atattgtagg                                              20
```

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 92

```
cctgaatcca atactgtagg                                              20
```

<210> SEQ ID NO 93
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 93

```
cctggctcca atactgtagg                                              20
```

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 94

```
gcattgagca agctaacagc                                              20
```

<210> SEQ ID NO 95
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 95
gcattgagca agctaactgc                                            20

<210> SEQ ID NO 96
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 96
gcattgagca agttaacagc                                            20

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
acattaagca agttaacagc                                            20

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
gcattaagca aactaacagc                                            20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
gcattgacga agctaacagc                                            20

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 100
gcattaagca agctaacagc                                            20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 101
gcgttgagca agctaacagc                                            20
```

<210> SEQ ID NO 102
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 102
tttttttttt tttttttttt tttttttttt tttttttttt tttttttttt tttttttttt     60
ttttgtgacg aggggtcgtt g     81

<210> SEQ ID NO 103
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 103
tttttttttt tttttttttt tttttttttt tttttttttt tttttttttt tttttttttt     60
ttttgtgacg aggggtcgct g     81

<210> SEQ ID NO 104
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 104
tttttttttt tttttttttt tttttttttt tttttttttt tttttttttt tttttttttt     60
ttttgtaacg aggggggcgtt g     81

<210> SEQ ID NO 105
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 105
tttttttttt tttttttttt tttttttttt tttttttttt tttttttttt tttttttttt     60
ttttgtgtcg aggggcgtt g     81

<210> SEQ ID NO 106
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 106
tttttttttt tttttttttt tttttttttt tttttttttt tttttttttt tttttttttt     60
ttttgctcct gtatctaata gagc     84

<210> SEQ ID NO 107
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 107
tttttttttt tttttttttt tttttttttt tttttttttt tttttttttt tttttttttt     60
ttttgctcct gtatctaata aagc                                             84

<210> SEQ ID NO 108
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 108
tttttttttt tttttttttt tttttttttt tttttttttt tttttttttt tttttttttt     60
ttttgctcct gtatctaaca gagc                                             84

<210> SEQ ID NO 109
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 109
tttttttttt tttttttttt tttttttttt tttttttttt tttttttttt tttttttttt     60
tttttttggt ttccatcttc ctgg                                             84

<210> SEQ ID NO 110
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 110
tttttttttt tttttttttt tttttttttt tttttttttt tttttttttt tttttttttt     60
tttttttggt ttccatcttc ctgc                                             84

<210> SEQ ID NO 111
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 111
tttttttttt tttttttttt tttttttttt tttttttttt tttttttttt tttttttttt     60
tttttttggc ttccatctcc ctgg                                             84

<210> SEQ ID NO 112
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 112
tttttttttt tttttttttt tttttttttt tttttttttt tttttttttt tttttttttt     60
tttttttggt ttccatttcc ctgg                                             84

<210> SEQ ID NO 113
<211> LENGTH: 84
<212> TYPE: DNA

<213> ORGANISM: Artificial Sequence
<220> FEATURE:
<223> OTHER INFORMATION: Synthetic Oligonucleotide

<400> SEQUENCE: 113
tttttttttt tttttttttt tttttttttt tttttttttt tttttttttt tttttttttt    60
tttttttggt ttccattttc ctgg                                            84

<210> SEQ ID NO 114
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 114
tttttttttt tttttttttt tttttttttt tttttttttt tttttttttt tttttttttt    60
tttttttgga taaacagcag ttgttgc                                         87

<210> SEQ ID NO 115
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 115
tttttttttt tttttttttt tttttttttt tttttttttt tttttttttt tttttttttt    60
tttttttgaa taaacagcag ttgttgt                                         87

<210> SEQ ID NO 116
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 116
tttttttttt tttttttttt tttttttttt tttttttttt tttttttttt tttttttttt    60
tttttttgaa taaacagcag ctgttgc                                         87

<210> SEQ ID NO 117
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 117
tttttttttt tttttttttt tttttttttt tttttttttt tttttttttt tttttttttt    60
tttttttatt ctgctatgtc gacaccc                                         87

<210> SEQ ID NO 118
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 118
tttttttttt tttttttttt tttttttttt tttttttttt tttttttttt tttttttttt    60
tttttttatt ctgctatgtc ggcgccc                                         87

<210> SEQ ID NO 119
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 119
tttttttttt tttttttttt tttttttttt tttttttttt tttttttttt tttttttttt      60
tttttttatt ctgctatgtc ggcaccc                                           87

<210> SEQ ID NO 120
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 120
tttttttttt tttttttttt tttttttttt tttttttttt tttttttttt tttttttttt      60
tttttttatt ctgctatgtt gacaccc                                           87

<210> SEQ ID NO 121
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 121
tttttttttt tttttttttt tttttttttt tttttttttt tttttttttt tttttttttt      60
tttttttctc catttcttgc tctcctc                                           87

<210> SEQ ID NO 122
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 122
tttttttttt tttttttttt tttttttttt tttttttttt tttttttttt tttttttttt      60
tttttttctc catttcttgc tcttctc                                           87

<210> SEQ ID NO 123
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 123
tttttttttt tttttttttt tttttttttt tttttttttt tttttttttt tttttttttt      60
tttttttcct gactccaata ctgtagg                                           87

<210> SEQ ID NO 124
<211> LENGTH: 87
<212> TYPE: DNA
<213> ORGANISM: Artificial Sequence
<220> FEATURE:
<223> OTHER INFORMATION: Synthetic Oligonucleotide

```
<400> SEQUENCE: 124
tttttttttt tttttttttt tttttttttt tttttttttt tttttttttt tttttttttt    60
tttttttcct gactccaata ctgcagg                                        87

<210> SEQ ID NO 125
<211> LENGTH: 87
<212> TYPE: DNA
<213> ORGANISM: Artificial Sequence
<220> FEATURE:
<223> OTHER INFORMATION: Synthetic Oligonucleotide

<400> SEQUENCE: 125
tttttttttt tttttttttt tttttttttt tttttttttt tttttttttt tttttttttt    60
tttttttcct gactccaata ttgtagg                                        87

<210> SEQ ID NO 126
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 126
tttttttttt tttttttttt tttttttttt tttttttttt tttttttttt tttttttttt    60
ttttgcattg agcaagctaa cagc                                           84

<210> SEQ ID NO 127
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 127
tttttttttt tttttttttt tttttttttt tttttttttt tttttttttt tttttttttt    60
ttttgcattg agcaagctaa ctgc                                           84

<210> SEQ ID NO 128
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 128
tttttttttt tttttttttt tttttttttt tttttttttt tttttttttt tttttttttt    60
ttttgcattg agcaagttaa cagc                                           84

<210> SEQ ID NO 129
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 129
tttttttttt tttttttttt tttttttttt tttttttttt tttttttttt tttttttttt    60
ttttgcatta agcaaactaa cagc                                           84

<210> SEQ ID NO 130
<211> LENGTH: 18
```

```
<212> TYPE: DNA
<213> ORGANISM: Artificial Sequence
<220> FEATURE:
<223> OTHER INFORMATION: Synthetic Oligonucleotide

<400> SEQUENCE: 130
ttaggcatct cctatggc                                                     18

<210> SEQ ID NO 131
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 131
ttaggcattt cctatggc                                                     18

<210> SEQ ID NO 132
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 132
ttaggcatct ccaatggc                                                     18

<210> SEQ ID NO 133
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 133
ccagtccccc cttttctttt                                                   20

<210> SEQ ID NO 134
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 134
taatacgact cactataggg agaccaccat gggagtgatg g                            41

<210> SEQ ID NO 135
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 135
taatacgact cactataggg agaccaccat gggagtgaag g                            41

<210> SEQ ID NO 136
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 136
```
taatacgact cactataggg agaccaccat gggagtgagg g        41

<210> SEQ ID NO 137
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 137
tttttttttt tttttttttt tttttttttt tttttttttt tttttttttt tttttttttt        60 tttttttatag caaagccctt tc        82

<210> SEQ ID NO 138
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 138
tagctgaggg gacagatag        19

<210> SEQ ID NO 139
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 139
tagctgaggg aacagatag        19

<210> SEQ ID NO 140
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 140
atgggtggca agtggtcaaa aag        23

<210> SEQ ID NO 141
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 141
atgggtggca agtggtcaaa acg        23

<210> SEQ ID NO 142
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 142
atgggtggca aatggtcaaa aag        23

<210> SEQ ID NO 143
<211> LENGTH: 23

```
<212> TYPE: DNA
<213> ORGANISM: Artificial Sequence
<220> FEATURE:
<223> OTHER INFORMATION: Synthetic Oligonucleotide

<400> SEQUENCE: 143
atgggtggca agtggtcaaa agg                                          23

<210> SEQ ID NO 144
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 144
ccagtacagg caaaaagc                                                18

<210> SEQ ID NO 145
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 145
cagtacaggc gaaaagc                                                 17

<210> SEQ ID NO 146
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 146
cagtacaggc aagaagc                                                 17

<210> SEQ ID NO 147
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 147
taatacgact cactataggg agaccaccat gggtggcaag tggtcaaaaa g           51

<210> SEQ ID NO 148
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 148
taatacgact cactataggg agaccaccat gggtggcaag tggtcaaaac g           51

<210> SEQ ID NO 149
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 149
```

```
tttttttttt tttttttttt tttttttttt tttttttttt tttttttttt tttttttttt      60 tttttttccag tacaggcaaa aagc                                              84

<210> SEQ ID NO 150
<211> LENGTH: 83
<212> TYPE: DNA
<213> ORGANISM: Artificial Sequence
<220> FEATURE:
<223> OTHER INFORMATION: Synthetic Oligonucleotide

<400> SEQUENCE: 150
tttttttttt tttttttttt tttttttttt tttttttttt tttttttttt tttttttttt      60 tttttttcagt acaggcgaaa agc                                               83

<210> SEQ ID NO 151
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 151
tttttttttt tttttttttt tttttttttt tttttttttt tttttttttt tttttttttt      60 tttttttccag tacaggcaag aagc                                              84

<210> SEQ ID NO 152
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 152
tttttttttt tttttttttt tttttttttt tttttttttt tttttttttt tttttttttt      60
tttttttgtc agcagtcttt                                                    80

<210> SEQ ID NO 153
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 153
tttttttttt tttttttttt tttttttttt tttttttttt tttttttttt tttttttttt      60
tttttttgtc agcagtctca                                                    80

<210> SEQ ID NO 154
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 154
tttttgacca cttgccaccc                                                    20

<210> SEQ ID NO 155
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 155
tttttgacca cttgccactc                                          20

<210> SEQ ID NO 156
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 156
tttttgacca cttgcccccc                                          20

<210> SEQ ID NO 157
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 157
tttttttttt tttttttttt tttttttttt tttttttttt tttttttttt tttttttttt    60 ttttttttttg accacttgcc accc                                         84

<210> SEQ ID NO 158
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 158
tttttttttt tttttttttt tttttttttt tttttttttt tttttttttt tttttttttt    60 ttttttttttg accacttgcc actc                                         84

<210> SEQ ID NO 159
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 159
tttttttttt tttttttttt tttttttttt tttttttttt tttttttttt tttttttttt    60 ttttttttttg accacttgcc cccc                                         84

<210> SEQ ID NO 160
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 160
taatacgact cactataggg agaccaccat ggtgggagca gtgtctca            48

<210> SEQ ID NO 161
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 161
taatacgact cactataggg agaccaccat ggaggcacaa gaggaagagg          50

<210> SEQ ID NO 162
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 162
tagtcagtgt ggaaaatctc tagcagtg          28

<210> SEQ ID NO 163
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 163
ctcgatgtca gcagttcttg aagtactc          28

<210> SEQ ID NO 164
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 164
cagacccttt tagtcagtgt ggaaaatc          28

<210> SEQ ID NO 165
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 165
gtctacttgt gtgctatatc tctttttc          28

<210> SEQ ID NO 166
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 166
gcattcccta caatccccaa ag          22

<210> SEQ ID NO 167
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 167
ggtctaacca gagagaccca gtacag          26

<210> SEQ ID NO 168
<211> LENGTH: 31

-continued

```
<212> TYPE: DNA
<213> ORGANISM: Artificial Sequence
<220> FEATURE:
<223> OTHER INFORMATION: Synthetic Oligonucleotide

<400> SEQUENCE: 168
agcttgcctt gagtgcttca agtagtgtgt g                                    31

<210> SEQ ID NO 169
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 169
tgccttgagt gcaagtagtg tgtgccc                                         27

<210> SEQ ID NO 170
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 170
aaaagggctg ttggaaatgt gg                                              22

<210> SEQ ID NO 171
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 171
ggaaggacac caaatgaaag attgtactga gag                                  33

<210> SEQ ID NO 172
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 172
gcctgtcttt cagtgcaatc tttcatttgg tgtcc                                35

<210> SEQ ID NO 173
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 173
tctgttctga ggaaaattcc ctggcctccc                                      30

<210> SEQ ID NO 174
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 174
```
attccctaca atccccaaag tcaag                                          25

<210> SEQ ID NO 175
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 175
attccctaca atccccaaag tc                                             22

<210> SEQ ID NO 176
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 176
tggaaaggtg aagggncagt agtaatacaa g                                   31

<210> SEQ ID NO 177
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 177
tggaaaggtg aagggncagt agtaataca                                      29

<210> SEQ ID NO 178
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 178
ctcatcctgt ctacttgcca cacaatcatc ac                                  32

<210> SEQ ID NO 179
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 179
ccctagtggg atgtgtactt ctgaac                                         26

<210> SEQ ID NO 180
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 180
taggagtagc acccaccaag gcaaagag                                       28

<210> SEQ ID NO 181
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 181
tggtgtgtag ttctgccaat cagggaag                                28

<210> SEQ ID NO 182
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 182
cttgaagcac tcaaggcaag ctttattg                                28

<210> SEQ ID NO 183
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 183
gggatttggg gttgctctgg                                         20

<210> SEQ ID NO 184
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 184
gggatttggg gctgctctgg                                         20

<210> SEQ ID NO 185
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 185
tgatagtagg aggcttggta gg                                      22

<210> SEQ ID NO 186
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 186
tgatagtagg aggcttaata gg                                      22

<210> SEQ ID NO 187
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 187
tgatagtagg aggcttgata gg                                      22

```
<210> SEQ ID NO 188
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 188
gttaggcagg gatattcacc                                               20

<210> SEQ ID NO 189
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 189
gttaggcagg gatactcacc                                               20

<210> SEQ ID NO 190
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 190
ccctgtctta ttcttctagg                                               20

<210> SEQ ID NO 191
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 191
ccctgtctta ttcttacagg                                               20

<210> SEQ ID NO 192
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 192
ccctgtctta ttcttgtagg                                               20

<210> SEQ ID NO 193
<211> LENGTH: 85
<212> TYPE: DNA
<213> ORGANISM: Artificial Sequence
<220> FEATURE:
<223> OTHER INFORMATION: Synthetic Oligonucleotide

<400> SEQUENCE: 193
tttttttttt tttttttttt tttttttttt tttttttttt tttttttttt tttttttttt    60
tttttccctg tcttattctt ctagg                                         85

<210> SEQ ID NO 194
<211> LENGTH: 85
<212> TYPE: DNA
<213> ORGANISM: Artificial Sequence
```

<220> FEATURE:
<223> OTHER INFORMATION: Synthetic Oligonucleotide

<400> SEQUENCE: 194
tttttttttt tttttttttt tttttttttt tttttttttt tttttttttt tttttttttt    60
tttttccctg tcttattctt acagg                                           85

<210> SEQ ID NO 195
<211> LENGTH: 85
<212> TYPE: DNA
<213> ORGANISM: Artificial Sequence
<220> FEATURE:
<223> OTHER INFORMATION: Synthetic Oligonucleotide

<400> SEQUENCE: 195
tttttttttt tttttttttt tttttttttt tttttttttt tttttttttt tttttttttt    60
tttttccctg tcttattctt gtagg                                           85

<210> SEQ ID NO 196
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 196
ttcttcctgc cataggagat gc                                              22

<210> SEQ ID NO 197
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 197
ttcttcctgc cataggaaat gc                                              22

<210> SEQ ID NO 198
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 198
gcagttgtag gctgacttcc                                                 20

<210> SEQ ID NO 199
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 199
gcagttgtag gctgactccc                                                 20

<210> SEQ ID NO 200
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 200
gcagttgtag gctggcttcc                                                    20

<210> SEQ ID NO 201
<211> LENGTH: 85
<212> TYPE: DNA
<213> ORGANISM: Artificial Sequence
<220> FEATURE:
<223> OTHER INFORMATION: Synthetic Oligonucleotide

<400> SEQUENCE: 201
tttttttttt tttttttttt tttttttttt tttttttttt tttttttttt tttttttttt        60
tttttgcagt tgtaggctga cttcc                                              85

<210> SEQ ID NO 202
<211> LENGTH: 85
<212> TYPE: DNA
<213> ORGANISM: Artificial Sequence
<220> FEATURE:
<223> OTHER INFORMATION: Synthetic Oligonucleotide

<400> SEQUENCE: 202
tttttttttt tttttttttt tttttttttt tttttttttt tttttttttt tttttttttt        60
tttttgcagt tgtaggctga ctccc                                              85

<210> SEQ ID NO 203
<211> LENGTH: 85
<212> TYPE: DNA
<213> ORGANISM: Artificial Sequence
<220> FEATURE:
<223> OTHER INFORMATION: Synthetic Oligonucleotide

<400> SEQUENCE: 203
tttttttttt tttttttttt tttttttttt tttttttttt tttttttttt tttttttttt        60
tttttgcagt tgtaggctgg cttcc                                              85

<210> SEQ ID NO 204
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 204
tagctggctg gacagatag                                                     19

<210> SEQ ID NO 205
<211> LENGTH: 87
<212> TYPE: DNA
<213> ORGANISM: Human immunodeficiency virus

<400> SEQUENCE: 205
aagatagggg ggcaactaaa ggaagctcta ttagatacag gagcagatga tacagtatta        60
gaagaaataa atttgccagg aagatgg                                            87

<210> SEQ ID NO 206
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 206
```

```
gtgcgagagc gt                                                          12

<210> SEQ ID NO 207
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 207
gtgcgagacc gt                                                          12

<210> SEQ ID NO 208
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 208
aacaagcccc ag                                                          12

<210> SEQ ID NO 209
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 209
aacaagcccc gg                                                          12

<210> SEQ ID NO 210
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 210
acccacctcc c                                                           11

<210> SEQ ID NO 211
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 211
acccgcctcc c                                                           11

<210> SEQ ID NO 212
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 212 gagtgatgg                                                               9

<210> SEQ ID NO 213
<211> LENGTH: 9
<212> TYPE: DNA
```

```
<213> ORGANISM: Artificial Sequence
<220> FEATURE:
<223> OTHER INFORMATION: Synthetic oligonucleotide

<400> SEQUENCE: 213 gagtgaagg                                                                 9

<210> SEQ ID NO 214
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 214 gagtgaggg                                                                 9

<210> SEQ ID NO 215
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 215
gtggcaagtg gtcaaaaag                                                     19

<210> SEQ ID NO 216
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 216
gtggcaagtg gtcaaaacg                                                     19

<210> SEQ ID NO 217
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 217
tgggagcagt gtctca                                                        16

<210> SEQ ID NO 218
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 218
aggcacaaga ggaagagg                                                      18

<210> SEQ ID NO 219
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 219
taatacgact cactataggg agaccaccat gg                                      32
```

<210> SEQ ID NO 220
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 220
gtgacgaggg gtcgttg                                                   17

<210> SEQ ID NO 221
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 221
gtgacgaggg gtcgctg                                                   17

<210> SEQ ID NO 222
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 222
gtaacgaggg gtcgttg                                                   17

<210> SEQ ID NO 223
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 223
gtgtcgaggg ggcgttg                                                   17

<210> SEQ ID NO 224
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 224
gctcctgtat ctaatagagc                                                20

<210> SEQ ID NO 225
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 225
gctcctgtat ctaataaagc                                                20

<210> SEQ ID NO 226
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 226
gctcctgtat ctaacagagc                                              20

<210> SEQ ID NO 227
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 227
ggtttccatc ttcctgg                                                 17

<210> SEQ ID NO 228
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 228
ggtttccatc ttcctgc                                                 17

<210> SEQ ID NO 229
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 229
ggcttccatc tccctgg                                                 17

<210> SEQ ID NO 230
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 230
ggtttccatt tccctgg                                                 17

<210> SEQ ID NO 231
<211> LENGTH: 87
<212> TYPE: DNA
<213> ORGANISM: Human immunodeficiency virus

<400> SEQUENCE: 231
aagatagggg ggcaactaaa ggaagcccta ttagataccg gagcagatga tacagtatta   60
gaagaaataa atttaccagg aagatgg                                       87

<210> SEQ ID NO 232
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 232
ggtttccatt ttcctgg                                                 17

```
<210> SEQ ID NO 233
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 233
ggataaacag cagttgttgc                                               20

<210> SEQ ID NO 234
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 234
gaataaacag cagttgttgt                                               20

<210> SEQ ID NO 235
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 235
gaataaacag cagctgttgc                                               20

<210> SEQ ID NO 236
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 236
attctgctat gtcgacaccc                                               20

<210> SEQ ID NO 237
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 237
attctgctat gtcggcgccc                                               20

<210> SEQ ID NO 238
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 238
attctgctat gtcggcaccc                                               20

<210> SEQ ID NO 239
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 239
attctgctat gttgacaccc                                              20

<210> SEQ ID NO 240
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 240
ctccatttct tgctctcctc                                              20

<210> SEQ ID NO 241
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 241
ctccatttct tgctcttctc                                              20

<210> SEQ ID NO 242
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 242
cctgactcca atactgtagg                                              20

<210> SEQ ID NO 243
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 243
cctgactcca atactgcagg                                              20

<210> SEQ ID NO 244
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 244
cctgactcca atattgtagg                                              20

<210> SEQ ID NO 245
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 245
gcattgagca agctaacagc                                              20

<210> SEQ ID NO 246
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 246
gcattgagca agctaactgc                                              20

<210> SEQ ID NO 247
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 247
gcattgagca agttaacagc                                              20

<210> SEQ ID NO 248
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 248
gcattaagca aactaacagc                                              20

<210> SEQ ID NO 249
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 249
atagcaaagc cctttc                                                  16

<210> SEQ ID NO 250
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 250
ccagtacagg caaaaagc                                                18

<210> SEQ ID NO 251
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 251
cagtacaggc gaaaagc                                                 17

<210> SEQ ID NO 252
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 252
```
ccagtacagg caagaagc                                         18

<210> SEQ ID NO 253
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 253
gtcagcagtc ttt                                              13

<210> SEQ ID NO 254
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 254
gtcagcagtc tca                                              13

<210> SEQ ID NO 255
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 255
gaccacttgc caccc                                            15

<210> SEQ ID NO 256
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 256
gaccacttgc cactc                                            15

<210> SEQ ID NO 257
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 257
gaccacttgc ccccc                                            15

<210> SEQ ID NO 258
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 258
ccctgtctta ttcttctagg                                       20

<210> SEQ ID NO 259
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 259
ccctgtctta ttcttacagg                      20

<210> SEQ ID NO 260
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 260
ccctgtctta ttcttgtagg                      20

<210> SEQ ID NO 261
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 261
gcagttgtag gctgacttcc                      20

<210> SEQ ID NO 262
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 262
gcagttgtag gctgactccc                      20

<210> SEQ ID NO 263
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 263
gcagttgtag gctggcttcc                      20

<210> SEQ ID NO 264
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 264
agcgaacaaa cagtagttgt tgcag                25

<210> SEQ ID NO 265
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 265
agcgaacaaa cagtagttgt tgcaa                25

<210> SEQ ID NO 266
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 266
agcgatcaaa cagcagttgt tgcag                                          25

<210> SEQ ID NO 267
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 267
agcgaacaaa cagtagttgt tgaag                                          25

<210> SEQ ID NO 268
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 268
agcgatcaaa cagtagttgt tgcag                                          25

<210> SEQ ID NO 269
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 269
tttttttttt tttttttttt tttttttttt tttttttttt tttttttttt tttttttttt   60
tttttagcga acaaacagta gttgttgcag                                     90

<210> SEQ ID NO 270
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 270
tttttttttt tttttttttt tttttttttt tttttttttt tttttttttt tttttttttt   60
tttttagcga acaaacagta gttgttgcaa                                     90

<210> SEQ ID NO 271
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 271
tttttttttt tttttttttt tttttttttt tttttttttt tttttttttt tttttttttt   60
tttttagcga tcaaacagca gttgttgcag                                     90

```
<210> SEQ ID NO 272
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 272
tttttttttt tttttttttt tttttttttt tttttttttt tttttttttt tttttttttt      60
tttttagcga acaaacagta gttgttgaag                                        90

<210> SEQ ID NO 273
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 273
tttttttttt tttttttttt tttttttttt tttttttttt tttttttttt tttttttttt      60
tttttagcga tcaaacagta gttgttgcag                                        90

<210> SEQ ID NO 274
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 274
ggcttaggca tctcctatgg cag                                               23

<210> SEQ ID NO 275
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 275
ggcttaggca tttcctatgg cag                                               23

<210> SEQ ID NO 276
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 276
agacagtggc aatgagagtg atgg                                              24

<210> SEQ ID NO 277
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 277
agacagtggc aatgagagtg aagg                                              24

<210> SEQ ID NO 278
<211> LENGTH: 24
<212> TYPE: DNA
```

```
<213> ORGANISM: Artificial Sequence
<220> FEATURE:
<223> OTHER INFORMATION: Synthetic oligonucleotide

<400> SEQUENCE: 278
agacagtggc aatgagagtg acgg                                              24

<210> SEQ ID NO 279
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 279
agacagtggc aatgagagtg aggg                                              24

<210> SEQ ID NO 280
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 280
ttaccctgtc ttattcttct agg                                               23

<210> SEQ ID NO 281
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 281
ttaccctgtc ttattcttgt agg                                               23

<210> SEQ ID NO 282
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 282
ttaccctgtc ttattcgtgt ggg                                               23

<210> SEQ ID NO 283
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 283
ttaccctgtc ttattcttac agg                                               23

<210> SEQ ID NO 284
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 284
ccttccagtc cccccttttc t                                                 21
```

<210> SEQ ID NO 285
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 285
ccatccagtc cccccttttc t                                              21

<210> SEQ ID NO 286
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 286
tttgaccact tgccacccat                                                20

<210> SEQ ID NO 287
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 287
tttgaccact tgcccccat                                                 20

<210> SEQ ID NO 288
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 288
tttgaccact tgttacccat                                                20

<210> SEQ ID NO 289
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 289
tttgaccact tgcctcccat                                                20

<210> SEQ ID NO 290
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 290
taatacgact cactataggg agaagacagt ggcaccacca tggagagtga tgg           53

<210> SEQ ID NO 291
<211> LENGTH: 53
<212> TYPE: DNA
<213> ORGANISM: Artificial Sequence
<220> FEATURE:

<223> OTHER INFORMATION: Synthetic oligonucleotide

<400> SEQUENCE: 291
taatacgact cactataggg agaagacagt ggcaccacca tggagagtga agg        53

<210> SEQ ID NO 292
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 292
taatacgact cactataggg agaagacagt ggcaccacca tggagagtga cgg        53

<210> SEQ ID NO 293
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 293
taatacgact cactataggg agaagacagt ggcaccacca tggagagtga ggg        53

<210> SEQ ID NO 294
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 294
tttttttttt tttttttttt tttttttttt tttttttttt tttttttttt tttttttttt        60
ttttccttcc agtccccct tttct        85

<210> SEQ ID NO 295
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 295
tttttttttt tttttttttt tttttttttt tttttttttt tttttttttt tttttttttt        60
ttttccatcc agtccccct tttct        85

<210> SEQ ID NO 296
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 296
tttttttttt tttttttttt tttttttttt tttttttttt tttttttttt tttttttttt        60
tttttttgac cacttgccac ccat        84

<210> SEQ ID NO 297
<211> LENGTH: 84
<212> TYPE: DNA
<213> ORGANISM: Artificial Sequence
<220> FEATURE:
<223> OTHER INFORMATION: Synthetic oligonucleotide -continued

<400> SEQUENCE: 297
tttttttttt tttttttttt tttttttttt tttttttttt tttttttttt tttttttttt    60
tttttttgac cacttgcccc ccat    84

<210> SEQ ID NO 298
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 298
tttttttttt tttttttttt tttttttttt tttttttttt tttttttttt tttttttttt    60
tttttttgac cacttgttac ccat    84

<210> SEQ ID NO 299
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 299
tttttttttt tttttttttt tttttttttt tttttttttt tttttttttt tttttttttt    60
tttttttgac cacttgcctc ccat    84

<210> SEQ ID NO 300
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 300
aagacagcag tacaaatggc ag    22

<210> SEQ ID NO 301
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 301
aagacagcag tacagatggc ag    22

<210> SEQ ID NO 302
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 302
aagacagcag tgcaaatggc ag    22

<210> SEQ ID NO 303
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 303
aagacagcag tactaatggc ag						22

<210> SEQ ID NO 304
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 304
tggaaaggtg aagggcagt ag						22

<210> SEQ ID NO 305
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 305
tggaaaggtg aagggcagt gg						22

<210> SEQ ID NO 306
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 306
tggaaaggtg aaggagcagt ag						22

<210> SEQ ID NO 307
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 307
tggaaaggtg aagggcggt ag						22

<210> SEQ ID NO 308
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 308
taatacgact cactataggg agaccaccat ggaaaacaga tggcaggtg			49

<210> SEQ ID NO 309
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 309
taatacgact cactataggg agaccaccat ggaaaacaga tggcaggta			49

<210> SEQ ID NO 310
<211> LENGTH: 49

```
<212> TYPE: DNA
<213> ORGANISM: Artificial Sequence
<220> FEATURE:
<223> OTHER INFORMATION: Synthetic oligonucleotide

<400> SEQUENCE: 310
taatacgact cactataggg agaccaccat ggaaaacaga tggcaggcg          49

<210> SEQ ID NO 311
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 311
taatacgact cactataggg agaccaccat ggaaaacaga tggcagggg          49

<210> SEQ ID NO 312
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 312
gaagcatcca ggaagtcagc                                          20

<210> SEQ ID NO 313
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 313
gaagcatcca ggaagccagc                                          20

<210> SEQ ID NO 314
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 314
gaagcatcca ggaagtcggc                                          20

<210> SEQ ID NO 315
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 315
gaagcatcca ggaagtcaac                                          20

<210> SEQ ID NO 316
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 316
```

```
gaagcatcca gggagtcagc                                                 20
```

<210> SEQ ID NO 317
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 317

```
gcatctccta tggcaggaag aa                                              22
```

<210> SEQ ID NO 318
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 318

```
gcatttccta tggcaggaag aa                                              22
```

<210> SEQ ID NO 319
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 319

```
gcatctccta tggcaggaag ag                                              22
```

<210> SEQ ID NO 320
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 320

```
ctgtgggtac acaggcatgt gt                                              22
```

<210> SEQ ID NO 321
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 321

```
ctgtgggtac acaggcatgc gt                                              22
```

<210> SEQ ID NO 322
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 322

```
ctgtgggtac acaagcatgt gt                                              22
```

<210> SEQ ID NO 323
<211> LENGTH: 22
<212> TYPE: DNA
<213> ORGANISM: Artificial Sequence

```
<220> FEATURE:
<223> OTHER INFORMATION: Synthetic oligonucleotide

<400> SEQUENCE: 323
ctgtgggtac acaggcttgt gt                                              22

<210> SEQ ID NO 324
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 324
gcacaataat gtatgggaat tgg                                             23

<210> SEQ ID NO 325
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 325
gcacaataat gtataggaat tgg                                             23

<210> SEQ ID NO 326
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 326
gcacaataat gtatggggat tgg                                             23

<210> SEQ ID NO 327
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 327
gcacaataat gtatgggaat cgg                                             23

<210> SEQ ID NO 328
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 328
gcacaataat gtatgggaat ggg                                             23

<210> SEQ ID NO 329
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 329
taatacgact cactataggg agatcctcta tcaaagcagt aag                       43
```

<210> SEQ ID NO 330
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 330
taatacgact cactataggg agatcctcta tcaaagcagt gag         43

<210> SEQ ID NO 331
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 331
taatacgact cactataggg agatcctcta tcagagcagt aag         43

<210> SEQ ID NO 332
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 332
taatacgact cactataggg agatcctcta ccaaagcagt aag         43

<210> SEQ ID NO 333
<211> LENGTH: 86
<212> TYPE: DNA
<213> ORGANISM: Artificial Sequence
<220> FEATURE:
<223> OTHER INFORMATION: Synthetic oligonucleotide

<400> SEQUENCE: 333
tttttttttt tttttttttt tttttttttt tttttttttt tttttttttt tttttttttt         60
ttttctgtgg gtacacaggc atgtgt         86

<210> SEQ ID NO 334
<211> LENGTH: 86
<212> TYPE: DNA
<213> ORGANISM: Artificial Sequence
<220> FEATURE:
<223> OTHER INFORMATION: Synthetic oligonucleotide

<400> SEQUENCE: 334
tttttttttt tttttttttt tttttttttt tttttttttt tttttttttt tttttttttt         60
ttttctgtgg gtacacaggc atgcgt         86

<210> SEQ ID NO 335
<211> LENGTH: 86
<212> TYPE: DNA
<213> ORGANISM: Artificial Sequence
<220> FEATURE:
<223> OTHER INFORMATION: Synthetic oligonucleotide

<400> SEQUENCE: 335
tttttttttt tttttttttt tttttttttt tttttttttt tttttttttt tttttttttt         60
ttttctgtgg gtacacaagc atgtgt         86

<210> SEQ ID NO 336
<211> LENGTH: 86
<212> TYPE: DNA
<213> ORGANISM: Artificial Sequence
<220> FEATURE:
<223> OTHER INFORMATION: Synthetic oligonucleotide

<400> SEQUENCE: 336
tttttttttt tttttttttt tttttttttt tttttttttt tttttttttt tttttttttt    60
ttttctgtgg gtacacaggc ttgtgt    86

<210> SEQ ID NO 337
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 337
aatgatgaca gcatgtc    17

<210> SEQ ID NO 338
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 338
aatgatgaca gcatgcc    17

<210> SEQ ID NO 339
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 339
aatgatggta gcctgtc    17

<210> SEQ ID NO 340
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 340
aagggctgtt ggaaatgtgg    20

<210> SEQ ID NO 341
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 341
aagggctgtt ggaaatgtag    20

<210> SEQ ID NO 342
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 342
aagggctgtt ggaaatgtaa                                              20

<210> SEQ ID NO 343
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 343
aagggctgtt ggaagtgtgg                                              20

<210> SEQ ID NO 344
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 344
aaaggttgct ggaaatgtgg                                              20

<210> SEQ ID NO 345
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 345
cctagtggga tgtgtacttc tga                                          23

<210> SEQ ID NO 346
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 346
cctagtggga tgtgtacttc cga                                          23

<210> SEQ ID NO 347
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 347
cctagtggga tgtgtatttc tga                                          23

<210> SEQ ID NO 348
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 348
cctagtggga tgtgcacttc tga                                          23
```

-continued

```
<210> SEQ ID NO 349
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 349
cctagtggga tatgtacttc tga                                              23

<210> SEQ ID NO 350
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 350
cctagtggga tgtatacacc tga                                              23

<210> SEQ ID NO 351
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 351
ccaagtattg tagagatcct acc                                              23

<210> SEQ ID NO 352
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 352
ccaagtattg tagagatctt acc                                              23

<210> SEQ ID NO 353
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 353
ccaagtattg tagagaccct acc                                              23

<210> SEQ ID NO 354
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 354
ccaagtattg tagggatcct acc                                              23

<210> SEQ ID NO 355
<211> LENGTH: 23
<212> TYPE: DNA
<213> ORGANISM: Artificial Sequence
<220> FEATURE:
<223> OTHER INFORMATION: Synthetic oligonucleotide
```

```
<400> SEQUENCE: 355
ccaagtattg tagtgtccct acc                                           23

<210> SEQ ID NO 356
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 356
taatacgact cactataggg agaccaccat ggggaaggcc aggaatttc c              51

<210> SEQ ID NO 357
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 357
taatacgact cactataggg agaccaccat ggggaaggcc aggaatttt c              51

<210> SEQ ID NO 358
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 358
taatacgact cactataggg agaccaccat ggggaaggcc aggaaatttc c             51

<210> SEQ ID NO 359
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 359
taatacgact cactataggg agaccaccat ggggaaggcc aggaaatttt c             51

<210> SEQ ID NO 360
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 360
taatacgact cactataggg agaccaccat ggggaaggcc aggaatttc c              51

<210> SEQ ID NO 361
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 361
tttttttttt tttttttttt tttttttttt tttttttttt tttttttttt tttttttttt   60
ttttcctagt gggatgtgta cttctga                                       87
```

```
<210> SEQ ID NO 362
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 362
tttttttttt tttttttttt tttttttttt tttttttttt tttttttttt tttttttttt    60
ttttcctagt gggatgtgta cttccga                                         87

<210> SEQ ID NO 363
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 363
tttttttttt tttttttttt tttttttttt tttttttttt tttttttttt tttttttttt    60
ttttcctagt gggatgtgta tttctga                                         87

<210> SEQ ID NO 364
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 364
tttttttttt tttttttttt tttttttttt tttttttttt tttttttttt tttttttttt    60
ttttcctagt gggatgtgca cttctga                                         87

<210> SEQ ID NO 365
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 365
tttttttttt tttttttttt tttttttttt tttttttttt tttttttttt tttttttttt    60
ttttcctagt gggatatgta cttctga                                         87

<210> SEQ ID NO 366
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 366
tttttttttt tttttttttt tttttttttt tttttttttt tttttttttt tttttttttt    60
ttttcctagt gggatgtata cacctga                                         87

<210> SEQ ID NO 367
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 367
```

-continued aagaaggtgg agagcaagac                                           20

<210> SEQ ID NO 368
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 368
aagaaggtgg agagcaaggc                                           20

<210> SEQ ID NO 369
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 369
aagaaggtgg agagagagac                                           20

<210> SEQ ID NO 370
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 370
aagaaggtgg cgagcaagac                                           20

<210> SEQ ID NO 371
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 371
aagaaggtgg cgagcaaggc                                           20

<210> SEQ ID NO 372
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 372
agagtgatgg                                                      10

<210> SEQ ID NO 373
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 373
agagtgaagg                                                      10

<210> SEQ ID NO 374
<211> LENGTH: 9
<212> TYPE: DNA
<213> ORGANISM: Artificial Sequence

```
<220> FEATURE:
<223> OTHER INFORMATION: Synthetic oligonucleotide

<400> SEQUENCE: 374 agagtgacg                                                              9

<210> SEQ ID NO 375
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 375
agagtgaggg                                                            10

<210> SEQ ID NO 376
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 376
aaacagatgg caggtg                                                     16

<210> SEQ ID NO 377
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 377
aaacagatgg caggta                                                     16

<210> SEQ ID NO 378
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 378
aaacagatgg caggcg                                                     16

<210> SEQ ID NO 379
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 379
aaacagatgg cagggg                                                     16

<210> SEQ ID NO 380
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 380
tctatcaaag cagtaag                                                    17
```

<210> SEQ ID NO 381
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 381
tctatcaaag cagtgag                                                    17

<210> SEQ ID NO 382
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 382
tctatcagag cagtaag                                                    17

<210> SEQ ID NO 383
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 383
tctaccaaag cagtaag                                                    17

<210> SEQ ID NO 384
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 384
ggaaggccag ggaatttcc                                                  19

<210> SEQ ID NO 385
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 385
ggaaggccag ggaattttc                                                  19

<210> SEQ ID NO 386
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 386
ggaaggccag ggaatttcc                                                  19

<210> SEQ ID NO 387
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 387
ggaaggccag gaaattttc						19

<210> SEQ ID NO 388
<211> LENGTH: 9184
<212> TYPE: DNA
<213> ORGANISM: Human immunodeficiency virus

<400> SEQUENCE: 388

| | | | | |
|---|---|---|---|---|
| ggtctctctg | gttagaccag | atctgagcct | gggagctctc | tggctaacta | gggaacccac | 60 |
| tgcttaagcc | tcaataaagc | ttgccttgag | tgcttcaagt | agtgtgtgcc | cgtctgttgt | 120 |
| gtgactctgg | taactagaga | tccctcagac | cctttagtc | agtgtggaaa | atctctagca | 180 |
| gtggcgcccg | aacagggacc | tgaaagcgaa | agggaaacca | gaggagctct | ctcgacgcag | 240 |
| gactcggctt | gctgaagcgc | gcacggcaag | aggcgagggg | cggcgactgg | tgagtacgcc | 300 |
| aaaaattttg | actagcggag | gctagaagga | gagagatggg | tgcgagagcg | tcagtattaa | 360 |
| gcggggggaga | attagatcga | tgggaaaaaa | ttcggttaag | gccagggggga | aagaaaaaat | 420 |
| ataaattaaa | acatatagta | tgggcaagca | gggagctaga | acgattcgca | gttaatcctg | 480 |
| gcctgttaga | aacatcagaa | ggctgtagac | aaatactggg | acagctacaa | ccatcccttc | 540 |
| agacaggatc | agaagaactt | agatcattat | ataatacagt | agcaaccctc | tattgtgtgc | 600 |
| atcaaaggat | agagataaaa | gacaccaagg | aagctttaga | caagatagag | gaagagcaaa | 660 |
| acaaaagtaa | gaaaaagca | cagcaagcag | cagctgacac | aggacacagc | aatcaggtca | 720 |
| gccaaaatta | ccctatagtg | cagaacatcc | aggggcaaat | ggtacatcag | gccatatcac | 780 |
| ctagaacttt | aaatgcatgg | gtaaaagtag | tagaagagaa | ggctttcagc | ccagaagtga | 840 |
| tacccatgtt | ttcagcatta | tcagaaggag | ccaccccaca | agatttaaac | accatgctaa | 900 |
| acacagtggg | gggacatcaa | gcagccatgc | aaatgttaaa | agagaccatc | aatgaggaag | 960 |
| ctgcagaatg | ggatagagtg | catccagtgc | atgcagggcc | tattgcacca | ggccagatga | 1020 |
| gagaaccaag | gggaagtgac | atagcaggaa | ctactagtac | ccttcaggaa | caaataggat | 1080 |
| ggatgacaaa | taatccacct | atcccagtag | gagaaattta | taaaagatgg | ataatcctgg | 1140 |
| gattaaataa | aatagtaaga | atgtatagcc | ctaccagcat | tctggacata | agacaaggac | 1200 |
| caaaggaacc | ctttagagac | tatgtagacc | ggttctataa | aactctaaga | gccgagcaag | 1260 |
| cttcacagga | ggtaaaaaat | tggatgacag | aaaccttgtt | ggtccaaaat | gcgaacccag | 1320 |
| attgtaagac | tattttaaaa | gcattgggac | cagcggctac | actagaagaa | atgatgacag | 1380 |
| catgtcaggg | agtaggagga | cccggccata | aggcaagagt | tttggctgaa | gcaatgagcc | 1440 |
| aagtaacaaa | ttcagctacc | ataatgatgc | agagaggcaa | ttttaggaac | caaagaaaga | 1500 |
| ttgttaagtg | tttcaattgt | ggcaaagaag | ggcacacagc | cagaaattgc | agggccccta | 1560 |
| ggaaaaaggg | ctgttggaaa | tgtggaaagg | aaggacacca | aatgaaagat | tgtactgaga | 1620 |
| gacaggctaa | ttttttaggg | aagatctggc | cttcctacaa | gggaaggcca | gggaattttc | 1680 |
| ttcagagcag | accagagcca | acagccccac | cagaagagag | cttcaggtct | ggggtagaga | 1740 |
| caacaactcc | ccctcagaag | caggagccga | tagacaagga | actgtatcct | ttaacttccc | 1800 |
| tcaggtcact | ctttggcaac | gacccctcgt | cacaataaag | atagggggggc | aactaaagga | 1860 |
| agctctatta | gatacaggag | cagatgatac | agtattagaa | gaaatgagtt | tgccaggaag | 1920 |
| atggaaacca | aaaatgatag | ggggaattgg | aggttttatc | aaagtaagac | agtatgatca | 1980 |

```
gatactcata gaaatctgtg gacataaagc tataggtaca gtattagtag gacctacacc    2040
tgtcaacata attggaagaa atctgttgac tcagattggt tgcactttaa attttcccat    2100
tagccctatt gagactgtac cagtaaaatt aaagccagga atggatggcc caaaagttaa    2160
acaatggcca ttgacagaag aaaaaataaa agcattagta gaaatttgta cagagatgga    2220
aaaggaaggg aaaatttcaa aaattgggcc tgaaaatcca tacaatactc cagtatttgc    2280
cataaagaaa aaagacagta ctaaatggag aaaattagta gatttcagag aacttaataa    2340
gagaactcaa gacttctggg aagttcaatt aggaatacca catcccgcag ggttaaaaaa    2400
gaaaaaatca gtaacagtac tggatgtggg tgatgcatat ttttcagttc ccttagatga    2460
agacttcagg aagtatactg catttaccat acctagtata aacaatgaga caccagggat    2520
tagatatcag tacaatgtgc ttccacaggg atggaaagga tcaccagcaa tattccaaag    2580
tagcatgaca aaaatcttag agccttttag aaaacaaaat ccagacatag ttatctatca    2640
atacatggat gatttgtatg taggatctga cttagaaata gggcagcata gaacaaaaat    2700
agaggagctg agacaacatc tgttgaggtg gggacttacc acaccagaca aaaaacatca    2760
gaaagaacct ccattccttt ggatgggtta tgaactccat cctgataaat ggacagtaca    2820
gcctatagtg ctgccagaaa aagacagctg gactgtcaat gacatacaga agttagtggg    2880
gaaattgaat tgggcaagtc agatttaccc agggattaaa gtaaggcaat tatgtaaact    2940
ccttagagga accaaagcac taacagaagt aataccacta acagaagaag cagagctaga    3000
actggcagaa aacagagaga ttctaaaaga accagtacat ggagtgtatt atgacccatc    3060
aaaagactta atagcagaaa tacagaagca ggggcaaggc caatggacat atcaaattta    3120
tcaagagcca tttaaaaatc tgaaaacagg aaaatatgca agaatgaggg gtgcccacac    3180
taatgatgta aaacaattaa cagaggcagt gcaaaaaata accacagaaa gcatagtaat    3240
atggggaaag actcctaaat ttaaactgcc catacaaaag gaaacatggg aaacatggtg    3300
gacagagtat tggcaagcca cctggattcc tgagtgggag tttgttaata cccctccctt    3360
agtgaaatta tggtaccagt tagagaaaga acccatagta ggagcagaaa ccttctatgt    3420
agatggggca gctaacaggg agactaaatt aggaaaagca ggatatgtta ctaatagagg    3480
aagacaaaaa gttgtcaccc taactgacac aacaaatcag aagactgagt tacaagcaat    3540
ttatctagct ttgcaggatt cgggattaga agtaaacata gtaacagact cacaatatgc    3600
attaggaatc attcaagcac aaccagatca aagtgaatca gagttagtca atcaaataat    3660
agagcagtta ataaaaaagg aaaaggtcta tctggcatgg gtaccagcac acaaaggaat    3720
tggaggaaat gaacaagtag ataaattagt cagtgctgga atcaggaaag tactattttt    3780
agatggaata gataaggccc aagatgaaca tgagaaatat cacagtaatt ggagagcaat    3840
ggctagtgat tttaacctgc cacctgtagt agcaaaagaa atagtagcca gctgtgataa    3900
atgtcagcta aaaggagaag ccatgcatgg acaagtagac tgtagtccag gaatatggca    3960
actagattgt acacatttag aaggaaaagt tatcctggta gcagttcatg tagccagtgg    4020
atatatagaa gcagaagtta ttccagcaga acagggcag gaaacagcat attttctttt    4080
aaaattagca ggaagatggc cagtaaaaac aatacatact gacaatggca gcaatttcac    4140
cggtgctacg gttagggccg cctgttggtg gcgggaatc aagcaggaat ttggaattcc    4200
ctacaatccc caaagtcaag gagtagtaga atctatgaat aaagaattaa agaaaattat    4260
aggacaggta agagatcagg ctgaacatct taagacagca gtacaaatgg cagtattcat    4320
ccacaatttt aaaagaaaag ggggattgg ggggtacagt gcaggggaaa gaatagtaga    4380
```

```
cataatagca acagacatac aaactaaaga attacaaaaa caaattacaa aaattcaaaa   4440
ttttcgggtt tattacaggg acagcagaaa tccactttgg aaaggaccag caaagctcct   4500
ctggaaaggt gaaggggcag tagtaataca agataatagt gacataaaag tagtgccaag   4560
aagaaaagca aagatcatta gggattatgg aaaacagatg gcaggtgatg attgtgtggc   4620
aagtagacag gatgaggatt agaacatgga aaagtttagt aaaacaccat atgtatgttt   4680
cagggaaagc taggggatgg ttttatagac atcactatga aagccctcat ccaagaataa   4740
gttcagaagt acacatccca ctaggggatg ctagattggt aataacaaca tattggggtc   4800
tgcatacagg agaaagagac tggcatttgg gtcagggagt ctccatagaa tggaggaaaa   4860
agagatatag cacacaagta gaccctgaac tagcagacca actaattcat ctgtattact   4920
ttgactgttt ttcagactct gctataagaa aggccttatt aggacacata gttagcccta   4980
ggtgtgaata tcaagcagga cataacaagg taggatctct acaatacttg gcactagcag   5040
cattaataac accaaaaaag ataaagccac ctttgcctag tgttacgaaa ctgacagagg   5100
atagatggaa caagccccag aagaccaagg gccacagagg gagccacaca atgaatggac   5160
actagagctt ttagaggagc ttaagaatga agctgttaga cattttccta ggatttggct   5220
ccatggctta gggcaacata tctatgaaac ttatggggat acttgggcag gagtggaagc   5280
cataataaga attctgcaac aactgctgtt tatccatttt cagaattggg tgtcgacata   5340
gcagaatagg cgttactcga cagaggagag caagaaatgg agccagtaga tcctagacta   5400
gagccctgga agcatccagg aagtcagcct aaaactgctt gtaccaattg ctattgtaaa   5460
aagtgttgct ttcattgcca agtttgtttc ataacaaaag ccttaggcat ctcctatggc   5520
aggaagaagc ggagacagcg acgaagagct catcagaaca gtcagactca tcaagcttct   5580
ctatcaaagc agtaagtagt acatgtaatg caacctatac caatagtagc aatagtagca   5640
ttagtagtag caataataat agcaatagtt gtgtggtcca tagtaatcat agaatatagg   5700
aaaatattaa gacaaagaaa aatagacagg ttaattgata gactaataga aagagcagaa   5760
gacagtggca atgagagtga aggagaaata tcagcacttg tggagatggg ggtggagatg   5820
gggcaccatg ctccttggga tgttgatgat ctgtagtgct acagaaaaat tgtgggtcac   5880
agtctattat ggggtacctg tgtggaagga agcaaccacc actctatttt gtgcatcaga   5940
tgctaaagca tatgatacag aggtacataa tgtttgggcc acacatgcct gtgtacccac   6000
agaccccaac ccacaagaag tagtattggt aaatgtgaca gaaaatttta acatgtggaa   6060
aaatgacatg gtagaacaga tgcatgagga tataatcagt ttatgggatc aaagcctaaa   6120
gccatgtgta aaattaaccc cactctgtgt tagtttaaag tgcactgatt tgaagaatga   6180
tactaatacc aatagtagta gcgggagaat gataatggag aaaggagaga taaaaaactg   6240
ctctttcaat atcagcacaa gcataagagg taaggtgcag aaagaatatg catttttta    6300
taaacttgat ataataccaa tagataatga tactaccagc tataagttga caagttgtaa   6360
cacctcagtc attacacagg cctgtccaaa ggtatccttt gagccaattc ccatacatta   6420
ttgtgccccg gctggttttg cgattctaaa atgtaataat aagacgttca atggaacagg   6480
accatgtaca aatgtcagca cagtacaatg tacacatgga attaggccag tagtatcaac   6540
tcaactgctg ttaaatggca gtctagcaga agaagaggta gtaattagat ctgtcaattt   6600
cacggacaat gctaaaacca taatagtaca gctgaacaca tctgtagaaa ttaattgtac   6660
aagacccaac aacaatacaa gaaaaagaat ccgtatccag agaggaccag ggagagcatt   6720
```

```
tgttacaata ggaaaaatag gaaatatgag acaagcacat tgtaacatta gtagagcaaa   6780
atggaataac actttaaaac agatagctag caaattaaga gaacaatttg gaaataataa   6840
aacaataatc tttaagcaat cctcaggagg ggacccagaa attgtaacgc acagttttaa   6900
ttgtggaggg gaatttttct actgtaattc aacacaactg tttaatagta cttggtttaa   6960
tagtacttgg agtactgaag ggtcaaataa cactgaagga agtgacacaa tcaccctccc   7020
atgcagaata aaacaaatta taaacatgtg gcagaaagta ggaaaagcaa tgtatgcccc   7080
tcccatcagt ggacaaatta gatgttcatc aaatattaca gggctgctat taacaagaga   7140
tggtggtaat agcaacaatg agtccgagat cttcagacct ggaggaggag atatgaggga   7200
caattggaga agtgaattat ataaatataa agtagtaaaa attgaaccat taggagtagc   7260
acccaccaag gcaaagagaa gagtggtgca gagagaaaaa agagcagtgg gaataggagc   7320
tttgttcctt gggttcttgg gagcagcagg aagcactatg ggcgcagcct caatgacgct   7380
gacggtacag gccagacaat tattgtctgg tatagtgcag cagcagaaca atttgctgag   7440
ggctattgag gcgcaacagc atctgttgca actcacagtc tggggcatca agcagctcca   7500
ggcaagaatc ctggctgtgg aaagatacct aaaggatcaa cagctcctgg ggatttgggg   7560
ttgctctgga aaactcattt gcaccactgc tgtgccttgg aatgctagtt ggagtaataa   7620
atctctggaa cagatttgga atcacacgac ctggatggag tgggacagag aaattaacaa   7680
ttacacaagc ttaatacact ccttaattga agaatcgcaa aaccagcaag aaaagaatga   7740
acaagaatta ttggaattag ataaatgggc aagtttgtgg aattggttta cataacaaa    7800 ttggctgtgg tatataaaat tattcataat gatagtagga ggcttggtag gtttaagaat   7860
agtttttgct gtactttcta tagtgaatag agttaggcag ggatattcac cattatcgtt   7920
tcagacccac ctcccaaccc cgaggggacc cgacaggccc gaaggaatag aagaagaagg   7980
tggagagaga gacagagaca gatccattcg attagtgaac ggatccttgg cacttatctg   8040
ggacgatctg cggagcctgt gcctcttcag ctaccaccgc ttgagagact tactcttgat   8100
tgtaacgagg attgtggaac ttctgggacg caggggtgg gaagccctca atattggtg    8160 gaatctccta cagtattgga gtcaggaact aaagaatagt gctgttagct tgctcaatgc   8220
cacagccata gcagtagctg aggggacaga tagggttata gaagtagtac aaggagcttg   8280
tagagctatt cgccacatac ctagaagaat aagacagggc ttggaaagga ttttgctata   8340
agatgggtgg caagtggtca aaaagtagtg tgattggatg gcctactgta agggaaagaa   8400
tgagacgagc tgagccagca gcagataggg tgggagcagc atctcgagac ctggaaaaac   8460
atggagcaat cacaagtagc aatacagcag ctaccaatgc tgcttgtgcc tggctagaag   8520
cacaagagga ggaggaggtg ggttttccag tcacacctca ggtacccttta agaccaatga   8580 cttacaaggc agctgtagat cttagccact ttttaaaaga aaaggggggga ctggaagggc   8640 taattcactc ccaaagaaga caagatatcc ttgatctgtg gatctaccac acacaaggct   8700
acttccctga ttagcagaac tacacaccag ggccaggggt cagatatcca ctgacctttg   8760
gatggtgcta caagctagta ccagttgagc cagataagat agaagaggcc aataaaggag   8820
agaacaccag cttgttacac cctgtgagcc tgcatgggat ggatgacccg gagagagaag   8880
tgttagagtg gaggtttgac agccgcctag catttcatca cgtggcccga gagctgcatc   8940
cggagtactt caagaactgc tgacatcgag cttgctacaa gggactttcc gctggggact   9000
ttccagggag gcgtggcctg ggcgggactg ggagtggcg agccctcaga tcctgcatat   9060
aagcagctgc ttttttgcctg tactgggtct ctctggttag accagatctg agcctgggag   9120
```

```
ctctctggct aactagggaa cccactgctt aagcctcaat aaagcttgcc ttgagtgctt    9180
caaa                                                                 9184

<210> SEQ ID NO 389
<211> LENGTH: 9184
<212> TYPE: DNA
<213> ORGANISM: Human immunodeficiency virus

<400> SEQUENCE: 389
gaagcactca aggcaagctt tattgaggct taagcagtgg gttccctagt tagccagaga      60
gctcccaggc tcagatctgg tctaaccaga gagacccagt acaggcaaaa agcagctgct     120
tatatgcagg atctgagggc tcgccactcc ccagtccgc ccaggccacg cctccctgga     180
aagtccccag cggaaagtcc cttgtagcaa gctcgatgtc agcagttctt gaagtactcc     240
ggatgcagct ctcgggccac gtgatgaaat gctaggcggc tgtcaaacct ccactctaac     300
acttctctct ccgggtcatc catcccatgc aggctcacag ggtgtaacaa gctggtgttc     360
tctcctttat tggcctcttc tatcttatct ggctcaactg gtactagctt gtagcaccat     420
ccaaaggtca gtggatatct gacccctggc cctggtgtgt agttctgcta atcagggaag     480
tagccttgtg tgtggtagat ccacagatca aggatatctt gtcttctttg ggagtgaatt     540
agcccttcca gtccccccctt ttcttttaaa aagtggctaa gatctacagc tgccttgtaa     600
gtcattggtc ttaaaggtac ctgaggtgtg actggaaaac ccacctcctc ctcctcttgt     660
gcttctagcc aggcacaagc agcattggta gctgctgtat tgctacttgt gattgctcca     720 tgttttttcca ggtctcgaga tgctgctccc accctatctg ctgctggctc agctcgtctc     780
attctttccc ttacagtagg ccatccaatc acactacttt tgaccacttt gccacccatc     840
ttatagcaaa atccttttcca agccctgtct tattcttcta ggtatgtggc gaatagctct     900
acaagctcct tgtactactt ctataaccct atctgtcccc tcagctactg ctatggctgt     960
ggcattgagc aagctaacag cactattctt tagttcctga ctccaatact gtaggagatt    1020
ccaccaatat ttgagggctt ccaccccccct gcgtcccaga agttccacaa tcctcgttac    1080
aatcaagagt aagtctctca gcggtggta gctgaagagg cacaggctcc gcagatcgtc    1140
ccagataagt gccaaggatc cgttcactaa tcgaatggat ctgtctctgt ctctctctcc    1200
accttcttct tctattcctt cgggcctgtc gggtcccctc ggggttggga ggtgggtctg    1260
aaacgataat ggtgaatatc cctgcctaac tctattcact atagaaagta cagcaaaaac    1320
tattcttaaa cctaccaagc ctcctactat cattatgaat aatttatat accacagcca    1380 atttgttatg ttaaaccaat tccacaaact tgcccattta tctaattcca ataattcttg    1440
ttcattcttt tcttgctggt tttgcgattc ttcaattaag gagtgtatta agcttgtgta    1500
attgttaatt tctctgtccc actccatcca ggtcgtgtga ttccaaatct gttccagaga    1560
tttattactc caactagcat tccaaggcac agcagtggtg caaatgagtt ttccagagca    1620 acccccaaatc cccaggagct gttgatcctt taggtatctt tccacagcca ggattcttgc    1680
ctggagctgc ttgatgcccc agactgtgag ttgcaacaga tgctgttgcg cctcaatagc    1740
cctcagcaaa ttgttctgct gctgcactat accagacaat aattgtctgg cctgtaccgt    1800
cagcgtcatt gaggctgcgc ccatagtgct tcctgctgct cccaagaacc caaggaacaa    1860
agctcctatt cccactgctc tttttttctct ctgcaccact cttctctttg ccttggtggg    1920
tgctactcct aatggttcaa ttttttactac tttatattta tataattcac ttctccaatt    1980
```

```
gtccctcata tctcctcctc caggtctgaa gatctcggac tcattgttgc tattaccacc    2040
atctcttgtt aatagcagcc ctgtaatatt tgatgaacat ctaatttgtc cactgatggg    2100
aggggcatac attgcttttc ctactttctg ccacatgttt ataatttgtt ttattctgca    2160
tgggagggtg attgtgtcac ttccttcagt gttatttgac ccttcagtac tccaagtact    2220
attaaaccaa gtactattaa acagttgtgt tgaattacag tagaaaaatt cccctccaca    2280
attaaaactg tgcgttacaa tttctgggtc ccctcctgag gattgcttaa agattattgt    2340
tttattattt ccaaattgtt ctcttaattt gctagctatc tgttttaaag tgttattcca    2400
ttttgctcta ctaatgttac aatgtgcttg tctcatattt cctatttttc ctattgtaac    2460
aaatgctctc cctggtcctc tctggatacg gattcttttt cttgtattgt tgttgggtct    2520
tgtacaatta atttctacag atgtgttcag ctgtactatt atggttttag cattgtccgt    2580
gaaattgaca gatctaatta ctacctcttc ttctgctaga ctgccattta acagcagttg    2640
agttgatact actggcctaa ttccatgtgt acattgtact gtgctgacat tgtacatgg     2700 tcctgttcca ttgaacgtct tattattaca ttttagaatc gcaaaaccag ccggggcaca    2760
ataatgtatg ggaattggct caaaggatac ctttggacag gcctgtgtaa tgactgaggt    2820
gttacaactt gtcaacttat agctggtagt atcattatct attggtatta tatcaagttt    2880
ataaaaaaat gcatattctt tctgcacctt acctcttatg cttgtgctga tattgaaaga    2940 gcagttttt atctctcctt tctccattat cattctcccg ctactactat ggtattagt     3000 atcattcttc aaatcagtgc actttaaact aacacagagt ggggttaatt ttacacatgg    3060
ctttaggctt tgatcccata aactgattat atcctcatgc atctgttcta ccatgtcatt    3120
tttccacatg ttaaaatttt ctgtcacatt taccaatact acttcttgtg gttggggtc    3180 tgtgggtaca caggcatgtg tggcccaaac attatgtacc tctgtatcat atgctttagc    3240
atctgatgca caaaatagag tggtggttgc ttccttccac acaggtaccc cataatagac    3300
tgtgacccac aatttttctg tagcactaca gatcatcaac atcccaagga gcatggtgcc    3360
ccatctccac ccccatctcc acaagtgctg atatttctcc ttcactctca ttgccactgt    3420
cttctgctct ttctattagt ctatcaatta acctgtctat ttttctttgt cttaatattt    3480
tcctatattc tatgattact atggaccaca caactattgc tattattatt gctactacta    3540
atgctactat tgctactatt ggtataggtt gcattacatg tactacttac tgctttgata    3600
gagaagcttg atgagtctga ctgttctgat gagctcttcg tcgctgtctc cgcttcttcc    3660
tgccatagga gatgcctaag gcttttgtta tgaaacaaac ttggcaatga agcaacact    3720 ttttacaata gcaattggta caagcagttt taggctgact tcctggatgc ttccagggct    3780
ctagtctagg atctactggc tccatttctt gctctcctct gtcgagtaac gcctattctg    3840
ctatgtcgac acccaattct gaaaatggat aaacagcagt tgttgcagaa ttcttattat    3900
ggcttccact cctgcccaag tatccccata gtttcatag atatgttgcc ctaagccatg    3960
gagccaaatc ctaggaaaat gtctaacagc ttcattctta agctcctcta aaagctctag    4020
tgtccattca ttgtgtggct ccctctgtgg cccttggtct tctggggctt gttccatcta    4080
tcctctgtca gttcgtaac actaggcaaa ggtggcttta tctttttgg tgttattaat      4140 gctgctagtg ccaagtattg tagagatcct accttgttat gtcctgcttg atattcacac    4200
ctagggctaa ctatgtgtcc taataaggcc tttcttatag cagagtctga aaaacagtca    4260
aagtaataca gatgaattag ttggtctgct agttcagggt ctacttgtgt gctatatctc    4320
tttttcctcc attctatgga gactccctga cccaaatgcc agtctctttc tcctgtatgc    4380
```

```
agaccccaat atgttgttat taccaatcta gcatcccta gtgggatgtg tacttctgaa    4440
cttattcttg gatgagggct ttcatagtga tgtctataaa accatcccct agctttccct    4500
gaaacataca tatggtgttt tactaaactt ttccatgttc taatcctcat cctgtctact    4560
tgccacacaa tcatcacctg ccatctgttt tccataatcc ctaatgatct ttgcttttct    4620
tcttggcact acttttatgt cactattatc ttgtattact actgcccctt cacctttcca    4680
gaggagcttt gctggtcctt tccaaagtgg atttctgctg tccctgtaat aaacccgaaa    4740
attttgaatt tttgtaattt gttttttgtaa ttctttagtt tgtatgtctg ttgctattat    4800
gtctactatt ctttcccctg cactgtaccc cccaatcccc ccttttcttt taaaattgtg    4860
gatgaatact gccatttgta ctgctgtctt aagatgttca gcctgatctc ttacctgtcc    4920
tataattttc tttaattctt tattcataga ttctactact ccttgacttt ggggattgta    4980
gggaattcca aattcctgct tgattcccgc ccaccaacag gcggccctaa ccgtagcacc    5040
ggtgaaattg ctgccattgt cagtatgtat tgttttact ggccatcttc ctgctaattt    5100
taaaagaaaa tatgctgttt cctgccctgt ttctgctgga ataacttctg cttctatata    5160
tccactggct acatgaactg ctaccaggat aacttttcct tctaaatgtg tacaatctag    5220
ttgccatatt cctggactac agtctacttg tccatgcatg gcttctcctt ttagctgaca    5280
tttatcacag ctggctacta tttcttttgc tactacaggt ggcaggttaa aatcactagc    5340
cattgctctc caattactgt gatatttctc atgttcatct tgggccttat ctattccatc    5400
taaaaatagt actttcctga ttccagcact gactaattta tctacttgtt catttcctcc    5460
aattcctttg tgtgctggta cccatgccag atagacctt tccttttta ttaactgctc    5520 tattatttga ttgactaact ctgattcact ttgatctggt tgtgcttgaa tgattcctaa    5580
tgcatattgt gagtctgtta ctatgtttac ttctaatccc gaatcctgca aagctagata    5640
aattgcttgt aactcagtct tctgatttgt tgtgtcagtt agggtgacaa cttttttgtct    5700 tcctctatta gtaacatatc ctgcttttcc taatttagtc tccctgttag ctgccccatc    5760
tacatagaag gttctgctc ctactatggg ttctttctct aactggtacc ataatttcac    5820
taagggaggg gtattaacaa actcccactc aggaatccag gtggcttgcc aatactctgt    5880
ccaccatgtt tcccatgttt cctttgtat gggcagttta aatttaggag tctttcccca    5940
tattactatg ctttctgtgg ttatttttg cactgcctct gttaattgtt ttacatcatt    6000
agtgtgggca ccctcattc ttgcatattt tcctgttttc agatttttaa atggctcttg    6060
ataaatttga tatgtccatt ggccttgccc ctgcttctgt atttctgcta ttaagtcttt    6120
tgatgggtca taatacactc catgtactgg ttcttttaga atctctctgt tttctgccag    6180
ttctagctct gcttcttctg ttagtggtat tacttctgtt agtgctttgg ttcctctaag    6240
gagtttacat aattgcctta ctttaatccc tgggtaaatc tgacttgccc aattcaattt    6300
ccccactaac ttctgtatgt cattgacagt ccagctgtct tttctggca gcactatagg    6360 ctgtactgtc catttatcag gatggagttc ataacccatc caaggaatg gaggttcttt    6420 ctgatgtttt ttgtctggtg tggtaagtcc ccacctcaac agatgttgtc tcagctcctc    6480 tattttttgtt ctatgctgcc ctattctaa gtcagatcct acatacaaat catccatgta    6540
ttgatagata actatgtctg gatttgtttt tctaaaaggc tctaagattt ttgtcatgct    6600
actttggaat attgctggtg atcctttcca tccctgtgga agcacattgt actgatatct    6660
aatccctggt gtctcattgt ttatactagg tatggtaaat gcagtatact tcctgaagtc    6720
```

```
ttcatctaag ggaactgaaa aatatgcatc acccacatcc agtactgtta ctgattttt      6780
cttttttaac cctgcgggat gtggtattcc taattgaact tcccagaagt cttgagttct      6840
cttattaagt tctctgaaat ctactaattt tctccattta gtactgtctt ttttctttat      6900
ggcaaatact ggagtattgt atggattttc aggcccaatt tttgaaattt tcccttcctt      6960
ttccatctct gtacaaattt ctactaatgc ttttattttt tcttctgtca atggccattg      7020
tttaacttt tgggccatcca ttcctggctt taattttact ggtacagtct caatagggct      7080
aatgggaaaa tttaaagtgc aaccaatctg agtcaacaga tttcttccaa ttatgttgac      7140
aggtgtaggt cctactaata ctgtacctat agctttatgt ccacagattt ctatgagtat      7200
ctgatcatac tgtcttactt tgataaaacc tccaattccc cctatcattt ttggtttcca      7260
tcttcctggc aaactcattt cttcaatac tgtatcatct gctcctgtat ctaatagagc       7320
ttcctttagt tgccccccta tctttattgt gacgaggggt cgttgccaaa gagtgacctg      7380
agggaagtta aaggatacag ttccttgtct atcggctcct gcttctgagg gggagttgtt      7440
gtctctaccc cagacctgaa gctctcttct ggtgggctg ttggctctgg tctgctctga       7500
agaaaattcc ctggccttcc cttgtaggaa ggccagatct tccctaaaaa attagcctgt      7560
ctctcagtac aatctttcat ttggtgtcct tcctttccac atttcaaca gccctttttc       7620
ctaggggccc tgcaatttct ggctgtgtgc ccttctttgc cacaattgaa acacttaaca      7680
atctttcttt ggttcctaaa attgcctctc tgcatcatta tggtagctga atttgttact      7740
tggctcattg cttcagccaa aactcttgcc ttatggccgg gtcctcctac tccctgacat      7800
gctgtcatca tttcttctag tgtagccgct ggtcccaatg cttttaaaat agtcttacaa      7860
tctgggttcg cattttggac caacaaggtt tctgtcatcc aatttttac ctcctgtgaa       7920
gcttgctcgg ctcttagagt tttatagaac cggtctacat agtctctaaa gggttccttt      7980
ggtccttgtc ttatgtccag aatgctggta gggctataca ttcttactat tttatttaat     8040
cccaggatta tccatctttt ataaatttct cctactggga taggtggatt atttgtcatc      8100
catcctattt gttcctgaag ggtactagta gttcctgcta tgtcacttcc ccttggttct     8160
ctcatctggc ctggtgcaat aggccctgca tgcactggat gcactctatc ccattctgca      8220
gcttcctcat tgatggtctc ttttaacatt tgcatggctg cttgatgtcc ccccactgtg      8280
tttagcatgt tgtttaaatc ttgtggggtg gctccttctg ataatgctga aaacatgggt      8340
atcacttctg ggctgaaagc cttctcttct actacttta cccatgcatt taaagttcta       8400
ggtgatatgg cctgatgtac catttgcccc tggatgttct gcactatagg gtaatttgg      8460
ctgacctgat tgctgtgtcc tgtgtcagct gctgcttgct gtgctttttt cttacttttg     8520
ttttgctctt cctctatctt gtctaaagct tccttggtgt cttttatctc tatcctttga     8580
tgcacacaat agagggttgc tactgtatta tataatgatc taagttcttc tgatcctgtc     8640
tgaagggatg gttgtagctg tcccagtatt tgtctacagc cttctgatgt ttctaacagg     8700
ccaggattaa ctgcgaatcg ttctagctcc ctgcttgccc atactatatg ttttaattta     8760
tattttttct ttcccctgg ccttaaccga atttttccc atcgatctaa ttctcccccg        8820
cttaatactg acgctctcgc acccatctct ctccttctag cctccgctag tcaaaatttt     8880
tggcgtactc accagtcgcc gcccctcgcc tcttgccgtg cgcgcttcag caagccgagt     8940
cctgcgtcga gagagctcct ctggtttccc tttcgctttc aggtccctgt tcgggcgcca     9000
ctgctagaga ttttccacac tgactaaaag ggtctgaggg atctctagtt accagagtca     9060
cacaacagac gggcacacac tacttgaagc actcaaggca agctttattg aggcttaagc     9120
```

```
agtgggttcc ctagttagcc agagagctcc caggctcaga tctggtctaa ccagagagac    9180
ccct                                                                 9184

<210> SEQ ID NO 390
<211> LENGTH: 87
<212> TYPE: DNA
<213> ORGANISM: Human immunodeficiency virus

<400> SEQUENCE: 390
aaaataggag acaactgaa agaagctcta ttagatacag gagcagatga tacagtatta     60
gaagatataa atttgccagg gaaatgg                                        87

<210> SEQ ID NO 391
<211> LENGTH: 87
<212> TYPE: DNA
<213> ORGANISM: Human immunodeficiency virus

<400> SEQUENCE: 391
aaagtaggag acagctaaa agaagctcta ttagacacag gagcagatga tacagtatta     60
gaagacataa atttgccagg aaaatgg                                        87

<210> SEQ ID NO 392
<211> LENGTH: 87
<212> TYPE: DNA
<213> ORGANISM: Human immunodeficiency virus

<400> SEQUENCE: 392 aagataggg ggcaactaaa ggaagctcta ttagatacag gagcagatga tacagtatta     60
gaagaaatga gtttgccagg aagatgg                                        87

<210> SEQ ID NO 393
<211> LENGTH: 185
<212> TYPE: DNA
<213> ORGANISM: Artificial Sequence
<220> FEATURE:
<223> OTHER INFORMATION: Consensus sequence

<400> SEQUENCE: 393
tycttcagag cagaccagag ccaacagccc caccatttct tcagagcaga ccagagccaa    60
cagccccacc agaagagagc ttcaggtctg gggtagagac aacaactccc cctcagaagc    120
aggagccgat agacaaggar mtgtatcctt trrcttccct cagatcactc tttggcaacg    180
acccc                                                                185

<210> SEQ ID NO 394
<211> LENGTH: 185
<212> TYPE: DNA
<213> ORGANISM: Human immunodeficiency virus

<400> SEQUENCE: 394
ttcttcagag cagaccagag ccaacagccc caccatttct tcagagcaga ccagagccaa    60
cagccccacc agaagagagc ttcaggtctg gggtagagac aacaactccc cctcagaagc    120
aggagccgat agacaaggag atgtatcctt tggcttccct cagatcactc tttggcaacg    180
acccc                                                                185

<210> SEQ ID NO 395
<211> LENGTH: 185
<212> TYPE: DNA
```

<213> ORGANISM: Human immunodeficiency virus

<400> SEQUENCE: 395

| ttcttcagag cagaccagag ccaacagccc caccatttct tcagagcaga ccagagccaa | 60 |
| cagccccacc agaagagagc ttcaggtctg gggtagagac aacaactccc cctcagaagc | 120 |
| aggagccgat agacaaggaa ctgtatcctt taacttccct cagatcactc tttggcaacg | 180 |
| acccc | 185 |

<210> SEQ ID NO 396
<211> LENGTH: 149
<212> TYPE: DNA
<213> ORGANISM: Human immunodeficiency virus

<400> SEQUENCE: 396

| tccttcagag cagaccagag ccaacagccc caccagcaga gagcttcagg tttggggaag | 60 |
| aggtaacaac tccctctcag aaacaggagc cgatagacaa ggagatgtat cctttggctt | 120 |
| ccctcagatc actctttggc aacgacccc | 149 |

<210> SEQ ID NO 397
<211> LENGTH: 149
<212> TYPE: DNA
<213> ORGANISM: Human immunodeficiency virus

<400> SEQUENCE: 397

| tccttcagag cagaccagag ccaacagccc caccagaaga gagcttcagg tctggggtag | 60 |
| agacaacaac tccccctcag aagcaggagc cgatagacaa ggaactgtat cctttaactt | 120 |
| ccctcagatc actctttggc aacgacccc | 149 |

<210> SEQ ID NO 398
<211> LENGTH: 100
<212> TYPE: DNA
<213> ORGANISM: Human immunodeficiency virus

<400> SEQUENCE: 398

| ttagataaga tagaggaaga gcaaaacaaa agtaagaaaa agacacagca agcagcagct | 60 |
| gacacaggaa acagcagcaa gcaggtcagc caaaattacc | 100 |

<210> SEQ ID NO 399
<211> LENGTH: 100
<212> TYPE: DNA
<213> ORGANISM: Human immunodeficiency virus

<400> SEQUENCE: 399

| atggacccac ctcccaaccc cgagggaacc cgacaggccc gaaggaatcg aagaagaagg | 60 |
| tggagagaga gacagagaca catccggaag attagtggat | 100 |

<210> SEQ ID NO 400
<211> LENGTH: 180
<212> TYPE: DNA
<213> ORGANISM: Human immunodeficiency virus

<400> SEQUENCE: 400

| gagcttttag aggagcttaa gaatgaagct gttagacatt ttcccaggcc atggcttcat | 60 |
| ggattggggc agcatatcta tgaaacttat ggggatactt ggacaggagt ggaagccata | 120 |
| ataagaattc tgcaacaact gctgtttatc catttcagaa ttgggtgtcg acatagcaga | 180 |

-continued

```
<210> SEQ ID NO 401
<211> LENGTH: 96
<212> TYPE: PRT
<213> ORGANISM: Human immunodeficiency virus

<400> SEQUENCE: 401

Met Glu Gln Ala Pro Glu Asp Gln Gly Pro Gln Arg Glu Pro His Asn
1               5                   10                  15

Glu Trp Thr Leu Glu Leu Leu Glu Glu Leu Lys Asn Glu Ala Val Arg
            20                  25                  30

His Phe Pro Arg Ile Trp Leu His Gly Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Arg His Ser Arg
65                  70                  75                  80

Ile Gly Val Thr Arg Gln Arg Arg Ala Arg Asn Gly Ala Ser Arg Ser
                85                  90                  95

<210> SEQ ID NO 402
<211> LENGTH: 40
<212> TYPE: PRT
<213> ORGANISM: Human immunodeficiency virus

<400> SEQUENCE: 402

Glu Leu Leu Glu Glu Leu Lys Asn Glu Ala Val Arg His Phe Pro Arg
1               5                   10                  15

Pro Trp Leu His Gly Leu Gly Gln His Ile Tyr Glu Thr Tyr Gly Asp
            20                  25                  30

Thr Trp Thr Gly Val Glu Ala Ile
        35                  40

<210> SEQ ID NO 403
<211> LENGTH: 21
<212> TYPE: PRT
<213> ORGANISM: Human immunodeficiency virus

<400> SEQUENCE: 403

Lys Ile Arg Leu Arg Pro Gly Gly Lys Lys Tyr Lys Leu Lys His
1               5                   10                  15

Ile Val Trp Ala Ser
            20

<210> SEQ ID NO 404
<211> LENGTH: 21
<212> TYPE: PRT
<213> ORGANISM: Human immunodeficiency virus

<400> SEQUENCE: 404

Lys Ile Arg Leu Arg Pro Gly Gly Arg Lys Tyr Lys Leu Lys His
1               5                   10                  15

Ile Val Trp Ala Ser
            20

<210> SEQ ID NO 405
<211> LENGTH: 18
<212> TYPE: PRT
<213> ORGANISM: Human immunodeficiency virus

<400> SEQUENCE: 405

Thr Gly Ser Glu Glu Leu Arg Ser Leu Tyr Asn Thr Val Ala Thr Leu
```

```
<210> SEQ ID NO 406
<211> LENGTH: 18
<212> TYPE: PRT
<213> ORGANISM: Human immunodeficiency virus

<400> SEQUENCE: 406

Thr Gly Ser Glu Glu Phe Arg Ser Leu Tyr Asn Thr Val Ala Thr Leu
1               5                   10                  15
Tyr Cys

<210> SEQ ID NO 407
<211> LENGTH: 1816
<212> TYPE: DNA
<213> ORGANISM: Homo sapiens

<400> SEQUENCE: 407
cttctctgcc agaagatacc atttcaactt taacacagca tgatcgaaac atacaaccaa     60
acttctcccc gatctgcggc cactggactg cccatcagca tgaaattttt tatgtattta    120
cttactgttt ttcttatcac ccagatgatt gggtcagcac ttttgctgt gtatcttcat     180 agaaggttgg acaagataga agatgaaagg aatcttcatg aagattttgt attcatgaaa    240
acgatacaga gatgcaacac aggagaaaga tccttatcct tactgaactg tgaggagatt    300
aaaagccagt ttgaaggctt tgtgaaggat ataatgttaa caaagagga gacgaagaaa     360 gaaaacagct ttgaaatgca aaaaggtgat cagaatcctc aaattgcggc acatgtcata    420
agtgaggcca gcagtaaaac aacatctgtg ttacagtggg ctgaaaaagg atactacacc    480
atgagcaaca acttggtaac cctggaaaat gggaaacagc tgaccgttaa agacaagga    540 ctctattata tctatgccca agtcaccttc tgttccaatc gggaagcttc gagtcaagct    600
ccatttatag ccagcctctg cctaaagtcc cccggtagat tcgagagaat cttactcaga    660
gctgcaaata cccacagttc cgccaaacct tgcgggcaac aatccattca cttgggagga    720
gtatttgaat tgcaaccagg tgcttcggtg tttgtcaatg tgactgatcc aagccaagtg    780
agccatggca ctggcttcac gtcctttggc ttactcaaac tctgaacagt gtcaccttgc    840
aggctgtggt ggagctgacg ctgggagtct tcataataca gcacagcggt taagcccacc    900
ccctgttaac tgcctatttta aaccctagg atcctcctta tggagaacta tttattatac    960
actccaaggc atgtagaact gtaataagtg aattacaggt cacatgaaac caaaacgggc   1020
cctgctccat aagagcttat atatctgaag cagcaacccc actgatgcag acatccagag   1080
agtcctatga aaagacaagg ccattatgca caggttgaat tctgagtaaa cagcagataa   1140
cttgccaagt tcagttttgt ttctttgcgt gcagtgtctt tccatggata atgcatttga   1200
tttatcagtg aagatgcaga agggaaatgg ggagcctcag ctcacattca gttatggttg   1260
actctgggtt cctatggcct tgttggaggg ggccaggctc tagaacgtct aacacagtgg   1320
agaaccgaaa ccccccccc cccccccgcc accctctcgg acagttattc attctctttc   1380
aatctctctc tctccatctc tctctttcag tctctctctc tcaacctctt tcttccaatc   1440
tctctttctc aatctctctg tttcccttg tcagtctctt ccctccccca gtctctcttc   1500 tcaatcccc tttctaacac acacacacac acacacacac acacacacac acacacacac   1560
acacacacac acacacacac agagtcaggc cgttgctagt cagttctctt ctttccaccc   1620
```

```
tgtccctatc tctaccacta tagatgaggg tgaggagtag ggagtgcagc cctgagcctg    1680
cccactcctc attacgaaat gactgtattt aaaggaaatc tattgtatct acctgcagtc    1740
tccattgttt ccagagtgaa cttgtaatta tcttgttatt tattttttga ataataaaga    1800
cctcttaaca ttaaaa                                                    1816

<210> SEQ ID NO 408
<211> LENGTH: 261
<212> TYPE: PRT
<213> ORGANISM: Homo sapiens

<400> SEQUENCE: 408

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```